United States Patent [19]
Arthur et al.

[11] Patent Number: 5,871,910
[45] Date of Patent: Feb. 16, 1999

[54] PROBES FOR THE DETECTION OF NUCLEOTIDE SEQUENCES IMPLICATED IN THE EXPRESSION OF RESISTANCE TO GLYCOPEPTIDES, IN PARTICULAR IN GRAM-POSITIVE BACTERIA

[75] Inventors: Michel Arthur, Paris; Sylvie Dukta-Malen, Fresnes; Catherine Molinas; Patrice Courvalin, both of Paris, all of France

[73] Assignee: Institut Pasteur, Paris Cedex, France

[21] Appl. No.: 286,819

[22] Filed: Aug. 5, 1994

Related U.S. Application Data

[63] Continuation of Ser. No. 174,682, Dec. 28, 1993, abandoned, which is a continuation of Ser. No. 917,146, Aug. 10, 1992, abandoned.

[30] Foreign Application Priority Data

Oct. 31, 1990 [FR] France ................................ 9013579

[51] Int. Cl.[6] ............................ C12Q 1/68; C12P 19/34; C07H 21/04
[52] U.S. Cl. ................... 435/6; 435/91.2; 536/24.32; 536/24.33
[58] Field of Search ............... 435/6, 91.1, 91.2, 435/810; 536/24.32, 24.33

[56] References Cited

FOREIGN PATENT DOCUMENTS 0229701  7/1987  European Pat. Off. .

OTHER PUBLICATIONS

Mol. Gen. Genet., vol. 224, No. 3, Dec. 1990, Springer Verlag, S. Dutka–Malen et al.: The VANA Glycopeptide Resistance Protein is Related to D–alanyl–D–alanine Ligase Cell Wall Biosynthesis Enzymes, pp. 364–372.

Biochemistry, vol. 30, No. 8, 26 Fevrier 1991, American Chemical Society: T.D.H. Bugg et al.: "Identification of Vancomycin Resistance Protein VanA as a D–alanine: D–alanine Ligase of altered Substrate Specificity", pp. 2017–2021.

Antimicrobian Agents and Chemotherapy, vol. 34, No. 5, May 1990, American Society for Microbiology; A. Brisson–Noel et al.:"Cloning and heterospecific expression of the resistanc determinant vanA encoding high–level resistance to glycopeptides in *Enterococcus faecium* BM4147", pp. 924–927.

Antimicrobian Agents and Chemotherapy, vol. 34, No. 10, Oct. 1990, American Society for Microbiology; S. Dutka–Malen et al.: "Phenotypic and genotypic heterogeneity of glycopeptide resistance determinants in Gram–positive bacteria", pp. 1875–1879.

Antimicrobian Agents and Chemotherapy, vol. 33, No. 2, Janvier 1989, American Society for Microbiology; R. Leclercq et al.: Transferable vancomycin and teicoplanin resistance in *Enterococcus faecium*:, pp. 10–15.

Robinson et al., *J. Bacteriol.* 167(3), 809–817 (1986).

Daub et al., *Biochemistry* 27, 3701–3708 (1988).

Varshney et al., *J. Biol. Chem.* 263(16), 7776–7784 (1988).

Arthur et al., *Gene* 103, 133–134 (1991).

*Primary Examiner*—Kenneth R. Horlick
*Attorney, Agent, or Firm*—Oblon, Spivak, McClelland, Maier & Neustadt, P.C.

[57] ABSTRACT

The invention relates to isolated polynucleotides and probes which are optionally labelled and which hybridize with polynucleotides encoding polypeptides implicated in the bacterial resistance to vancomycin, teicoplanin and to both vancomycin and teicoplanin. The invention also relates to the utilization of these polynucleotide probes for the diagnosis of resistance to the glycopeptides.

8 Claims, 94 Drawing Sheets

```
AAGCTTTCTTTTGCTTCATTTGTTAGAGATTTACTAACCGTATTAAATAGCTTCTTTTC
AGCCATTGCCCTTGCTTCTTCCACACCATTCTTCAAGTGTAGTGATAGCAGGCAGTATAAT
TTTGTTTTTCTTAGAAAATCTATGCATTCATGCAGTAGATGAATGGCATCACCATTTTC
CAAAGCTAATTGATGAAGGTACTTAAATTCTTCAAATGTCATTCGATATTCACTCAGGGTAAAGTTAC
AAAGTCGTATTCACTTCGAGGATGGAGTGTATGAGTGTTTCTTCCCAAAGTGTATTTCCCTTGAGG
ATAATGATCAAGCGAGGATGGACTAACACCAATCTGTTTCGATATATATTGTATGACCGA
ATCTGGGATGCTTTTGATATGAGTGTATGGCCAACCGGGATACCGAAGAACAGCTAATTG
AACAGCAAATCCTAAACGGTTTTCTTCCCTTCGCTTATTCTTCAGGATTTGCATAAAAGC
TTTGGAAAAAGTGAAGTAGGTCCCCAGTATCCATTCTTCCAATTTCATTCAGTATCATTC
CTGTCTCTGTTCCGGTGTAAGCAATTTATTAGTTCAATTCAATAGAGTCTCTAAGACTTGTCTCAAAA
CATTTCTGTATTTCAATTTATTAGTTCAATTCAATAGAGTCTCATAAGACTTGTCTCAAAA
ACAAATGTAGTAGATAGACTGATAAAATCATAGTTAAGAGCGTCTCATAAGACTGTCTCAAAA
ATGAGGTGATATTTGCGGAAAATCGGTTATATTCGTGTGTCAGTTCGACTAACCAGAATCC
TTCAAGACAATTTCAGCAGTGAACGAGATCGGAATGGATATTATAAAGAGAAAGTTT
CAGGAGCAACAAAGGATCGCGAGCAACTTCGAATCACTCGATTTACAGGATTACAGGAGATG
ACATCATTTATGTTACACATAGAGATCTTATTCGAATCACTAAAGATACATGGCTTG
TAATCGATAACAAGATAATCCATACGAGCTTAACTCGATGAGACAACGTGAAGGATTGAATTGGCTAAGAATGATG
ATTTATCAGAGCGAGATTTATTCGGATGAGAGAACGTGAAGGATTGAATTGGCTAAGAATGATG
AATTAGAGCGAGTTTAAGGTCGATTAAAGAAGGAAATATGACTGTAAATCAAATTTGTGAATTACTAAT
AGGAAAGTTTAAGGTCGATTAAAGAAGGAAATATGACTGTAAATCAAATTTGTGAATTACTAAT
CGGXXAAAGCTATATAAAGGAAATTACAGGAAATTATCAGAAGTGATAATAAAATATTAACAGCTCCT
GTATCTAGGGCTTCATTATACAGGAAATTTTAAGAAGAAGAAAAAAGAATCATCTCCTTAGTCA
CCGCTAATGGGCAATATTTTAAGAAGAAGAAAAAAGAATCATCTTAAGAAATTCTTAGTCA
AGCGATGCCGAAAAGCCTTGATAAATTCGGCCCTATAATCTGATAATCTGATAAATTATTAAGGGCAAAC
TTTATTATGTAAATGCTTATAAATTCGGCCCTATAATCTGATAATCTGATAAATTATTAAGGGCAAAC
```

```
GCTCTCATCATGCGGCAAATGGAATATCATGCAATGAAGCGCAAAATCGCAGACGTTTGC
GCTCCATCATGGAAAACAGTGGGTTTGAAGCATATAGCCTCGAATGGTGGCACTATGTAT
TAAGAGACGAACCATACCCAATAGCTATTTGATTTCCCGTTAAATAAACTTTTAACC
GTTGCACGGACAAACTAACTCTTTCGGCAGGAAACCCGACGTATGTAACTG
GTTCTTAGGGAATTTATATAGTAGATAGTATTGAAGATGTAAGGCAGAGCGATATTGC
GGTCATTATCTGCGTGCGCTGCAAGATAGCCTGATAATAAGACTGATCGCATAGAGG
GGTGGTATTTCACACCGCCCATTGTCAACAGGCAGTTCAGCCTCGTTAAATTCAGCATGG
GTATCACTTATGAAAATTCATCTACATTGGTGATAATAGTAAATCGAGATTGTGCCGAAATA
ATTGACTGTAATTTACGGGCAAAACGCACAATCTCAAACGAGATTGTGCCGTTAAGG
GGAAGATTCTAGAAATATTTCATACTTCCAACTATATAGTTAAGGAGGAGACTGAAAATG
AAGAAGTTGTTTTTTATTGTTATTCTTAATATACTTAGGTTATGACTACGTT
AATGAAGCACTGTTTCTCAGGAAAAAAGTCGAATTCAAATTATGATCAAAATCCCAAA
GAACATTTAGAAATAGTGGGACTTCTGAAAATACCCAAGAGAAACAATTACAGAAGAA
CAGGTTTATCAAGGAAATCTGCTATTAATCAATAGTAAATCATATCCTGTTCGCCAAGAAGTG
TGAAGTCAGATATCGTGTTATTATCTCAAAGAAATAGCGAATTAATAATTTCAGAGATGGTCAATG
TTGATAGTAAAGGGTGGCGTTAGTCATTTTCATTTTAATTGGGGCTGAGTATCGAGACTTTGATG
ATGCTGTAAAGTGTGCTTTACCAGTTTATCACTAGATGTAGGATCAAGCTTGACGAAATGGAACGAGCCC
AGCATAATTCAGGTTTATCACTAGATGTAGGATCAAGCTTGACGAAATGGAACGAGCCC
CTGAAGGAAACAGAGTTAACAGGAATTC
AGGACAAAACAGAGTTAACAGGAATTC
```

```
LysLeuPhePheLeuLeuIleCys***ArgPheThrAsnArgIleLys***LeuLeuPhe
SerPheSerPheCysSerPheValArgAspLeuLeuThrValLeuAsnSerPheSer
AlaPheLeuPheAlaHisLeuLeuGluIleTyr***ProTyr***IleAlaSerPheGln
AAGCTTTTCTTTTTGCTCATTTGTTAGAGATTACTAACCGTATTAAATAGCTTCTTTTC

SerHisCysProCysPheProHisSerPheLysCysSerAspSerArgGlnTyrAsn
AlaIleAlaLeuAlaSerHisThrIleLeuSerSerValValIleAlaGlySerIleIle
ProLeuProLeuProThrProPhePheGlnVal******GlnAlaVal***Phe
AGCCATTGCCCTTGCTTCCCACACCATTCTTTCAAGTGTAGTGATAGCAGGCAGTATAAT
                                100

PheValPheSer***LysIleTyrAlaPheMetGln***MetAsnGlyIleThrIlePhe
LeuPhePheLeuArgLysSerMetHisSerCysSerArg***MetAlaSerProPheSer
CysPhePheLeuGluAsnLeuCysIleHisAlaValAspGluTrpHisHisPhePro
TTTGTTTTTTCTTAGAAAATCTATGCATTCATGCAGTAGATGAATGGCATCACCATTTTC
```

GlnSer***LeuMetLysValLeuLysCysHisSerIlePheThrGlnGlyLysSerTyr

LysAlaAsn*****ArgTyrLeuAsnValIleArgTyrSerLeuArgValLysValThr

LysLeuIleAspGluGlyThr*MetSerPheAspIleHisSerGly*LysLeuGln

CAAAGCTAATTGATGAAGTACTTAAATGTCATTCGATATTCACTCAGGTAAAAGTTAC
                              .                              200                              .

LysValValPheThrSerAsnPhePheGlnMetIleProLysCysIlePheProLeuArg

LysSerTyrSerLeuArgIleSerPheLys*SerGlnSerValPheSerLeu*Gly

SerArgIleHisPheGluPheLeuSerAsnAspProLysValTyrPheProPheGluAsp

AAAGTCGTATTCACTTCGAATTTCTTTCAAATGATCCCAAAGTGTATTTCCCTTTGAGG
                              .                              300                              .

FIG. 5B ileMetIleLysArgGlyTrpThrAsnThrAsnLeuPheArgTyrIleLeuTyrAspArg
****SerSerGluAspGlyLeuThrProIleCysPheAspIleTyrCysMetThrGlu
AsnAspGlnAlaArgMetAsp*HisGlnSerValSerIleTyrIleVal*ProAsn
ATAATGATCAAGCGAGGATGGACTAACACCAATCTGTTCGATATATATTGTATGACCGA IleTrpAspAlaPheAspMetSerValTrpProThrGlyIleProLysAsnSer***Leu
SerGlyMetLeuLeuIle*ValTyrGlyGlnProGlyTyrArgArgThrAlaAsn*
LeuGlyCysPhe***TyrGluCysMetAlaAsnArgAspThrGluGlnLeuIleGlu
ATCTGGGATGCTTTTGATATGAGTGTATGGCCAACCGGGATACCGAAGAACAGCTAATTG
                                400

AsnSerLysSer*ThrValPhePheProProSerLeuIleAsnTyrPhe*IlePro
ThrAlaAsnProLysArgPheSerSerLeuLeuArgLeuLeuThrIleSerLysSerArg
GlnGlnIleLeuAsnGlyPheLeuProSerPheAlaTyr***LeuPheLeuAsnProVal
AACAGCAAATCCTAAACGGTTTCTTCCCTCCTTCGCTTATTAACTATTCTAAATCCG

FIG. 5C

```
PheGlyLysSerGluValGlyProGlnTyrProPheIlePheArgAspLeuHisLysSer
LeuGluLysValLys***ValProSerIleHisSerSerGlyIleCysIleLysAla
TrpLysLys***SerArgSerProValSerIleHisLeuGlnGlyPheAla***LysPro
TTTGGAAAAAGTGAAGTAGGTCCCCAGTATCCATTCATCTTCAGGGATTTGCATAAAAGC
                             500
LeuSerLeuPheArgCysLysGlnPheSerThrSerArgAsnPheHisSerValSerPhe
CysLeuCysSerGlyValSerAsnSerLeuProLeuAlaIlePheIleGlnTyrHisSer
ValSerValPro Val***AlaIleLeuTyrLeuSerGlnPheSerPheSerIleIlePro
CTGTCTCTGTTCCGGTGTAAGCAATTCTCTACCTCTCGCAATTTCATTCAGTATCATTC
                                                         600
```

```
HisPheCysIlePheAsnLeuLeuValGlnLeuTyrIleAsnArgValTyrSerIleAsp
IleSerValPheSerIleTyr***PheAsnTyrIleSerIleIleGluCysThrLeuLeuIle
PheLeuTyrPheGlnPheIleSerSerIleIleTyrGln***SerValLeuTyr***Tyr
CATTTCTGTATTTCAATTATTAGTTCAATTATATCAATAGAGTGTACTCTTATTGAT

ThrAsnValValAsp******AsnHisSer***GluArgLeuIleArgLeuValSerLys
GlnMet******ThrAspLysIleIleValLysSerValSer***AspLeuSerGlnLys
LysCysSerArgLeuIleLeuLysSer***LeuArgAlaSerHisLysThrCysLeuLysAsn
ACAAATGTAGTAGACTGATAAAATCATAGTTAAGAGCGTCTCATAAGACTTGTCTCAAAA
                                        700

MetArg***TyrPheAlaGluAsnArgLeuTyrSerCysGlnPheAsp***ProGluSer
***GlyAspIleLeuArgLysIleGlyTyrIleArgValSerThrAsnGlnAsnPro
GluValIlePheCysGlyLysSerValIlePheValSerValArgLeuThrArgIleLeu
ATGAGGTGATATTTGCGGAAAATCGGTTATATTCGTGTCAGTTCGACTAACCAGAATCC
```

```
PheLysThrIleSerAlaValGluArgAspArgAsnGlyTyrTyrIleLysArgLysPhe

SerArgGlnPheGlnGlnLeuAsnGluIleGlyMetAspIleIle***ArgGluSerPhe

GlnAspAsnPheSerSer***ThrArgSerGluTrpIleLeuTyrLysGluLysValSer
TTCAAGACAATTTCAGCAGTTGAACGAGATCGGAATGGATATATAAAGAGAAAGTTT
                    .                    .
                   800

GlnGluGlnArgIleAlaSerAsnPheLysLysCys***ThrIleTyrArgLysMet

ArgSerAsnLysGlySerArgAlaThrSerLysSerValArgArgPheThrGlyArg***

GlyAlaThrLysAspArgGluGlnLeuGlnLysValLeuAspAspLeuGlnGluAspAsp
CAGGAGCAACAAAGGATCGCGAGCAACTTCAAAAGTGTTAGACGATTACAGGAAGATG
                    .                    .
                                         900
```

FIG. 5F

ThrSerPheMetLeuGlnThr***LeuGluSerLeuValValHisLysIleTyrLeuAsn
HisHisLeuCysTyrArgLeuAsnSerAsnHisSer*TyrThrArgSerIle*Ile
IleIleTyrValThrArgIleThrArgIleThrArgSerThrArgGlnAspLeuPheGluLeu
ACATCATTATGTTACAGACTTAACTCGAATCACTCGTAGTACACAGATCTATTGAAT

*SerIleThrTyrGluIleLysArgGlnVal*AsnHis***LysIleHisGlyLeu
AsnArg*HisThrArg*LysGlyLysPheLysIleThrLysArgTyrMetAla***
IleAspAsnIleArgAspLysLysAlaSerLeuLysSerLeuLysAspThrTrpLeuAsp
TAATCGATAACATACGAGATAAAAGGCAAGTTAAAATCACTAAAAGATACATGGCTTG
                                1000

IleTyrGlnLysIleIleIleHisThrAlaAsnSer*LeuLeu*TrpLeuValLeuThr
PheIleArgArg*SerIleGlnProIleLeuAsnTyrCysAsnGlyTrpCys*Pro
LeuSerGluAspAsnProTyrSerGlnPheLeuIleThrValMetAlaGlyValAsnGln
ATTTATCAGAAGATAATCCATACAGCCAATTCTTAATTACTGTAATGGCTGGTGTTAACC

FIG. 5G

```
Asn***SerGluIleLeuPheGly***AspAsnValLysGlyLeuAsnTrpLeuArgLys
IleArgAlaArgSerTyrSerAspGluThrThr***ArgAsp***IleGly***GluArg
LeuGluArgAspLeuIleArgMetArgGlnArgGluGlyIleGluLeuAlaLysLysGlu
AATTAGAGCGAGATCTTATTCGGATGAGACAACGTGAAGGATTGAATTGGCTAAGAAAG
              .              1100              .              .
LysGluSerLeuLysValAsp***ArgSerIleIleLysIleThrGlnGlu***IleMet
ArgLysVal***ArgSerIleLysGluValSer***LysSerArgArgAsnGluLeuCys
GlyLysPheLysGlyArgLeuLysTyrHisLysAsnHisAlaGlyMetAsnTyrAla
AAGGAAAGTTTAAAGGTCGATTAAAGAAGAAGTATCATAAAAATCACGCAGGAATGAATTATG
              .              .              .             1200
```

```
ArgArgLysLeuTyrLysGluGlyAsnMetThrValAsnGlnIleCysGluIleThrAsn
GlyGluSerTyrIleLysLysGluIle***Leu***IleLysPheValLysLeuLeuMet
AlaLysAlaIle***ArgArgLysTyrAspCysLysSerAsnLeu***AsnTyr***Cys
CGGXXAAAGCTATATAAAGAAGGAAATGACTGTAAATCAAATTTGTGAAATTACTAAT

ValSerArgAlaSerLeuTyrArgLysLeuSerGluValAlaAsnAsn***ProPheCysIle
TyrLeuGlyLeuHisTyrThrGlyAsnTyrGlnLys***IleIleSerHisSerValPhe
Ile***GlyPheIleIleGlnGluIleIleArgSerGlu***LeuAlaIleLeuTyrSer
GTATCTAGGGCTTCATTATACAGGAAATTATCAGAAGTGAATAATTAGCCATTCTGTATT
                                    1300

ProLeuMetGlyAsnIlePheLysGluGluLysGluLysLysLeu***AsnIleAsnSerLeuLeu
Arg***TrpAlaIlePheLeuLysLysLysArgLysLeu***AsnIleAsnSerLeuLeu
AlaAsnGlyGlnTyrPhe***ArgArgLysGlyAsnTyrLysIleLeuThrAlaSer***
CCGCTAATGGGCAATATTTTTAAAGAAGAAAAGGAAACTATAAAATATTAACAGCCTCC
```

SerAspAlaGluLysProPheAspLysLysArgIleIleIleLeuArgAsnSer***Ser

AlaMetProLysSerProLeuIleLysLysGluSerSerSer***GluIleLeuSerHis

ArgCysArgLysAlaLeu******LysLysAsnHisHisLeuLysLysPheLeuValIle

AGCGATGCCGAAAAGCCCTTTGATAAAAAAGAATCATCATCTTAAGAAATTCTTAGTCA
                    .                  1400                  .

PheIleMet*MetLeuIleAsnSerAlaLeu*SerAspLysLeuLeuArgAlaAsn

LeuLeuCysLysCysLeu*IleArgProTyrAsnLeuIleAsnTyr*GlyGlnThr

TyrTyrValAsnAlaTyrLysPheGlyProIleIle*****IleIleLysGlyLysLeu

TTTATTATGTAAATGCTTATTAATTCGGCCCTATAATCTGATAAATTATTAAGGGCAAAC
                    .                  1500

FIG. 5J

```
LeuCysGluArgValIleThrMetSerAspLysIleLeuIleValAspAspGluHisGlu
TyrValLysGly***Leu***AlaIleLysTyrLeuLeuTrpMetMetAsnMetLys
Met***LysGlyAspAsnTyrGluArg***AsnThrTyrCysGly*****Thr***Asn
TTATGTGAAAGGGTGATAACTATGAGCGATAAAATACTTATTGTGGATGATGAACATGAA

IleAlaAspLeuValGluLeuTyrLeuLysAsnGluAsnTyrThrValPheLysTyrTyr
LeuProIleTrpLeuAsnTyrThr***LysThrArgIleIleArgPheSerAsnThrIle
CysArgPheGly***IleIleLeuLysArgGluLeuTyrGlyPheGlnIleLeuTyr
ATTGCCGATTGGTTGAATTATACTTAAAAAACGAGAATTATACGGTTTCAAATACTAT
                              1600

ThrAlaLysGluAlaLeuGluCysIleAspLysSerGluIleAspLeuAlaIleLeuAsp
ProProLysHisTrpAsnVal***ThrSerLeuArgLeuThrLeuProTyrTrpThr
ArgGlnArgSerIleGlyMetTyrArgGlnVal***Asp***ProCysHisIleGlyHis
ACCGCCAAAGAAGCATTGGAATGTATAGACAAGTCTGAGATTGACCTTGCCATATTGGAC
```

FIG. 5K

```
IleMetLeuProGlyThrSerGlyLeuThrIleCysGlnLysIleArgAspLysHisThr
SerCysPheProAlaGlnAlaAlaLeuLeuSerValLysLys***GlyThrSerThrPro
HisAlaSerArgHisLysArgProTyrTyrLeuSerLysAsnLysGlyGlnAlaHisLeu
ATCATGCTTCCCGGCACAAGCGGCCTTACTATCTGTCAAAAATAAGGACAAGCACACC
                     .              1700                .
TyrProIleMetLeuThrGlyLysAspThrGluValAspLysIleThrGlyLeuThr
IleArgLeuSerCys***ProGlyLysIleGlnArg***IleLysLeuGlnGly***Gln
SerAspTyrHisAlaAspArgGluArgTyrArgGlyArg***AsnTyrArgValAsnAsn
TATCCGATTATCATGCTGACCGGGAAAGATACAGAGGTAGATAAAATTACAGGGTTAACA
                     .              1800
```

FIG. 5L

IleGlyAlaAspAspTyrIleThrLysProPheArgProLeuGluLeuIleAlaArgVal
SerAlaArgMetIleIle*ArgSerProPheAlaHisTrpSer*LeuLeuGly***
ArgArgGly***LeuTyrAsnGluAlaLeuSerProThrGlyValAsnCysSerGlyLys
ATCGGCGCGGATGATTATATAACGAAGCCCTTTCGCCCACTGAGTTAATTGCTCGGGTA

LysAlaGlnLeuArgArgTyrLysLysPheSerGlyValValLysGluGlnAsnGluAsnVal
ArgProSerCysAlaAspThrLysAsnSerValGlu***ArgSerArgThrLysMetLeu
GlyProValAlaProIleGlnLysIleGlnTrpSerLysGlyAlaGluArgLysCysTyr
AAGGCCCAGTTGCGCCGATACAAAAATTCAGTGGAGTAAAGGAGCAGACGAAAATGTT
                                    1900

IleValHisSerGlyLeuValIleAlaAsnValAsnThrHisGluCysTyrLeuAsnGluLys
SerSerThrProAlaLeuSerMetLeuThrProMetSerValIle***ThrArgSer
ArgProLeuArgProCysHis*Cys*HisPro***ValLeuSerGluArgGluAla
ATCGTCCACTCCGGCCTTGTCATTAATGTTAACACCCATGAGTGTTATCTGAACGAGAAG

FIG. 5M

GlnLeuSerLeuThrProThrGluPheSerIleLeuArgIleLeuCysGluAsnLysGly
SerTyrProLeuLeuProProSerPheGlnTyrCysGluSerSerValLysThrArgGly
ValIleProTyrSerHisArgValPheAsnThrAlaAsnProLeu***LysGlnGlyGlu
CAGTTATCCCTTACTCCCACCGAGTTTTCAATACTGCGAATCCCTCTGAAAACAAGGGG
                         2000
AsnValValSerSerGluLeuLeuPheHisGluIleTrpGlyAspGluTyrPheSerLys
MetTrpLeuAlaProSerCysTyrPheMetArgTyrGlyAlaThrAsnIleSerAlaArg
CysGly*LeuArgAlaAlaIleSer*AspMetGlyArgArgIlePheGlnGlnGlu
AATGTGGTTAGCTCCGAGCTGCTATTTCATGAGATATGGGGCGACGAATATTTCAGCAAG
                                                    2100

SerAsnAsnThrIleThrValHisIleArgHisLeuArgGluLysMetAsnAspThrIle
AlaThrProSerProCysIleSerGlyIleCysAlaLysLys***ThrThrProLeu
GlnGlnHisHisArgAlaTyrProAlaPheAlaArgLysAsnGluArgHisHis***
AGCAACAACACCATCACCGTGCATATCCGGCATTGCGGAAAAATGAACGACACCATT

AspAsnProLysTyrIleLysThrValTrpGlyValGlyTyrLysIleGluLys***Lys
IleIleArgAsnIle***LysArgTyrGlyGlyLeuValIleLeuLysLeuLysAsnLysLys
*SerGluIleTyrLysAsnGlyMetGlyGlyTrpLeu*Asn***LysIleLysLys
GATAATCCGAAATATATAAAACGGTATGGGGGTTGGTTATAAAATTGAAAAATAAAA

2200

LysArgLeuPheGlnThrArgThrLysThrLeuHisValTyrArgCysAsnCysCysGly
AsnAspTyrSerLysLeuGluArgLysLeuTyrMetTyrIleValAlaIleValValVal
ThrThrIleProAsn*AsnGluAsnPheThrCysIleSerLeuGlnLeuLeuTrp*
AAACGACTATTCCAAACTAGAACGAAAACTTTACATGTATATCGTTGCAATTGTTGGT

SerAsnCysIleArgValValTyrSerPheAsnAspProArgGluThrTrpGlyLeuAsp
AlaIleValPheValLeuTyrIleArgSerMetIleArgGlyLysLeuGlyAspTrpIle
GlnLeuTyrSerCysCysIlePheValGln***SerGluGlyAsnLeuGlyIleGlySer
AGCAATTGTATTCGTGTTGTATATTCGTTCAATGATCCGAGGGAAACTTGGGGATTGGAT
                              .                              
                            2300                              
LeuLysTyrPheGlyLysGlnIle***LeuLysSerProGlyArgAspGluIleIleSer
LeuSerIleLeuGluAsnLysTyrAspLeuAsnHisLeuAspAlaMetLysLeuTyrGln
*ValPheTrpLysThrAsnMetThr*IleThrTrpThrArg***AsnTyrIleAsn
CTTAAGTATTTGGAAAACAAATATGACTTAAATCACCTGGACGCGATGAAATTATATCA
                              .                              
                            2400

```
IlePheHisThrGluGlnTyrArgTyrLeuTyrCysGlyAspCysHis***TyrSer
TyrSerIleArgAsnAsnIleAspIlePheIleTyrValAlaIleValIleSerIleLeu
IleProTyrGlyThrIle***IleSerLeuPheMetTrpArgLeuSerLeuValPheLeu
ATATTCCATACGGAACAATATAGATATCTTTATTTATGTGGGATTGTCATTAGTATTCT

TyrSerMetSerArgHisAlaPheLysIleArgLysIleLeu***ArgAspLysTyrArg
IleLeuCysArgValMetLeuSerLysPheAlaLysTyrPheAspGluIleAsnThrGly
PheTyrValAlaSerCysPheGlnAsnSerGlnAsnThrLeuThrArg***IleProAla
TATTCTATGTCGCGTCATGCTTTCAAAATTCGCAAAATACTTTGACGAGATAAATACCGG
                                   2500

His***CysThrTyrSerGluArgArg***ThrAsn***AlaPheCysGlyAsnGlyCys
IleAspValLeuIleGlnAsnGluAspLysGlnIleGluLeuSerAlaGluMetAspVal
LeuMetTyrLeuPheArgThrLysIleAsnLysLeuSerPheLeuArgLysTrpMetLeu
CATTGATGTACTTATTCAGAACGAAGATAAACAAATTGAGCTTTCTGCGGAAATGGATGT
```

TyrGlyThrLysAlaGlnHisIleLysThrAspSerGlyLysAlaArgAlaGlyCysLys
MetGluGlnLysLeuAsnThrLeuLysArgThrLeuGluLysArgGluGlnAspAlaLys
TrpAsnLysSerSerThrHis***AsnGlyLeuTrpLysSerGluSerArgMetGlnSer
TATGGAACAAAAGCTCAACACATTAAAACGGACTCTGGAAAAGCGAGAGCAGGATGCAAA
                              2600
AlaGlyArgThrLysLysLys*ArgCysTyrValLeuGlyAlaArgTyr*AsnAla
LeuAlaGluGlnArgLysAsnAspValValMetTyrLeuAlaHisAspIleLysThrPro
TrpProAsnLysGluLysMetThrLeuLeuCysThrTrpArgThrIleLeuLysArgPro
GCTGGCCGAACAAAGAAAAAAATGACGTTGTTATGTACTTGGCGCACGATATTAAAACGCC
                                                        2700

ProTyrIleHisTyrArgLeuPheGluProAla***ArgGlySerArgHisAlaGlyArg
LeuThrSerIleIleGlyTyrLeuSerLeuAspGluAlaProAspMetProValAsp
LeuHisProLeuSerValIle*AlaCysLeuThrArgLeuGlnThrCysArg*Ile
CCTTACATCCATTATCGGTTATTTGAGCCTGCTTGACGAGGTCCAGACATGCCGGTAGA

SerLysGlyLysValCysAlaTyrHisValGlyGlnSerValSerThrArgThrAlaAsn
GlnLysAlaLysTyrValHisIleThrLeuAspLysAlaTyrArgLeuGluGlnLeuIle
LysArgGlnSerMetCysIleSerArgTrpThrLysArgIleAspSerAsnSer***Ser
TCAAAAGGCAAGTATGTGCATATCACGTTGGACAAAGGTATCGACTCGAACAGCTAAT
                                    2800

ArgArgValPhe*AspTyrThrVal*ProThrAsnAspAsnAlaAsnLysAsnAla
AspGluPhePheGluIleThrArgTyrAsnLeuGlnThrIleThrLeuThrLysThrHis
ThrSerPheLeuArgLeuHisGlyIleThrTyrLysArg*Arg*GlnLysArgThr
CGACGAGTTTTTGAGATTACACGGTATAACCTACAAACGATAACGCTAACAAAACGCA

```
HisArgProIleLeuTyrAlaGlyAlaAspAspArg***IleLeuSerSerAlaPheArg
IleAspLeuTyrTyrMetLeuValGlnMetThrAspGluPheTyrProGlnLeuSerAla
*ThrTyrThrIleCysTrpCysArg*ProMetAsnPheIleLeuSerPheProHis
CATAGACCTATACTATATGCTGGTGCAGATGACCGATGAATTTATCCTCAGCTTTCCGC
                    .         2900         .                
ThrTrpLysThrGlyGlyTyrSerArgProArgGlySerAspArgValArgArgPro***
HisGlyLysGlnAlaValIleHisAlaProGluAspLeuThrValSerGlyAspProAsp
MetGluAsnArgArgLeuPheThrProProArgIle***ProCysProAlaThrLeuIle
ACATGGAAAACAGGCGGTTATTCACGCCCCCGAGGATCTGACCGTGTCCGGGACCCTGA
                    .         3000         .                
```

```
*ThrArgGluSerLeu*GlnHisPheGluLysArgArgCysIleGln*Gly*
LysLeuAlaArgValPheAsnAsnIleLeuLysAsnAlaAlaAlaTyrSerGluAspAsn
AsnSerArgGluSerLeuThrThrPhe***LysThrProLeuHisThrValArgIleThr
TAAACTCGGAGAGTCTTTAACAACATTTGAAAAACGCCTGCATACAGTGAGGATAA

GlnHisHis***HisTyrArgGlyProLeuArgGlyCysGlyValAsnArgIleGlnGlu
SerIleIleAspIleThrAlaGlyLeuSerGlyAspValValSerIleGluPheLysAsn
AlaSerLeuThrProArgAlaSerProGlyMetTrpCysGlnSerAsnSerArgThr
CAGCATCATTGACATTACCGGGGCCCTCTCCGGGGATGTGGTCAATCGAATTCAAGAA
                           3100

HisTrpLysHisProLysArg***AlaSerCysHisIle***LysValLeu***AlaGly
ThrGlySerIleProLysAspLysLeuAlaAlaIlePheGluLysPheTyrArgLeuAsp
LeuGluAlaSerGlnLysIleSer***LeuProTyrLeuLysSerSerIleGlyTrpThr
CACTGGAAGCATCCCAAAAGATAAGCTAGCTGCCATATTTGAAAAGTTCTATAGGCTGGA
```

```
GlnPheSerPheArgTyrGlyTyrTrpArgGlyThrTrpIleGlyAspCysLysArgAsn
AsnSerArgSerSerAspThrGlyGlyAlaGlyLeuGlyLeuAlaIleAlaLysGluIle
IleLeuValLeuProIleArgValAlaArgAspLeuAspTrpArgLeuGlnLysLysLeu
CAATTCTCGTTCTTCCGATACGGGTGGCGCGGGACTTGGATTGGCGATTGCAAAAGAAAT
                        .                                  .
                       3200
TyrCysSerAlaTrpArgAlaAspLeuArgGlyLysLeu*****LeuTyrAspVal***
IleValGlnHisGlyGlyGlnIleTyrAlaGluSerTyrAspAsnTyrThrThrPheArg
LeuPheSerMetGluGlyArgPheThrArgLysAlaMetIleThrIleArgArgLeuGly
TATTGTTCAGCATGGAGGGCAGATTTACGCGGAAAGCTATGATAACTATACGACGTTTAG
                        .                                  .
                                                          3300
```

FIG. 5V

GlyArgAlaSerSerAspAlaArgLeuGly***LysGluValLeuArgAspValTyr
ValGluLeuProAlaMetProAspLeuValAspLysArgArgSer***GluMetTyrIle
*SerPheGlnArgCysGlnThrTrpLeuIleLysGlyGlyProLysArgCysIle*
GGTAGAGCTTCCAGCGATGCCAGACTTGGTTGATAAAGGAGTCCTAAGAGATGTATAT

AsnPheLeuGlyLysSerGlnGlyTyrLeuTyrPhePheLeuGlyAsn***GlnPheAsn
IlePhe*GluAsnLeuLysValIlePheThrPheSer*GluIleAsnAsnLeuIle
PhePheArgLysIleSerArgLeuSerLeuLeuPheLeuArgLysLeuThrIle***Tyr
AATTTTTAGGAAAATCTCAAGGTTATCTTACTTTTTCTTAGAAATTAACAATTAAT
                                3400

IleLysLysArgLeuValLeuThrArg*Thr*TyrArgLysAsnGluProPheSer
LeuArgAsnGlySerPheLeuHisGlyArgLeuAsnThrValArgThrSerArgPheArg
*GluThrAlaArgSerTyrThrValAspLeuIlePro*GluArgAlaValPheVal
ATTAAGAAACGGCTCGTTCTTACACGGTAGACTTAATACCGTAGAACGAGCCGTTTCG

FIG. 5W

PhePheArgGluArgPheAspLysIleThrIleGlyIleProValIleProPheGlyAlaPhe
SerSerGluLysAspLeuThrArgLeuProLeuAlaSerProPheTyrLeuValProPhe
LeuGlnArgLysIle***GlnAspTyrHisProArgPheIleTrpCysLeuSer
TTCTTCAGAGAAGATTTGACAAGATTACCATTGGCATCCCCGTTTATTTGGTGCCTTT
                              3500
HisArgLysGlyTrpSer*Leu*IleThrSerAlaLeuPheMetAspValSer
ThrGluArgValGlyLeuGlyGlu*HisArgHisTyrCysLeuTrpMet*Ala
GlnLysGlyLeuValLeuIleMetAsnAsnIleGlyIleThrValTyrGlyCysGluGln
CACAGAAAGGGTTGGTCTTAATTATGAATAACATCGGCATTACTGTTTATGGATGTGAGC
                                                     3600

```
ArgMetArgGlnMetHisSerMetLeuPheArgLeuAlaAlaLeuAlaLeuTrpGlnArg***
Gly***GlyArgCysIleProCysSerPheAlaSerLeuTrpArgTyrGlyAsnAspAsn
AspGluAlaAspAlaPheHisAlaLeuSerProArgPheGlyValMetAlaThrIleIle
AGGATGAGGCAGATGCATTCCATGCTCTTTCGCCTCGCTTTGGCGTTATGGCAACGATAA

LeuThrProThrCysArgAsnProThrProArgLeuSerIleAsnValSerVal
***ArgGlnArgValGlyIleGlnArgGlnIleArgAlaPheGlnSerMetTyrGlnCys
AsnAlaAsnValSerGluSerAsnAlaLysSerAlaProPheAsnGlnCysIleSerVal
TTAACGCCAACGTGTCGGAATCCAACGCCAAATCCGGCCTTCAATCAATGTATCAGTG
                                 3700

TrpAspIleAsnGlnArgPheProProLeuPhePheLeuArg***ArgGluProVal
GlyThr***IleArgAspPheArgLeuTyrSerSerCysAlaGluSerArgCysGlu
GlyHisLysSerGluIleSerAlaSerIleLeuLeuAlaLeuLeuLysAr=gAlaGlyValLys
TGGGACATAAATCAGAGATTTCCGCCCTCTATTCTTCTTCTTGGCTGAAGAGAGCCGGTGTGA
```

AsnIlePheLeuProGluAlaSerAlaAlaAlaIleIle***IleGlnLeuLeuLeuArgGlu
IleTyrPheTyrProLysHisArgLeuGlnSerTyrArgTyrAsnCysCys***GluAsn
TyrIleSerThrArgSerIleGlyCysAsnHisIleAspThrThrAlaAlaLysArgMet
AATATATTTCTACCCGAAGCATCGGCTGCAATCATATAGATACAACTGCTAAGAGAA
                              3800
TrpAlaSerLeuSerThrMetTrpArgThrArgArgIleAlaLeuProIleIleLeu***
GlyHisCysArgGlnCysGlyValLeuAlaGly***ArgCysArgLeuTyrTyrAsp
GlyIleThrValAspAsnValAlaTyrSerProAspSerValAlaAspTyrThrMetMet
TGGGCATCACTGTCGACAATGTGGCCTACTCGCCCGGATAGCGGTTGCCGATTATACTATGA
                                                3900

FIG. 5Z

```
Cys***PheLeuTrpGlnTyrAlaThr***AsnArgLeuCysAlaLeuTrpLysAsnMet
AlaAsnSerTyrGlySerThrGlnArgLysIleAspCysAlaLeuCysGlyLysThr***
LeuIleLeuMetAlaValArgAsnValLysSerIleValArgSerValGluLysHisAsp
TGCTAATTCTTATGGCAGTACGCAACGTAAAATCGATTGTGGCCTCTGTGGAAAAACATG

IleSerGlyTrpThrAlaThrValAlaAlaArgTyrSerAlaThr***GlnLeuValTrpTrp
PheGlnValGlyGlnArgProTrpGlnGlyThrGlnArgHisAspSerTrpCysGlyGly
PheArgLeuAspSerAspArgGlyLysValLeuSerAspMetThrValGlyValValValGly
ATTTCAGGTTGGGACACAGGCGACCGTGGCCAAGGTACTCAGCAGCACATGACAGTTGGTGTGGTGG

4000

GluArgAlaArg***AlaLysArgLeuLeuSerGlyCysGluAspLeuAspValLysCys
AsnGlyProAspArgGlnSerGlyTyr***AlaAlaAlaAlaArgIleTrpMet***SerVal
ThrGlyGlnIleGlyLysValAlaValIleGluArgLeuArgGlyPheGlyCysLysValLeu
GAACGGGCCAGATAGGCAAAGCGGTTATTGAGCGGCTGCGAGGATTTGGATGTAAAGTGT
```

FIG. 5AA

```
TrpLeuIleValAlaAlaGluVal***Arg***ThrMetTyrArgLeuMetSerCysCys
GlyLeu***SerGlnProLysTyrArgGlyLysLeuCysThrVal****ValAlaAla
AlaTyrSerArgSerArgSerIleGluValAlaAsnTyrValProPheAspGluLeuLeuGln
TGGCTTATAGTCGCAGCCGAAGTATAGAGGTAAACTATGTACCGTTTGATGAGTTGCTGC
                         .                         .
                        4100
LysIleAlaIleSerLeuArgPheMetCysArgSerIleArgThrIleLeuSer
Lys***ArgTyrArgTyrAlaSerCysAlaAlaGlnTyrGlyTyrAlaLeuTyrTyrGln
AsnSerAspIleValThrLeuHisValProLeuAsnThrAspThrHisTyrIleIleSer
AAAATAGCGATATCGTTACGCTTCATGTGCCGCTCAATACGGATACGCACTATATTATCA
                         .                         .
                                                  4200
```

AlaThrAsnLysTyrArgGlu***SerLysGluHisPheLeuSerIleLeuGlyAlaVal
ProArgThrAsnThrGluAsnGluAlaArgSerIleSerTyrGlnTyrTrpAlaArgSer
HisGluGlnIleGlnArgMetLysGlnGlyAlaPheLeuIleAsnThrGlyArgGlyPro
GCCACGAACAAATACAGAGAATGAAGCAAGGAGCATTTCTTATCAATACTGGGCGCGGTC

HisLeu*IleProMetSerTrpLeuLysHis****LysThrGlyAsnTrpAlaValPro
ThrCysArgTyrLeu*ValGly*SerIleArgLysArgGluThrGlyArgCysArg
LeuValAspThrTyrGluLeuValLysAlaLeuGluAsnGlyLysLeuGlyGlyAlaAla
CACTTGTAGATACCTATGAGTTGGTTAAAGCATTAGAAACGGGAAACTGGGCGGTGCCG
                                        4300

HisTrpMetTyrTrpLysGluArgLysSerPheSerThrLeuIleAlaProLysAsnGln
IleGlyCysIleGlyArgArgGlyArgValPheLeuLeu***LeuHisProLysThrAsn
LeuAspValLeuGluGlyGluGluPhePheTyrSerAspCysThrGlnLysProIle
CATTGGATGTATTGGAAGGAGAAGAGTTTTCTACTCTGATTGCACCCAAAACCAA

```
LeuIleIleAsnPheTyrLeuAsnPheLysGluCysLeuThr******SerHisArgIle
******SerIlePheThr***ThrSerLysAsnAla***ArgAspAsnHisThrAlaTyr
AspAsnGlnPheLeuLeuLysLeuGlnArgMetProAsnValIleIleThrProHisThr
TTGATAATCAATTTTTACTTAAACTTCAAAGAATGCCTAACGTGATAATCACACCGCATA
                    .                    .                    
                                         4400
ArgProIleProSerLysArgCysValIleProLeuLysLysProLeuLysThrVal
GlyLeuLeuTyrArgAlaSerValAla***TyrArg***LysAsnHis***LysLeuPhe
AlaTyrTyrThrGluGlnAlaLeuArgAspThrValGluLysThrIleLysAsnCysLeu
CGGCCTATTATACCGAGCAAGCGTTGCGTGATACCGTTGAAAAAACCATTAAAAACTGTT
                    .                    .                    
                                                          4500
```

FIG. 5DD

TrpIleLeuLysGlyAspArgSerMetAsnArgIleLysValAlaIleLeuPheGlyGly
GlyPhe*LysGluThrGlyAla*IleGlu***LysLeuGlnTyrCysLeuGlyVal
AspPheGluArgArgGlnHisGlu***AsnLysSerCysAsnThrValTrpGlyLeu
TGGATTTTGAAAGGAGACAGGAGCATGAATAGAATAAAAGTTGCAATACTGTTTGGGGGT

CysSerGluHisAspValSerAlaIleGluIleAlaAlaAsnIleAsn
AlaGlnArgSerMetThrTyrArg*AsnLeuGln*Arg***ProLeuThrLeuIle
LeuArgGlyAla*ArgIleGlyLysIleCysAsnArgAspSerArg*His******
TGCTCAGAGGAGCATGACGTATCGGTAAAATCTGCAATAGAGATAGCCGCTAACATTAAT
                                    4600

LysGluLysTyrGluProLeuTyrIleGlyIleThrLysSerGlyValTrpLysMetCys
LysLysAsnThrSerArgTyrThrLeuGluLeuArgAsnLeuValTyrGlyLysCysAla
ArgLysIleArgAlaValIleHisTrpAsnTyrGluIleTrpCysMetGluAsnValArg
AAAGAAAAATACGAGCCGTTATACATTGGAATTACGAAATCTGGTATGGAAAATGTGC

FIG. 5EE

GluLysProCysAlaGluTrpGluAsnAspAsnCysTyrSerAlaValLeuSerProAsp
LysAsnLeuAlaArgAsnGlyLysThrThrIleAlaIleGlnLeuTyrSerArgArgIle
LysThrLeuArgGlyMetGlyLysArgGlnLeuLeuPheSerCysThrLeuAlaGly***
GAAAACCTTGCGCGGGAATGGGAAAACGACAATTGCTATTCAGCTGTACTCTCGCCGGAT
            .                          4700                         .
LysLysMetHisGlyLeuLeuValLysLysAsnHisGluTyrGluIleAsnHisValAsp
LysLysCysThrAspTyrLeuLeuLysArgThrMetAsnMetLysSerThrMetLeuMet
LysAsnAlaArgIleThrCys*LysGluPro*Ile*AsnGlnProCys*Cys
AAAAAAATGCACGGATTACTTGTTAAAAGAACCATGAATATGAAATCAACCATGTTGAT
            .                          .                         4800

FIG. 5FF

```
ValAlaPheSerAlaLeuHisGlyLysLysSerGlyGluAspGlySerIleGlnGlyLeuPhe
***HisPheGlnLeuCysMetAlaSerGlnValLysMetAspProTyrLysValCysLeu
  SerIlePheSerPheAlaTrpGlnValArg***ArgTrpIleHisThrArgSerVal***
GTAGCATTTTCAGCTTTGCATGGCAAGTCAGGTGAAGATGGATCCATACAAGGTCTGTTT

GluLeuSerGlyIleProPheValGlyCysAspIleGlnSerSerAlaIleCysMetAsp
AsnCysProValSerLeuLeu***AlaAlaIlePheLysAlaGlnPheValTrpThr
  IleValArgTyrProPheCysArgLeuArgTyrSerLysLeuSerAsnLeuTyrGlyGln
GAATTGTCCGGTATCCCTTTTGTAGGCTGCGATATTCAAAGCTCAGCAATTGTATGGAC
                              4900

LysSerLeuThrTyrIleValAlaAlaLysAsnAlaGlyIleAlaAlaThrProAlaPheTrpVal
AsnArg***HisThrSerLeuArgLysMetLeuGly***LeuLeuProProPheGlyLeu
  IleValAspIleHisArgCysGluLysCysTrpAspSerTyrSerArgLeuLeuGlyTyr
AAATCGTTGACATACATCGTTGCGAAAAATGCTGGGATAGCTACTCCCGCCTTTTGGGTT
```

FIG. 5GG

```
IleAsnLysAspAspArgProValAlaAlaThrPheThrTyrProValPheValLysPro
LeuIleLysMetIleGlyArgTrpGlnLeuArgLeuProIleLeuPheLeuLeuSerArg
******Arg*****AlaGlyGlySerTyrValTyrLeuSerCysPheCys***AlaGly
ATTAATAAAGATGATAGGCCGGTGGCAGCTACGTTTACCTATCCTGTTTTGTTAAGCCG
                          .         5000          .          .
AlaArgSerGlySerSerPheGlyValLysLysValAsnSerAlaAspGluLeuAspTyr
ArgValGlnAlaHisProSerVal***LysLysSerIleAlaArgThrAsnTrpThrThr
AlaPheArgLeuIleLeuArgCysGluLysSerGln***ArgGlyArgIleGlyLeuArg
GCGCGTTCAGGCTCATCCTTCGGTGTGAAAAAGTCAATAGCCGGACGAATTGGACTAC
                          .         .         .         5100
```

```
AlaIleGluSerAlaArgGlnTyrAspSerLysIleLeuIleGluGlnAlaValSerGly
GlnLeuAsnArgGlnAspAsnMetThrAlaLysSer***LeuSerArgLeuPheArgAla
Asn***IleGlyLysThrIle***GlnGlnAsnLeuAsn***AlaGlyCysPheGlyLeu
GCAATTGAATCGGCAAGACAATATGACAGCAAAATCTTAATGAGCAGGCTGTTTCGGGC

CysGluValGlyCysAlaValLeuGlyAsnSerAlaAlaLeuValValGlyGluValAsp
ValArgSerValValArgTyrTrpGluThrValProArg***LeuLeuAlaArgTrpThr
***GlyArgLeuCysGlyIleGlyLysGlnCysArgValSerCysTrpArgGlyGlyPro
TGTGAGGTCGGTTGTGCGGTTATTGGGAAACAGTGCCGCGTTAGTGTGGCGAGGTGGAC
                                5200

GlnIleArgLeuGlnTyrGlyIleIlePheArgIleHisGlnGluValGluProGluLysGly
LysSerGlyCysSerThrGluSerPheValPheIleArgLysSerSerArgLysLysAla
AsnGlnAlaAlaValArgAsnLeuSerTyrSerSerGlySerArgAlaGlyLysArgLeu
CAAATCAGGCTGCAGTACGGAATCTTTCGTATTCATCAGGAAGTCGAGCCGGAAAAGGC
```

```
SerGluAsnAlaValIleThrValProAlaAspLeuSerAlaGluArgGlyArgIle
LeuLysThrGlnLeu***ProPheProGlnThrPheGlnArgSerGluAspGlyTyr
***LysArgSerTyrAsnArgSerArgArgProPheSerArgGlyAlaArgThrAspThr
TCTGAAAACGCAGTTATAACCGTTCCCGCAGACCTTTCAGCAGAGGAGCGAGGACGGATA
                          5300
GlnGluThrAlaLysLysIleTyrLysAlaLeuGlyCysArgArgGlyLeuAlaArgValAsp
ArgLysArgGlnLysLysTyrIleLysArgSerAlaValGluVal***ProValTrpIle
GlyAsnGlyLysLysAsnIle***SerAlaArgLeu***ArgSerSerProCysGlyTyr
CAGGAAACGGCAAAAAAATATATAAAGCGCTCGGCTGTAGAGGTCTAGCCCGTGTGGAT
                                                    5400
```

```
MetPheLeuGlnAspAsnGlyArgIleValLeuAsnGluValLysnThrLeuProGlyPhe
CysPheTyrLysIleThrAlaAlaAlaLeuTyr***ThrLysSerIleLeuCysProValSer
ValPheThrArg***ArgProHisCysThrArgSerGlnTyrSerAlaArgPheHis
ATGTTTTTACAAGATAACGGCCGCATTGTACTGAACGAAGTCATACTCTGCCCGGTTTC
                                              .
ThrSerTyrSerArgTyrProArgMetMetAlaAlaAlaGlyIleAlaLeuProGluLeu
ArgHisThrValValIleProVal***TrpProLeuGlnValLeuHisPheProAsn***
ValIleGlnSerLeuSerProTyrAspGlyArgCysArgTyrCysThrSerArgThrAsp
ACGTCATACAGTCGTTATCCCCGTATGATGGCCGCTGCAGGTATTGCACTTCCCGAACTG
                     5500                       .
IleAspArgLeuIleValLeuAlaAlaLeuLysGly*****AlaTrpLys***AspLeuLeu
LeuThrAla***SerTyr***Arg***ArgGlyAspLysHisGlyAsnArgIleTyrPhe
***ProLeuAspArgIleSerValLysGlyValIleSerMetGluIleGlyPheThrPhe
ATTGACCGCTTGATCGTATTAGCGTTAAAGGGGTGATAAGCATGGAAATAGGATTTACTT
```

Phe\*\*\*MetLys\*\*\*TyrThrValPheValGlyThrLeuAsnMetProLeuGlyIleIle
PheArg\*\*\*AsnSerThrArgCysSerLeuGlyArg\*\*\*IleCysHisLeuGly\*\*\*Phe
LeuAspGluIleValHisGlyValArgTrpAspAlaLysTyrAlaThrTrpAspAsnPhe
TTTAGATGAAATAGTACACGGTGTTCGTTGGGACGCTAAATATGCCACTTGGATAATT
                              5600
SerProGluAsnArgLeuThrValMetLys\*\*\*IleAlaLeu\*\*\*GlyHisThrSerTrp
HisArgLysThrGly\*\*\*ArgLeu\*\*\*SerLysSerHisCysArgAspIleArgValGly
ThrGlyLysProValAspGlyTyrGluValAsnArgIleValGlyThrTyrGluLeuAla
TCACCGGAAAACCGGTTGACGGTTATGAAGTAAATCGCATTGTAGGACATACGAGTTGG
                                                5700

FIG. 5LL

LeuAsnArgPhe***ArgGlnLysAsnTrpLeuLeuProLysGlyThrAspCysPheTyr
***IleAlaPheGluGlyLysArgThrGlyCysTyrProArgValArgIleAlaSerMet
GluSerLeuLeuLysAlaLysGluLeuAlaAlaThrGlnGlyTyrGlyLeuLeuLeuTrp
CTGAATCGCTTTTGAAGGCAAAAGAACTGGCTGCTACCCAAGGGTACGGATTGCTTCTAT

GlyThrValThrValLeuSerValLeu***ThrValLeuCysAsnGlyLeuHisSerArg
GlyArgLeuProSer***AlaCysCysLysLeuPheTyrAlaMetGlyCysThrAlaGly
AspGlyTyrArgProLysArgAlaValAlaAsnCysPheMetGlnTrpAlaAlaGlnProGlu
GGGACGGGTTACCGTCCTAAGCGTGCTGTAAACTGTTTTATGCAATGGGCTGCACAGCCGG
                                  5800

LysIleThr*GlnArgLysValIleIleProIleLeuThrGluLeuArg*PheGln
Lys*ProAspLysGlyLysLeuLysLeuLeuSerGlnTyr*ProAsn***AspAspPheLys
AsnAsnLeuThrLysGluSerTyrTyrProAsnIleAspArgThrGluMetIleSerLys
AAAATAACCTGACAAAGGAAAGTTATTATCCCAATATTGACCGAACTGAGATGATTTCAA

FIG. 5MM

LysAspThrTrpLeuGlnAsnGlnAlaIleAlaAlaAlaValProLeuIleLeuArgPhe
ArgIleArgGlyPheLysIleLysPro*ProArgGlnCysHis*SerTyrAlaLeu
GlyTyrValAlaSerLysSerHisSerSerArgGlySerAlaIleAspLeuThrLeuTyr
AAGGATACGTGGCTTCAAAATCAAGCCCGCGGCAGTGCCATTGATCTTACGCTTT
       .               5900              .
IleAsp***ThrArgValSerLeuTyrGlnTrpGlyAlaAspLeuIleLeuTrpMetAsn
SerIleArgHisGly*AlaCysThrAsnGlyGluProIle*PheTyrGly***Thr
ArgLeuAspThrGlyGluLeuValProMetGlySerArgPheAspPheMetAspGluArg
ATCGATTAGACACGGGTGAGCTTGTACCAATGGGGAGCCGATTGATTTATGGATGAAC
       .                 .             6000

FIG. 5NN

```
AlaLeuIleMetArgGlnMetGluTyrHisAlaMetLysArgIleAlaAspValCys
LeuSerSerCysGlyLysTrpAsnIleMetGln***SerAlaLysSerGlnThrPheAla
SerHisAlaAlaAsnGlyIleSerCysAsnGluAlaGlnAsnArgArgArgLeuArg
GCTCTCATCATGCGGCAAATGGAATATCATGCAATGAAGCGCAAAATCGCAGACGTTTGC
                      .                      .
AlaProSerTrpLysThrValGlyLeuLysHisIleAlaSerAsnGlyGlyThrMetTyr
LeuHisHisGlyLeuLysGlnTrpVal***SerIle***ProArgMetValAlaLeuCysIle
SerIleMetGluAsnSerGlyPheGluAlaTyrSerLeuTrpGluTrpTrpHisTyrValLeu
GCTCCATCATGGAAAACAGTGGGTTTGAAGCATATAGCCTCGAATGGTGGCACTATGTAT
                      6100
***GluThrAsnHisThrProIleAlaIleLeuIleSerProLeuAsnLysLeuLeuThr
LysArgArgThrIleProGln***LeuPhe***PheProArg***IleAsnPhe***Pro
ArgAspGluProTyrProAsnSerTyrPheAspPheProValLys***ThrPheAsnArg
TAAGAGACGAACCATACCCCAATAGCTATTTTGATTCCCGTTAAATAAACTTTTAACC
```

FIG. 500

```
ValAlaArgThrAsnTyrIleSer***LeuPheArgGlnGluThrArgArgMet***Leu

LeuHisGlyGlnThrIle***AlaAsnSerPheGlyArgLysProAspValCysAsnTrp

CysThrAspLysLeuTyrLysLeuThrLeuSerAlaGlyAsnProThrTyrValThrGly

GTTGCACGGACAAACTATATAAGCTAACTCTTTCGCAGGAAACCCGACGTATGTAACTG
         .                  6200                  .

ValLeuArgGluPheIleTyrSerArg***Tyr***ArgCysLysAlaGluArgTyrCys

PheLeuGlyAsnLeuTyrIleValAspSerIleGluAspValArgGlnSerAspIleAla

Ser***GlyIleTyrIle*****IleValLeuLysMet***GlyArgAlaIleLeuArg

GTTCTTAGGGAATTTATATATAGTAGATATTGAAGATGTAAGGCAGAGCGATATTGC
         .                  .                     6300
```

GlyHisTyrLeuArgAlaLeuArgGlnAspSerLeuIleArgLeuIleAla***Arg
ValIleIleCysValArgCysGlyLysIleAla******Asp*SerHisArgGly
SerLeuSerAlaCysAlaAlaAlaArg***ProAspAsnLysThrAspArgIleGluGly
GGTCATTATCTGCGTGCGCTGCGCCAAGATAGCCTGATAATAAGACTGATCGCATAGAGG

GlyGlyIleSerHisArgProLeuSerThrGlySerSerAlaSerLeuAsnSerAlaTrp
ValValPheHisThrAlaHisCysGlnGlnAlaValGlnProArg***IleGlnHisGly
TrpTyrPheThrProProIleValAsnArgGlnPheSerLeuValLysPheSerMetGly
GGTGGTATTCACACCGCCCATTGTCAACAGGCAGTTCAGCCTCGTTAAATTCAGCATGG

6400

ValSerLeuMetLysIleHisLeuHisTrp******IleGln*GlyGluIle
TyrHisLeu*LysPheIleTyrIleGlyTyrAspAsnSerLysSerSerArgAlaLys*
IleThrTyrGluAsnSerSerThrLeuValIleIleValAsnProValGlyArgAsnAsn
GTATCACTTATGAAAATTCATCTACATTGGTGATAAATAGTAAATCCAGTAGGGCGAAATA

IleAspCysAsnLeuArgGlyLysThrAlaGlnSerGlnThrArgLeuCysArgLeuArg

LeuThrValIleTyrGlyAlaLysArgHisAsnLeuLysArgAspCysAlaVal***Gly

*Leu*PheThrGlyGlnAsnGlyThrIleSerAsnGluIleValProPheLysGly

ATTGACTGTAATTACGGGGCAAAACGGCACAATCTCAAACGGATTGTGCCGTTTAAGG
                              6500

GlyArgPhe*LysTyrPheIleLeuProThrIle*LeuArgArgArgLeuLysMet

GluAspSerArgAsnIleSerTyrPheGlnLeuTyrSer*GlyGlyAsp*Lys***

LysIleLeuGluIlePheHisThrSerAsnTyrIleValLysGluThrGluAsnGlu

GGAAGATTCTAGAAATATTTCATACTTCCAACTATATAGTTAAGGAGGAGACTGAAAATG
                                                     6600

FIG. 5RR

```
LysLysLeuPhePheLeuLeuLeuPheLeuIleTyrLeuGlyTyrAspTyrVal
ArgSerCysPhePheTyrCysTyrCysTyrSer***TyrThr***ValMetThrThrLeu
GluValValPheIleValIleValIleLeuValIleLeuAsnIleLeuArgLeu***LeuArg***
AAGAAGTTGTTTTTTTATTGTTATTGTTATTCTTAATATACTAGGTATGACTACGTT

AsnGluAlaLeuPheSerGlnGluLysValGluPheGlnAsnTyrAspGlnAsnProLys
MetLysHisCysPheLeuArgLysLysSerAsnPheLysIleMetIleLysIleProLys
*SerThrValPheSerGlyLysSerArgIleSerLysLeu*SerLysSerGlnArg
AATGAAGCACTGTTTCTCAGGAAAAAGTCGAATTCAAAATTATGATCAAATCCAAA
                                    6700
GluHisLeuGluAsnSerGlyThrSerGluAsnThrGlnGluLysThrIleThrGluGlu
AsnIle***LysIleValGlyLeuLeuLysIleProLysArgLysGlnLeuGlnLysAsn
ThrPheArgLys***TrpAspPhe***LysTyrProArgGluAsnAsnTyrArgArgThr
GAACATTTAGAAAATAGTGGGACTTCTGAAAATACCCAAGAGAAAACAATTACAGAAGAA
```

FIG. 5SS

GlnValTyrGlnGlyAsnLeuLeuLeuIleAsnSerLysTyrProValArgGlnGluVal
ArgPheIleLysGluIleCysTyr***SerIleValAsnIleLeuPheAlaAlaLysCys
GlyLeuSerArgLysSerAlaIleAsnGln*****IleSerCysSerProArgSerVal
CAGGTTTATCAAGGAAATCTGCTATTAATCAATAGTAAATATCCTGTTCGCCAAGAAGTG
                              6800
*SerGlnIleSer*IleTyrLeuAsnMetThrAsn*****MetAspThrGlyCys
GluValArgTyrArgGluPheIle*Thr*ArgIleAsnLysTrpIleArgValAla
LysSerAspIleValAsnLeuSerLysHisAspGluLeuIleAsnGlyTyrGlyLeuLeu
TGAAGTCAGATATCGTGAATTTATCTAAACATGACGAATTAATAAATGGATACGGGTTGC
                                                        6900

```
LeuIleValIlePheIleCysGlnLysLys***HisLysAsnPheGlnArgTrpSerMet
******TyrLeuTyrValLysArgAsnSerThrLysIlePheArgAspGlyGln***
AspSerAsnIleTyrMetSerLysGluIleAlaGlnLysPheSerGluMetValAsnAsp
TTGATAGTAATATTTATATGTCAAAAGAAATAGCACAAAAATTTCAGAGATGGTCAATG

MetLeu***ArgValAlaLeuValIleLeuLeuIleValAlaIleGluThrLeuMet
CysCysLysGlyTrpArg***SerPheTyrTyr******TrpLeuSerArgLeu******
AlaValLysGlyGlyValSerHisPheIleIleAsnSerGlyTyrArgAspPheAspGlu
ATGCTGTAAAGGGTGGCGTTAGTCATTTATTATTAATAGTGCTATCGAGACTTTGATG
                                    7000
SerLysValCysPheThrLysLysTrpGlyLeuSerMetProTyrGlnGlnValIleVal
AlaLysCysAlaLeuProArgAsnGlyGly***ValCysLeuThrSerArgLeu******
GlnSerValLeuTyrGlnGluMetGlyAlaGluTyrAlaLeuProAlaGlyTyrSerGlu
AGCAAAGTGTGCTTACCAAGAAATGGGGCTGAGTATGCCTTACCAGCAGGTTATAGTG
```

```
SerIleIleGlnValTyrHis***Met***AspGlnAla***ArgLysTrpAsnGluPro
Ala***PheArgPheIleThrArgCysArgIleLysLeuAspGluAsnGlyThrSerPro
HisAsnSerGlyLeuSerLeuAspValGlySerSerLeuThrLysMetGluArgAlaPro
AGCATAATTCAGGTTTATCACTAGATGTAGGATCAAGCTTGACGAAAATGGAACGAGCCC
                              .                              
                             7100                            
LeuLysGluSerGly***LysLysMetLeuGlyAsnThrGlySerPheTyrValIleGln
***ArgLysValAspArgArgLysCysLeuGluIleArgValHisPheThrLeuSerArg
GluGlyLysTrpIleGluGluAsnAlaTrpLysTyrGlyPheIleLeuArgTyrProGlu
CTGAAGGAAAGTGGATAGAAGAAAATGCTTGGAAATACGGGTTCATTTTACGTTATCCAG
                              .                              
                             7200                            
```

FIG. 5VV

ArgThrLysGlnSer**GlnGluPhe
GlyGlnAsnArgValAsnArgAsnSer
AspLysThrGluLeuThrGlyIleGln
AGGACAAAACAGAGTTAACAGGAATTC
                    7227

FIG. 5WW

EcoRV

GATATCGTTACGCTTCATGTGCCGCTCAATACGGATACGCACTATATTATCAGCCACGAACAAA 64

TACAGAGAATGAAGCAAGGAGCATTTCTTATCAATACTGGGCGCGGTCCACTTGTAGATACCTATGAGTTGGTTAAAGCATTAGAAAACGG 155

GAAACTGGGCGGTGCCGCATTGGAAGTGTATTGGAAGGAGAGGAAGAGTTTTCTACTCTGATTGCACCCAAAAACCAATTGATAATCAATTT 246

TTACTTAAACTTCAAAGAATGCCTAACGTGATAATCACACCGCATAATCACCGAGCAAGCGTTGCGTGATACCGTTGAAAAAA 337
                                        HaeIII
        RBS                ▼MET ASN ARG ILE LYS VAL ALA ILE LEU PHE GLY GLY CYS
CCATTAAAAACTGTTTGGATTTGAAAGGAGACAGGAGC ATG AAT AGA ATA AAA GTT GCA ATA CTG TTT GGG GGT TGC 415
                                              NlaIII

SER GLU HIS ASP VAL LYS SER ALA ILE GLU ILE ALA ALA ASN LYS GLU LYS TYR
TCA GAG CAT GAC GTA AAA TCT GCA ATA GAG ATA GCC GCT AAC AAA GAA AAA TAC 484

GLU PRO LEU TYR ILE GLY ILE THR LYS SER GLY VAL TRP LYS MET CYS GLU LYS PRO CYS ALA GLU TRP
GAG CCG TTA TAC ATT GGA ATT ACG AAA TCT GGT GTA TGG AAA ATG TGC GAA AAA CCT TGC GCG GAA TGG 553

GLU ASN ASP ASN CYS TYR SER ALA VAL LEU SER PRO ASP LYS LYS MET HIS GLY LEU LEU VAL LYS LYS
GAA AAC GAC AAT TGC TAT TCA GCT GTA CTC TCG CCG GAT AAA AAA ATG CAC GGA TTA CTT GTT AAA AAG 622

ASN HIS GLU TYR GLU ILE ASN HIS VAL ASP PHE ALA SER ALA LEU HIS GLY LYS SER GLY GLU ASP
AAC CAT GAA TAT GAA ATC AAC CAT GTT GAT GTA GCA TTT TCA GCT TTG CAT GGC AAG TCA GGT GAA GAT 691

GLY SER ILE GLN GLY LEU PHE GLU LEU PRO PHE ILE VAL ALA GLY ILE CYS ASP ILE GLN SER SER ALA
GGA TCC ATA CAA GGT CTG TTT GAA TTG CCT TTT GTA GCA GGT ATC TGC GAT ATT CAA AGC TCA GCA 760

ILE CYS MET ASP LYS SER LEU ASP ARG ASP ALA LYS ASN ALA ALA GLY ILE ALA THR PRO ALA PHE TRP
ATT TGT ATG GAC AAA TCG TTG ACA GAT GCG AAA AAT GCT GGG ATA GCT ACT CCC GCC TTT TGG 829

VAL ILE ASN LYS ASP ASP ARG PRO VAL ALA ALA THR PHE THR TYR PRO VAL PHE VAL LYS PRO ALA ARG
GTT ATT AAT AAA GAT GAT AGG CCG GTG GCA GCT ACG TTT ACC TAT CCT GTT TTT GTT AAG CCG GCG CGT 898

FIG.6A

```
SER GLY SER SER PHE GLY VAL LYS LYS VAL ASN SER ALA ASP TYR ALA ILE GLU SER ALA
TCA GGC TCA TCC TTC GGT GTG AAA AAA GTC AAT AGC GCG GAC TAC GCA ATT GAA TCG GCA  967

ARG GLN TYR ASP SER LYS ILE LEU ILE GLU GLN ALA VAL SER GLY CYS GLU VAL GLY VAL LEU
AGA CAA TAT GAC AGC AAA ATC TTA ATT GAG CAG GCT GTT TCG GGC TGT GAG GTC GGT GTA TTG 1036

GLY ASN SER ALA ALA LEU VAL VAL GLY GLU LEU VAL ASP ILE LEU ARG GLN TYR GLY ILE PHE ARG ILE
GGA AAC AGT GCC GCG TTA GTT GTT GGC GAG GTG GAC CAA ATC AGG CTG CAA TAC GGA ATC TTT CGT ATT 1105

HIS GLN GLU VAL GLU PRO GLU LYS PRO GLY LYS SER ASN ALA VAL ILE THR PRO ALA ASP LEU SER ALA
CAT CAG GAA GTC GAG CCG GAA AAA CCG GGC TCT GAA AAC GCA GTT ATA ACC GTT CCC GCA GAC CTT TCA GCA 1174

GLU GLU ARG GLY ARG ILL GLN GLU THR ALA LYS ILE TYR LYS ALA LEU GLY CYS ARG GLY LEU ALA
GAG GAG CGA GGA CGG ATA CAG GAA ACG GCA AAA ATA TAT AAA GCG CTC GGC TGT AGA GGT CTA GCC 1243

ARG VAL ASP MET PHL LEU GLN ASP ASN GLY ARG ILE VAL LEU ASN GLU VAL ASN THR LEU PRO GLY PHE
CGT GTG GAT ATG TTT TTA CAA GAT AAC GGC CGC ATT GTA CTG AAC GAA GTC AAT ACT CTG CCC GGT TTC 1312

THR SER TYR SER ARG TYR PRO ARG MET MET ALA ALA ALA GLY ILE ALA LEU PRO GLU LEU ILE ASP ARG
ACG TCA TAC AGT CGT TAT CCC CGT ATG ATG GCC GCT GCA GGT ATT GCA CTT CCC GAA CTG ATT GAC CGC 1381

LEU ILE VAL LEU ALA LEU LYS GLY *** ***
TTG ATC GTA TTA GCG TTA AAG GGG TGA TAA GCATGGAAATAGGATTTACTTTTTTAGATGAAATAGTACACGGTGTTCGTT 1462
                                     ▲  NlaIII
GGGACGCTAAATATGCCACTTGGGATAATTTCACCGGAAAACCGGTTGACGGTTATGAAGTAAATCGCATTGTAGGGACATACGAGTTGGC 1553
TGAATCGCTTTTGAAGGCAAAAGAACTGGCTGCTACCCAAGGTGTTGCTTCTATGGGACGGTTACCGTCCTAAGCGTGCTGTAAAC 1644
TGTTTTATGCAATGGGCTGCACAGCCGGAAAATAACCTGACAAAGGAAAGTTATTATCCCAATATTGACCGAACTGAGATGATTTCAAAAG 1735
     sacII
GGATACGTGGCTTCAAAATCAAGCCATAGCCGCG                                                       1769
```

FIG.6B

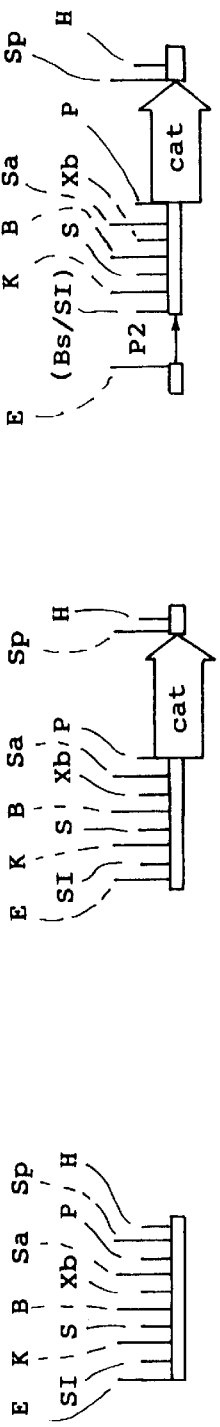
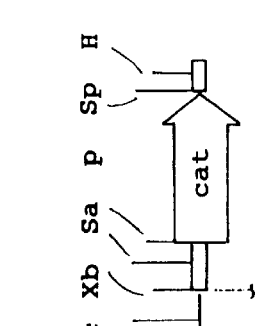
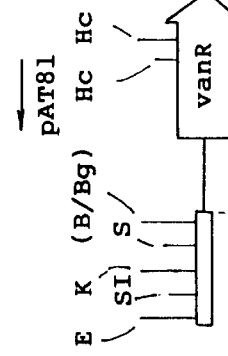
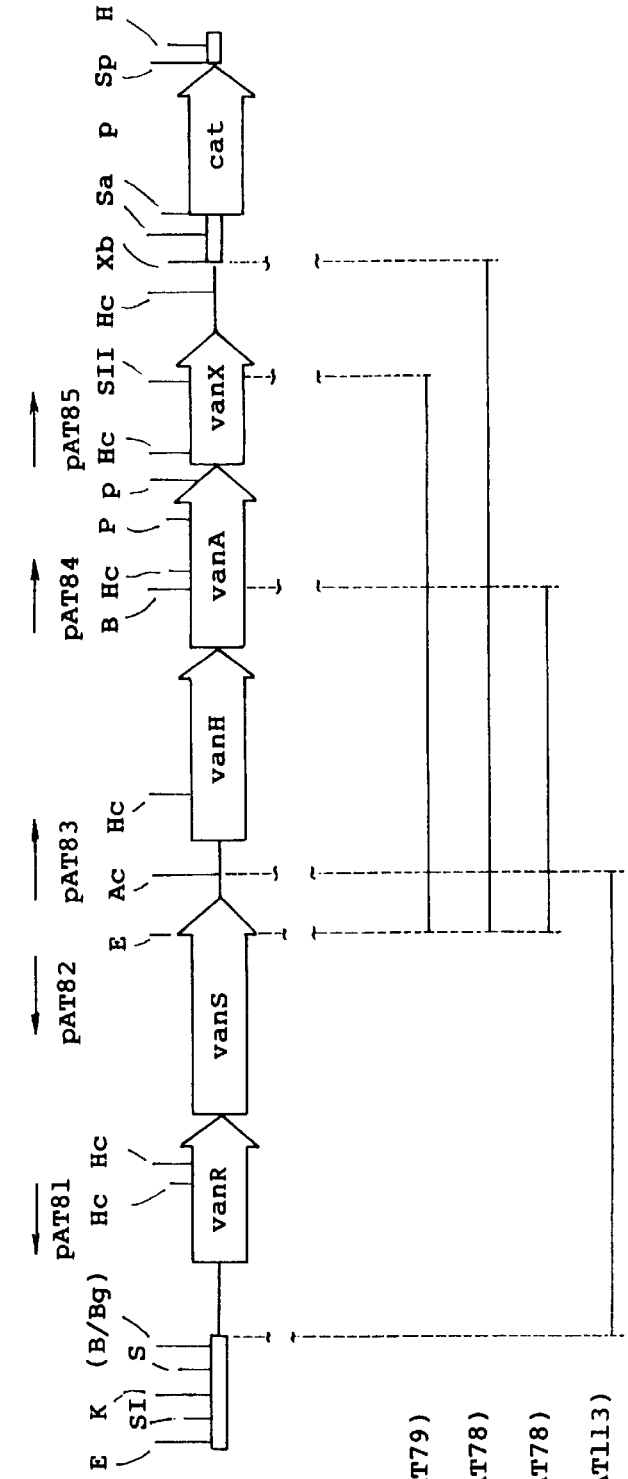
FIG. 7B  FIG. 7C  FIG. 7D la. brin "+"

```
1    GGG GTA GCG TCA GGA AAA TGC GGA TTT ACA ACG CTA AGC CTA TTT TCC TGA CGA ATC CCT
61   CGT TTT TAA CAA CGT TAA GAA AGT TTT AGT GGT CTT AAA GAA TTT AAT GAG ACT ACT TTC
121  TCT GAG TTA AAA TGG TAT TCT CCT AGT AAA TTA ATA TGT TCC CAA CCT AAG GGC GAC ATA
181  TGG TGT AAC AAA TCT TCA TTA AAG CTA CCT GTC CGT TTT TTA TAT TCA ACT GCT GTT GTT
241  AGG TGG AGA GTA TTC CAA ATA CTT ATA GCA TTG ATA ATT ATG TTT AAA GCA CTG GCT CTT
301  TGC AAT TGA TGC TGT ATG GTG CGT TCT CTA AGC TCA CCT TGT TTT CCG AAG AAA ATA GCT
361  CTT GCC AAT CCA TTC ATG GCT TCT CCT TTA TTC AAT CCT CTT TGT ATT TTT CTT CTT AAT
421  GAT TCA TCC GAT ATA TAA TTC AAA ATA AAG ATC GTT TTT TCT ATT CGG CCC ATC TCA CGT
481  AAG GCT GTA GCT AAG CTG TTT TGT CTT GAA TAG GAA CCT AGC TTC CCC ATA ATA AGG GAT
541  GCT GAA ACT GTT CCC TCC CTT ATA GAA TGA GCT AAT CGC AAA ACA TCC TCA TAA TTT TCT
601  TTA ATG ACC TTT GTA TTT ATT TGT CCA CGT AAA ATG GCT TCT AGT TTT GGA TAC TCA CTT
```

FIG. 8A

```
 661 GCT TTA TCT ATC GTA AAT AAT TTT GAG TCC GAT AAA TCC CTT ATT CTT GGG GCA AAT TTA
 721 AAT CCT AAT AAA TGA GTC AGT CCG AAT ATT TGG TCA GTG TAA CCG GCA GTG TCT GTA TAA
 781 TGT TCC TCT ATG TTT AGA TCC GTC TCA TGA TGT AAC AAA CCA TCC AAA ACA TGA ATC GCA
 841 TCT CTT GAA TTA GTA TGA ATA ATC TTT GTG TAG TAA GAA GAG AAT TGA TCA CTT GTA AAT
 901 CGG TAG ATG GTG GCT CCT TTT CCA GTT CCA TAA TGT GGA TTT GCA TCT GCA TGT AGT GAT
 961 GAA ACA CCT AGC TGC ATT CTC ATA CCA TCT GAC GAA GAT GTT ACT CCG TCG CCC CAA TAG
1021 AAA GGC AAT TGT AAT TTA TGA TGA AAG TTT ACT AAT ATG GCT TTA TAT GTA AGT CCG GGT GTG
1081 TCT TCA TAC ATG CGC ATT CTG CTC AAG CCA CAT TGA GAT ACA TTG GCT AGT TGC TTC ATG GCA
1141 GCT TCG GCC ATC TTG CTC AAG CCA ATA TTC ATT CCC ATT CCT AAA AGG GCA GCC ATG ATA
1201 ATG ATT GTT TCT TCC TTA TCT GGT TTT CGA TTA TCT GGA GCA TGA GTG AAT TGC TCA TGA
1261 AAT CCT GTT ATA TGG GCC ACA TCC ATG AGT TTT GCT TCT AAT TTT ATT CTT GGT AGC ATC
1321 TGA TAA AGG CTT GCA CTA AAT TTT TTT TCA AGA GAA ACC CCA TCT AAC TTA TTG GAA TTG GCA GCT GCA
1381 AGT GAT AGC TTT CCT TTT TCA AGA GAA ACC CCA TCT AAC CCA TCT AAC TTA TTG GAA TTG GCA GCT AAC
1441 CAC TTT AAC CTT TCA TTA AAG CTG CTG GTT CTC TCC GTT ATA TAA TCT TCG AAT GAT AAA
```

FIG. 8B

```
1501 CTA ACT GAT AAT CTC GTA TTC CCC TTC GAT TGA TTC CAT GTA TCT TCC GAA AAC AAA TAT
1561 TCC TCA AAA TCC CTA TAT TGT GTT AAA ACA GCC ATT TCA TAG TAA TGA CGA ATG GAA ACA TCT CCT GCC CGA ACA TGC
1621 TCC CGA AGT TCT GTT AAA ACA TGT CTT TTC CAT CGT TTT GAA ATA AAA TCC ACA GGT TTA ATT GTT GTA CCA TCA
1681 TCC TCG TAT AAA TGT CTT TTC CAT CGT TTT GAA ATA AAA TCC ACA GGT GAG TCA TCA GGC
1741 ACT TTT CGC TTT CCA GAT TCG TTC ATT CCT CGG ATA ATC TCA ACA GCT TGT AAA AGT GGC
1801 TCA TTT GCC TTT GTA GAA TGA AAT ACT CTT AAT AGC GTT GGC GTA TAT TTT CTT
1861 AGT GAA TAA AAC CGT TTT TGC AGT AAG TCT AAA TAA TCA TAG TCG GCA GGA CGT GCA AGT
1921 TCC TGA GCC TCT TCT ACT GAA GAG ACA AAG GTA TTC CAT TCA ATA ACC GAT TCT AAA ACC
1981 TTA AAA ACG TCT AAT TTT TCC TCT CTT GCT TTA CCG TTT TGT TTC TGG ATT TCC TCT TGA GCC TTA
2041 TGT ATA ACT TTC TCA TTT AGC TTT TTA CCG TTT TGT TTC TGG ATT TCC TCT TGA GCC TTA
2101 CGA CCT TTT GAT AAC AAA CTA AGT ATT TGC CTA TCA TGA ATT TCA AAC GCT TTA TCC GTT
2161 AGC TCC TGA GTA AGT TGT AAT AAA TAG ATG GTT AAT ATC GAA TAA CGT TTA TTT TCT TGA
2221 AAG TCA CGG AAT GCA TAC GGC TCG TAT CTT GAG CCT AAG CGA GAC AGC TGC AAC AGG CGG
2281 TTA CGG TGC AAA TGA CTA ATT TGC ACT GTT TCT AAA TCC ATT CCT CGT ATG TAT TCG AGT
2341
```

FIG. 8C

```
2401 CGT TCT ATT ATT TTT AGA AAA GTT TCG GGT GAA GGA TGA CCC GGT GGC TCT TTT AAC CAA
2461 CCC AAT ATC GTT TTA TTG GAT TCG GAT GGA TGC GAG GTA ATA ATC CCT TCA AGC TTT
2521 TCT TTT TGC TCA TTT GTT AGA GAT TTA CTA ACC GTA TTA AAT AGC TTC TTT TCA GCC ATT
2581 GCC CTT GCT TCC CAC ACC ATT CTT TCA AGT GTA GTG ATA GCA GGC AGT ATA ATT TTG TTT
2641 TTT CTT AGA AAA TCT ATG CAT TCA TGC AGT AGA TGA ATG GCA TCA CCA TTT TCC AAA GCT
2701 AAT TGA TGA AGG TAC TTA AAT GTC ATT CGA TAT TCA CTC AGG GTA AAA GTT ACA AAG TCG
2761 TAT TCA CTT CGA ATT TCT TTC AAA TGA TCC CAA AGT GTA TTT TCC CTT TGA GGA TAA TGA
2821 TCA AGC GAG GAT GGA CTA ACA CCA ATC TGT GGC CAA CCG GGA TAC CGA AGA ACA GCT AAT TGA ACA GCA
2881 ATG CTT TTG ATA TGA GTG TAT TCT TCC CTC CTT CGC TTA TTA ACT ATT TCT AAA TCC CGT TTG GAA
2941 AAT CCT AAA CGG TTT TCT TCC CCC AGT ATC CAT TCA TCT TCA GGG ATT TTC ATT TGC ATA AAA GCC TGT CTC
3001 AAA GTG AAG TAG GTC CCC AGT ATC CAT TCA TCT TCA GGG ATT TTC ATT TGC ATA AAA GCC TGT CTC
3061 TGT TCC GGT GTA AGC AAT TCT CTA CCT CTC GCA ATT TCA ATA GAG TGT ACT CTA TTG ATA CAA ATG
3121 GTA TTT TCA ATT TAT TAG TTC AAT TAT ATA TCA ATA GAG TGT ACT CTA TTG ATA CAA ATG
     TAG TAG ACT GAT AAA ATC ATA GTT AAG AGC GTC TCA TAA GAC TTG TCT CAA AAA TGA GGT
```

```
3181     resolvase
         LEU ARG LYS ILE GLY TYR ILE ARG VAL SER SER THR ASN GLN ASN PRO SER ARG
         TTG CGG AAA ATC GGT TAT ATT CGT GTC AGT TCG ACT AAC CAG AAT CCT TCA AGA
3241 GAT ATT
3301 CAA TTT CAG CAG TTG AAC GAG ATC GGA ATG GAT ATT TAT GAA GAG AAA GTT TCA GGA
     GLN PHE GLN GLN LEU ASN GLU ILE GLY MET ASP ILE TYR ILE GLU GLU LYS VAL SER GLY
3361 GCA ACA AAG GAT CGC GAG CAA CTT CAA AAA GTG TTA GAC TTA CAG GAA GAT GAC ATC
     ALA THR LYS ASP ARG GLU GLN LEU GLN LYS VAL LEU ASP LEU GLN GLU ASP ASP ILE
3421 ATT TAT GTT ACA GAC TTA ACT CGA ATC CGT AGT ACT CGT AGT CAA CAA GAT CTA TTA ATC
     ILE TYR VAL THR ASP LEU THR ARG ILE ARG SER THR ARG GLN GLN ASP LEU LEU ILE
3481 GAT AAC ATA CGA GAT AAA AAG GCA AGT TCA CTA AAA GAT ACA TGG CTT GAT TTA
     ASP ASN ILE ARG ASP LYS LYS ALA SER LEU LYS ASP THR TRP LEU ASP LEU
3541 TCA GAA GAT AAT CCA TAC AGC CAA TTC TTA ATT ACT GTA ATG GCT GGT GTT AAC CAA TTA
     SER GLU ASP ASN PRO TYR SER GLN PHE LEU ILE THR VAL MET ALA GLY VAL ASN GLN LEU
3601 GAG CGA GAT CTT ATT CGG AGA CAA CGT GAA GGG ATT GAA CTG GCT AAG AAA GAA GGA
     GLU ARG ASP LEU ILE ARG ARG GLN ARG GLU GLY ILE GLU LEU ALA LYS LYS GLU GLY
3661 AAG TTT AAA GGT CGA TTA AAG AAG TAT CAT CAT AAA AAT CAC GCA GGA ATG AAT TAT GCG GTA
     LYS PHE LYS GLY ARG LEU LYS LYS TYR HIS LYS ASN HIS ALA GLY MET ASN TYR ALA VAL
3721 AAG CTA TAT AAA GAA GGA AAT ATG ACT GTA GAA ATT TGT GAA ATT ACT AAT GTA TCT
     LYS LEU TYR LYS GLU GLY ASN MET THR VAL ASN GLN ILE CYS GLU ILE THR ASN VAL SER
     AGG GCT TCA CTA TTA TAC AGG AAA TTA TCA GAA GTG AAT AAT TAG CCA TTC TGT ATT CCG CTA
     ARG ALA SER LEU TYR ARG LYS LEU SER GLU VAL ASN ASN
```

```
3781
ATG GGC AAT ATT TTT AAA GAA GAA AAG GAA ACT ATA AAA TAT TAA CAG CCT CCT AGC GAT
3841
GCC GAA AAG CCC TTT GAT AAA AAA AGA ATC ATC TTA AGA AAT TCT TAG TCA TTT ATT
3901
ATG TAA ATG CTT ATA AAT TCG GCC CTA TAA TCT GAT AAA TTA TTA AGG GCA AAC TTA TGT

3961        VanR MET SER ASP LYS ILE LEU ILE VAL ASP ASP GLU HIS GLU ILE ALA
GAA AGG GTG ATA ACT ATG AGC GAT AAA ATA CTT ATT GTG GAT GAT GAA CAT GAA ATT GCC
4021
ASP VAL GLU LEU TYR LEU LYS ASN TYR THR VAL PHE LYS TYR TYR THR ALA
GAT GTT GAA TTA TAC CTT AAA AAC TAT ACG GTT TTC AAA TAC TAT ACC GCC
4081
LYS GLU ALA LEU GLU CYS ILE ASP LYS SER GLU ILE ALA ILE LEU ASP ILE MET
AAA GAA GCA TTG GAA TGT ATA GAC AAG TCT GAG ATT GCC CTT GAC ATC ATG
4141
LEU PRO GLY THR SER GLY LEU THR ILE CYS GLN LYS ILE ARG ASP LYS HIS THR TYR PRO
CTT CCC GGC ACA AGC GGC CTT ACT ATC TGT CAA AAA ATA AGG GAC CAC ACC TAT CCG
4201
ILE ILE MET LEU THR GLY LYS ASP THR GLU VAL ASP LYS ILE THR GLY LEU THR ILE GLY
ATT ATC ATG CTG ACC GGG AAA GAT ACA GAG GTA GAT AAA ATT ACA GGG TTA ACA ATC GGC
4261
ALA ASP TYR ILE THR LYS PRO PHE ARG PRO LEU GLU LEU ILE ALA ARG VAL LYS ALA
GCG GAT TAT ATA ACG AAG CCC TTT CGC CCA CTG GAG TTA ATT GCT CGG GTA AAG GCC
4321
GLN LEU ARG ARG TYR LYS LYS PHE SER GLY VAL LYS GLU GLN ASN GLU ASN VAL ILE VAL
CAG TTG CGC CGA TAC AAA AAA TTC AGT GGA GTA AAG GAG CAG AAC GAA AAT GTT ATC GTC
```

FIG. 8F

```
4381
HIS SER GLY LEU VAL ILE ASN VAL ASN THR HIS GLU CYS TYR LEU ASN GLU LYS GLN LEU
CAC TCC GGC CTT GTC ATT AAT GTT AAC ACC CAT GAG TGT TAT CTG AAC GAG AAG CAG TTA
4441
SER LEU THR PRO THR GLU PHE SER ILE LEU ARG ILE LEU CYS GLU ASN LYS GLY ASN VAL
TCC CTT ACT CCC ACC GAG TTT TCA ATA CTG CGA ATC CTC TGT GAA AAC AAG GGG AAT GTG
4501
VAL SER SER GLU LEU LEU PHE HIS GLU ILE TRP GLY ASP GLU TYR PHE SER LYS SER ASN
GTT AGC TCC GAG CTG CTA TTT CAT GAG ATA TGG GGC GAC GAA TAT TTC AGC AAG AGC AAC
4561
ASN THR ILE THR VAL HIS ILE ARG HIS LEU ARG GLU LYS MET ASN ASP THR ILE ASP ASN
AAC ACC ATC ACC GTG CAT ATC CGG CAT TTG CGC GAA AAA ATG AAC GAC ACC ATT GAT AAT
4621
PRO LYS TYR ILE LYS THR VAL TRP GLY VALGLYTYRLYSILEGLULYS
CCG AAA TAT ATA AAA ACG GTA TGG GGG GTTGGTTATAAAATTGAAAAT AAA AAA AAC GAC
                                       VanS              LEUVALILELYSLEULYSASN LYS LYS ASN ASP
4682
TYR SER LYS LEU GLU ARG LYS LEU TYR MET TYR ILE VAL ALA ILE VAL VAL ALA ILE
TAT TCC AAA CTA GAA CGA AAA CTT TAC ATG TAT ATC GTT GCA ATT GTG GTA GCA ATT
4742
VAL PHE VAL LEU TYR ILE ARG SER MET ILE ARG GLY LYS LEU GLY ASP TRP ILE LEU SER
GTA TTC GTG TTG TAT ATT CGT TCA ATG ATC CGA GGG AAA CTT GGG GAT TGG ATC TTA AGT
4802
ILE LEU GLU ASN ASN LYS TYR ASP ILE LYS ASP ALA MET LYS LEU TYR GLN TYR SER
ATT TTG GAA AAC AAT AAA TAT GAC ATC AAA GAC GCG ATG AAA TTA TAT CAA TAT TCC
4862
ILE ARG ASN ASN ILE ASP ILE PHE ILE TYR VAL ALA ILE VAL ILE SER ILE LEU ILE LEU
ATA CGG AAC AAT ATA GAT ATC TTT ATT TAT GTG GCG ATT GTC ATT AGT ATT CTT ATT CTA
4922
CYS ARG VAL MET LEU SER LYS PHE ALA LYS TYR PHE ASP GLU ILE ASN THR GLY ILE ASP
TGT CGC GTC ATG CTT TCA AAA TTC GCA AAA TAC TTT GAC GAG ATA ACC GGC ATT GAT
```

FIG. 8G

```
4982
     VAL LEU ILE GLN ASN GLU ASP LYS GLN ILE GLU LEU SER ALA GLU MET ASP VAL MET GLU
     GTA CTT ATT CAG AAC GAA GAT AAA CAA ATT GAG CTT TCT GCG GAA ATG GAT GTT ATG GAA
5042
     GLN LYS LEU ASN THR LEU LYS ARG THR LEU GLU LYS ARG GLU GLN ASP ALA LYS LEU ALA
     CAA AAG CTC AAC ACA TTA AAA CGG ACT CTG GAA AAG CGA GAG CAG GAT GCA AAG CTG GCC
5102
     GLU GLN ARG LYS ASN ASP VAL VAL MET TYR LEU ALA HIS ASP ILE LYS THR PRO LEU THR
     GAA CAA AGA AAT GAC GTT GTT ATG TAC TTG GCG CAC GAT ATT AAA ACG CCC CTT ACA
5162
     SER ILE ILE GLY TYR LEU SER LEU LEU ASP GLU ALA PRO MET PRO VAL ASP GLN LYS
     TCC ATT ATC GGT TAT TTG AGC CTG CTT GAC GAG GCT CCA ATG CCG GTA GAT CAA AAG
5222
     ALA LYS TYR VAL HIS ILE THR ARG LEU ASP LYS ALA TYR ARG LEU GLU LEU ILE ASP GLU
     GCA AAG TAT GTG CAT ATC ACA CGG TTG GAC AAA GCG TAT CGA GAA CTC ATC GAC GAG
5282
     PHE PHE GLU ILE THR ARG TYR ASN LEU GLN THR ILE THR LEU THR LYS THR HIS ILE ASP
     TTT TTT GAG ATT ACA CGG TAT AAC CTA CAA ACG ATA ACG CTA ACA AAA ACG CAC ATA GAC
5342
     LEU TYR TYR MET LEU VAL GLN MET THR ASP GLU PHE TYR PRO GLN LEU SER ALA HIS GLY
     CTA TAC TAT ATG CTG GTG CAG ATG ACC GAT GAA TTT TAT CCT CAG CTT TCC GCA CAT GGA
5402
     LYS GLN ALA VAL ILE HIS ALA PRO GLU ASP LEU THR VAL SER GLY ASP PRO ASP LYS LEU
     AAA CAG GCG GTT ATT CAC GCC CCC GAG GAT CTG ACC GTG TCC GGC GAC CCT GAT AAA CTC
5462
     ALA ARG VAL PHE ASN ASN ILE LEU LYS ASN ALA ALA ALA TYR SER GLU ASP ASN SER ILE
     GCG AGA GTC TTT AAC AAC ATT TTG AAA AAC GCC GCT GCA TAC AGT GAG GAT AAC AGC ATC
```

FIG. 8H

```
5522
ILE ASP ILE THR ALA GLY LEU SER GLY ASP VAL VAL SER ILE GLU PHE LYS ASN THR GLY
ATT GAC ATT ACC GCG GGC CTC TCC GGG GAT GTG GTG TCA ATC GAA TTC AAG AAC ACT GGA
5582
SER ILE PRO LYS ASP LYS LEU ALA ALA ILE PHE GLU LYS PHE TYR ARG LEU ASP ASN ALA
AGC ATC CCA AAA GAT AAG CTA GCT GCC ATA TTT GAA AAG TTC TAT AGG CTG GAC AAT GCT
5642
ARG SER SER ASP THR GLY GLY ALA GLY LEU ALA ILE ALA LYS GLU ILE ILE VAL
CGT TCT TCC GAT ACG GGT GGC GCG GGA CTT GCA ATT GCA AAA GAA ATT ATT GTT
5702
GLN HIS GLY GLY GLN ILE TYR ALA GLU SER ASN ASP ASN TYR THR THR PHE ARG VAL GLU
CAG CAT GGA GGG CAG ATT TAC GCG GAA AGC AAT GAT AAC TAT ACG ACG TTT AGG GTA GAG
5762
LEU PRO ALA MET PRO ASP LEU VAL ASP LYS ARG ARG SER
CTT CCA GCG ATG CCA GAC TTG GTT GAT AAA AGG AGG TCC TAA GA GAT GTA TAT AAT TTT
5821
TTA GGA AAA TCT CAA GGT TAT CTT TAC TTT TTC TTA GGA AAT TAA CAA TTT AAT ATT AAG
5881
AAA CGG CTC GTT CTT ACA CGG TAG ACT TAA TAC CGT AAG AAC GAG CCG TTT TCG TTC TTC
5941
AGA GAA AGA TTT GAC AAG ATT ACC ATT GGC ATC CCC GTT TTA TTT GGT GCC TTT CAC AGA
6001
                  VanH        MET ASN ASN ILE GLY ILE THR VAL TYR GLY CYS GLU GLN ASP GLU
AAGGGTTGG TCT TAA TT ATG AAT AAC ATC GGC ATT ACT GTT TAT GGA TGT GAG CAG GAT GAG
6063
ALA ASP ALA PHE HIS ALA LEU SER PRO ARG PHE GLY VAL MET ALA THR ILE ILE ASN ALA
GCA GAT GCA TTC CAT GCT CTT TCG CCT CGC TTT GGC GTT ATG GCA ACG ATA ATT AAC GCC
6123
```

FIG. 8I

```
     ASN VAL SER GLU SER ASN ALA LYS SER ALA PRO PHE ASN GLN CYS ILE SER VAL GLY HIS
     AAC GTG TCG GAA TCC AAC GCC AAA TCC GCG CCT TTC AAT CAA TGT ATC AGT GTG GGA CAT
6183
     LYS SER GLU ILE SER ALA SER ILE LEU LEU ALA LEU LYS ARG ALA GLY VAL LYS TYR ILE
     AAA TCA GAG ATT TCC GCC TCT ATT CTT CTT GCG CTG AAG AGA GCC GGT GTG AAA TAT ATT
6243
     SER THR ARG SER ILE GLY CYS ASN HIS ILE ASP THR THR ALA ALA LYS ARG MET GLY ILE
     TCT ACC CGA AGC ATC GGC TGC AAT CAT ATA GAT ACA ACT GCT AAG AGA ATG GGC ATC
6303
     THR VAL ASP ASN VAL ALA TYR SER PRO ASP TYR SER VAL ALA ASP TYR THR MET MET LEU ILE
     ACT GTC GAC AAT GTG GCG TAC TCG CCG GAT AGC GTT GCC GAT TAT ACT ATG ATG CTA ATT
6363
     LEU MET ALA VAL ARG ASN VAL LYS SER ILE VAL ARG SER VAL GLU LYS HIS ASP PHE ARG
     CTT ATG GCA GTA CGC AAC GTA AAA TCG ATT GTG CGC TCT GAA AAA CAT GAT TTC AGG
6423
     LEU ASP SER ASP ARG GLY LYS VAL LEU SER ASP MET THR VAL GLY VAL GLY THR GLY
     TTG GAC AGC GAC CGT GGC AAG GTA CTC AGC GAC ATG ACA GTT GGT GTG GGA ACG GGC
6483
     GLN ILE GLY LYS ALA VAL ILE GLU ARG LEU ARG GLY PHE GLY CYS LYS VAL LEU ALA TYR
     CAG ATA GGC AAA GCG GTT ATT GAG CGG CTG CGA GGA TTT GGA TGT AAA GTG TTG GCT TAT
6543
     SER ARG SER ARG SER ILE GLU VAL ASN TYR VAL PRO ASP PHE GLU LEU LEU GLN ASN SER
     AGT CGC AGC AGT ATA GAG GTA AAC TAT GTA CCG GAT TTT GAG TTG CTG CAA AAT AGC
6603
     ASP ILE VAL THR LEU HIS VAL PRO LEU ASN THR ASP THR HIS TYR ILE ILE SER HIS GLU
     GAT ATC GTT ACG CTT CAT GTG CCG CTC AAT ACG GAT ACG CAC TAT ATC AGC CAC GAA
6663
     GLN ILE GLN ARG MET LYS GLN GLY ALA PHE LEU ILE ASN THR GLY ARG GLY PRO LEU VAL
     CAA ATA CAG AGA ATG AAG CAA GGA GCA TTT CTT ATC AAT ACT GGG CGC GGT CCA CTT GTA
```

FIG. 8J

```
6723
ASP THR TYR GLU LEU VAL LYS ALA LEU GLY ASN GLY LYS LEU GLY GLY ALA ALA LEU ASP
GAT ACC TAT GAG TTG GTT AAA GCA TTA GAA AAC GGG AAA CTG GGC GGT GCC GCA TTG GAT
6783
VAL LEU GLY GLY GLU GLU PHE TYR PHE TYR SER ASP CYS THR GLN LYS PRO ILE ASP ASN
GTA TTG GAA GGA GAG GAA GAG TTT TAC TTC TAC TCT GAT TGC ACC CAA AAA CCA ATT GAT AAT
6843
GLN PHE LEU LYS LEU LEU GLN ARG MET PRO ASN VAL ILE PRO HIS THR ALA TYR
CAA TTT TTA CTT AAA CTT CAA AGA ATG CCT AAC GTG ATC ACA CCG CAT ACG GCC TAT
6903
TYR THR GLU GLN ALA LEU ARG ASP THR VAL GLU LYS THR ILE LYS ASN CYS LEU ASP PHE
TAT ACC GAG CAA GCG TTG CGT GAT ACC GTT GAA AAA ACC ATT AAA AAC TGT TTG GAT TTT
6963
                     VanA  METASN ARG ILE LYS VAL ALA ILE LEU PHE GLY GLY CYS SER
GAA AGG AGA CAG GAG CATGAAT AGA ATA AAA GTT GCA ATA CTG TTT GGG GGT TGC TCA
GLU ARG ARG GLN GLU HISGLU
7021
GLU GLU HIS ASP VAL SER ALA ILE GLU ILE ALA ALA ASN ILE ASN LYS GLU
GAG GAG CAT GAC GTA TCG GCA ATA GAG ATA GCC GCT AAC ATT AAT AAA GAA
7081
LYS TYR GLU PRO LEU TYR ILE GLY ILE THR LYS SER GLY VAL TRP LYS MET CYS GLU LYS
AAA TAC GAG CCG TTA TAC ATT GGA ATT ACG AAA TCT GGT GTA TGG AAA ATG TGC GAA AAA
7141
PRO CYS ALA GLU TRP GLU ASN ASP ASN CYS TYR SER ALA VAL LEU SER PRO ASP LYS LYS
CCT TGC GCG GAA TGG GAA AAC GAC AAT TGC TAT TCA GCT GTA CTC TCG CCG GAT AAA AAA
7201
MET HIS GLY LEU LEU VAL LYS LYS ASN HIS GLU TYR GLU ILE ASN HIS VAL ASP VAL ALA
ATG CAC GGA TTA CTT GTT AAA AAG AAC CAT GAA TAT GAA ATC AAC CAT GTT GAT GTA GCA
7261
```

FIG. 8K

```
      PHE SER ALA LEU HIS GLY LYS SER GLY GLU ILE GLN GLY LEU PHE GLU LEU
      TTT TCA GCT TTG CAT GGC AAG TCA GGA GAA ATA CAA GGT CTG TTT GAA TTG
      7321
      SER GLY ILE PRO PHE VAL GLY CYS ASP ILE SER ALA ILE CYS MET ASP LYS SER
      TCC GGT ATC CCT TTT GTA GGC TGC GAT ATT TCA GCA ATT TGT ATG GAC AAA TCG
      7381
      LEU THR TYR ILE VAL ALA LYS ASN ALA GLY ILE ALA THR PRO ALA PHE TRP VAL ILE ASN
      TTG ACA TAC ATC GTT GCG AAA AAT GCT GGG ATA GCT ACT CCC GCC TTT TGG GTT ATT AAT
      7441
      LYS ASP ASP ARG PRO VAL ALA ALA THR PHE THR TYR PRO VAL PHE VAL LYS PRO ALA ARG
      AAA GAT GAT AGG CCG GTG GCA GCT ACG TTT ACC TAT CCT GTT TTT AAG CCG GCG CGT
      7501
      SER GLY SER SER PHE GLY VAL LYS LYS VAL ASN SER ALA ASP GLU LEU ASP TYR ALA ILE
      TCA GGC TCA TCC TTC GGT GTG AAA AAG GTC AAT AGC GAC GAA TTG GAC TAC GCA ATT
      7561
      GLU SER ALA ARG GLN TYR ASP SER LYS ASN SER ALA VAL GLY GLU VAL ASP GLN ILE
      GAA TCG GCA AGA CAA TAT GAC AGC AAA AAT AGT GCC GCG GTT GAG CAG GTG GAC CAA ATC
      7621
      VAL GLY CYS ALA VAL LEU GLY ILE PHE ARG ILE HIS GLN GLU VAL GLU PRO GLU LYS SER GLU
      GTC GGT TGT GCG GTA TTG GGA ATC TTT CGT ATT CAT CAG GAA GTC GAG CCG GAA AAA TCT GAA
      7681
      ARG LEU GLN TYR GLY ILE PHE ARG ILE HIS GLN GLU VAL GLU PRO GLU LYS GLY SER GLU
      AGG CTG CAG TAC GGA ATC TTT CGT ATT CAT CAG GAA GTC GAG CCG GAA AAA GGC TCT GAA
      7741
      ASN ALA VAL ILE THR VAL PRO ALA ASP LEU SER ALA GLU GLU ARG GLY ARG ILE GLN GLU
      AAC GCA GTT ACC GTT CCC GCA GAC CTT TCA GCA GAG GAG CGA GGA CGG ATA CAG GAA
      7801
      THR ALA LYS LYS ILE TYR LYS ALA LEU GLY CYS ARG GLY LEU ALA ARG VAL ASP MET PHE
      ACG GCA AAA AAA ATA TAT AAA GCG CTC GGC TGT AGA GGT CTA GCC CGT GTG GAT ATG TTT

FIG. 8L
```

```
7861
LEU GLN ASP ASN GLY ARG ILE VAL LEU ASN GLU VAL ASN THR LEU PRO GLY PHE THR SER
TTA CAA GAT AAC GGC CGC ATT GTA CTG AAC GAA GTC AAT ACT CTG CCC GGT TTC ACG TCA
7921
TYR SER ARG TYR PRO ARG MET MET ALA ALA GLY ILE ALA LEU PRO GLU LEU ILE ASP
TAC AGT CGT TAT CCC CGT ATG ATG GCC GCT GGT ATT GCA CTT CCC GAA CTG ATT GAC
7981
ARG LEU ILE VAL LEU ALA LEU LYS GLY
CGC TTG ATC GTA TTA GCG TTA AAG GGG TGATAAGC ATG GAA ATA GGA TTT ACT TTT TTA GAT
                                    VanX    MET GLU ILE GLY PHE THR PHE LEU ASP
8043
GLU ILE VAL HIS GLY VAL ARG TRP ASP ALA LYS TYR ALA THR TRP ASP ASN PHE THR GLY
GAA ATA GTA CAC GGT GTT CGT TGG GAC GCT AAA TAT GCC ACT TGG GAT AAT TTC ACC GGA
8103
LYS PRO VAL ASP GLY TYR GLU VAL ASN ARG ILE ALA THR GLN GLY TYR GLU LEU ALA GLU SER
AAA CCG GTT GAC GGT TAT GAA GTA AAT CGC ATT ACC CAA GGG TAC GAG TTG GCT GAA TCG
8163
LEU LEU LYS ALA LYS GLU LEU ALA ALA ALA ASN CYS PHE MET GLN TRP ALA LEU LEU TRP ASP GLY ASN ASN
CTT TTG AAG GCA AAA GAA CTG GCT GCT GTA AAC TGT TTT ATG CAA TGG GCA CAG CCG GAA AAT AAC
8223
TYR ARG PRO LYS ARG ALA VAL ALA ASN CYS PHE MET GLN TRP ALA GLN PRO GLU ASN ASN
TAC CGT CCT AAG CGT GCT GTA AAC TGT TTT ATG CAA TGG GCA CAG CCG GAA AAT AAC
8283
LEU THR LYS GLU LYS TYR TYR PRO ASN ILE ASP ARG THR GLU MET ILE SER LYS GLY TYR
CTG ACA AAG GAA AGT TAT TAT CCC AAT ATT GAC CGA ACT GAG ATG ATT TCA AAA GGA TAC
8343
VAL ALA SER LYS SER SER HIS SER ARG GLY SER ALA ILE ASP LEU THR LEU TYR ARG LEU
GTG GCT TCA AAA TCA AGC CAT AGC CGC GGC AGT GCC ATT GAT CTT ACG CTT TAT CGA TTA
8403
ASP THR GLY GLU LEU VAL PRO MET GLY SER ARG PHE ASP PHE MET ASP GLU ARG SER HIS
GAC ACG GGT GAG CTT GTA CCA ATG GGG AGC AGC CGA TTT GAT TTT ATG GAT GAA CGC TCT CAT

FIG. 8M
```

```
     HIS ALA ALA ASN GLY ILE SER CYS ASN GLU ALA GLN ASN ARG ARG ARG LEU ARG SER ILE
8463 CAT GCG GCA AAT GGA ATA TCA TGC AAT GAA GCG CAA AAT CGC AGA CGT TTG CGC TCC ATC
     MET GLU ASN SER GLY PHE GLU ALA TYR SER LEU GLU TRP TRP HIS TYR VAL LEU ARG ASP
8523 ATG GAA AAC AGT GGG TTT GAA GCA TAT AGC CTC GAA TGG TGG CAC TAT GTA TTA AGA GAC
     GLU PRO TYR PRO ASN SER TYR PHE ASP PHE PRO VAL LYS
8583 GAA CCA TAC CCC AAT AGC TAT TTT GAT TTC CCC GTT AAA TAAA CTT TTA ACC GTT GCA
8641 CGG ACA AAC TAT ATA AGC TAA CTC TTT CGG CAG GAA ACC CGA CGT ATG TAA CTG GTT CTT
8701 AGG GAA TTT ATA TAT AGT AGA TAT TGA AGA TGT AAG GCA GAG CGA TAT TGC GGT CAT
8761 TAT CTG CGT GCG CTG CGG CAA GAT AGC AGT TCA ACA GGC AGT TCA GCA TAG AGG GGT GGT
8821 ATT TCA CAC CGC CCA TTG TCA CTA CAT TGG TGA TAA TAG TAA ATC CAG TAG GGC GAA ATA ATT GAC
8881 CTT ATG AAA ATT CAT CTA CAT TGG GGC AAA ACG GCA CAA TCT CAA ACG AGA TTG TGC CGT TTA AGG GGA AGA
                                                                          VanY MET LYS LYS
8941 TGT AAT TTA CGG GGC AAA ACG GCA CAA TCT CAA ACG AGA TTG TGC CGT TTA AGG AGA CTG AAA ATG AAG
     LEU PHE PHE LEU LEU LEU ILE TYR LEU GLY TYR ASP TYR VAL ASN GLU
9001 TTC TAG AAA TAT TTC ATA CTT CCA ACT ATA TAG TTA AGG AGA CTG AAA ATG AAG
9061 TTG TTT TTT TTA TTG TTA TTC TTA ATA TAC TTA GGT TAT GAC TAC GTT AAT GAA
```

FIG. 8N

```
9121
ALA LEU PHE SER GLN GLU LYS VAL GLU PHE GLN ASN TYR ASP GLN ASN PRO LYS GLU HIS
GCA CTG TTT TCT CAG GAA AAA GTC GAA TTT CAA AAT TAT GAT CAA AAT CCC AAA GAA CAT
9181
LEU GLU ASN SER GLY THR SER GLU ASN THR GLN GLU LYS THR GLU GLU GLN VAL
TTA GAA AAT AGT GGG ACT TCT GAA AAT ACC CAA GAG AAA ACA GAA GAA CAG GTT
9241
TYR GLN GLY ASN LEU LEU ILE ASN SER LYS TYR PRO VAL ARG GLN GLU SER VAL LYS
TAT CAA GGA AAT CTG CTA ATC AAT AGT AAA TAT CCT GTT CGC CAA GAA AGT GTG AAG
9301
SER ASP ILE VAL ASN LEU SER LYS HIS ASP LEU ILE ASN GLY TYR GLY LEU LEU ASP
TCA GAT ATC GTG AAT TTA TCT AAA CAT GAC GAA ATA AAT GGA TAC GGG TTG CTT GAT
9361
SER ASN ILE TYR MET SER LYS GLU ILE ALA GLN LYS PHE SER GLU MET VAL ASN ASP ALA
AGT AAT ATT TAT ATG TCA AAA GAA ATA GCA CAA AAA TTT TCA GAG ATG GTC AAT GAT GCT
9421
VAL LYS GLY VAL SER HIS PHE ILE ASN SER GLY TYR ARG ASP PHE ASP GLU HIS GLN GLN
GTA AAG GGT GGC GTT AGT CAT TTT ATT AAT AGT GGC TAT CGA GAC TTT GAT GAG CAA
9481
SER VAL LEU TYR GLN MET GLU MET GLY ALA GLY TYR ALA LEU PRO ALA GLY TYR SER GLU HIS
AGT GTG CTT TAC CAA GAA ATG GGG GCT GAG TAT GCC TTA CCA GCA GGT TAT AGT GAG CAT
9541
ASN SER GLY LEU SER LEU ASP VAL GLY SER SER LEU THR LYS MET GLU ARG ALA PRO GLU
AAT TCA GGT CTT TCA GAT GTA GGA TCA AGC TTG ACG AAA ATG GAA CGA GCC CCT GAA
9601
GLY LYS TRP ILE GLU ASN ALA TRP LYS TYR GLY PHE ILE LEU ARG TYR PRO GLU ASP
GGA AAG TGG ATA GAA AAT GCT TGG AAA TAC GGG TTC ATT TTA CGT TAT CCA GAG GAC
9661
LYS THR GLU LEU THR GLY ILE GLN TYR GLU PRO TRP HIS ILE ARG TYR VAL GLY LEU PRO
AAA ACA GAG TTA ACA GGA ATT CAA TAT GAA CCA TGG CAT ATT CGC TAT GTT GGT TTA CCA
9721
```

FIG. 80

```
              HIS SER ALA ILE MET LYS GLU LYS ASN PHE VAL LEU GLU GLU TYR MET ASP TYR LEU LYS
              CAT AGT GCG ATT ATG AAA GAA AAG AAT TTC GTT CTC GAG GAA TAT ATG GAT TAC CTA AAA
9781
              GLU GLU LYS THR ILE SER VAL SER VAL ASN GLY GLU LYS TYR GLU ILE PHE TYR TYR PRO
              GAA GAA AAA ACC ATT TCT GTT AGT GTA AAT GGG GAA AAA TAT GAG ATC TTT TAT TAT CCT
9841
              VAL THR LYS ASN THR THR ILE HIS VAL PRO THR ASN LEU ARG TYR GLU ILE SER GLY ASN
              GTT ACT AAA AAT ACC ACC ATT CAT GTG CCG ACT AAT CTT CGT TAT GAG ATA TCA GGA AAC
9901
              ASN ILE ASP GLY VAL ILE VAL THR VAL PHE PRO GLY SER THR HIS THR ASN SER ARG ARG
              AAT ATA GAC GGT GTA ATT GTG ACA GTG TTT CCC GGA TCA ACA CAT ACT AAT TCA AGG AGG
9961
              TAA GGA TGG CGG AAT GAA ACC AAC GAA ATT AAT GAA CAG CAT TAT TGT ACT AGC ACT TTT
10021
              GGG GTA ACG TTA GCT TTT TAA TTT AAA ACC CAC GTT AAC TAG GAC ATT GCT ATA CTA ATG
                                    Vanz      LEU GLY LYS ILE LEU SER ARG GLY LEU
10081
              ATA CAA CTT AAA CAA AAG AATTAGAGG AAA TTA TA TTG GGA AAA ATA TCT AGA GGA TTG
10143
              LEU ALA LEU TYR LEU VAL THR LEU ILE TRP LEU VAL LEU PHE LYS LEU GLN TYR ASN ILE
              CTA GCT TTA TAT TTA GTG ACA CTA ATC TGG TTA GTG TTA TTC AAA TTA CAA TAC AAT ATT
10203
              LEU SER VAL PHE ASN TYR HIS GLN ARG SER LEU ASN LEU THR PRO PHE THR ALA THR GLY
              TTA TCA GTA TTT AAT TAT CAT CAA AGA AGT CTT AAC TTG ACT CCA TTT ACT GCT ACT GGG
10263
              ASN PHE ARG GLU MET ILE ASP ASN VAL ILE ILE PHE ILE PRO PHE GLY LEU LEU LEU ASN
              AAT TTC AGA GAG ATG ATA GAT AAT GTT ATA ATC TTT ATT CCA TTT GGC TTG CTT TTG AAT
```

FIG. 8P

```
10323
VAL ASN PHE LYS GLU ILE GLY PHE LEU PRO LYS PHE ALA PHE VAL LEU SER LEU
GTC AAT TTT AAA GAA ATC GGA TTT TTA CCT AAG TTT GCT TTT GTA CTG TTA AGT CTT
10383
THR PHE GLU ILE ILE GLN PHE ILE PHE ALA ILE GLY ALA THR ASP ILE THR ASP VAL ILE
ACT TTT GAA ATA ATT CAA TTT ATC GCT ATT GGA GCG ACA GAC ATA ACA GAT GTA ATT
10443
THR ASN THR VAL GLY GLY PHE LEU GLY PHE LEU TYR GLY LEU SER ASN LYS HIS MET
ACA AAT ACT GTT GGA GGC TTT CTT GGA CTG TTA TAT GGT TTA AGC AAT AAG CAT ATG
10503
ASN GLN LYS LYS LEU ASP ARG VAL ILE ILE PHE VAL GLY ILE LEU LEU VAL LEU LEU
AAT CAA AAA AAA TTA GAC AGA GTT ATT ATT TTT GTA GGT ATA CTT TTG CTC GTA TTA TTG
10563
LEU VAL TYR ARG THR HIS LEU ARG ILE ASN TYR VAL
CTC GTT TAC CGT ACC CAT TTA AGA ATA AAT TAC GTG TAAG ATG TCT AAA TCA AGC AAT
10621
CTG ATC TTT CAT ACA CAT AAA GAT ATT GAA TGA TTA GAT GGA AAA CGG GAT GTG
10681
GGG AAA CTC GCC CGT AGG TGT GAA GTG AGG GGA AAA CCG GTG ATA AAG TAA AAA GCT TAC
10741
CTA ACA CTA TAG TAA CAA AGA AAG CCC AAT TAT CAA TTT TAG TGC TGA GGA ATT GGT CTC
10801
TTT AAT AAA TTT CCT TAA CGT TGT AAA TCC GCA TTT TCC TGA CGG TAC CCC
```

FIG. 8Q

Ib brin(-)
1
CAA AAT ATC ACC TCA TTT TTG AGA CAA GTC TTA TGA GAC GCT CTT AAC TAT GAT TTT ATC
61
AGT CTA CTA CAT TTG TAT CAA TAG AGT ACA CTC TAT TGA TAT ATA ATT GAA CTA ATA AAT Transposase                MET LYS ILE ALA ARG GLY ARG GLU LEU LEU THR
121
TGA AAA TAC AGA AAT GGA ATGATACTG AA ATG AAA ATT GCG AGA GGT AGA GAA TTG CTT ACA
182
PRO GLU GLN ARG GLN ALA PHE MET GLN ILE PRO GLU ASP GLU TRP ILE LEU GLY THR TYR
CCG GAA CAG AGA CAG GCT TTT ATG CAA ATC CCT GAA GAT GAA TGG ATA CTG GGG ACC TAC
242
PHE THR PHE SER LYS ARG ASP LEU GLU ILE VAL ASN LYS ARG ARG ARG GLU GLU ASN ARG
TTC ACT TTT TCC AAA CGG GAT TTA GAA ATA GTT AAT AAG CGA AGG AGG GAA GAA AAC CGT
302
LEU GLY PHE ALA VAL GLN LEU ALA VAL LEU ARG TYR PRO GLY TRP PRO TYR THR HIS ILE
TTA GGA TTT GCT GTT CAA TTA GCT GTT CTT CGG TAT CCC GGT TGG CCA TAC ACT CAT ATC
362
LYS SER ILE PRO ASP SER VAL ILE GLN TYR ILE SER LYS GLN ILE GLY VAL SER PRO SER
AAA AGC ATC CCA GAT TCG GTC ATA CAA TAT ATA TCG AAA CAG ATT GGT GTT AGT CCA TCC
422
SER LEU ASP HIS TYR PRO GLN ARG GLU ASN THR LEU TRP ASP HIS LEU LYS GLU ILE ARG
TCG CTT GAT CAT TAT CCT CAA AGG GAA AAT ACA CTT TGG GAT CAT TTG AAA GAA ATT CGA

FIG. 8R

```
482
SER GLU TYR ASP PHE VAL THR PHE THR LEU SER GLU TYR ARG MET THR PHE LYS TYR LEU
AGT GAA TAC GAC TTT GTA ACT TTT ACC CTG AGT GAA TAT CGA ATG ACA TTT AAG TAC CTT
542
HIS GLN LEU ALA LEU GLU ASN LYS ILE GLU ASP ALA ILE HIS LEU HIS GLU CYS ILE ASP PHE
CAT CAA TTA GCT TTG GAA AAT AAA ATT GAT GCC ATT CAT CTA CTG CAT GAA TGC ATA GAT TTT
602
LEU ARG LYS ASN LYS ILE ILE LEU PRO ALA ILE THR THR LEU GLU ARG MET VAL TRP GLU
CTA AGA AAA AAC ATT ATA CTG CCT GCT ATC ACT ACA CTT GAA AGA ATG GTG TGG GAA
662
ALA ARG ALA MET ALA GLU LYS LEU PHE ASN THR VAL SER LYS SER LEU THR ASN GLU
GCA AGG GCA ATG GCT GAA AAG CTA TTT AAT ACG GTT AGT AAA TCT CTA ACA AAT GAG
722
GLN LYS GLU LEU GLU GLY ILE ILE THR SER GLN HIS PRO SER GLU SER ASN LYS THR
CAA AAA GAA CTT GAA GGG ATT ACC TCG CAG CAT CCA TCC GAA TCC AAT AAA ACG
782
ILE LEU GLY TRP LEU LYS GLU PRO PRO GLY HIS PRO SER PRO GLU THR PHE LEU LYS ILE
ATA TTG GGT TGG TTA AAA GAG CCA CCG GGT CAT CCT TCA CCC GAA ACT TTT CTA AAA ATA
842
ILE GLU ARG LEU GLU TYR ILE ARG ILE GLU THR VAL GLN ILE SER HIS LEU
ATA GAA CGA CTC GAA TAC ATA CGA ATA GAA ACA GTG CAA ATT AGT CAT TTG
902
HIS ARG ASN ARG LEU GLN LEU SER ARG LEU GLY SER ARG TYR GLU PRO TYR ALA PHE
CAC CGT AAC CGC CTG CAG CTG TCT CGC TTA GGC TCA AGA TAC GAG CCG TAT GCA TTC
962
ARG ASP PHE GLN ASN LYS ARG TYR SER ILE LEU THR ILE TYR LEU GLN LEU THR
CGT GAC TTT CAA GAA AAT AAA CGT TAT TCG ATA TTA ACC TAT TTA CAA CTT ACT
1022
GLN GLU LEU THR ASP LYS ALA PHE GLU ILE HIS ASP ARG GLN ILE LEU SER LEU SER
CAG GAG CTA ACG GAT AAA GCG TTT GAA ATT CAT GAT AGG CAA ATA CTT AGT TTG TTA TCA
```

FIG. 8S

```
1082
LYS GLY ARG LYS ALA GLN GLU ILE GLU GLN LYS ASN GLY LYS LEU LYS LEU ASN GLU LYS
AAA GGT CGT AAG GCT CAA GAG ATC GAA CAG AAA AAC GGT AAA AAG CTA AAT GAG AAA
1142
VAL ILE HIS PHE THR ASN ILE GLY GLN ALA LEU ILE LYS ALA ARG GLU GLU LYS LEU ASP
GTT ATA CAC TTT ACG AAC ATC GGA CAA GCA TTA ATT AAA GCA AGA GAG GAA TTA GAC
1202
VAL PHE LYS VAL LEU GLU SER VAL ILE GLU TRP ASN THR PHE VAL SER SER VAL GLU GLU
GTT TTT AAG GTT TTA GAA TCG GTT ATT GAA TGG AAT ACC TTT GTC TCT TCA GTA GAA GAG
1262
ALA GLN GLU LEU ALA ARG PRO ALA ASP TYR LEU ASP LEU GLN LEU GLU PHE HIS SER ARG PHE
GCT CAG GAA CTT GCA CGT CCT GAC TAT TTA GAC TTA CTG CAA TTT CAT CGG TTT
1322
TYR SER LEU ARG LYS TYR THR PRO THR LEU ARG VAL LEU GLU VAL LEU GLU SER THR LYS
TAT TCA CTA AGA AAA TAT ACG CCA ACG CTA AGA GTA TTG GAA GTA TCT CAT ACA AAG
1382
ALA ASN GLU PRO LEU LEU GLN ALA VAL GLU ILE ILE ARG GLY MET ASN GLU SER GLY LYS
GCA AAT GAG CCA CTT TTA CAA GCT GTT GAG ATT ATC CGA GGA ATG AAC GAA TCT GGA AAG
1442
ARG LYS VAL PRO ASP ASP SER PRO VAL ASP PHE ILE SER LYS TRP LYS ARG HIS LEU
CGA AAA GTG CCT GAT GAC TCA CCT GTG GAT TTT ATT TCA AAA CGA TGG AAA CAT TTA
1502
TYR GLU ASP ASP GLY THR THR ILE ASN ARG HIS TYR TYR GLU MET ALA VAL LEU THR GLU
TAC GAG GAT GAT GGT ACA ACA ATT AAT CGT CAT TAC GAA ATG GCT GTT TTA ACA GAA
1562
LEU ARG GLU HIS VAL ARG ALA GLY ASP VAL SER ILE VAL GLY SER ARG GLN TYR ARG ASP
CTT CGG GAG CAT GTT CGG GCA GGA GAT GTT TCC ATT GTT GGC AGC AGA CAA TAT AGG GAT
```

FIG. 8T

```
1622
PHE GLU GLU TYR LEU PHE SER GLU ASP THR TRP ASN GLN SER LYS GLY ASN THR ARG LEU
TTT GAG GAA TAT TTG TTT TCG GAA GAT ACA TGG AAT CAA TCG AAG GGG AAT ACG AGA TTA
1682
SER VAL SER LEU SER PHE GLU ASP TYR ILE THR GLU ARG THR SER SER PHE ASN GLU ARG
TCA GTT AGT TTA TCA TTC GAA GAT TAT ATA ACG GAG AGA ACC AGC AGC TTT AAT GAA AGG
1742
LEU LYS TRP LEU ALA ALA ASN SER ASN LYS LEU ASP GLY VAL SER LEU GLU LYS GLY LYS
TTA AAG TGG TTA GCT GCC AAT TCC AAT AAG TTA GAT GGG GTT TCT CTT GAA AAA GGA AAG
1802
LEU SER LEU ALA ARG LEU GLU LYS ASP VAL PRO GLU GLU ALA LYS LYS PHE SER ALA SER
CTA TCA CTT GCA CGC TTA GAA AAA GAT GTT CCA GAA GAA GCA AAA AAA TTT AGT GCA AGC
1862
LEU TYR GLN MET LEU PRO ARG ILE LYS LEU THR ASP LEU LEU MET ASP VAL ALA HIS ILE
CTT TAT CAG ATG CTA CCA AGA ATA AAA TTA ACT GAT TTA CTC ATG GAT GTG GCC CAT ATA
1922
THR GLY PHE HIS GLU GLN PHE THR HIS ALA SER ASN ASN ARG LYS PRO ASP LYS GLU GLU
ACA GGA TTT CAT GAG CAA TTC ACT CAT GCT TCC AAT AAT CGA AAA CCA GAT AAG GAA GAA
1982
THR ILE ILE MET ALA ALA LEU LEU GLY MET ASN ILE GLY LEU SER LYS MET
ACA ATC ATT ATG GCT GCC CTT TTA GGA ATG ATT GGC TTG AGC AAG ATG
2042
ALA GLU ALA THR PRO GLY LEU THR TYR LYS GLN LEU ALA ASN VAL SER GLN TRP ARG MET
GCC GAA GCA ACA CCC GGA CTT ACA TAT AAG CAA CTA GCC AAT GTA TCT CAA TGG CGC ATG
2102
TYR ASP ALA MET ASN LYS ALA GLN ALA ILE LEU VAL ASN PHE HIS HIS LYS LEU GLN
TAT GAT GCC ATG AAT AAA GCC CAA GCC ATA TTA GTA AAC TTT CAT CAT AAA TTA CAA
2162
LEU PRO PHE TYR TRP GLY ASP GLY THR THR THR SER SER ASP GLY MET ARG MET GLN LEU
TTG CCT TTC TAT TGG GGC GAC GGT ACA ACA TCT TCG TCA GAT GGT ATG AGA ATG CAG CTA

FIG. 8U
```

```
2222
GLY VAL SER SER LEU HIS ALA ASP ALA ASN PRO HIS TYR GLY THR GLY LYS GLY ALA THR
GGT GTT TCA TCA CTA CAT GCA GAT GCA AAT CCA CAT TAT GGA ACT GGA AAA GGA GCC ACC
2282
ILE TYR ARG PHE THR SER ASP GLN PHE SER SER TYR TYR THR LYS ILE ILE HIS THR ASN
ATC TAC CGA TTT ACA AGT GAT CAA TTC TCT TCT TAC TAC ACA AAG ATT ATT CAT ACT AAT
2342
SER ARG ASP ALA ILE HIS VAL LEU ASP GLY LEU LEU HIS HIS GLU THR ASP LEU ASN ILE
TCA AGA GAT GCG ATT CAT GTT TTG GAT GGT TTA CAT CAT GAG ACG GAT CTA AAC ATA
2402
GLU GLU HIS TYR THR ASP THR ALA GLY TYR THR ASP GLN ILE PHE GLY LEU THR HIS LEU
GAG GAA CAT TAT ACA GAC ACT GCC GGT TAC ACT GAC CAA ATA TTC GGA CTG ACT CAT TTA
2462
LEU GLY PHE LYS PHE ALA PRO ARG ILE ARG ASP LEU SER LYS LEU PHE THR ILE
TTA GGA TTT AAA TTT GCC CCA AGA ATA AGG GAT TTA TCG GAC TCA AAA TTA TTT ACG ATA
2522
ASP LYS ALA SER GLU TYR PRO LYS LEU ARG GLY ALA ILE LEU ARG GLY GLN ILE ASN THR LYS
GAT AAA GCA AGT GAG TAT CCA AAA CTA CGT GGA GAA GCC ATT TTA CGT GGA CAA ATA AAT ACA AAG
2582
VAL ILE LYS GLU ASP VAL LEU ARG ALA HIS SER ILE ARG GLU GLY THR
GTC ATT AAA GAA GAT GTT TTG CGA GCT CAT TCT ATA AGG GAG GGA ACA
2642
AGT TTC AGC ATC CCT TAT TAT GGG GAA GCT AGG TTC CTA TTC AAG ACA AAA CAG CTT AGC
VAL SER ALA SER LEU ILE MET GLY LYS LEU GLY SER TYR SER ARG GLN ASN SER LEU ALA
GTT TCA GCA TCC CTT ATT ATG GGG AAG CTA GGT TCC TAT TCA AGA CAA AAC AGC TTA GCT
2702
THR ALA LEU ARG GLU MET GLY ARG ILE GLU LYS THR ILE PHE ILE LEU ASN TYR ILE SER
ACA GCC TTA CGT GAG ATG GGC CGA ATA GAA AAA ACG ATC TTT ATT TTG AAT TAT ATA TCG
```

FIG. 8V

```
2762
ASP GLU SER LEU ARG ARG ARG LYS ILE GLN ARG GLY LEU ASN LYS ILE GLN ARG GLY ALA MET ASN GLY
GAT GAA TCA TTA AGA AGA AGA AAA ATA CAA AGA GGA TTG AAT AAA GGA GAA GCC ATG AAT GGA
2822
LEU ALA ARG ALA ILE PHE PHE GLY LYS GLN GLY GLU LEU ARG GLU ARG THR ILE GLN HIS
TTG GCA AGA GCT ATT TTC TTC GGA AAA CAA GGT GAG CTT AGA GAA ACC ATA CAG CAT
2882
GLN LEU GLN ARG ALA SER ALA LEU ASN ILE ILE ILE ASN ALA ILE SER ILE TRP ASN THR
CAA TTG CAA AGA GCC AGT GCT TTA AAC ATA ATT ATC AAT GCT ATA AGT ATT TGG AAT ACT
2942
TCT CCA CCT AAC AAC AGC AGT TGA ATA TAA AAA ACG GAC AGG TAG CTT TAA TGA AGA TTT
LEU HIS LEU THR THR ALA VAL GLU TYR LYS ARG THR GLY SER PHE ASN GLU ASP LEU
CTC CAC CTA ACA ACA GCA GTT GAA TAT AAA AAA CGG ACA GGT AGC TTT AAT GAA GAT TTG
3002
LEU HIS HIS MET SER PRO LEU GLY TRP GLU HIS ILE ASN LEU LEU GLY GLU TYR HIS PHE
TTA CAC CAT ATG TCG CCC TTA GGT TGG GAA CAT ATT AAT TTA CTA GGA GAA TAC CAT TTT
3062
ASN SER GLU LYS VAL VAL SER LEU ASN SER LEU ARG PRO LEU LYS LEU SER
AAC TCA GAG AAA GTA GTC TCA TTA AAT TCT TTA AGA CCA CTA AAA CTT TCT TAA CGT TG
3121
TTA AAA ACG AGG GAT TCG TCA GGA AAA TAG GCT TAG CGT TGT AAA TCC GCA TTT TCC TGA
3181
CGC TAC CCC
```

FIG. 8W

```
                                                                                 SacI
        CATTGATCACTAACAATAGCTTCCTTCCTTCAACGGCCACTTCTGTACCAAGAGTTGTTGTC          42
        TCATAAAATACGAGAAGACACAGGAAGACCGCAAATTTCTTTTCTTTTCCTAGTACACTGAATG        111
                      RBS                     M  K  K  I  A  V  L  F  G  G     180
        TAACCTTAAAGAAAAAGGAAGAAAAATGATGAAAAAAATTGCCGTTTTATTGGAGG                244

N  S  P  E  Y  S  V  S  L  T  S  A  A  S  V  I  Q  A  I  D
        AATTCTCCAGAATATCTCAGTGTCCACTAACCTCAGCAGCAAGTGTGATCCAAGCTATTGAC           304

P  L  K  Y  E  V  M  T  I  G  I  A  P  T  M  D  W  Y  W  Y
        CCGCTGAAATATGAAGTAATGACCATTGGCATTGCACCAACAATGGATTGGTATTGGTAT            364

Q  G  N  L  A  N  V  R  N  D  T  W  L  E  D  H  K  N  C  H
        CAAGGAAACCTCGCGAATGTTCGCAATGATACTTGGCTAGAAGATCACAAAAACTGTCAC           424

Q  L  T  F  S  S  Q  G  F  I  L  G  E  K  R  I  V  P  D  V
        CAGCTGACTTTTTCTAGCCAAGGATTTATATTAGGAGAAAAACGAATCGTCCCTGATGTC          484

L  F  P  V  L  H  G  K  Y  G  E  D  G  C  I  Q  G  L  L  E
        CTCTTTCCAGTCTTGCATGGGAAGTATGGCGAGGATGGCTGTATCCAAGGACTGCTTGAA           544

L  M  N  L  P  Y  V  G  C  H  V  A  A  S  A  L  C  M  N  K
        CTAATGAACCTGCCTTATGTTGGTTGCCATGTCGCCGCTTCCGCATTATGTATGAACAAA          604

FIG. 9A
```

```
    W  L  L  H  Q  L  A  D  T  M  G  I  A  S  A  P  T  L  L  L
    TGGCTCTTGCATCAACTTGCTGATACCATGGGAATCGCTAGTGCTCCCACTTTGCTTTTA    664

S  R  Y  E  N  D  P  A  T  I  D  R  F  I  Q  D  H  G  F  P
    TCCCGCTATGAAAACGATCCTGCCACAATCGATCGTTTATTCAAGACCATGGATTCCCG     724

I  F  I  K  P  N  E  A  G  S  S  K  G  I  T  K  V  T  D  K
    ATCTTTATCAAGCCGAATGAAGCCGGTTCTTCAAAAGGGATCACAAAAGTAACTGACAAA    784

T  A  L  Q  S  A  L  T  T  A  F  A  Y  G  S  T  V  L  I  Q
    ACAGCGCTCCAATCTGCATTAACGACTGCTTTTGCTTACGGTTCTACTGTGTTGATCCAA    844

K  A  I  A  G  I  E  I  G  C  G  I  L  G  N  E  Q  L  T  I
    AAGGCGATAGCGGGGTATTGAAATTGGCTGCGGGCATCTTAGGAAATGAGCAATTGACGATT   904

G  A  C  D  A  I  S  L  V  D  G  F  F  D  F  F  E  E  K  Y  Q
    GGTGCTTGTGATGCGCCACGATCACTGTCCCAGACGGTTTTTTTGATTTTGAAGAGAAATACCAA   964

L  I  S  A  T  I  H  T  V  P  A  P  L  P  L  A  L  E  S  Q  I
    TTAATCAGCGCCACGATCCACACTGTCCCAGCACCATTGCCTCTCGCCTTGAATCACAGATC   1024

K  E  Q  A  Q  L  Y  R  N  L  G  L  T  G  L  A  R  I  D
    AAGGAGCAGGCACAGCTGCTTTATCGAAACTTGGGATTGACGGGTCTGGCTCGAATCGAT    1084

F  F  V  T  N  Q  G  A  I  Y  L  N  E  I  N  T  M  P  G  F
    TTTTCGTCACCAATCAAGGAGAGCGATTTATTAAACGAAATCAACACCATGCCGGGATTT   1144
```

FIG. 9B

```
      T   G   H   S   R   Y   P   A   M   M   A   E   V   G   L   S   Y   E   I   L
ACTGGGCACTCCCGCTACCCGGCTATGATGGCGGAGAGTCGGGTTATCCTACGAAATATTA        1204

V   E   Q   L   E   A   L   A   E   E   D   K   R   *
GTAGAGCAATTGATTGCACTGGCAGAGGAGGACAAACGATGAACACATTACAATTGATCAATA     1267

AAAACCATCCATTGAAAAAAATCAAGAGCCCCGCACTTAGTGCTAGCTCCTTTTAGCCGATCACGATG   1336

TTTACCTGCAG                                                              1347
   PstI
```

FIG. 9C

```
VanC  --MKKIAVLF GGNSPEYSVS LTSAASVIQA IDPLKYEVMT IGIAPTMDWY WYQGNLANVR NDTWLEDHKN CHQLTFSSQG FILGEKRIVP ---------D
VanA  MNRIKVAILF GGCSEEHDVS VKSAIEIAAN INKEKYEPLY IGITKSGVWK MCEKPCAEWE NDNCYSAVLS PDKKMHGLLV KKNHEYEINH --------VD
Dd1A  MEKLRVGIVF GGKSAEHEVS LQSAKNIVDA IDKSRFDVVL LGIDKQGQWH VSDASHYLLN ADDPAHIALR PSATSLAQVP GKHEHQLIDA QNGQPLPTVD
Dd1B  -MTDKAIVLL GGTSAEREVS LNSGAAVLAG LREGGIDAYP VDPKEVDVTQ LKSMGFQKV- ---------- ---------- ---------- ----------
               CCCCCC  IIII IICIC C    C    C      CC         CC
                                              domaine 1

<--1-->
VanC  VLFPVLHGKY GEDGCIQGLL ELMNLPYVGC HVAASALCMN KWLLHQLADT MGIASAPTLL LSRYEND--- PATIDRFIQD HGFPIFIKPN EAGSSKGITK
VanA  VAFSALHGKS GEDGSIQGLF ELSGIPFVGC DIQSSAICMD KSLTYIVAKN AGIATPAFWV INKDDRP--- -----VAAT  FTYPVFVKPA RSGSSFGVKK
Dd1A  VIFPIVHGTL GEDGSLQGML RVANLPFVGS DVLASAACMD KDVTKRLLRD AGLNIAPFIT LTRANRHNIS FAE--VESK  LGLPLFVKPA NQGSSVGVSK
Dd1B  --FIALHGRG GEDGTLQGML ELMGLPYTGS GVMASALSMD KLRSKLLWQG AGLPVAPWVA LTRAEFEKGL SDKQLAEISA LGLPVIVKPS REGSSVGMSK
              I    IIIICIICC      CI IC   II CI     I    C       IC         IC         CCC              ICCCII    III IC I
                                              domaine 2

VanC  VTDKTALQSA LTTAFAYGST VLIQKAIAGI EIGCGILGNE -QLTIGACDA ISLVDGFFDF EEKYQLIS-- -ATITVPAP  LPLALESQIK EQAQLLYRNL
VanA  VNSADELDYA IESARQYDSK ILIEQAVSGC EVGCAVLGNS EVGCAVLGNS EIECAVLGND NP---QAST  CGEIVLTSDF HQEVEPEKGS ENAVITVPAD LSAEERGRIQ ETAKKIYKAL
Dd1A  VTSEEQYATA VALAFEFDHK VIVEQGIKGR EIECAVLGND NP----QAST CGEIVLTSDF YAYDTKYIDE DGAKVVVPAA IAPEINDKIR AIAVQAYQTL
Dd1B  VVAENALQDA LRLAFQHDEE VLIEKWLSGP EFTVAILGEE IL-------P SIRIQPSGTF YDYEAKYLSD ETQYFC-PAG LEASQEANLQ ALVLKAWTTL
            I    ICI          CC CC   I      IC     CC II     IC  CCII                C      C
                                              domaine 3

<--2-->
VanC  GLTGLARIDF FVTNQGAIYL NEINTMPGFT GHSRYPAMMA EVGLSYEILV EQLIALAEED KR
VanA  GCRGLARVDM FLQDNGRIVL NEVNTLPGFT SYSRYPRMMA AAGIALPELI DRLIVLALKG
Dd1A  GCAGMARVDV FLTPENEVVI NEINTLPGFT NISMYPKLWQ ASGLGYTDLI TRLIELALER HAANNALKTT M
Dd1B  GCKGWGRIDV MLDSDGQFYL LEANTSPGMT SHSLVPMAAR QAGMSFSQLV VRILELAD
            I I  CICIC CC    CC   I IIICI I      I   IC    IC    II    CC II
                                              domaine 4
```

PROBES FOR THE DETECTION OF NUCLEOTIDE SEQUENCES IMPLICATED IN THE EXPRESSION OF RESISTANCE TO GLYCOPEPTIDES, IN PARTICULAR IN GRAM-POSITIVE BACTERIA

This is a continuation of application Ser. No. 08/174,682, filed Dec. 28, 1993, abandoned, which is a continuation of application Ser. No. 07/917,146, filed Aug. 10, 1992, abandoned.

The invention relates to the polypeptides associated with the expression of resistance to antibiotics of the glycopeptide family, in particular in Gram-positive bacteria, in particular in the family of the Gram-positive cocci. The invention also relates to a nucleotide sequence coding for these polypeptides. It also relates to the use of these polypeptides and their nucleotide sequence as agents for the in vitro detection of resistance to glycopeptides. Among the Gram-positive cocci, the invention relates most particularly to the enterococci, the streptococci and the staphylococci which are of particular importance for the implementation of the invention.

The glycopeptides, which include vancomycin and teicoplanin are antibiotics which inhibit the synthesis of the bacterial cell wall. These antibiotics are very much used for the treatment of severe infections due to Gram-positive cocci (enterococci, streptococci and staphylococci), in particular in light of allergy and resistance to the penicillins. In spite of long clinical usage of vancomycin, this antibiotic has remained active towards almost all of the strains up to 1986, the date at which the first resistant strains were isolated. Since then, resistance to the glycopeptides has been detected by many microbiologists in Europe and in the United States, in particular in strains isolated from immunodepressive patients, making necessary a systematic evaluation of the sensitivity of the microbes in hospital environments.

The activity of the glycopeptides depends on the formation of a complex between the antibiotic and the precursors of the peptidoglycan, more than on the direct interaction with enzymes of cell wall metabolism. In particular, it has been observed that the glycopeptides bind to the terminal D-alanyl-D-alanine residues (D-ala-D-ala) of the precursors of the peptidoglycan.

The recent emergence of resistance to the glycopeptides, in particular in the enterococci, has led to certain results being obtained with regard to knowledge of the factors conferring this resistance.

For example it has been observed in a particular strain of enterococci, *Enterococcus faecium* BM4147, that the determinant of resistance to the glycopeptides is localized on a plasmid of 34 kb, the plasmid pIP816. This determinant has been cloned in *E.coli* (Brisson Noel et al., 1990, Antimicrob Agents Chemother 34, 924–927).

According to the results hitherto obtained, the resistance to the glycopeptides is associated with the production of a protein of molecular weight of about 40 kDa, the synthesis of this protein being induced by sub-inhibitory concentrations of certain glycopeptides such as vancomycin.

By carrying out a more detailed study of the resistance of certain strains of Gram-positive cocci towards glycopeptides, in particular vancomycin or teicoplanin, the inventors have observed that this resistance might be linked to the expression of several proteins or polypeptides encoded in sequences usually borne by plasmids in the resistant strains. The recent results obtained by the inventors also make it possible to distinguish the genes coding for two phenotypes of resistance, on the one hand strains highly resistant to the glycopeptides, and, on the other, strains with a low level of resistance.

By strain with a high level of resistance is meant a strain of bacteria, in particular a strain of Gram-positive cocci, for which the minimal inhibitory concentrations (MIC) of vancomycin and teichoplaninare higher than 32 and 8 μg/ml, respectively. The MIC of vancomycin towards strains with low-level resistance are included between 16 and 32 μg/ml. These strains are apparently sensitive to teicoplanin.

The inventors have isolated and purified, among the components necessary for the expression of the resistance to the glycopeptides, a particular protein designated VANA or VanA which exhibits a certain homology with D-alanine-D-alanine ligases. VanA is nonetheless functionally distinct from the ligases.

In principle, a gene sequence will be designated by "van . . . " and an amino acid sequence by "Van . . . "

The invention relates to polypeptides or proteins implicated in the expression of resistance to antibiotics of the glycopeptide family and, in particular, to vancomycin and/or teicoplanin as well as to the nucleotide sequences coding for such complexes.

The invention also relates to nucleotide probes which can be used for the detection of resistance to the glycopeptides, in particular by means of the polymerase chain reaction (PCR), or by tests involving antibodies.

The invention relates to a composition of polypeptides, characterized in that it contains at least one protein or part of a protein selected from the amino acid sequences identified in the list of the sequences as SEQ ID NO 2 (VanH), SEQ ID NO 4 (VanA), SEQ ID NO 6 (VanX) or SEQ ID NO 8 (VanC), or any protein or part of a protein recognized by the antibodies directed against VanH, VanA, VanX or VanC, or any protein or part of a protein encoded in a sequence hybridizing with one of the nucleotide sequences identified in the list of the sequences as SEQ ID NO 1, SEQ ID NO 3, SEQ ID NO 5 or SEQ ID NO 7 or with one of the following sequences V1 (SEQ ID NO:9) or V2 (SEQ ID NO:10) under stringent or only slightly stringent conditions:

```
V1 : GGX  GAA  GAT  GGX  TCX  TTX  CAA  GGX
          G    C         AG   C         G
                                   A

V2 : AAT  ACX  ATX  CCX  GGX  TTT  AC
     C         T               C
                C
```

A first particular composition according to the invention implicated in the expression of the resistance to the glycopeptides is characterized in that it comprises at least 3 proteins or any part of one or more of these proteins necessary to confer to Gram-positive bacteria the resistance to antibiotics of the glycopeptide family, in particular to vancomycin and/or teicoplanin or to promote this resistance, in particular in strains of the family of the Gram-positive cocci, these proteins or parts of proteins being a) recognized by antibodies directed against one of the sequences identified in the list of the sequences as SEQ ID NO 2, SEQ ID NO 4, SEQ ID NO 6.

b) or encoded in genes containing a sequence identified as SEQ ID NO 1, SEQ ID NO 3 or SEQ ID NO 5 or hybridizing with one of these sequences or its complementary sequence or with the sequences V1 (SEQ ID NO:9) or V2 (SEQ ID NO:10), under stringent or only slightly stringent conditions.

These sequences are also designated, respectively, by ORF3, ORF1 containing the gene VanH, vanA (or ORF2);

they characterize the proteins responsible for resistance as obtained from the strain *Enterococcus faecium* BM4147 described by leclerq et al (N. Engl. J. Med. 319:157–161).

Another protein, VanC (SEQ ID NO:8), related to the D-Ala-D-Ala ligases but of different specificity has been characterized in *Enterococcus gallinarum* BM4173; the vanC gene (SEQ ID NO:7) possesses domains having sufficient homology with the vanA gene for probes corresponding to defined regions of vanA to make possible its detection.

*E.gallinarum* is a constitutive isolate resistant to low levels of vancomycin (Dutka-Malen et al., Antimicrob. Agents Chemother 34 (1990b) 1875–1879).

By the expression "polypeptides" is meant any sequence of amino acids constituting proteins or being of a size less than that of a protein.

The stringent conditions mentioned above are defined according to the usual conditions pertaining to the hybridization of nucleotide sequences. As an example, in the case of the sequences which hybridize with the sequence of the vanA gene (SEQ ID NO 1) it will be possible to apply the following conditions:

for hybridization under conditions of high stringency:
a reaction temperature of 65° C. overnight in a solution containing 0.1% SDS, 0.7% skimmed milk powder, 6×SSC (1×SSC=0.15M NaCl and 0.015M sodium citrate at pH=7.0)
washes at 65° C. in 2×SSC–0.1% SDS;

for hybridization under slightly stringent conditions, the hybridization temperature is 60° C. overnight and the temperature of the washings is 45° C.

The expression of resistance to glycopeptides may be expressed by the persistence of an infection due to microbes usually sensitive to the glycopeptides.

A polypeptide or a protein is necessary for the expression of resistance to the glycopeptides, if its absence makes the strain which contains this polypeptide or this protein more sensitive to the glycopeptides and if this polypeptide or protein is not present in sensitive strains.

Different levels of resistance to the glycopeptides exist in the strains of Gram-positive cocci, in particular.

According to a preferred embodiment of the invention, the polypeptides included in the composition defined above correspond to the combination of the proteins identified in the list of the sequences as SEQ ID NO 2 (VanH), SEQ ID NO 4 (VanA), SEQ ID NO 6 (VanX).

The inventors have thus observed that the expression of resistance to the glycopeptides in Gram-positive bacteria requires the expression of at least three proteins or of polypeptides derived from these proteins.

According to a first particular embodiment of the invention, the polypeptides of the composition are also characterized in that the amino acid sequences necessary for the expression of resistance to antibiotics of the glycopeptide family are under the control of regulatory elements, in particular of the proteins corresponding to the sequences designated by SEQ ID NO 12 and SEQ ID NO 14 in the list of the sequences, and which correspond to a regulatory sequence R and to a sensor sequence S, respectively.

VanS and VanR constitute a two-component regulatory system, VanR being an activator of transcription and VanS stimulating the transcription dependent on VanR. VanS is capable of modulating the level of phosphorylation of VanR in response to the vancomycin present in the external medium and is thus involved in the control of the transcription of the genes for resistance to vancomycin.

These regulatory sequences are in particular capable of increasing the level of resistance, to the extent to which they promote the expression of the proteins responsible for resistance comprised in the polypeptides of the invention.

According to another advantageous embodiment of the invention, the polypeptides of the above composition are encoded in the sequence SEQ ID NO 15 identified in the list of the sequences, which represents the sequence coding for the 5 proteins previously described.

Another sequence according to the invention is designated by SEQ ID NO 16 which contains the sequence SEQ ID NO 15 as well as a sequence upstream from SEQ ID NO 15 coding for a transposase (encoded in the (−) strand of the sequence, and a sequence downstream from SEQ ID NO 15 corresponding to the genes vanY and vanZ and at each end reverse repeated sequences of 38 bp. SEQ ID NO 16 constitutes a transposon, the genes of which are implicated at different levels in the establishment of resistance to the glycopeptides.

The invention also relates to the purified proteins belonging to the composition and to the polypeptides described previously. In particular, the invention relates to the purified protein VanA, characterized in that it corresponds to the amino acid sequence SEQ ID NO 4 in the list of the sequences or a protein VanC, encoded in a gene capable of hybridizing with the vanA gene.

The protein VanA contains 343 amino acids and has a calculated molecular mass of 37400 Da. The protein VanC contains 343 amino acids and has a calculated molecular mass of 37504 Da.

Other interesting proteins in the framework of the invention correspond to the sequences identified as SEQ ID NO 2 (VanH), SEQ ID NO 6 (VanX), SEQ ID NO 12 (VanR), SEQ ID NO 14 (VanS) in the list of the sequences.

The sequence identified by the abbreviation SEQ ID NO 2 contains the protein VanH encoded in the gene vanH, this protein contains 322 amino acids and begins with a methionine. This protein is an enzyme implicated in the synthesis of the peptidoglycan and has a molecular mass of 35,754 kDA. VanH exhibits some similarities to dehydrogenases which catalyze the NAD$^+$-dependent oxidation of 2-hydroxy-carboxylic acids to form the corresponding 2-keto-carboxylic acids. In fact, the VanH protein might use NADP$^+$ rather than NAD$^+$. The VanH protein also contains several residues of reactive sites which probably participate directly in the binding of the substrate and in catalysis. VanH might be implicated in the synthesis of a substrate of the ligase VanA. This substrate of VanA might be a D-α-hydroxy-carboxylic acid, which might be condensed by VanA with D-alanine in the place of a D-amino acid, which might affect the binding of the precursor of the peptidoglycan with vancomycin, as a result of the loss of a hydrogen bond because one of the hydrogen bonds formed between vancomycin and N-acetyl-D-Ala-D-Ala occurs with the NH group of the terminal D-alanine residue. Let it be recalled that "Ala" is the abbreviation for "alanine".

The inventors have been able to detect some interactions between the proteins VanA and VanH and have in particular been able to describe the following: the nature of the VanA protein (D-alanine: D-alanine ligase with reduced specificity for its substrate) which has made possible resistance to glycopeptides, implies the biosynthesis by VanA of a novel compound different from D-Ala-D-Ala, a peptide which may be incorporated into the peptidoglycans but which is not recognized by vancomycin. In particular, the observation of similarities between the product of the vanH gene and the D-specific α-keto-acid reductases has made it possible to determine that this compound cannot be a D-amino acid but is a D hydroxy acid, which when it is bound to D-alanine by VanH, can generate the novel depsipeptide precursor of the peptidoglycan.

The invention also relates to any combination of these different proteins in a resistance complex, as well as to hybrid proteins comprising one or several of the above proteins, or part of these proteins, in combination with a defined amino acid sequence.

Also included in the framework of the invention are nucleotide sequences coding for one of the amino acid sequences described above.

A particular sequence is the nucleotide sequence of about 7.3 kb, corresponding to the HindIII-EcoRI restriction fragment, such as that obtained starting from the plasmid pIP816 described in the publication of Leclerq et al—1988, cited above.

This sequence of 7.3 kb comprises the nucleotide sequence coding for the 3 resistance proteins and the 2 regulatory proteins referred to above. This coding sequence is included in an internal BglII-XbaI fragment. It also comprises a part of the sequences coding for the transposase and the resolvase.

The invention also relates to any nucleotide fragment comprising the above-mentioned restriction fragment as well as any part of the HindIII-EcoRI fragment, in particular the EcoRI-XbaI fragment of about 3.4 kb coding for the 3 resistance proteins or the EcoRV-SacII fragment of about 1.7 kb coding for VanA or also HindIII-EcoRI fragment of about 3.3 kb coding for the 2 regulatory proteins VanR and VanS.

Another definition of a nucleotide sequence of the invention corresponds to a nucleotide fragment containing the following restriction sites in the following order, such as obtained starting from pIP816 mentioned above:

HindIII, BglII, BglII, EcoRI, BamHI, XbaI, EcoRI.

Another nucleotide sequence according to the invention is characterized in that it corresponds to a sequence selected from the sequences identified as SEQ ID NO 15, SEQ ID NO 17, or SEQ ID NO 16, or in that it includes this sequence or any part of this sequence, or also any sequence or part of the sequence of the complementary DNA or any sequence of RNA corresponding to one of these DNAs, capable, either of constituting a hybridization probe for the detection of resistance to antibiotics of the glycopeptide family, in particular to vancomycin and/or teicoplanin in particular in strains of the family of the Gram-positive cocci, or of coding for a sequence necessary or associated with the expression of resistance to antibiotics of the glycopeptide family, in particular to vancomycin and/or teicoplanin., in particular in strains of the family of the Gram-positive cocci.

The sequence SEQ ID NO 17 codes for the 3 resistance proteins VanH, VanA and VanX.

The sequence SEQ ID NO 16 includes a transposon shown in FIG. 7a; this transposon contains the genes necessary for the expression of resistance to the glycopeptides as well as the genes associated with this resistance implicated, for example, in the regulation of the expression of the genes necessary to produce the resistance phenotype or implicated in the amount of resistance polypeptide produced.

A specific sequence corresponding to the above definition is one of the following sequences:

V1 (SEQ ID NO:9) :
GGX GAA GAT GGX TCX TTX CAA GGX
      G    C         AG   C       G
                             A or

V2 (SEQ ID NO:10) :
AAT ACX ATX CCX GGX TTT AC
     C      T                 T
             C

V1 and V2 make possible the constitution of probes, if necessary, in combination with other nucleotides, depending on the degree of specificity desired in order to detect vanA and vanC and may also be used as primers in polymerase chain reactions.

Other preferred nucleotide sequences are the sequences SEQ ID NO 1, SEQ ID NO 3, SEQ ID NO 5, SEQ ID NO 7, SEQ ID NO 18 (transposase), SEQ ID NO 20 (resolvase), SEQ ID NO 22 (vanY), SEQ ID NO 24 (vanZ), SEQ ID NO 11 (vanR), SEQ ID NO 13 (vanS) or a variant of one of these sequences provided that it codes for a protein having immunological and/or functional properties similar to those of the proteins encoded in the sequences SEQ ID NO 1 (vanA), SEQ ID NO 3 (vanH), SEQ ID NO 10 (vanX), or SEQ ID NO 21 (vanC), SEQ ID NO 18 (transposase), SEQ ID NO 20 (resolvase), SEQ ID NO 22 (vanY), SEQ ID NO 24 (vanZ), SEQ ID NO 11 (vanR), SEQ ID NO 13 (vanS) or in that it makes possible the detection of strains resistant to antibiotics of the glycopeptide family.

Variants include all of the fragments of the sequences having the following properties.

These sequences code for the resistance proteins VanH, VanA and VanX.

The nucleotide sequence designated by SEQ ID NO 1 corresponds to a DNA fragment of 1029 bp situated between the ATG codon at position 377 and the TGA codon at position 1406 on the plasmid pAT214 (FIG. 6).

The invention also relates to a nucleotide sequence coding for the sequence SEQ ID NO 15 corresponding to the sequence coding for the 5 proteins (2 regulatory proteins and 3 resistance proteins), and also comprising the flanking sequences associated with these coding sequences, or comprising this sequence.

Also included in the framework of the invention is a sequence modified with respect to SEQ ID NO 15, characterized in that it lacks the flanking sequences. These flanking sequences are the sequences shown in the following pages and defined as follows:

sequence upstream from the sequence coding for R: between the bases 1 and 1476 of the sequence shown in FIG. 5, sequence between the sequence coding for the sensor protein S and ORF1: between the bases 3347 and 3500 of the sequence shown in FIG. 5, sequence downstream from the sequence coding for ORF3: between the bases 6168 and 7227 of the sequence shown in FIG. 5.

The sequence designated by SEQ ID NO 15 is also characterized by the fragment bearing the restriction sites in the following order:

BglIII-EcoRI-BamHI-EcoRI

The location of the regulatory proteins and the resistance proteins is shown in FIG. 3.

The inventors have identified upstream and downstream from the genes vanR, vanS, vanH, vanA and vanX, which are necessary for or associated with the expression of resistance to glycopeptides at a given level, genes coding for a transposase and a resolvase (upstream from the group previously mentioned) and genes vanY and vanZ, downstream from this group. The genes for the transposase and resolvase might be implicated in transposition functions and the vanY gene coding for a D,D-carboxy peptidase might be implicated in the metabolism of the peptidoglycan, and might contribute to resistance to the glycopeptides in *E. faecium* BM4147 even though vanR, vanS, vanH, vanA and vanX borne by a plasmid in a high number of copies, alone confer a high level of resistance.

Let it be noted that the sequence coding for the transposase (SEQ ID NO:18) is located on the (−) strand of the sequence ID NO 16 which codes for vanR, vanS, vanH, vanA, vanX, vanY, vanZ and the resolvase.

The invention relates not only to the DNA sequences identified in the list of the sequences but also to the complementary DNA sequences and the corresponding RNA sequences. The invention concerns in addition sequences which are equivalent to the former, either in terms of expression of proteins, polypeptides or their fragments described above, or in terms of the capacity to detect, for example by chain polymerization procedures, strains of Gram-positive bacteria exhibiting resistance to antibiotics of the glycopeptide family such as vancomycin or teicoplanin.

Recombinant sequences characterized in that they comprise one of the above nucleotide sequences also form part of the invention.

The invention also relates to a recombinant vector characterized in that it includes one of the above nucleotide sequences at a site inessential for its replication, under the control of regulatory elements likely to be implemented in the expression of the resistance to antibiotics of the glycopeptide family, in particular to vancomycin or teicoplanin in a defined host.

Particularly advantageous recombinant vectors for the implementation of the invention are the following vectors: pAT214 containing the EcoRV-SacII fragment of 1761 bp containing a nucleotide sequence coding for the VanA protein; in these vectors the sequences of the invention are advantageously placed under the control of promoters such as the lac promoter.

The invention also relates to a recombinant cell host containing a nucleotide sequence such as that previously described or a vector such as that described above under conditions which make possible the expression of resistance to antibiotics of the glycopeptide family, in particular resistance to vancomycin and/or this host being for example selected from the bacteria, in particular the Gram-positive cocci.

In certain applications it is also possible to use yeasts, fungi, insect or mammalian cells.

The invention also relates to a nucleotide probe characterized in that it is capable of hybridizing with a sequence previously described, this probe being labelled if necessary. These probes may or may not be specific for the proteins of resistance to glycopeptides.

Labels which can be used for the requirements of the invention are the known radioactive labels as well as other labels such as enzymatic labels or chemoluminescent labels.

Probes thus labelled may be used in hybridization tests in order to detect resistance to glycopeptides in Gram-positive bacteria. In this case, conditions of low stringency will be used.

Nucleotide probes according to the invention may be characterized in that they are specific in Gram-positive bacteria for the sequences coding for a resistance protein to the glycopeptides, in particular to vancomycin and/or teicoplanin these probes being in addition universal among these sequences.

By these specific probes is meant any oligonucleotide hybridizing with a nucleotide sequence coding for one of the proteins according to the invention, such as described in the preceding pages, and not exhibiting a cross hybridization reaction or amplification reaction (PCR) with sequences present in all of the sensitive strains.

The universal character of the oligonucleotide which can be used in PCR is defined by their capacity to promote specifically the amplification of a nucleotide sequence implicated in resistance in any one strain of Gram-positive bacteria, resistant to the antibiotics of the glycopeptide family.

The size of the nucleotide probes according to the invention may vary depending on the use desired. For the oligonucleotides which are used in PCR, recourse will be had to fragments of a length which is usual in this procedure. In order to construct probes, it is possible to take any part of the sequences of the invention, for example probe fragments of 200 nucleotides.

According to a particular embodiment of the invention, a nucleotide probe is selected for its specificity towards a nucleotide sequence coding for a protein necessary for the expression in Gram-positive bacteria of a high level of resistance to antibiotics of the glycopeptide family, in particular to vancomycin and teicoplanin.

As examples, useful probes may be selected from the intragenic part of the vanA gene.

Other useful probes for carrying out the invention are characterized by their universal character, according to the preceding definition, but are not specific for the resistance genes. They may also be used as primers in PCR, and are for example:

```
V1  (SEQ ID NO:9) :
GGX  GAA  GAT  GGX  TCX  TTX  CAA  GGX
      G    C         AG   C         G
                          A

V2  (SEQ ID NO:10) :
AAT  ACX  ATX  CCX  GGX  TTT  AC
 C    T                   C
      C
```

V1 and V2 hybridize with vanA and vanC and are capable of leading to the detection of proteins associated with resistance to glycopeptides in other micro-organisms.

Other particular probes of the invention have the specific character of a nucleotide sequence coding for a protein necessary for the expression in Gram-positive bacteria of a low level of resistance to antibiotics of the glycopeptide family, in particular to vancomycin in Gram-positive bacteria.

It should also be mentioned that oligonucleotide probes which might be derived from the sequence of the vanA gene coding for the VanA protein may be used indiscriminantly to detect high-level or low-level resistance.

In a particularly preferred manner, a probe of the invention is characterized in that it hybridizes with a chromosomal or non-chromosomal nucleotide sequence of a Gram-positive strain resistant to glycopeptides, in particular to vancomycin and/or teicoplanin, in particular in that it hybridizes with a chromosomal or non-chromosomal nucleotide sequence of a strain of Gram-positive cocci, for example an enterococcal strain and preferably *E. faecium* 4147 or *E. gallinarum*.

In order to distinguish strains with a high level of resistance from strains with a low level of resistance it is possible to carry out a hybridization test using conditions of high stringency.

The oligonucleotides of the invention may be obtained from the sequences of the invention by cutting with restriction enzymes, or by chemical synthesis according to the standard methods.

Furthermore, the invention relates to polyclonal or monoclonal antibodies, characterized in that they recognize the polypeptide(s) described above or an amino acid sequence described above.

These antibodies may be obtained according to standard methods for antibody production. In particular, in the case of the preparation of monoclonal antibodies, recourse will be had to the method of Köhler and Milstein according to which monoclonal antibodies are prepared by cell fusion between myeloma cells and mouse spleen cells previously immunized with a polypeptide or a composition according to the invention, in conformity with the standard procedure.

The antibodies of the invention can advantageously be used for the detection of the presence of proteins characteristic of resistance to the glycopeptides, in particular to vancomycin and teicoplanin.

Particularly useful antibodies are polyclonal or monoclonal antibodies directed against the protein VanA or VanC. Such antibodies advantageously make it possible to detect strains of bacteria, in particular Gram-positive cocci, exhibiting high-level resistance to the antibiotics of the glycopeptide family. If necessary, a step entailing lysis of the cells of the sample undergoing detection is performed prior to the placing in contact of the sample with the antibodies.

In order to carry out this detection, recourse will advantageously be had to antibodies labelled for example with a radioactive substance or other type of label.

Hence, tests for the detection in Gram-positive bacteria of resistance to the glycopeptides, in particular tests making use of the ELISA procedures, are included in the framework of the invention.

A kit for the in vitro diagnosis of the presence of Gram-positive strains, resistant to the glycopeptides, in particular to vancomycin and/or teicoplanin, these strains belonging in particular to the Gram-positive cocci for example enterococci, for example *E. faecium* or *E. gallinarum* is characterized in that it comprises:

antibodies corresponding to the above definition, labelled if necessary,
  a reagent for the detection of an immunological reaction of the antigen-antibody type,
  if necessary, reagents to effect the lysis of the cells of the sample to be tested.

Furthermore, the agents developed by the inventors offer the very useful advantage of being suitable for the development of a rapid and reliable test or kit for the detection of Gram-positive strains resistant to the glycopeptides by means of the polymerase chain reaction (PCR). Such a test makes it possible to improve the sensitivity of the existing tests which remain rather unreliable and, in certain cases, may make possible the detection of all of the representatives of the family of the genes coding for resistance proteins to the glycopeptides in Gram-positive bacteria.

The carrying out of a test by means of the method of amplification of the genes of these proteins is done by the PCR procedure or by the RPCR procedure (RPCR : abbreviation for reverse polymerase chain reaction).

The RPCR technique makes possible the amplification of the $NH_2$ and COOH terminal regions of the genes it is desired to detect.

Some specific primers make it possible to amplify the genes of the strains with low-level resistance. These primers are selected, for example, from the sequence coding for the resistance protein VanA.

As examples, the following sequences can be used as primers for the preparation of probes for the detection of an amplification by means of the PCR or RPCR method.

V1 (SEQ ID NO:9) :
GGX GAA GAT GGX TCX TTX CAA GGX
 G   C       AG  C      G
                        A

V2 (SEQ ID NO:10) :
AAT ACX ATX CCX GGX TTT AC
 C   T                C
     C

X represents one of the bases A,T,C or G or also corresponds in all cases to inosine.

Naturally, the invention relates to the complementary probes of the oligonucleotides previously described as well as possibly to the RNA probes which correspond to them.

A kit for the in vitro diagnosis of the presence of strains of Gram-positive bacteria resistant to the glycopeptides, in particular resistant to vancomycin and/or teicoplanin these strains belonging in particular to the Gram-positive cocci, in particular that they are strains of enterococci, for example *E. faecium* or *E. gallinarum*, is characterized in that it contains:

a nucleotide probe complying with the above specifications and if necessary,
  oligonucleoside triphosphates in an amount sufficient to make possible the amplification of the desired sequence,
  a hybridization buffer,
  a DNA polymerization agent.

The invention also relates to a procedure for the in vitro detection of the presence of Gram-positive strains resistant to the glycopeptides, in particular to vancomycin and/or teicoplanin these strains belonging in particular to the family of the Gram-positive cocci, in particular in that they are strains of enterococci, for example *E. faecium* or *E. gallinarum*, characterized in that it comprises:

a) the placing of a biological sample likely to contain the resistant strains in contact with a primer constituted by a nucleotide sequence described above, or any part of a sequence previously described, capable of hybridizing with a desired nucleotide sequence necessary for the expression of resistance to the glycopeptides, this sequence being used as matrix in the presence of the 4 different nucleoside triphosphates and a polymerization agent under conditions of hybridization such that for each nucleotide sequence which has hybridized with a primer, an elongation product of each primer complementary to the matrix is synthesized,
  b) the separation of the matrix from the elongation product obtained, this latter then also being capable of behaving as a matrix,
  c) the repetition of step a) so as to produce a detectable amount of the desired nucleotide sequences,
  d) the detection of the product of amplification of the nucleotide sequences.

The detection of the elongation products of the desired sequence may be carried out by a probe identical with the primers used to carry out the PCR or RPCR procedure, or also by a probe different from these primers, this probe being labelled if necessary.

Details relating to the implementation of the PCR procedures may be obtained from the patent applications EP 0229701 and EP 0200362.

Other advantages and characteristics of the invention will become apparent in the examples which follow and from the figures.

BRIEF DESCRIPTION OF THE DRAWINGS

FIG. 2A: Restriction maps of the inserts of the plasmids pAT213 and pAT214. The vector and the DNA insert are distinguished by light and dark segments, respectively. The open arrow represents the vanA gene.

FIG. 2B: Strategy for the nucleotide sequencing of the insert of 1761 bp in the plasmid pAT214. The arrows indicate the direction and extent of the sequencing reactions by the dideoxy method. The synthetic oligonucleotide primer (5' ATGCTCCTGTCTCCTTTC 3' OH; SEQ ID NO:27) is complementary to the sequence between the positions 361 and 378. Only the pertinent restriction sites are given.

FIG. 4: representation of SEQ ID NO 15.

FIG. 5: representation of SEQ ID NO 15 and the corresponding protein (SEQ ID NOS:27,28 and 29).

FIG. 6: sequence of the vanA gene and the corresponding protein.

FIGS. 7a–76C:

FIG. 7a: Localization of the genes vanR, vanS, vanH, vanA, vanX, vanY, vanZ of the gene for the transposase and of the gene for the resolvase as well as the repeated reverse terminal sequences of 38 bp at the end of the transposon.

FIGS. 76A–76C: Mapping of the plasmids. (76A) Polylinker pAT29 and derivatives constructed in this study. The arrow labelled P2 indicates the position and orientation of the P2 promoter of aphA-3 (Caillaud et al., 1987, Mol. Gen. Genet. 207:509–513). (76B) Insert pAT80. The white rectangles indicate the DNA of pAT29 but they are not shown to scale. The rectangles terminating in an arrow indicate the coding sequences. The arrows shown in vertical and horizontal full lines indicate the position and orientation, respectively, of the apha-1 gene in the derivatives of pAT80. Restriction sites: Ac, AccI; B, BamHI; Bg, BglII; Bs, BssHII; E, EcoRI; H, HindIII; Hc, HincII; K, KpnI; P, PstI; S, SmaI; SI, SacI; SII, SacII; Sa, SalI; Sp, SphI; Xb, XbaI. (76C) Inserts in pAT86, pAT87, pAT88 and pAT89. The inserts are shown by full lines and the corresponding vectors are indicated in parentheses.

FIG. 8: nucleotide sequence of the transposon shown in FIG. 7 (SEQ ID NOS:16 and 30) and amino acid sequence of the corresponding proteins (SEQ ID NOS:2, 4, 6, 12, 14, 19 and 21). The nucleotide sequence is shown for the (+) strand (SEQ ID NO:16) and for the (−) strand (SEQ ID NO:90) (corresponding to the complementary sequence of the (+) strand for the positions 1 to 3189) on which the coding sequence of the transposase is located.

FIG. 9: Nucleotide sequence of the SacI-PstI fragment of 1347 bp of the plasmid pAT216 containing the vanC gene (SEQ ID NO:31). The numbering starts at the first base G of the SacI restriction site. The potential RBS sequence upstream from the initiation codon ATG of translation at position 215 is underlined. The STOP codon (TGA) is indicated by *. The region coding for the vanC and the deduced amino acid sequence are indicated in bold characters. Sequential overlapping clones were generated by restriction fragments of subcloning of pAT216 in the bacteriophage M13mp10 (Amersham, England). The universal primer (New England Biolabs Beverly Mass.) was used to sequence the insert in the recombinant phages. The sequencing was performed by the enzymatic dideoxy nucleotide method (Sanger et al., 1977 PNAS 74: 5463–5467) by using the T7 DNA polymerase (Sequenase US B CORP, Cleveland, Ohio) and [α-$^{35}$S]dATP (Amersham, England). The reaction products were loaded onto 6% denaturing polyacrylamide gels.

FIG. 10: alignment of the amino acid sequences of VanC (SEQ ID NO:2), VanA (SEQ ID NO:4), DdlA (SEQ ID NO:32) and DdlB (SEQ ID NO:33). The identical (I) amino acids and the conservative (C) substitutions in the 4 sequences are indicated in the alignment. In order to classify the conservative substitutions, the amino acids were grouped as follows: RK, LFPMVI (SEQ ID NO:34), STQNC (SEQ ID NO:35), AGW, H, ED and Y. The regions of high homology corresponding to the domains 1, 2, 3 and 4 are underlined. The sequences corresponding to the peptides 1 and 2 are indicated by the arrows.

FIG. 11B: Target peptides (SEQ ID NOS:36–39) and deduced nucleotide sequence. X represents any base of the DNA. Peptide 2 in DdlB (SEQ ID NO:39) differs from the target peptide at 2 positions (*).

FIG. 11C: Nucleotide sequence of V1 and V2. Alternate nucleotides and deoxyinosine (I) which may correspond to any base in the DNA, were used at the positions at which the nucleotide sequences coding for the target peptides vary. The arrows indicate the direction of DNA synthesis. The oligonucleotides were synthesized by the methoxyphosphoramidite method with a Biosystem DNA 380B machine (Applied Biosystem, Foster City, Calif.). The DNA was isolated from bacterial lysates by extraction with hexadecyl trimethyl ammonium bromide (Inst. biotechnologies, Inc., New Haven, Colo.) (Le Bouguénec et al., 1990, J. Bacteriol. 172:727–734) and used as matrix for the amplification by means of PCR with a controlled heating system "Intelligent Heating Block" IBH101 (Hybarid Ltd., GB) according to the description of Mabilat et al. (1990, Plasmid 23:27–34). The amplification products were revealed by electrophoresis on a 0.8% gel, after staining with ethidium bromide.

FIG. 12A: The plasmid pAT217 was constructed by litigation of the EcoRI-HincII fragment of pAT216 to the suicide vector pAT114 (Trieu-Cuot et al., 1991, Gene 106:21–27), digested with EcoRI and SmaI.

FIG. 12B: vanC region of the chromosomal DNA of BM4174.

FIG. 12C: vanC region after integration of pAT217.

Figure 14:
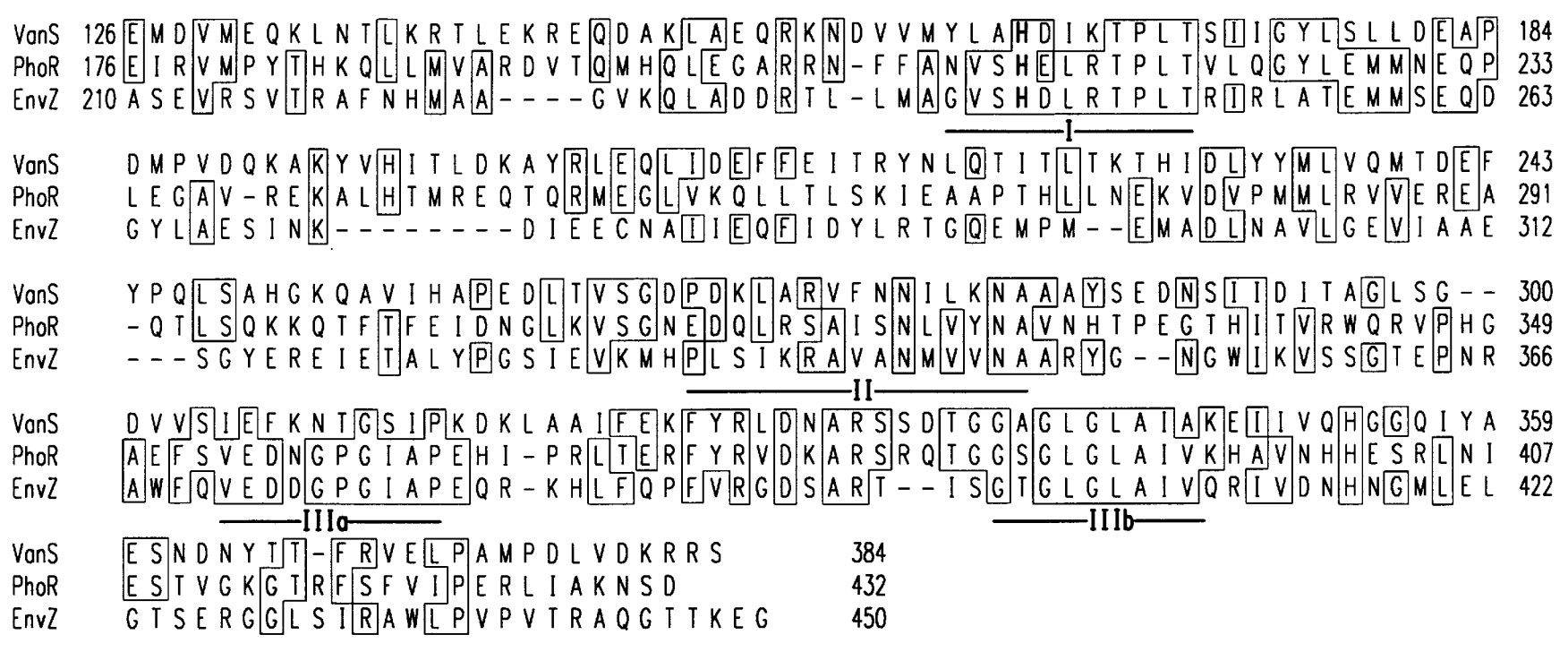

FIG. 14: alignment of the deduced amino acid sequences of VanS derived from *E. faecium* BM4147 (SEQ ID NO:40) and of PhoR (SEQ ID NO:41) and EnvZ (SEQ ID NO:42) from *E.coli*. The numbers on the left refer to the position of the first amino acid in the alignment. The numbers on the right refer to the position of the last amino acid of the corresponding line. The identical amino acids are placed in boxes. The dotted lines indicate gaps introduced in order to optimize their similarity. The dashes indicate the positions of the amino acid residues conserved in other HPK. The histidine residues in bold characters in section 1 are potential sites of autophosphorylation.

Figure 15:
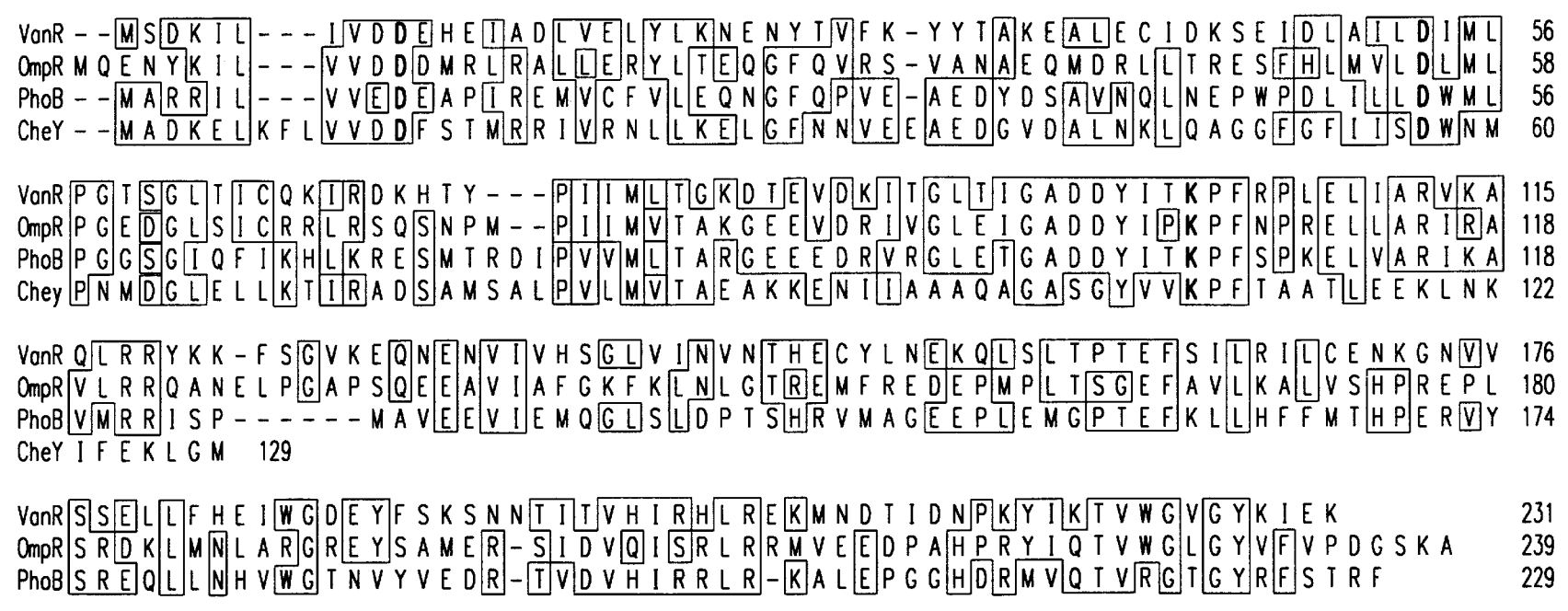

FIG. 15: alignment of the deduced amino acid sequences of VanR from *E. faecium* BM4147 (SEQ ID NO:43), OmpR (SEQ ID NO:44) and PhoB (SEQ ID NO:45) from *E. coli* as well as that of CheY from *Salmonella typhimurium* (SEQ ID NO:46). The numbers on the right indicate the position of the last amino acid of the corresponding line. The identical amino acids are placed in boxes. The dotted lines indicate the gaps introduced in order to optimize the homologies. The residues in bold characters correspond to the amino acids strongly conserved in the effector domains of other RR. The aspartic acid residue 57 of CheY is phosphorylated by the HPK associated with CheA.

I—IDENTIFICATION OF vanA

Figure 1:
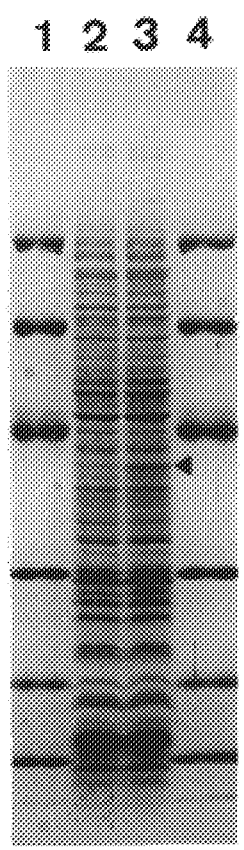
FIG. 1: electrophoresis on SDS-polyacrylamide gel (SDS-PAGE) of the proteins of the membrane fractions line 1 and line 4, molecular weight standards; line 2, *E. faecium* BM4147 placed in culture in the absence of vancomycin; line 3, BM4147 placed in culture in the presence of 10 μg/ml of vancomycin. The head of the arrow indicates the position of the VanA protein.

Materials and Methods for the Identification and Characterization of the VanA Gene Bacterial strains and plasmids The origin of the plasmids used is given in the table below.

| Strain or plasmid | Source or reference |
| --- | --- |
| *Escherichia coli* | |
| JM83 | Messing (1979) |
| AR1062 | Rambach and Hogness (1977) |
| JM103 | Hannshan (1983) |
| ST640 | Lugtenberg and van Schijndel van-Dam (1973) |
| *Enterococcus faecium* | |
| BM4147 | Leclercq et al (1988) |
| Plasmid pUC18 | Norrander et al (1983) |
| pAT213 | Brisson-Noel et al (1990) |
| pAT214 | Described in this text |

Preparation of the Enterococcal Membranes

*Enterococcus faecium* BM4147 was cultivated in 500 ml of heart-brain broth (BHI broth medium) until the optical density ($OD_{600}$) reached 0.7. Induction was effected with 10 µg/ml of vancomycin (Eli Lilly Indianapolis Ind). The subsequent steps were performed at 4° C. The cells were recovered by centrifugation for 10 minutes at 6000 g, washed with a TE buffer (0.01M TRIS-HCl, 0.002M EDTA, pH 7.0) and lysed by glass beads (100 µm in diameter) in a Braun apparatus for 2 minutes. The cell debris were separated by centrifugation for 10 minutes at 6000 g. The membranes were collected by centrifugation for 1 hour at 65000 g and resuspended in 0.5 ml of TE buffer.

Preparation of the Minicells

Plasmids were introduced by transformation into the strain *E. coli* AR1062 prepared in the form of bacterial vesicles. The bacterial vesicles were recovered on sucrose gradients and the proteins were labelled with 50 µCi of [$^{35}S$]-L-methionine (Amersham, Great Britain) according to the method of Rambach and Hogness (1977, P.N.A.S. USA, 74; 5041–5045).

Preparation of the Membrane Fractions and the Cytoplasmic Fractions of *E. coli*

*E. coli* JM83 and strains derived from it were placed in culture in BHI medium until an optical density ($OD_{600}$) of 0.7 was attained, washed and suspended in a TE buffer. The cell suspension was treated by sonication (ultrasound) for 20 seconds at doses of 50 W in a cell fragmentation apparatus in a Branson B7 sonication apparatus and the intact cells were removed by centrifugation for 10 minutes at 6000 g. The supernatant was fractionated into membrane and cytoplasmic fractions by means of centrifugation for 1 hour at 100,000 g.

Electrophoresis on SDS-Polyacrylamide Gel (SDS-PAGE)

The proteins from the bacterial fractions were separated by means of SDS-PAGE on linear gradients of polyacrylamide gels (7.5% –15%) (Laemmli 1970, Nature 227: 680–685). The electrophoresis was carried out for 1 hour at 200 V, then for 3 hours at 350 V. The gels were stained with Coomassie blue. The proteins of the extracts were separated on 10% polyacrylamide gels and visualized by means of autoradiography.

Purification of the Protein Band and Determination of the N-terminal Sequence

The proteins of the membrane fractions of an induced culture of *E. faecium* BM4147 were separated by means of SDS-PAGE. The gel was electrotransferred for 1 hour at 200 mA to a polyvinylidene difluoride membrane (Immobilon Transfer, Millipore) by using a transfer apparatus (Electrophoresis Unit LKB 2117 Multiphor II) in accordance with the instructions of the manufacturer. The transferred proteins were stained with Ponceau red. The portion of membrane bearing the protein of interest was excised, centered on a Teflon filter and placed in the cartridge of a sequencer (Sequencer Applied Biosystems model 470A). The protein was sequenced by means of the automated Edman degradation (1967, Eur. J. Biochem. 1; 80–81).

Construction of Plasmids

Figure 2:
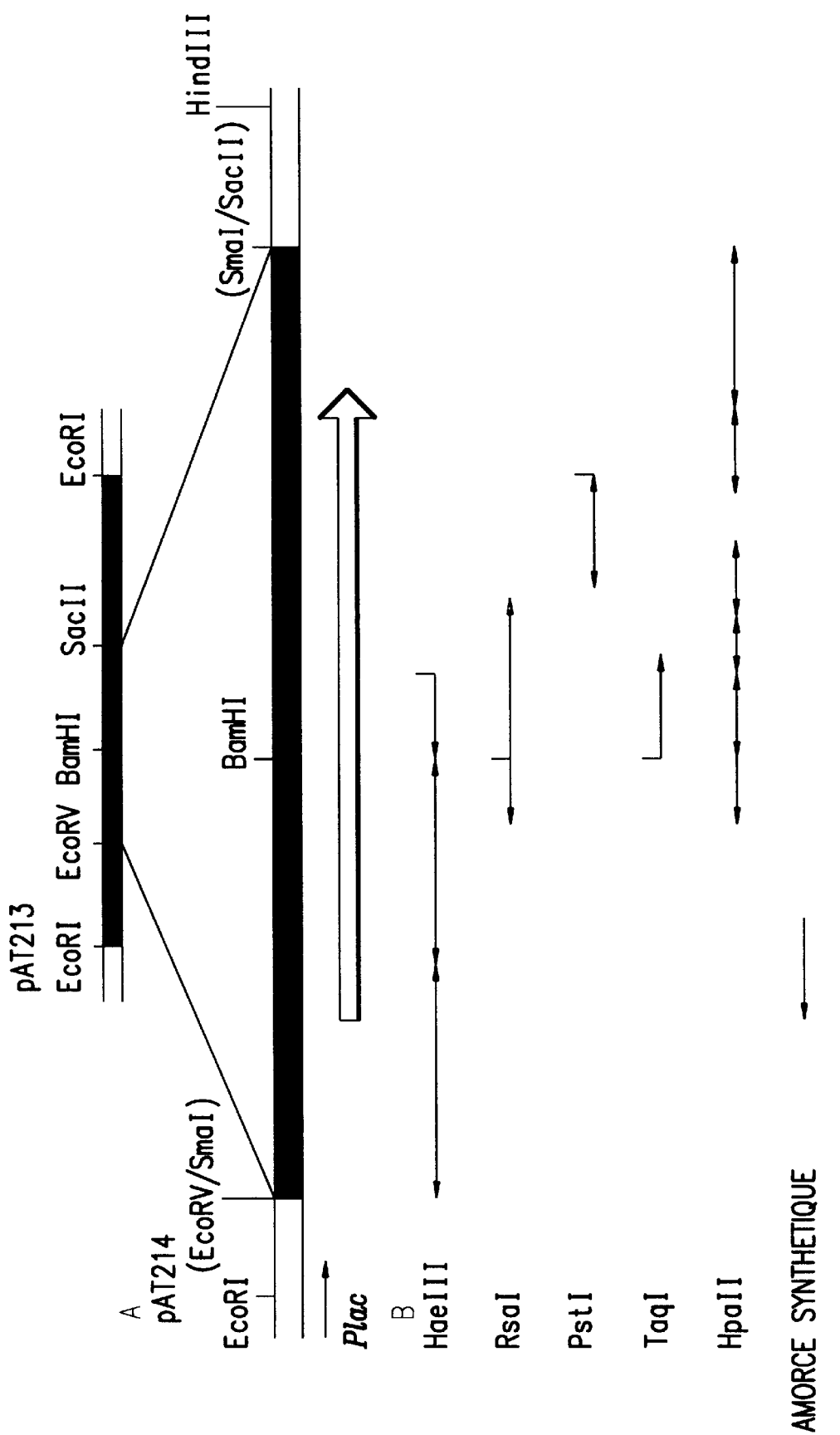
FIGS. 2A–2B.

The plasmid pAT213 (Brisson-Noel et al., 1990, Antimicrob. Agents Chemother., 34; 924–927) consists of a EcoRI fragment of DNA of 4.0 kb of the enterococcal plasmid pIP816 cloned at the EcoRI site of a Gram-positive-Gram-negative shuttle vector pAT187 (Trieu-Cuot et al., 1987, FEMS Microbiol. Lett. 48; 289–294). In order to construct pAT214, the EcoRV-SacII DNA fragment of 1761 bp of pAT213 was purified, treated with the Klenow fragment of the DNA polymerase I of E. coli and ligated to the DNA of pUC18 which had previously been digested with SmaI and dephosphorylated (FIG. 2). The cloning (Maniatis et al., 1982 Cold Spring Harbor Laboratory Press) was carried out with restriction endonucleases (Boehringer Mannheim and Pharmacia), with the T4 DNA ligase (Pharmacia) and alkaline phosphatase (Pharmacia) according to the instructions of the manufacturer.

Subcloning in M13 and Nucleotide Sequence

The DNA restriction fragments were subcloned in the polylinker of the replicative forms of the derivatives mp18 and mp19 of the bacteriophage M13 (Norrander et al., 1983, Gene 26; 101–106), obtained from Pharmacia P-L Biochemicals. E.coli JM103 was transfected with recombinant phages and the single-stranded DNA was prepared. The nucleotide sequencing was carried out by the enzymatic di-deoxy nucleotide method (Sanger et al., 1977, P.N.A.S. USA 74; 5463–5467) by using a T7 DNA polymerase (Sequenase, United States Biochemical Corporation, Cleveland, Ohio) and [α-$^{35}$S]dATP (Amersham, Great Britain). The reaction products were revealed on 6% polyacrylamide gels containing a denaturing buffer.

Data-Processing Analysis and Data on the Sequence

The complete DNA sequence was assembled by using the computer programs DBCOMP and DBUTIL (Staden, 1980, Nucleic Acids Res 8; 3673–3694). The protein data bank PSEQIP of the Pasteur Institute was screened using an algorithm developed by Claverie (1984, Nucleic Acids Res 12; 397–407). The alignments between the pairs of amino acid sequences were constructed using the algorithm of Wilbur et al (1983, P.N.A.S. USA 80; 726–730). The statistical significance of the homology was evaluated with the algorithm of Lipman and Pearson (1985, Science 227; 1435–1440).

For each comparison 20 amino acid sequences were used to calculate the mean values and the standard deviations of the random results.

Genetic Complementation Tests

The plasmids were introduced by transformation into E.coli ST640, a temperature-sensitive mutant with an unmodified D-ala-D-ala ligase (Lugtenberg et al 1973, J. Bacteriol 110; 26–34). The transformants were selected at 30° C. on plates containing 100 μg/ml of ampicillin and the presence of the plasmid DNA of the expected size and the restriction maps were verified. Single colonies grown at 30° C. in BHI broth medium containing ampicillin were placed on a BHI agar medium containing both 100 μg/ml of ampicillin and 50 μM of isopropyl-1-thio-β-D-galactopyranoside (IPTG) and the plates were incubated at a permissive temperature of 30° C. and at a non-permissive temperature of 42° C. The complementation test was considered to be positive if the colonies were present after 18 hours of incubation at 42° C.

RESULTS

Identification of the VanA Protein and its N-terminal Sequence

The membrane fractions of the E. faecium BM4147 cells placed in culture, on the one hand, under conditions of induction, and, on the other, in the absence of induction, were analysed by means of SDS-PAGE. The sole difference which could be detected,related to the exposure to subinhibitory concentrations of vancomycin, was the marked intensification of a band which corresponded to a protein of an estimated molecular weight of about 40 kDa. In the induced cells and in the non-induced cells, the protein band represents the same protein because this band is absent from membranes of a derivative of BM4147 which has lost the pIP816 plasmid. The inducible protein, designated as VanA, was purified after SDS-PAGE and automated Edman degradation was carried out on a 50 pmol. sample. Nine amino acids of the N-terminal sequence of VanA were identified: Met Asn Arg Ile Lys Val Ala Ile Leu (SEQ ID NO:47).

Sub-cloning of the VanA Gene

The insert of 4.0 kb of the plasmid pAT213 bears the determinant for resistance to the glycopeptides of E. faecium BM4147. Various restriction fragments of this insert were subcloned in pUC18 and the recombinant plasmids specific for vanA in E. coli were identified by SDS-PAGE analysis of the proteins of the cytoplasmic and membrane fractions or of the extracts of the bacterial vesicles. This approach was used since E. coli is intrinsically resistant to the glycopeptide. The EcoRV-SacII insert of the pAT214 plasmid (FIG. 2) codes for a unique polypeptide of 40 kDa which migrates together with VanA, derived from the membrane preparations of E. faecium BM4147.

Figure 3A:
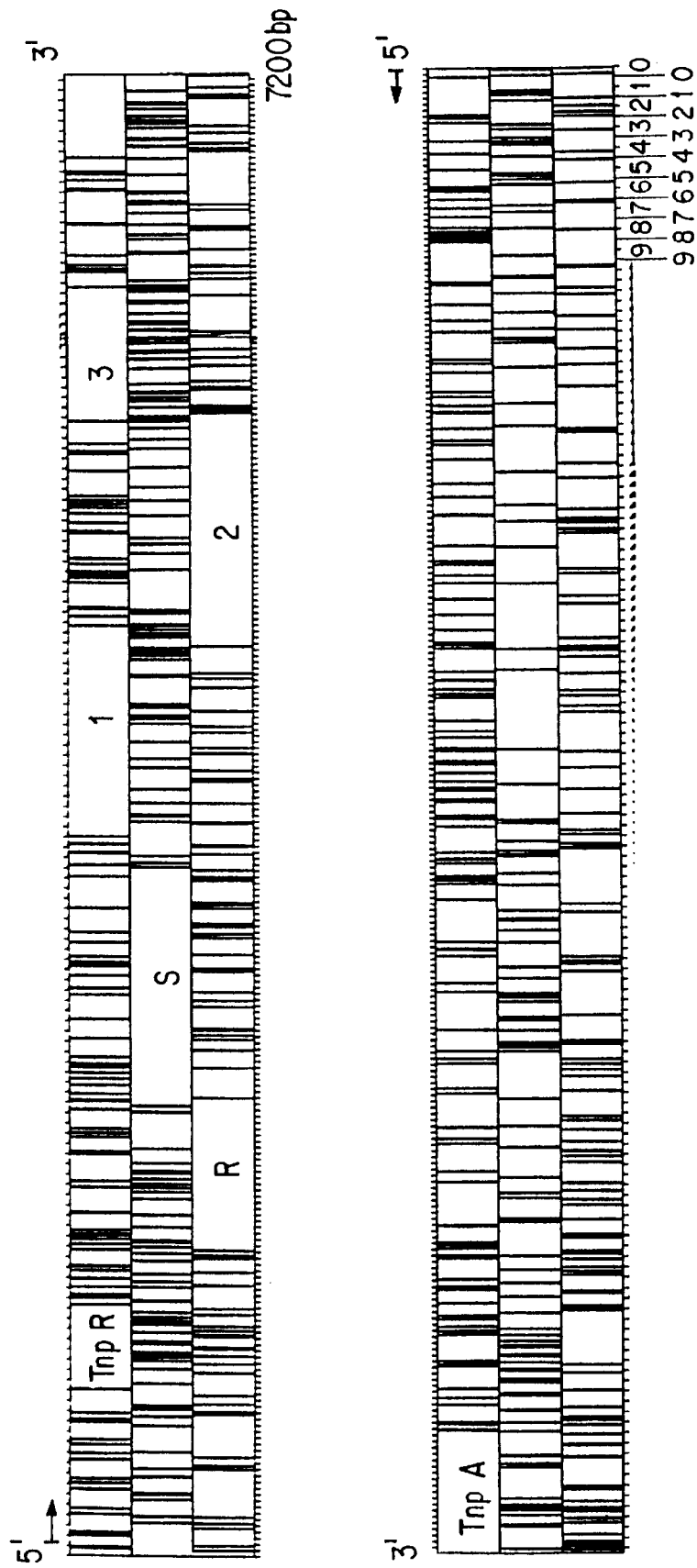
FIG. 3: position of the sequences R, S, ORF1, ORF2, ORF3.
Figure 3B:
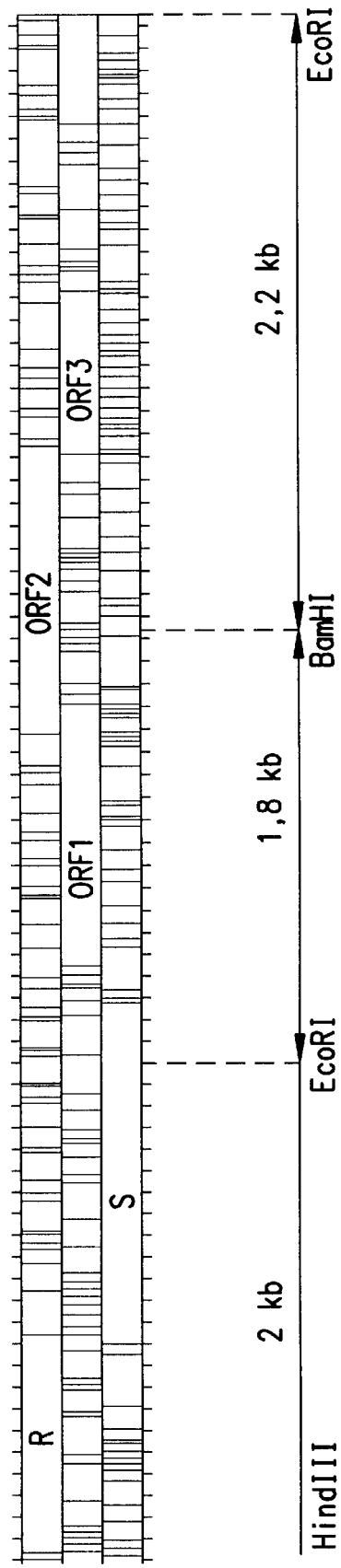
Figure 7A:
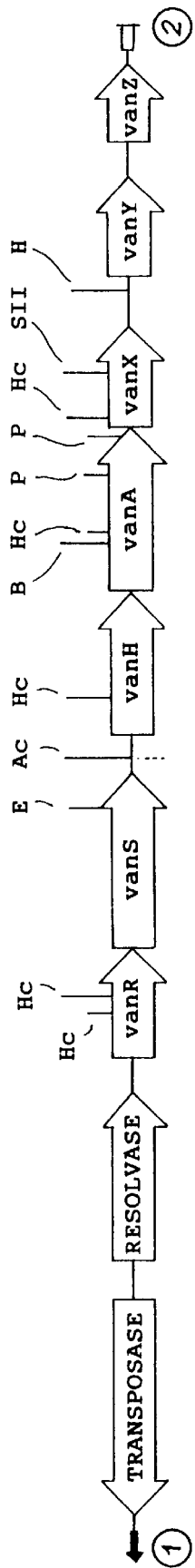
Figure 11:
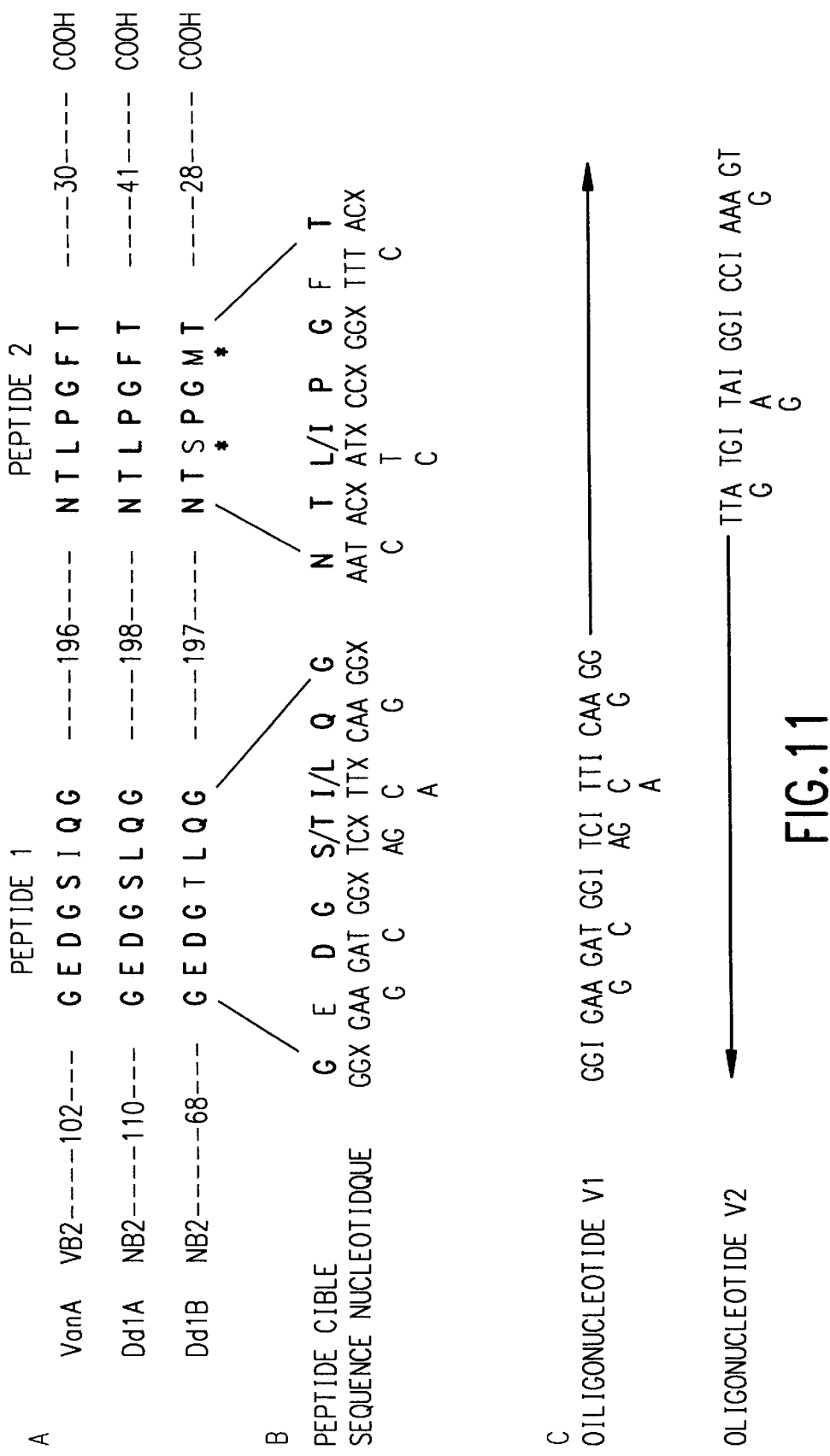
FIGS. 11A–11C: description of the oligonucleotides V1 (SEQ ID NO:9) and V2 (SEQ ID NO:10) (FIG. 11A): Amino acid sequence of the peptides 1 (SEQ ID NO:36) and 2 (SEQ ID NO:37) of VanA and of the D-Ala-D-Ala ligases (SEQ ID NO:36–39). The number of amino acids between the N-terminus and peptide 1, between the peptides 1 and 2 and the peptide 2 and the C-terminus is indicated. The identical amino acids between at least 2 of the 3 sequences are indicated in bold characters.
Figure 12:
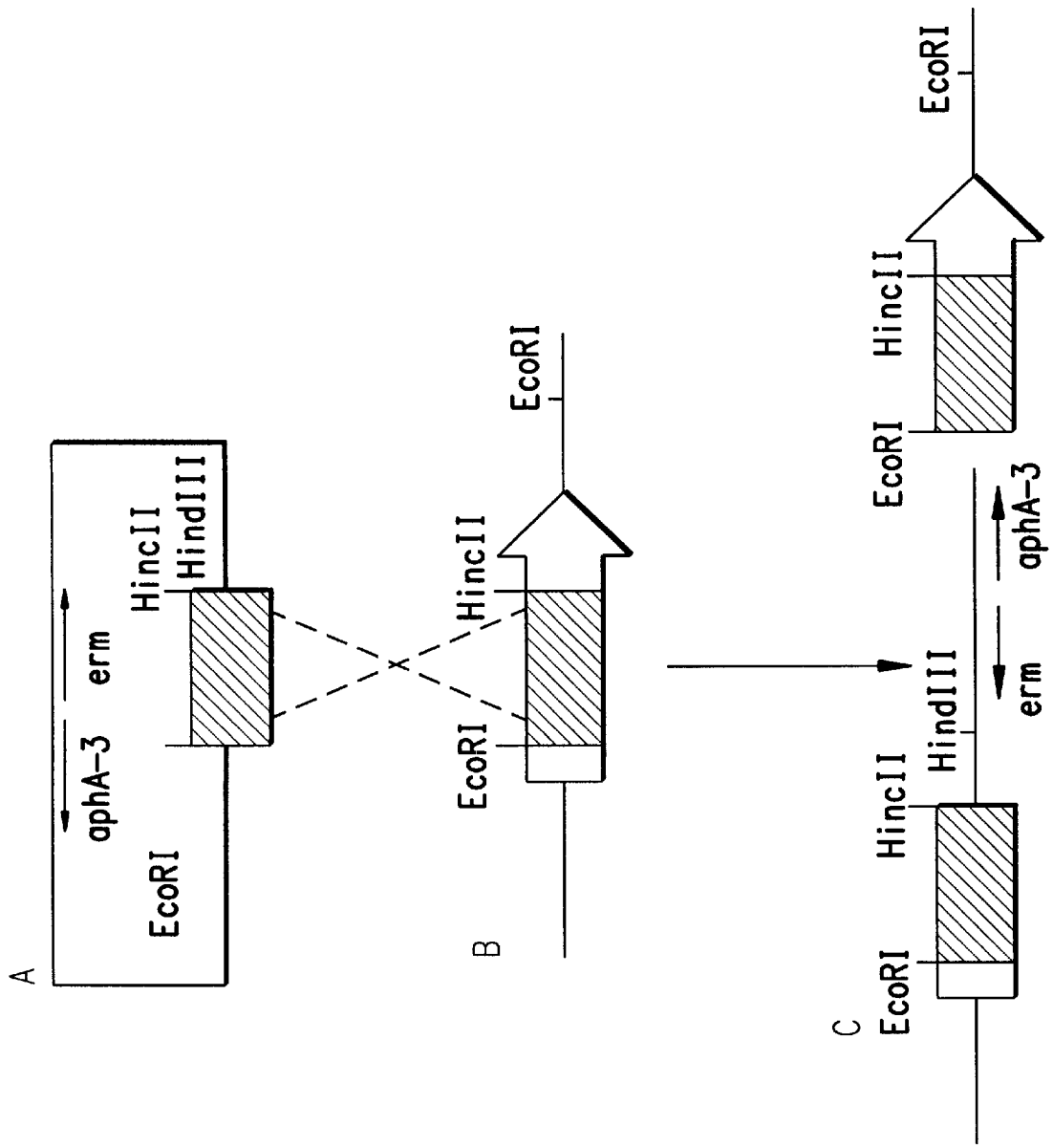
FIGS. 12A–12C: Inactivation by insertion of vanC. The vanC gene is shown by an open arrow and the internal EcoRI-HincII fragment of 690 bp is hatched. The DNA of pAT114 is shown by a thin line; the chromosomal DNA of PM4174 by a thick line; the arrows indicate the genes for resistance to the antibiotics: aphA-3 is the gene coding for the 3'-aminoglycoside phosphotransferase; erm is the gene coding for the ER$^R$ methyl transferase.
Figure 13:
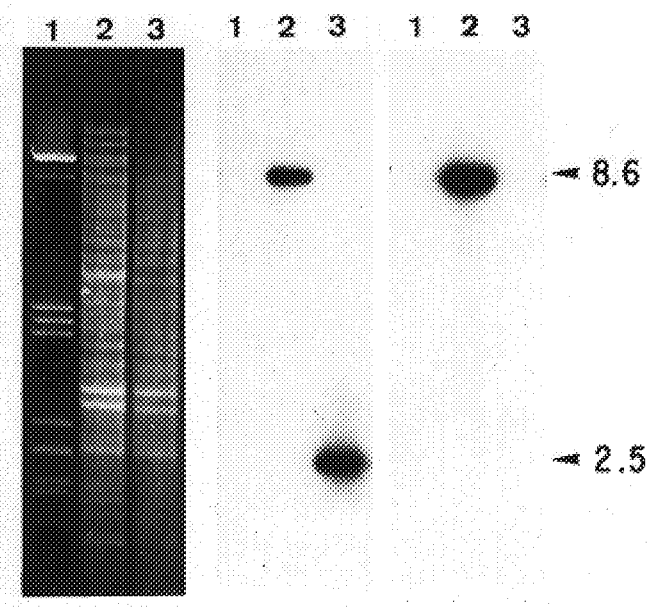
FIG. 13: Southern blot analysis of the integration of pAT217 into the vanC gene of BM4174. (left hand side): Total DNA of BM4175 (line 2) and BM4174 (line 3) digested with EcoRI and resolved by means of electrophoresis on a 1% agarose gel. The DNA of the bacteriophage lambda digested with PstI was used as molecular mass standard (line 1). The DNA was transferred under vacuum to a Nytran membrane (Schleicher and Schül, Germany) by using a Trans-Vac TE80 apparatus (Höfer Scientific Instruments, San Francisco, Calif.) and bound to the membrane through the intermediary of UV light. The hybridization was carried out with the probe C (Middle) or the probe aphA-3 specific for pAT114 (Lambert et al., 1985, Annales de l'Institut Pasteur/Microbiol. 136(b): 135–150). (right hand side): the probes were labelled with $^{32}P$ by nick translation. The molecular masses (kb) are indicated.

Nucleotide Sequence of the Insert in pAT214 and Identification of the VanA Coding Sequence The nucleotide sequence of the EcoRV-SacII insert of 1761 bp in pAT214 was determined on both strands of the DNA according to the strategy described in FIG. 2. The location of the termination codons (TGA, TAA, TAG) in three reading frames on each DNA strand showed the presence of a unique open reading frame (ORF) which was sufficiently long to code for the VanA protein. This reading frame ORF is located between the TAA codon at position 281 and the TAG codon at position 1406. The amino acid sequence deduced for ORF was compared with that of the N-terminus of VanA. The nine amino acids identified by protein sequencing are encoded in the nucleotide sequence beginning with the ATG (methionine) codon at position 377 (FIG. 3). This codon for the initiation of translation is preceded by a sequence (TGAAAGGAGA (SEQ ID NO:48), characteristic of a ribosomal binding site (RBS) in Gram-positive bacteria which is complementary to the 8 bases of the rRNA of the 16S subunit of Bacillus subtilis in its sequence (3'OH UCUUUCCUCC (SEQ ID NO:49) 5') (Moran et al., 1982, Mol. Gen. Genet. 186; 339–346). In this ORF, there is no other ATG or GTG initiation codon between the positions 281 and 377. The sequence of 1029 bp which extends from the ATG codon at position 377 to the TGA codon at position 1406 codes for a protein containing 343 amino acid residues. The calculated molecular weight of this protein is 37400 Da, which is in agreement with the estimation of 40 kDa obtained by SDS-PAGE analysis.

Homology of the Amino Acid Sequences of VanA and the D-ala-D-ala Ligase Enzymes

The screening of the protein data bank PSEQIP has shown the existence of a sequence homology between VanA and the D-ala-D-ala ligases of E.coli (ECOALA, Robinson et al., 1986, J. Bacteriol. 167; 809–817) and of Salmonella typhimurium (DALIG, Daub et al., 1988, Biochemistry 27;

3701–3708). The calculated percentage of homology between pairs of proteins was included between 28% and 36% for the identical amino acids and between 48% and 55% by taking into consideration homologous amino acids. VanA (SEQ ID NO:4) and DALIG are more closely related. The statistical significance of these similarities wa evaluated by aligning VANA and sequences containing the same composition of amino acids as DALIG or ECOALA (Lipman and Pearson, 1985, Science 227; 1435–1440).

Genetic Complementation Test for the Activity of D-ala-D-ala Ligase

The *E.coli* strain ST640 is a thermosensitive mutant exhibiting a deficient D-ala-D-ala ligase activity (Lugtenberg et al., 1973, J. Bacteriol. 113: 96–104). The plasmids pUC18 and pAT214 were introduced into *E.coli* ST640 by transformation. The strains ST640 and ST640 (pUC18) grew normally only at the permissive temperature (30° C.) whereas *E.coli* ST640 (pAT214) grew both at the permissive temperature and at the non-permissive temperature (42° C.).

This test shows that VANA is functionally related to the D-Ala-D-Ala ligases in *E.coli* and is probably capable of catalysing the same ligation reaction as DALIG.

II—VanS-VanR Two-Component Regulation System for the Control of the Synthesis of Depsipeptides of the Precursor of Peptidoglycans

MATERIALS AND METHODS

Strains, Plasmids and Conditions of Culture

The restriction fragments of pIP816 (Tra$^-$, Mob$^+$, Vm$^r$) were cloned in derivatives of the vector pAT29 which constitutes a shuttle vector between the Gram-positive and Gram-negative bacteria (oriR pAMβ1, oriR pUC, oriT RK2, spc, lacZ) (Trieu-Cuot et al., 1990, Nucleic Acids Res. 18:4296). This vector was constructed by the inventors and used to transform the strain *E.coli* JM103 ((lac-proAB), supE, thi, strA, sbcB15, endA, hspR4, F traD36, proAB, lacI$^q$, lacZ M15) (Messing et al., 1983, Methods Enzymol. 101:20–78). The plasmid DNA was prepared by an alkaline lysis protocol on a small scale (Sambrook et al., 1982, Molecular cloning, a laboratory manual. Cold Spring Harbor laboratory, Cold Spring Harbor N.Y.) and introduced by electroporation (Cruz-Rodz A. L. et al., 1990, Mol. Gen. Genet. 224:152–154) in *E.faecalis* JH2-2 (Fus$^R$, Rif$^R$) (Jacob A. E. et al., 1974, J. Bacteriol. 117: 360–372), by using a Gene Pulser apparatus (Bio-Rad Laboratories, Richmond, Calif.). The restriction profiles of the purified plasmids from *E. faecalis* and *E. coli* were compared in order to detect possible rearrangements of DNA.

The integrative plasmid pAT113 (Mob$^+$, Em$^R$, Km$^R$, oriR PACYC184, attTn1545, LacZ ) (Trieu-Cuot et al., Gene 106:21–27) carries the joined ends of the transposon Tn1545. This vector does not replicate in Gram-positive bacteria but is integrated into the chromosome of the host by illegitimate recombination mediated by the integrase of Tn1545 or of Tn916 (Trieu-Cuot et al. previously mentioned). The integrative plasmids were introduced into *E. faecalis* BM4148 (strain JH2-2::Tn916) by means of electroporation. This strain is modified by the transposon Tn917 described by Franque A. E. et al. (1981, J. Bacteriol. 145:494–502).

The cultures were grown in brain-heart broth (BHI—Brain Heart Infusion Broth) or on agar at 37° C. The method of Steers et al (Antibiot. Chemother. Basel. 9:307–311) was used to determine the minimal inhibitory concentrations (MICs) of the antibiotics on a Mueller-Hinton gelose agar medium.

Recombinant DNA Procedures

The cleavage of DNA with restriction endonucleases (Boehringer Mannheim and Pharmacia), the purification of the DNA restriction fragments from agarose gels, the conversion of the cohesive ends to blunt ends with the Klenow fragment of the DNA polymerase I of *E.coli* (Boehringer Mannheim), the dephosphorylation of the ends of the DNA with calf intestinal phosphatase (Boehringer Mannheim), the ligation of the DNA fragments with the T4 DNA ligase (Amersham) were carried out according to the standard methods of Sambrook et al (1982, Molecular Cloning, a Laboratory Manual. Cold Spring Harbor Laboratory. Cold Spring Harbor N.Y.).

Construction of Plasmids

The origin of the vectors and the inserts used for the recombinant plasmids constructed here is the following:

(i) vector pAT78 for the recognition of the promoter: the amplified DNA of the cat gene for chloramphenicol acetyltransferase of the plasmid pC194 of *Staphylococcus aureus* (Horinouchi et al., 1982, J. Bacteriol. 150:815–825) was inserted between the PstI and SphI restriction sites of the shuttle vector pAT29. Amplification by means of the polymerase chain reaction was carried out by means of primers A1 and A2 which were synthesized by the methoxy phosphoramidite method (Mabilat et al., 1990, Plasmid 23:27–34). The sequence of the primer A1 (SEQ ID NO:50) (5' G CTGCAGATAAAAATTTAGGAGG) is composed of a PstI recognition site (underlined) and 18 bases (positions 6 to 23) of pC194 which include the ribosomal binding site (RBS ; AGGAGG positions 18 to 23) of the cat gene. The sequence of the primer A2 (SEQ ID NO:51) (5' CGCATGCTATTATAAAA GCCAGTC) contains the SphI cleavage site (underlined) and is complementary (positions 8 to 24) to 17 bases at the 3' end of the cat gene. The triplet ATT at positions 9 to 11 corresponds to the TAA stop codon of cat. The DNA fragments amplified with the primers A1 and A2 hence consist of an open reading frame (orf) and a ribosomal binding site for CAT (positions 1234 to 1912 according to the numbering of Horinouchi et al. (1982, J. Bacteriol. 150:815–825) flanked by the PstI and SphI sites. The position 1234 is located at the interior of the loop of the secondary structure of the mRNA which blocks translation in the absence of chloramphenicol. Thus, the amplified sequence does not contain the cat promoter nor the sequence complementary to the RBS which is essential for the regulation of translation Ambulos, N. P. et al., 1984, Gene 28:171–176).

(ii) expression vector pAT79: the ClaI-BssHII fragment of 243 bp bearing the P2 promoter of the aphA-3 gene of the enterococcal plasmid pJH1 (Caillaud et al., 1987, Mol. Gen. Genet. 207:509–513) was inserted between the EcoRI and SacI restriction sites of pAT78.

(iii) plasmid pAT80 and its derivatives: the BglII-XbaI fragment of 5.5 kb of pIP816 was inserted between the BamHI and XbaI sites of pAT78. The resulting plasmid, designated as pAT80 was partially digested with HincII and ligated with the EcoRV fragment containing a gene related to the apha-I gene of the transposon Tn903 (Oka A. et al., 1981, J. Mol. Biol. 147:217–226. This fragment contains the aphA-I gene which codes for the 3'aminoglycoside phosphotransferase of type I conferring resistance to kanamycin. The insertion of aphAI was carried out at three different sites in pAT80, generating the plasmids pAT81, pAT83 and pAT85. The cassettes BamHI and EcoRI containing aphA-I were inserted at the BamHI (to form the plasmid pAT84) and EcoRI (to form the plasmid pAT82) sites of pAT80.

(iv) plasmids pAT86, pAT87, pAT88 and pAT89: the plasmid pAT86 was constructed by cloning the EcoRI-SacII fragment of 2.803 bp of pAT80 coding for VanH and VanA at a SmaI site of pAT79. pAT87 was obtained by inserting the EcoRI-XbaI fragment of 3.4 kb of pAT80 upstream from the cat gene of the detection vector of promoter pAT78. The plasmid pAT88 resulted from the ligation of pAT78 digested with EcoRI and BamHI to the EcoRI-BamHI fragment of 1.731 bp of pAT80. The BglII-AccI fragment (positions 1 to 2356) of pAT80 was inserted into the polylinker of the integrative vector pAT113, generating pAT89.

Sub-Cloning in M13 and Sequencing

The DNA restriction fragments were subcloned in a polylinker of replicative derivatives of the bacteriophage M13, these derivatives being called mp18 and mp19 (Norrander et al., 1983, Gene 26:101–106). *E.coli* JM103 was transfected with the recombinant phages and a single-stranded DNA was prepared. The sequencing of the nucleotides was carried out according to the conditions described by Sanger et al. (Proc. Natl. Acad. Sci. USA, 1977, 74:5463–5467) by using the modified T7 DNA polymerase (Sequenase, United States, Biochemical Corporation Cleveland Ohio) and [$\alpha$-$^{35}$S]dATP (Amersham). The reaction products were resolved on gradient gels of polyacrylamide in a 6% buffer.

Enzymatic Test

The JH2-2 derivatives of *E. faecalis* were grown to an optical density $OD_{600}$ of 0.7 in a BHI broth supplemented with spectinomycin (300 µg/ml). The cells were treated with lysozyme, lysed by sonication and the cell debris were centrifuged for 45 minutes at 100,000 g according to the description given by Courvalin et al. (1978, Antimicrob. Agents Chemother. 13:716–725). The formation of 5-thio-2-nitrobenzoate was measured at 37° C. in the presence and in the absence of chloramphenicol and the specific CAT activity was expressed in micromole per minute and per milligram of proteins (Shaw et al., 1975, Methods Enzymol. 43:737–755).

RESULTS

The vanH and vanA genes of pIP816 were cloned in a plasmid pAT79 under the control of the heterologous promoter P2 (Caillaud et al., 1987, Mol. Gen. Genet. 207:509–513) and the plasmid pAT86 formed did not confer resistance to vancomycin on the strain *E. faecalis* JH2-2. These genes are thus not sufficient for the synthesis of peptoglycan in the absence of the antibiotic. Different restriction fragments of pIP816 were cloned in the vector pAT78. The BglII-XbaI fragment of 5.5 kb of pAT80 is the smallest fragment obtained which conferred resistance to vancomycin.

Nucleotide Sequence of the VanR and VanS Genes

The sequence of the insert in pAT80 was determined on both strands of the DNA from the BglII site to the ATG initiation codon for the translation of VanH. Two open reading frames (orf) were detected within the sequence of 2475 bp: the first open reading frame extends from the nucleotide 386 to the nucleotide 1123; at position 431 a sequence characteristic of the RBS sequences in Gram-positive bacteria is found, 6 base pairs upstream from the ATG initiation codon for translation (T<u>GAAAGG</u>GTG (SEQ ID NO:52)); the other initiation codons for translation in this orf are not preceded by this type of sequence. The sequence of 693 bp extending from the ATG codon at position 431 to the TAA codon at position 1124 is capable of coding for a protein of 231 amino acids with a molecular mass of 26,612 Da which is designated as VanR.

In the case of the second open reading frame (from nucleotide 1089 to nucleotide 2255) the amino acid sequence deduced from the first initiation codon in phase (TTG at position 1104) would code for a protein of 384 amino acids having a molecular mass of 43,847 Da and designated as VanS. The TTG codon at position 1116 and the ATG codon at position 1164 are in-phase initiation codons for translation preceded by sequences with low complementarity with the 3'OH terminus of the 16S sub-unit of the rRNA of *B. subtilis* (G<u>GGGGG</u>TTGG-N8-TTG (SEQ ID NO:53) and A<u>GAACGA</u>AAA-N6-ATG (SEQ ID NO:54), respectively).

Between the last codon of vanS and the initiation codon ATG for the translation of vanH a sequence of 217 bp is to be observed which contains a repeated reverse sequence of 17 bp. This sequence does not function as a terminator of strong transcription.

The comparison of the sequences obtained with data bases has shown that the conserved amino acid residues identified by Stock et al. (1989, Microbiol. Rev. 53:450–490) in the kinase domain of 16 HPK (Histidine Protein Kinase) were detected in the C-terminal part of VanS (SEQ ID NO:14). VanS possesses two groups of hydrophobic amino acids in the N-terminal region. The histidine residue 164 of VAnS is aligned with the residue His216 of PhoR (SEQ ID NO:41) (Makino et al., 1986, J. Mol. Biol. 192: 549–556) and His 243 of EnvZ (SEQ ID NO:42) (Comeau et al., 1985, 164:578–584) which are presumed sites of autophosphorylation in these proteins.

Similarly, the amino acids 1 to 122 of VanR (SEQ ID NO:12) exhibit similarities with the effector domains of response regulators RR. The aspartic acid 53 of VanR might be a phosphorylation site because this residue is aligned with Asp 57 of Che Y (SEQ ID NO:46) which is phosphorylated by HPK associated with CheA and corresponds to an invariant position in other proteins of the RR type (Stock et al previously mentioned). VanR might belong to the sub-class OmpR-PhoB of RR which activates the initiation of transcription mediated by the RNA polymerase containing the 70S factor of *E.coli* (Stock et al. previously mentioned).

Inactivation of the Van Genes by Insertion

Cassettes of resistance to kanamycin inserted in the group of van genes in the plasmid pAT80 have shown the following: the insertion in vanR suppresses resistance to vancomycin and chloramphenicol; VanR is an activator of transcription necessary for the expression of the genes for resistance to vancomycin. The inactivation of vanS leads to a two-fold reduction of the minimal inhibitory concentration (MIC) of chloramphenicol and to a three-fold reduction of the specific CAT activity but the minimal inhibitory concentration of vancomycin remains unchanged. Hence, VanS is necessary to produce a high level of transcription of the genes for resistance to vancomycin although it is not required for the expression of the phenotype of resistance to vancomycin.

Derivatives of pAT80 bearing insertions in vanH (pAT83), vanA (pAT84) or in the region 1.0 kb downstream from vanA (pAT85) have made it possible to obtain resistance to chloramphenicol but not to vancomycin. This dissociated phenotype corresponds to the inactivation of genes coding for enzymes which synthesize the depsipeptide precursors necessary for the assembly of the bacterial cell walls in the presence of vancomycin.

Downstream from the vanA gene the presence of an inactivated orf has been detected in pAT85 in the region of the sequence of 365 bp after the TGA codon of vanA and before the SacII site and this orf contains an in-phase ATG initiation codon preceded by a RBS-like sequence. This sequence codes for a protein necessary for resistance to the glycopeptide, designated as VanX and which comprises maximally about 330 amino acids.

Trans-Activation of the Transcription of the Van Genes

The integrative plasmid pAT89 coding for VanR and VanS was introduced into the chromosome of E. faecalis BM4138. The plasmid pAT87 bearing the genes vanH, vanA and vanX cloned upstream from the cat gene lacking the promoter for pAT78 conferred resistance to vancomycin on this strain but not to E. faecalis JH2-2. The level of expression of the cat gene of pAT87 in the strains BM4138::pAT89 and JH2-2 indicated that VanR activates the transcription of the reporter gene localized at the 3' end of the group of van genes. Similar levels of CAT synthesis were observed for pAT88 which bears a transcription fusion between the 5' parts of vanA and the cat gene. These results show that in E. faecalis BM4138::pAT89 (pAT87) VanR and VanS encoded in the chromosome activate in a trans manner the transcription of vanA, vanH and vanX of pAT87 making possible the production of resistance to vancomycin.

Moreover, it has been observed that the expression of the gene was essentially constitutive when vanR and vanS were borne by a multicopy plasmid pAT80 and weakly inducible by vancomycin when the genes for the regulatory proteins were present on the chromosome of the host.

III—Characterization of the Sequence of the vanC gene of *Enterococcus gallinarum* BM4174

Definition and use of universal primers for the amplification of genes coding for D-Ala-D-Ala ligases and related proteins implicated in resistance to vancomycin The protein VanA necessary for the expression of a high level of resistance to the glycopeptides in *E. faecium* BM4147 shares a similarity of about 28 to 36% as regards its amino acids with the D-Ala-D-Ala ligases of *E.coli* but possesses a different substrate specificity from that of these ligases. Peptides designated as 1 and 2 which are conserved in the sequences of the DdlA and DdlB ligases (Zawadzke, 1991 Biochemistry 30:1673–1682) of *E.coli* and in the protein VanA were selected in order to synthesize universal primers intended to amplify internal fragments of genes coding for D-Ala-D-Ala ligases or related enzymes. The peptide targets GEDG(S/T) (I/L)QG and NT(I/L)PGFT were translated back as is shown in FIG. IV.1 in order to obtain degenerate oligonucleotides V1 and V2. As the peptides 1 and 2 of VanA, DdlA and DdlB are separated by amino acid sequences of similar length, the predicted size for the amplification product was about 640 bp.

Amplification by means of PCR with the DNA of *E.coli* JM83 and of *E. faecium* BM4147 made it possible to amplify products corresponding to the expected size which have then been purified and cloned in the bacteriophage M13mp10 (Norrander et al., 1983, Gene 26:101–106). The sequencing of the insert obtained with *E.coli* JM83 has shown that the product of PCR was an internal fragment of ddlA. A probe generated starting from a recombinant phage obtained with the amplification fragment of BM4147 was used for the Southern blot analysis of a DNA of BM4147 and BM4147-1 which is a derivative of BM4147 sensitive to vancomycin and which lacks the plasmid pIP816 (Leclercq et al., 1988, N. Engl. J. Med. 319:157–161). The probe hybridized with the EcoRI DNA fragment of 4 kb from BM4147 but not with the DNA from *E. faecium* BM4147-1. As the vanA gene is borne by the EcoRI fragment of 4 kb from pIP816, these results indicate that the primers also make possible the amplification of a part of vanA. Thus the oligonucleotides V1 and V2 may amplify fragments of genes coding for different proteins related to the D-Ala-D-Ala ligases, and may do this in different species.

Amplification, Cloning and Sequencing of the vanC gene

Amplification by means of PCR was carried out on the total DNA of *E. gallinarum* BM4174 and the amplification product obtained of about 640 bp was cloned in the bacteriophage M13mp10. The single-stranded DNA isolated from the recombinant phage was used to construct a probe C (Hu et al., 1982, Gene 17:2171–2177). In Southern analysis the probe hybridized with a PstI fragment of 1.7 kb from BM4174 but not with the DNA of BM4147 and BM4147-1.

The DNA of BM4174 was digested with PstI and fragments of 1.5 and 2 kb were purified by electrophoresis on agarose gel and cloned in pUC18 (Norrander et al., 1983, mentioned previously). The recombinant plasmids were introduced into *E.coli* JM83 by transformation and screened by hybridization on colonies (Sambrook et al., 1989, Molecular cloning, a laboratory manual. Cold Spring Harbor Laboratory Press, Cold Spring Harbor, N.Y.) by using the probe C. A homology was detected with a transformant harbouring a plasmid called pAT216 which contained a PstI insert of 1.7 kb. The sequence of the SacI-PstI part of 1347 bp of the insert of pAT216 was determined on both strands of the DNA. The location of the termination codons in the three reading frames of each strand of DNA revealed the presence of an ORF phase located between the TGA codons at positions 47 and 1244. The initiation codon of transcription ATG at position 215 is preceded by a sequence GAAAGGAAGA characteristic of the RBS sequences complementary to the RNA of the 16S subunit of *B. subtilis* (Moran et al., 1982, Mol. Gen. Genet. 186:339–346). The sequence of 1029 bp which extends from the ATG codon at position 215 to the TGA codon at position 1244 might code for a protein of 343 amino acids having a calculated molecular mass of 37504 Da designated as VanC. A sequence homology was detected between VanC, VanA and the D-Ala-D-Ala ligases of *E.coli*. In particular, four domains of strong homology previously found between VanA and the D-Ala-D-Ala ligases of the enterobacteria are also present in VanC. The percentage of identical amino acids calculated for these proteins taken two at a time varied between 29 and 38%. The alignment of the four sequences revealed the presence of 57 invariant amino acids which include the conserved residues of the peptides 1 and 2 used to define the oligonucleotide probes V1 and V2.

Inactivation of the vanC gene by Insertion

In order to evaluate the contribution of vanC to resistance to vancomycin in *E. gallinarum* BM4174, the vanC gene was inactivated by insertion. A EcoRI-HincII fragment of 690 bp, internal to vanC was cloned in pAT114 which does not replicate in Gram-positive bacteria. The resulting pAT217 plasmid was introduced into BM4174 by electroporation (Cruz-Rodz et al., 1990, Mol. Gen. Genet. 224:152–154) and the clones supposed to result from a homologous recombination leading to the integration of pAT217 into vanC were selected on erythromycin. The clone BM4175 was compared with BM4174 by Southern hybridization using the probe C and aphA-3 specific for pAT114. The two probes hybridized with the EcoRI fragment of 8.6 kb from BM4175. The probe C hybridized with a fragment of 2.5 kb from BM4174 whereas no signal was observed with the probe aphA-3. The results indicate that the plasmid pAT217 of 6.1 kb was integrated into the vanC gene. The determination of the minimal inhibitory concentration of vancomycin for BM4174 (16 mg/l) and BM4175 (2 mg/l) indicated that the inactivation by insertion in vanC abolishes resistance to vancomycin.

VanC is thus required for resistance to vancomycin. It may thus be supposed that this protein synthesizes a dipeptide or a depsipeptide which is incorporated into the precursors of peptido-glycans and is not recognized by vancomycin.

The sequences which are the object of the invention are given in the following pages after the list of the sequences containing the description of these sequences. In this list of the sequences, the proteins are identified with respect to the position of the nucleotide bases corresponding to the amino acids of the extremities of the proteins.

List of the Sequences
(contained in the sequences I (Ia, Ib), II presented below or in the sequence shown in FIG. 5).
Amino acid sequences
SEQ ID NO 2 (VanH): sequence of the first resistance protein, corresponding to the amino acid sequence of the open reading frame No. 3, starting at the base 3501 and terminating at the base 4529, containing the sequence coding for the vanH gene between the bases 3564 and 4529 with respect to the sequence shown in FIG. 5 or corresponding to the sequence between the positions of the nucleotides 6018 and 6983 of the sequence Ia.
SEQ ID NO 4 (VanA): sequence of the VanA protein, corresponding to the amino acid sequence of the open reading frame No. 1, starting at the base 4429 and terminating at the base 5553 with respect to the sequence shown in FIG. 5 or corresponding to the sequence between the positions of the nucleotides 6977 and 7807 of the sequence Ia.
SEQ ID NO 6 (VanX): sequence of the third resistance protein, corresponding to the amino acid sequence of the open reading frame No. 3, starting at the base 5526 and terminating at the base 6167 with respect to the sequence shown in FIG. 5 or corresponding to the sequence between the positions of the nucleotides 7816 and 8621 of the sequence Ia.
SEQ ID NO 12 (VanR): sequence of the regulatory protein R, corresponding to the amino acid sequence of the open reading frame No. 1, starting at the base 1477 and terminating at the base 2214 with respect to the sequence shown in FIG. 5 or corresponding to the sequence between the positions of the nucleotides 3976 and 4668 of the sequence Ia.
SEQ ID NO 14 (VanS): sequence of the sensor protein S, corresponding to the amino acid sequence of the open reading frame No. 2, starting at the base 2180 and terminating at the base 3346 with respect to the sequence shown in FIG. 5 or corresponding to the sequence between the positions of the nucleotides 4648 and 5800 of the sequence Ia.
SEQ ID NO 19: sequence of the transposase corresponding to the amino acids included between the nucleotides 150 and 3112 of the sequence Ib.
SEQ ID NO 21: sequence of the resolvase comprising the amino acids situated between the positions of the nucleotides 3187 and 3759 of the sequence Ia.
SEQ ID NO 23: VanY sequence comprising the amino acids situated between the positions of the nucleotides 9046 and 9960 of the sequence Ia.
SEQ ID NO 25: VanZ sequence comprising the amino acids situated between the positions of the nucleotides 10116 and 10598 of the sequence Ia.
SEQ ID NO 8: VanC amino acid sequence shown in list II.
Nucleotide sequences
SEQ ID NO 15: nucleotide sequence containing the sequence coding for the 5 proteins as well as the flanking sequences, shown in FIG. 5.
SEQ ID NO 17: sequence containing the sequence coding for the 3 resistance proteins as well as the flanking sequences and starting at the base 3501 and terminating at the base 6167, shown in FIG. 5.
SEQ ID NO 3: sequence of the vanA gene, starting at the base 4429 and terminating at the base 5553 of the sequence shown in FIG. 5, or corresponding to the nucleotide sequence situated between the nucleotides 6977 and 7807 of the sequence Ia.
SEQ ID NO 1: sequence coding for the first resistance protein called VanH, starting at the base 3501 and terminating at the base 4529, in particular the sequence vanH, the coding sequence of which is located between the bases 3564 and 4529 of the sequence shown in FIG. 5, or corresponding to the nucleotide sequence situated between the nucleotides 6018 and 6983 of the sequence Ia.
SEQ ID NO 5: sequence coding for the third resistance protein VanX, starting at the base 5526 and terminating at the base 6167 of the sequence shown in FIG. 5, or corresponding to the nucleotide sequence situated between the nucleotides 7816 and 8621 of the sequence Ia.
SEQ ID NO 16: sequence of the transposon coding for the transposase, the resolvase, vanR, VAnS, VanH, VanA, VanX, VanY and VanZ and containing the repeated reverse sequence of 38 bp at its N- and C-termini and corresponding to the sequence Ia.
SEQ ID NO 18: sequence coding for the transposase, starting at the base 150 and terminating at the base 3112 of the sequence Ib.
SEQ ID NO 20: sequence coding for the resolvase, starting at the base 3187 and terminating at the base 3759 of the sequence Ia.
SEQ ID NO 22: sequence coding for VanY, starting at the base 9046 and terminating at the base 9960 of the sequence Ia.
SEQ ID NO 24: sequence coding for VanZ, starting at the base 10116 and terminating at the base 10598 of the sequence Ia.
SEQ ID NO 7: sequence coding for VanC, shown in the list II in relation to the protein VanC.
SEQ ID NO 16: complete sequence Ia of the transposon of *E. faecium*, starting at the base 1 and terminating at the base 10851.
SEQ ID NO 11: sequence coding for the protein VanR, starting at the base 3976 and terminating at the base 4668 of the sequence Ia.
SEQ ID NO 23: sequence coding for the protein VanS, starting at the base 4648 and terminating at the base 5800 of the sequence Ia.

I. Nucleotide sequence of the transposon and translation

Ia. (+) Strand

```
1
GGG GTA GCG TCA GGA AAA TGC GGA TTT ACA ACG CTA AGC CTA TTT TCC TGA CGA ATC CCT

61
CGT TTT TAA CAA CGT TAA GAA AGT TTT AGT GGT CTT AAA GAA TTT AAT GAG ACT ACT TTC

121
TCT GAG TTA AAA TGG TAT TCT CCT AGT AAA TTA ATA TGT TCC CAA CCT AAG GGC GAC ATA

181
TGG TGT AAC AAA TCT TCA TTA AAG CTA CCT GTC CGT TTT TTA TAT TCA ACT GCT GTT GTT

241
AGG TGG AGA GTA TTC CAA ATA CTT ATA GCA TTG ATA ATT ATG TTT AAA GCA CTG GCT CTT

301
TGC AAT TGA TGC TGT ATG GTG CGT TCT CTA AGC TCA CCT TGT TTT CCG AAG AAA ATA GCT

361
CTT GCC AAT CCA TTC ATG GCT TCT CCT TTA TTC AAT CCT CTT TGT ATT TTT CTT CTT AAT

421
GAT TCA TCC GAT ATA TAA TTC AAA ATA AAG ATC GTT TTT TCT ATT CGG CCC ATC TCA CGT

481
AAG GCT GTA GCT AAG CTG TTT TGT CTT GAA TAG GAA CCT AGC TTC CCC ATA ATA AGG GAT

541
GCT GAA ACT GTT CCC TCC CTT ATA GAA TGA GCT AAT CGC AAA ACA TCC TCA TAA TTT TCT

601
TTA ATG ACC TTT GTA TTT ATT TGT CCA CGT AAA ATG GCT TCT AGT TTT GGA TAC TCA CTT

661
GCT TTA TCT ATC GTA AAT AAT TTT GAG TCC GAT AAA TCC CTT ATT CTT GGG GCA AAT TTA

721
AAT CCT AAT AAA TGA GTC AGT CCG AAT ATT TGG TCA GTG TAA CCG GCA GTG TCT GTA TAA

781
TGT TCC TCT ATG TTT AGA TCC GTC TCA TGA TGT AAC AAA CCA TCC AAA ACA TGA ATC GCA

841
TCT CTT GAA TTA GTA TGA ATA ATC TTT GTG TAG TAA GAA GAG AAT TGA TCA CTT GTA AAT

901
CGG TAG ATG GTG GCT CCT TTT CCA GTT CCA TAA TGT GGA TTT GCA TCT GCA TGT AGT GAT

961
GAA ACA CCT AGC TGC ATT CTC ATA CCA TCT GAC GAA GAT GTT GTA CCG TCG CCC CAA TAG

1021
AAA GGC AAT TGT AAT TTA TGA TGA AAG TTT ACT AAT ATG GCT TGG GCT TTA TTC ATG GCA

1081
TCT TCA TAC ATG CGC CAT TGA GAT ACA TTG GCT AGT TGC TTA TAT GTA AGT CCG GGT GTG

1141
GCT TCG GCC ATC TTG CTC AAG CCA ATA TTC ATT CCC ATT CCT AAA AGG GCA GCC ATG ATA

1201
ATG ATT GTT TCT TCC TTA TCT GGT TTT CGA TTA TTG GAA GCA TGA GTG AAT TGC TCA TGA

1261
AAT CCT GTT ATA TGG GCC ACA TCC ATG AGT AAA TCA GTT AAT TTT ATT CTT GGT AGC ATC

1321
TGA TAA AGG CTT GCA CTA AAT TTT TTT GCT TCT TCT GGA ACA TCT TTT TCT AAG CGT GCA

1381
AGT GAT AGC TTT CCT TTT TCA AGA GAA ACC CCA TCT AAC TTA TTG GAA TTG GCA GCT AAC

1441
CAC TTT AAC CTT TCA TTA AAG CTG CTG GTT CTC TCC GTT ATA TAA TCT TCG AAT GAT AAA

1501
CTA ACT GAT AAT CTC GTA TTC CCC TTC GAT TGA TTC CAT GTA TCT TCC GAA AAC AAA TAT

1561
TCC TCA AAA TCC CTA TAT TGT CTG CTG CCA ACA ATG GAA ACA TCT CCT GCC CGA ACA TGC
```

```
1621
TCC CGA AGT TCT GTT AAA ACA GCC ATT TCA TAG TAA TGA CGA TTA ATT GTT GTA CCA TCA

1681
TCC TCG TAT AAA TGT CTT TTC CAT CGT TTT GAA ATA AAA TCC ACA GGT GAG TCA TCA GGC

1741
ACT TTT CGC TTT CCA GAT TCG TTC ATT CCT CGG ATA ATC TCA ACA GCT TGT AAA AGT GGC

1801
TCA TTT GCC TTT GTA GAA TGA AAT TCC AAT ACT CTT AAT AGC GTT GGC GTA TAT TTT CTT

1861
AGT GAA TAA AAC CGT TTT TGC AGT AAG TCT AAA TAA TCA TAG TCG GCA GGA CGT GCA AGT

1921
TCC TGA GCC TCT TCT ACT GAA GAG ACA AAG GTA TTC CAT TCA ATA ACC GAT TCT AAA ACC

1981
TTA AAA ACG TCT AAT TTT TCC TCT CTT GCT TTA ATT AAT GCT TGT CCG ATG TTC GTA AAG

2041
TGT ATA ACT TTC TCA TTT AGC TTT TTA CCG TTT TGT TTC TGG ATT TCC TCT TGA GCC TTA

2101
CGA CCT TTT GAT AAC AAA CTA AGT ATT TGC CTA TCA TGA ATT TCA AAC GCT TTA TCC GTT

2161
AGC TCC TGA GTA AGT TGT AAT AAA TAG ATG GTT AAT ATC GAA TAA CGT TTA TTT TCT TGA

2221
AAG TCA CGG AAT GCA TAC GGC TCG TAT CTT GAG CCT AAG CGA GAC AGC TGC AAC AGG CGG

2281
TTA CGG TGC AAA TGA CTA ATT TGC ACT GTT TCT AAA TCC ATT CCT CGT ATG TAT TCG AGT

2341
CGT TCT ATT ATT TTT AGA AAA GTT TCG GGT GAA GGA TGA CCC GGT GGC TCT TTT AAC CAA

2401
CCC AAT ATC GTT TTA TTG GAT TCG GAT GGA TGC TGC GAG GTA ATA ATC CCT TCA AGC TTT

2461
TCT TTT TGC TCA TTT GTT AGA GAT TTA CTA ACC GTA TTA AAT AGC TTC TTT TCA GCC ATT

2521
GCC CTT GCT TCC CAC ACC ATT CTT TCA AGT GTA GTG ATA GCA GGC AGT ATA ATT TTG TTT

2581
TTT CTT AGA AAA TCT ATG CAT TCA TGC AGT AGA TGA ATG GCA TCA CCA TTT TCC AAA GCT

2641
AAT TGA TGA AGG TAC TTA AAT GTC ATT CGA TAT TCA CTC AGG GTA AAA GTT ACA AAG TCG

2701
TAT TCA CTT CGA ATT TCT TTC AAA TGA TCC CAA AGT GTA TTT TCC CTT TGA GGA TAA TGA

2761
TCA AGC GAG GAT GGA CTA ACA CCA ATC TGT TTC GAT ATA TAT TGT ATG ACC GAA TCT GGG

2821
ATG CTT TTG ATA TGA GTG TAT GGC CAA CCG GGA TAC CGA AGA ACA GCT AAT TGA ACA GCA

2881
AAT CCT AAA CGG TTT TCT TCC CTC CTT CGC TTA TTA ACT ATT TCT AAA TCC CGT TTG GAA

2941
AAA GTG AAG TAG GTC CCC AGT ATC CAT TCA TCT TCA GGG ATT TGC ATA AAA GCC TGT CTC

3001
TGT TCC GGT GTA AGC AAT TCT CTA CCT CTC GCA ATT TTC ATT CAG TAT CAT TCC ATT TCT

3061
GTA TTT TCA ATT TAT TAG TTC AAT TAT ATA TCA ATA GAG TGT ACT CTA TTG ATA CAA ATG

3121
TAG TAG ACT GAT AAA ATC ATA GTT AAG AGC GTC TCA TAA GAC TTG TCT CAA AAA TGA GGT
```

```
              résolvase
3181          LEU ARG LYS ILE GLY TYR ILE ARG VAL SER SER THR ASN GLN ASN PRO SER ARG
     GAT ATT TTG CGG AAA ATC GGT TAT ATT CGT GTC AGT TCG ACT AAC CAG AAT CCT TCA AGA
```

```
3241
GLN  PHE  GLN  GLN  LEU  ASN  GLU  ILE  GLY  MET  ASP  ILE  ILE  TYR  GLU  GLU  LYS  VAL  SER  GLY
CAA  TTT  CAG  CAG  TTG  AAC  GAG  ATC  GGA  ATG  GAT  ATT  ATA  TAT  GAA  GAG  AAA  GTT  TCA  GGA

3301
ALA  THR  LYS  ASP  ARG  GLU  GLN  LEU  GLN  LYS  VAL  LEU  ASP  ASP  LEU  GLN  GLU  ASP  ASP  ILE
GCA  ACA  AAG  GAT  CGC  GAG  CAA  CTT  CAA  AAA  GTG  TTA  GAC  GAT  TTA  CAG  GAA  GAT  GAC  ATC

3361
ILE  TYR  VAL  THR  ASP  LEU  THR  ARG  ILE  THR  ARG  SER  THR  GLN  ASP  LEU  PHE  GLU  LEU  ILE
ATT  TAT  GTT  ACA  GAC  TTA  ACT  CGA  ATC  ACT  CGT  AGT  ACA  CAA  GAT  CTA  TTT  GAA  TTA  ATC

3421
ASP  ASN  ILE  ARG  ASP  LYS  LYS  ALA  SER  LEU  LYS  SER  LEU  LYS  ASP  THR  TRP  LEU  ASP  LEU
GAT  AAC  ATA  CGA  GAT  AAA  AAG  GCA  AGT  TTA  AAA  TCA  CTA  AAA  GAT  ACA  TGG  CTT  GAT  TTA

3481
SER  GLU  ASP  ASN  PRO  TYR  SER  GLN  PHE  LEU  ILE  THR  VAL  MET  ALA  GLY  VAL  ASN  GLN  LEU
TCA  GAA  GAT  AAT  CCA  TAC  AGC  CAA  TTC  TTA  ATT  ACT  GTA  ATG  GCT  GGT  GTT  AAC  CAA  TTA

3541
GLU  ARG  ASP  LEU  ILE  ARG  MET  ARG  GLN  ARG  GLU  GLY  ILE  GLU  LEU  ALA  LYS  LYS  GLU  GLY
GAG  CGA  GAT  CTT  ATT  CGG  ATG  AGA  CAA  CGT  GAA  GGG  ATT  GAA  TTG  GCT  AAG  AAA  GAA  GGA

3601
LYS  PHE  LYS  GLY  ARG  LEU  LYS  LYS  TYR  HIS  LYS  ASN  HIS  ALA  GLY  MET  ASN  TYR  ALA  VAL
AAG  TTT  AAA  GGT  CGA  TTA  AAG  AAG  TAT  CAT  AAA  AAT  CAC  GCA  GGA  ATG  AAT  TAT  GCG  GTA

3661
LYS  LEU  TYR  LYS  GLU  GLY  ASN  MET  THR  VAL  ASN  GLN  ILE  CYS  GLU  ILE  THR  ASN  VAL  SER
AAG  CTA  TAT  AAA  GAA  GGA  AAT  ATG  ACT  GTA  AAT  CAA  ATT  TGT  GAA  ATT  ACT  AAT  GTA  TCT

3721
AGR  ALA  SER  LEU  TYR  ARG  LYS  LEU  SER  GLU  VAL  ASN  ASN
AGG  GCT  TCA  TTA  TAC  AGG  AAA  TTA  TCA  GAA  GTG  AAT  AAT  TAG  CCA  TTC  TGT  ATT  CCG  CTA

3781
ATG  GGC  AAT  ATT  TTT  AAA  GAA  GAA  AAG  GAA  ACT  ATA  AAA  TAT  TAA  CAG  CCT  CCT  AGC  GAT

3841
GCC  GAA  AAG  CCC  TTT  GAT  AAA  AAA  AGA  ATC  ATC  ATC  TTA  AGA  AAT  TCT  TAG  TCA  TTT  ATT

3901
ATG  TAA  ATG  CTT  ATA  AAT  TCG  GCC  CTA  TAA  TCT  GAT  AAA  TTA  TTA  AGG  GCA  AAC  TTA  TGT

3961                VanR       MET  SER  ASP  LYS  ILE  LEU  ILE  VAL  ASP  ASP  GLU  HIS  GLU  ILE  ALA
GAA  AGG  GTG  ATA  ACT  ATG  AGC  GAT  AAA  ATA  CTT  ATT  GTG  GAT  GAT  GAA  CAT  AAA  ATT  GCC

4021
ASP  LEU  VAL  GLU  LEU  TYR  LEU  LYS  ASN  GLU  ASN  TYR  THR  VAL  PHE  LYS  TYR  TYR  THR  ALA
GAT  TTG  GTT  GAA  TTA  TAC  TTA  AAA  AAC  GAG  AAT  TAT  ACG  GTT  TTC  AAA  TAC  TAT  ACC  GCC

4081
LYS  GLU  ALA  LEU  GLU  CYS  ILE  ASP  LYS  SER  GLU  ILE  ASP  LEU  ALA  ILE  LEU  ASP  ILE  MET
AAA  GAA  GCA  TTG  GAA  TGT  ATA  GAC  AAG  TCT  GAG  ATT  GAC  CTT  GCC  ATA  TTG  GAC  ATC  ATG

4141
LEU  PRO  GLY  THR  SER  GLY  LEU  THR  ILE  CYS  GLN  LYS  ILE  ARG  ASP  LYS  HIS  THR  TYR  PRO
CTT  CCC  GGC  ACA  AGC  GGC  CTT  ACT  ATC  TGT  CAA  AAA  ATA  AGG  GAC  AAG  CAC  ACC  TAT  CCG

4201
ILE  ILE  MET  LEU  THR  GLY  LYS  ASP  THR  GLU  VAL  ASP  LYS  ILE  THR  GLY  LEU  THR  ILE  GLY
ATT  ATC  ATG  CTG  ACC  GGG  AAA  GAT  ACA  GAG  GTA  GAT  AAA  ATT  ACA  GGG  TTA  ACA  ATC  GGC

4261
ALA  ASP  ASP  TYR  ILE  THR  LYS  PRO  PHE  ARG  PRO  LEU  GLU  LEU  ILE  ALA  ARG  VAL  LYS  ALA
GCG  GAT  GAT  TAT  ATA  ACG  AAG  CCC  TTT  CGC  CCA  CTG  GAG  TTA  ATT  GCT  CGG  GTA  AAG  GCC

4321
GLN  LEU  ARG  ARG  TYR  LYS  LYS  PHE  SER  GLY  VAL  LYS  GLU  GLN  ASN  GLU  ASN  VAL  ILE  VAL
CAG  TTG  CGC  CGA  TAC  AAA  AAA  TTC  AGT  GGA  GTA  AAG  GAG  CAG  AAC  GAA  AAT  GTT  ATC  GTC

4381
HIS  SER  GLY  LEU  VAL  ILE  ASN  VAL  ASN  THR  HIS  GLU  CYS  TYR  LEU  ASN  GLU  LYS  GLN  LEU
CAC  TCC  GGC  CTT  GTC  ATT  AAT  GTT  AAC  ACC  CAT  GAG  TGT  TAT  CTG  AAC  GAG  AAG  CAG  TTA

4441
SER  LEU  THR  PRO  THR  GLU  PHE  SER  ILE  LEU  ARG  ILE  LEU  CYS  GLU  ASN  LYS  GLY  ASN  VAL
TCC  CTT  ACT  CCC  ACC  GAG  TTT  TCA  ATA  CTG  CGA  ATC  CTC  TGT  GAA  AAC  AAG  GGG  AAT  GTG

4501
VAL  SER  SER  GLU  LEU  LEU  PHE  HIS  GLU  ILE  TRP  GLY  ASP  GLU  TYR  PHE  SER  LYS  SER  ASN
GTT  AGC  TCC  GAG  CTG  CTA  TTT  CAT  GAG  ATA  TGG  GGC  GAC  GAA  TAT  TTC  AGC  AAG  AGC  AAC
```

```
4561
ASN THR ILE THR VAL HIS ILE ARG HIS LEU ARG GLU LYS MET ASN ASP THR ILE ASP ASN
AAC ACC ATC ACC GTG CAT ATC CGG CAT TTG CGC GAA AAA ATG AAC GAC ACC ATT GAT AAT

4621
PRO LYS TYR ILE LYS THR VAL TRP GLY VAL GLY LYS ILE LEU LYS
CCG AAA TAT ATA AAA ACG GTA TGG GGG GTT GGT TAT AAA ATT GAA AAT AAA AAA AAC GAC
                                VanS        LEU VAL ILE LEU LYS LEU LYS ASN LYS LYS ASN ASP

4682
TYR SER LYS LEU GLU ARG LYS LEU TYR MET TYR ILE VAL ALA ILE VAL VAL VAL ALA ILE
TAT TCC AAA CTA GAA CGA AAA CTT TAC ATG TAT ATC GTT GCA ATT GTT GTG GTA GCA ATT

4742
VAL PHE VAL LEU TYR ILE ARG SER MET ILE ARG GLY LYS LEU GLY ASP TRP ILE LEU SER
GTA TTC GTG TTG TAT ATT CGT TCA ATG ATC CGA GGG AAA CTT GGG GAT TGG ATC TTA AGT

4802
ILE LEU GLU ASN LYS TYR ASP LEU ASN HIS LEU ASP ALA MET LYS LEU TYR GLN TYR SER
ATT TTG GAA AAC AAA TAT GAC TTA AAT CAC CTG GAC GCG ATG AAA TTA TAT CAA TAT TCC

4862
ILE ARG ASN ASN ILE ASP ILE PHE ILE TYR VAL ALA ILE VAL ILE SER ILE LEU ILE LEU
ATA CGG AAC AAT ATA GAT ATC TTT ATT TAT GTG GCG ATT GTC ATT AGT ATT CTT ATT CTA

4922
CYS ARG VAL MET LEU SER LYS PHE ALA LYS TYR PHE ASP GLU ILE ASN THR GLY ILE ASP
TGT CGC GTC ATG CTT TCA AAA TTC GCA AAA TAC TTT GAC GAG ATA AAT ACC GGC ATT GAT

4982
VAL LEU ILE GLN ASN GLU ASP LYS GLN ILE GLU LEU SER ALA GLU MET ASP VAL MET GLU
GTA CTT ATT CAG AAC GAA GAT AAA CAA ATT GAG CTT TCT GCG GAA ATG GAT GTT ATG GAA

5042
GLN LYS LEU ASN THR LEU LYS ARG THR LEU GLU LYS ARG GLU GLN ASP ALA LYS LEU ALA
CAA AAG CTC AAC ACA TTA AAA CGG ACT CTG GAA AAG CGA GAG CAG GAT GCA AAG CTG GCC

5102
GLU GLN ARG LYS ASN ASP VAL VAL MET TYR LEU ALA HIS ASP ILE LYS THR PRO LEU THR
GAA CAA AGA AAA AAT GAC GTT GTT ATG TAC TTG GCG CAC GAT ATT AAA ACG CCC CTT ACA

5162
SER ILE ILE GLY TYR LEU SER LEU LEU ASP GLU ALA PRO ASP MET PRO VAL ASP GLN LYS
TCC ATT ATC GGT TAT TTG AGC CTG CTT GAC GAG GCT CCA GAC ATG CCG GTA GAT CAA AAG

5222
ALA LYS TYR VAL HIS ILE THR LEU ASP LYS ALA TYR ARG LEU GLU GLN LEU ILE ASP GLU
GCA AAG TAT GTG CAT ATC ACG TTG GAC AAA GCG TAT CGA CTC GAA CAG CTA ATC GAC GAG

5282
PHE PHE GLU ILE THR ARG TYR ASN LEU GLN THR ILE THR LEU THR LYS THR HIS ILE ASP
TTT TTT GAG ATT ACA CGG TAT AAC CTA CAA ACG ATA ACG CTA ACA AAA ACG CAC ATA GAC

5342
LEU TYR TYR MET LEU VAL GLN MET THR ASP GLU PHE TYR PRO GLN LEU SER ALA HIS GLY
CTA TAC TAT ATG CTG GTG CAG ATG ACC GAT GAA TTT TAT CCT CAG CTT TCC GCA CAT GGA

5402
LYS GLN ALA VAL ILE HIS ALA PRO GLU ASP LEU THR VAL SER GLY ASP PRO ASP LYS LEU
AAA CAG GCG GTT ATT CAC GCC CCC GAG GAT CTG ACC GTG TCC GGC GAC CCT GAT AAA CTC

5462
ALA ARG VAL PHE ASN ASN ILE LEU LYS ASN ALA ALA ALA TYR SER GLU ASP ASN SER ILE
GCG AGA GTC TTT AAC AAC ATT TTG AAA AAC GCC GCT GCA TAC AGT GAG GAT AAC AGC ATC

5522
ILE ASP ILE THR ALA GLY LEU SER GLY ASP VAL VAL SER ILE GLU PHE LYS ASN THR GLY
ATT GAC ATT ACC GCG GGC CTC TCC GGG GAT GTG GTG TCA ATC GAA TTC AAG AAC ACT GGA

5582
SER ILE PRO LYS ASP LYS LEU ALA ALA ILE PHE GLU LYS PHE TYR ARG LEU ASP ASN ALA
AGC ATC CCA AAA GAT AAG CTA GCT GCC ATA TTT GAA AAG TTC TAT AGG CTG GAC AAT GCT

5642
ARG SER SER ASP THR GLY GLY ALA GLY LEU GLY LEU ALA ILE ALA LYS GLU ILE ILE VAL
CGT TCT TCC GAT ACG GGT GGC GCG GGA CTT GGA TTG GCG ATT GCA AAA GAA ATT ATT GTT

5702
GLN HIS GLY GLY GLN ILE TYR ALA GLU SER ASN ASP ASN TYR THR THR PHE ARG VAL GLU
CAG CAT GGA GGG CAG ATT TAC GCG GAA AGC AAT GAT AAC TAT ACG ACG TTT AGG GTA GAG
```

```
5762
LEU  PRO  ALA  MET  PRO  ASP  LEU  VAL  ASP  LYS  ARG  ARG  SER
CTT  CCA  GCG  ATG  CCA  GAC  TTG  GTT  GAT  AAA  AGG  AGG  TCC  TAA  GA   GAT  GTA  TAT  AAT  TTT

5821
TTA  GGA  AAA  TCT  CAA  GGT  TAT  CTT  TAC  TTT  TTC  TTA  GGA  AAT  TAA  CAA  TTT  AAT  ATT  AAG
5881
AAA  CGG  CTC  GTT  CTT  ACA  CGG  TAG  ACT  TAA  TAC  CGT  AAG  AAC  GAG  CCG  TTT  TCG  TTC  TTC

5941
AGA  GAA  AGA  TTT  GAC  AAG  ATT  ACC  ATT  GGC  ATC  CCC  GTT  TTA  TTT  GGT  GCC  TTT  CAC  AGA

6001
          VanH                      MET  ASN  ASN  ILE  GLY  ILE  THR  VAL  TYR  GLY  CYS  GLU  GLN  ASP  GLU
AAGGGTTGG  TCT  TAA  TT  ATG  AAT  AAC  ATC  GGC  ATT  ACT  GTT  TAT  GGA  TGT  GAG  CAG  GAT  GAG

6063
ALA  ASP  ALA  PHE  HIS  ALA  LEU  SER  PRO  ARG  PHE  GLY  VAL  MET  ALA  THR  ILE  ILE  ASN  ALA
GCA  GAT  GCA  TTC  CAT  GCT  CTT  TCG  CCT  CGC  TTT  GGC  GTT  ATG  GCA  ACG  ATA  ATT  AAC  GCC

6123
ASN  VAL  SER  GLU  SER  ASN  ALA  LYS  SER  ALA  PRO  PHE  ASN  GLN  CYS  ILE  SER  VAL  GLY  HIS
AAC  GTG  TCG  GAA  TCC  AAC  GCC  AAA  TCC  GCG  CCT  TTC  AAT  CAA  TGT  ATC  AGT  GTG  GGA  CAT

6183
LYS  SER  GLU  ILE  SER  ALA  SER  ILE  LEU  LEU  ALA  LEU  LYS  ARG  ALA  GLY  VAL  LYS  TYR  ILE
AAA  TCA  GAG  ATT  TCC  GCC  TCT  ATT  CTT  CTT  GCG  CTG  AAG  AGA  GCC  GGT  GTG  AAA  TAT  ATT

6243
SER  THR  ARG  SER  ILE  GLY  CYS  ASN  HIS  ILE  ASP  THR  THR  ALA  ALA  LYS  ARG  MET  GLY  ILE
TCT  ACC  CGA  AGC  ATC  GGC  TGC  AAT  CAT  ATA  GAT  ACA  ACT  GCT  GCT  AAG  AGA  ATG  GGC  ATC

6303
THR  VAL  ASP  ASN  VAL  ALA  TYR  SER  PRO  ASP  SER  VAL  ALA  ASP  TYR  THR  MET  MET  LEU  ILE
ACT  GTC  GAC  AAT  GTG  GCG  TAC  TCG  CCG  GAT  AGC  GTT  GCC  GAT  TAT  ACT  ATG  ATG  CTA  ATT

6363
LEU  MET  ALA  VAL  ARG  ASN  VAL  LYS  SER  ILE  VAL  ARG  SER  VAL  GLU  LYS  HIS  ASP  PHE  ARG
CTT  ATG  GCA  GTA  CGC  AAC  GTA  AAA  TCG  ATT  GTG  CGC  TCT  GTG  GAA  AAA  CAT  GAT  TTC  AGG

6423
LEU  ASP  SER  ASP  ARG  GLY  LYS  VAL  LEU  SER  ASP  MET  THR  VAL  GLY  VAL  VAL  GLY  THR  GLY
TTG  GAC  AGC  GAC  CGT  GGC  AAG  GTA  CTC  AGC  GAC  ATG  ACA  GTT  GGT  GTG  GTG  GGA  ACG  GGC

6483
GLN  ILE  GLY  LYS  ALA  VAL  ILE  GLU  ARG  LEU  ARG  GLY  PHE  GLY  CYS  LYS  VAL  LEU  ALA  TYR
CAG  ATA  GGC  AAA  GCG  GTT  ATT  GAG  CGG  CTG  CGA  GGA  TTT  GGA  TGT  AAA  GTG  TTG  GCT  TAT

6543
SER  ARG  SER  ARG  SER  ILE  GLU  VAL  ASN  TYR  VAL  PRO  PHE  ASP  GLU  LEU  LEU  GLN  ASN  SER
AGT  CGC  AGC  CGA  AGT  ATA  GAG  GTA  AAC  TAT  GTA  CCG  TTT  GAT  GAG  TTG  CTG  CAA  AAT  AGC

6603
ASP  ILE  VAL  THR  LEU  HIS  VAL  PRO  LEU  ASN  THR  ASP  THR  HIS  TYR  ILE  ILE  SER  HIS  GLU
GAT  ATC  GTT  ACG  CTT  CAT  GTG  CCG  CTC  AAT  ACG  GAT  ACG  CAC  TAT  ATT  ATC  AGC  CAC  GAA

6663
GLN  ILE  GLN  ARG  MET  LYS  GLN  GLY  ALA  PHE  LEU  ILE  ASN  THR  GLY  ARG  GLY  PRO  LEU  VAL
CAA  ATA  CAG  AGA  ATG  AAG  CAA  GGA  GCA  TTT  CTT  ATC  AAT  ACT  GGG  CGC  GGT  CCA  CTT  GTA

6723
ASP  THR  TYR  GLU  LEU  VAL  LYS  ALA  LEU  GLU  ASN  GLY  LYS  LEU  GLY  GLY  ALA  ALA  LEU  ASP
GAT  ACC  TAT  GAG  TTG  GTT  AAA  GCA  TTA  GAA  AAC  GGG  AAA  CTG  GGC  GGT  GCC  GCA  TTG  GAT

6783
VAL  LEU  GLU  GLY  GLU  GLU  GLU  PHE  PHE  TYR  SER  ASP  CYS  THR  GLN  LYS  PRO  ILE  ASP  ASN
GTA  TTG  GAA  GGA  GAG  GAA  GAG  TTT  TTC  TAC  TCT  GAT  TGC  ACC  CAA  AAA  CCA  ATT  GAT  AAT

6843
GLN  PHE  LEU  LEU  LYS  LEU  GLN  ARG  MET  PRO  ASN  VAL  ILE  ILE  THR  PRO  HIS  THR  ALA  TYR
CAA  TTT  TTA  CTT  AAA  CTT  CAA  AGA  ATG  CCT  AAC  GTG  ATA  ATC  ACA  CCG  CAT  ACG  GCC  TAT

6903
TYR  THR  GLU  GLN  ALA  LEU  ARG  ASP  THR  VAL  GLU  LYS  THR  ILE  LYS  ASN  CYS  LEU  ASP  PHE
TAT  ACC  GAG  CAA  GCG  TTG  CGT  GAT  ACC  GTT  GAA  AAA  ACC  ATT  AAA  AAC  TGT  TTG  GAT  TTT

6963
        VanA       METASN  ARG  ILE  LYS  VAL  ALA  ILE  LEU  PHE  GLY  GLY  CYS  SER
GAA  AGG  AGA  CAG  GAG  CATGAAT  AGA  ATA  AAA  GTT  GCA  ATA  CTG  TTT  GGG  GGT  TGC  TCA
GLU  ARG  ARG  GLN  GLU  HISGLU
```

```
7021
GLU GLU HIS ASP VAL SER VAL LYS SER ALA ILE GLU ILE ALA ALA ASN ILE ASN LYS GLU
GAG GAG CAT GAC GTA TCG GTA AAA TCT GCA ATA GAG ATA GCC GCT AAC ATT AAT AAA GAA

7081
LYS TYR GLU PRO LEU TYR ILE GLY ILE THR LYS SER GLY VAL TRP LYS MET CYS GLU LYS
AAA TAC GAG CCG TTA TAC ATT GGA ATT ACG AAA TCT GGT GTA TGG AAA ATG TGC GAA AAA

7141
PRO CYS ALA GLU TRP GLU ASN ASP ASN CYS TYR SER ALA VAL LEU SER PRO ASP LYS LYS
CCT TGC GCG GAA TGG GAA AAC GAC AAT TGC TAT TCA GCT GTA CTC TCG CCG GAT AAA AAA

7201
MET HIS GLY LEU LEU VAL LYS LYS ASN HIS GLU TYR GLU ILE ASN HIS VAL ASP VAL ALA
ATG CAC GGA TTA CTT GTT AAA AAG AAC CAT GAA TAT GAA ATC AAC CAT GTT GAT GTA GCA

7261
PHE SER ALA LEU HIS GLY LYS SER GLY GLU ASP GLY SER ILE GLN GLY LEU PHE GLU LEU
TTT TCA GCT TTG CAT GGC AAG TCA GGT GAA GAT GGA TCC ATA CAA GGT CTG TTT GAA TTG

7321
SER GLY ILE PRO PHE VAL GLY CYS ASP ILE GLN SER SER ALA ILE CYS MET ASP LYS SER
TCC GGT ATC CCT TTT GTA GGC TGC GAT ATT CAA AGC TCA GCA ATT TGT ATG GAC AAA TCG

7381
LEU THR TYR ILE VAL ALA LYS ASN ALA GLY ILE ALA THR PRO ALA PHE TRP VAL ILE ASN
TTG ACA TAC ATC GTT GCG AAA AAT GCT GGG ATA GCT ACT CCC GCC TTT TGG GTT ATT AAT

7441
LYS ASP ASP ARG PRO VAL ALA ALA THR PHE THR TYR PRO VAL PHE VAL LYS PRO ALA ARG
AAA GAT GAT AGG CCG GTG GCA GCT ACG TTT ACC TAT CCT GTT TTT GTT AAG CCG GCG CGT

7501
SER GLY SER SER PHE GLY VAL LYS LYS VAL ASN SER ALA ASP GLU LEU ASP TYR ALA ILE
TCA GGC TCA TCC TTC GGT GTG AAA AAA GTC AAT AGC GCG GAC GAA TTG GAC TAC GCA ATT

7561
GLU SER ALA ARG GLN TYR ASP SER LYS ILE LEU ILE GLU GLN ALA VAL SER GLY CYS GLU
GAA TCG GCA AGA CAA TAT GAC AGC AAA ATC TTA ATT GAG CAG GCT GTT TCG GGC TGT GAG

7621
VAL GLY CYS ALA VAL LEU GLY ASN SER ALA ALA LEU VAL VAL GLY GLU VAL ASP GLN ILE
GTC GGT TGT GCG GTA TTG GGA AAC AGT GCC GCG TTA GTT GTT GGC GAG GTG GAC CAA ATC

7681
ARG LEU GLN TYR GLY ILE PHE ARG ILE HIS GLN GLU VAL GLU PRO GLU LYS GLY SER GLU
AGG CTG CAG TAC GGA ATC TTT CGT ATT CAT CAG GAA GTC GAG CCG GAA AAA GGC TCT GAA

7741
ASN ALA VAL ILE THR VAL PRO ALA ASP LEU SER ALA GLU GLU ARG GLY ARG ILE GLN GLU
AAC GCA GTT ATA ACC GTT CCC GCA GAC CTT TCA GCA GAG GAG CGA GGA CGG ATA CAG GAA

7801
THR ALA LYS LYS ILE TYR LYS ALA LEU GLY CYS ARG GLY LEU ALA ARG VAL ASP MET PHE
ACG GCA AAA AAA ATA TAT AAA GCG CTC GGC TGT AGA GGT CTA GCC CGT GTG GAT ATG TTT

7861
LEU GLN ASP ASN GLY ARG ILE VAL LEU ASN GLU VAL ASN THR LEU PRO GLY PHE THR SER
TTA CCA GAT AAC GGC CGC ATT GTA CTG AAC GAA GTC AAT ACT CTG CCC GGT TTC ACG TCA

7921
TYR SER ARG TYR PRO ARG MET MET ALA ALA ALA GLY ILE ALA LEU PRO GLU LEU ILE ASP
TAC AGT CGT TAT CCC CGT ATG ATG GCC GCT GCA GGT ATT GCA CTT CCC GAA CTG ATT GAC

7981
ARG LEU ILE VAL LEU ALA LEU LYS GLY
CGC TTG ATC GTA TTA GCG TTA AAG GGG TGATAAGC ATG GAA ATA GGA TTT ACT TTT TTA GAT
                                            VanX     MET GLU ILE GLY PHE THR PHE LEU ASP

8043
GLU ILE VAL HIS GLY VAL ARG TRP ASP ALA LYS TYR ALA THR TRP ASP ASN PHE THR GLY
GAA ATA GTA CAC GGT GTT CGT TGG GAC GCT AAA TAT GCC ACT TGG GAT AAT TTC ACC GGA

8103
LYS PRO VAL ASP GLY TYR GLU VAL ASN ARG ILE VAL GLY THR TYR GLU LEU ALA GLU SER
AAA CCG GTT GAC GGT TAT GAA GTA AAT CGC ATT GTA GGG ACA TAC GAG TTG GCT GAA TCG

8163
LEU LEU LYS ALA LYS GLU LEU ALA ALA THR GLN GLY TYR GLY LEU LEU LEU TRP ASP GLY
CTT TTG AAG GCA AAA GAA CTG GCT GCT ACC CAA GGG TAC GGA TTG CTT CTA TGG GAC GGT
```

```
8223
TYR ARG PRO LYS ARG ALA VAL ASN CYS PHE MET GLN TRP ALA ALA GLN PRO GLU ASN ASN
TAC CGT CCT AAG CGT GCT GTA AAC TGT TTT ATG CAA TGG GCT GCA CAG CCG GAA AAT AAC

8283
LEU THR LYS GLU SER TYR TYR PRO ASN ILE ASP ARG THR GLU MET ILE SER LYS GLY TYR
CTG ACA AAG GAA AGT TAT TAT CCC AAT ATT GAC CGA ACT GAG ATG ATT TCA AAA GGA TAC

8343
VAL ALA SER LYS SER SER HIS SER ARG GLY SER ALA ILE ASP LEU THR LEU TYR ARG LEU
GTG GCT TCA AAA TCA AGC CAT AGC CGC GGC AGT GCC ATT GAT CTT ACG CTT TAT CGA TTA

8403
ASP THR GLY GLU LEU VAL PRO MET GLY SER ARG PHE ASP PHE MET ASP GLU ARG SER HIS
GAC ACG GGT GAG CTT GTA CCA ATG GGG AGC CGA TTT GAT TTT ATG GAT GAA CGC TCT CAT

8463
HIS ALA ALA ASN GLY ILE SER CYS ASN GLU ALA GLN ASN ARG ARG ARG LEU ARG SER ILE
CAT GCG GCA AAT GGA ATA TCA TGC AAT GAA GCG CAA AAT CGC AGA CGT TTG CGC TCC ATC

8523
MET GLU ASN SER GLY PHE GLU ALA TYR SER LEU GLU TRP TRP HIS TYR VAL LEU ARG ASP
ATG GAA AAC AGT GGG TTT GAA GCA TAT AGC CTC GAA TGG TGG CAC TAT GTA TTA AGA GAC

8583
GLU PRO TYR PRO ASN SER TYR PHE ASP PHE PRO VAL LYS
GAA CCA TAC CCC AAT AGC TAT TTT GAT TTC CCC GTT AAA TAAACTT TTA ACC GTT GCA

8641
CGG ACA AAC TAT ATA AGC TAA CTC TTT CGG CAG GAA ACC CGA CGT ATG TAA CTG GTT CTT

8701
AGG GAA TTT ATA TAT AGT AGA TAG TAT TGA AGA TGT AAG GCA GAG CGA TAT TGC GGT CAT

8761
TAT CTG CGT GCG CTG CGG CAA GAT AGC CTG ATA ATA AGA CTG ATC GCA TAG AGG GGT GGT

8821
ATT TCA CAC CGC CCA TTG TCA ACA GGC AGT TCA GCC TCG TTA AAT TCA GCA TGG GTA TCA

8881
CTT ATG AAA ATT CAT CTA CAT TGG TGA TAA TAG TAA ATC CAG TAG GGC GAA ATA ATT GAC

8941
TGT AAT TTA CGG GGC AAA ACG GCA CAA TCT CAA ACG AGA TTG TGC CGT TTA AGG GGA AGA

9001                                                                VanY
                                                                         MET LYS LYS
TTC TAG AAA TAT TTC ATA CTT CCA ACT ATA TAG TTA AGG AGG AGA CTG AAA ATG AAG AAG

9061
LEU PHE PHE LEU LEU LEU LEU LEU PHE LEU ILE TYR LEU GLY TYR ASP TYR VAL ASN GLU
TTG TTT TTT TTA TTG TTA TTG TTA TTC TTA ATA TAC TTA GGT TAT GAC TAC GTT AAT GAA

9121
ALA LEU PHE SER GLN GLU LYS VAL GLU PHE GLN ASN TYR ASP GLN ASN PRO LYS GLU HIS
GCA CTG TTT TCT CAG GAA AAA GTC GAA TTT CAA AAT TAT GAT CAA AAT CCC AAA GAA CAT

9181
LEU GLU ASN SER GLY THR SER GLU ASN THR GLN GLU LYS THR ILE THR GLU GLU GLN VAL
TTA GAA AAT AGT GGG ACT TCT GAA AAT ACC CAA GAG AAA ACA ATT ACA GAA GAA CAG GTT

9241
TYR GLN GLY ASN LEU LEU LEU ILE ASN SER LYS TYR PRO VAL ARG GLN GLU SER VAL LYS
TAT CAA GGA AAT CTG CTA TTA ATC AAT AGT AAA TAT CCT GTT CGC CAA GAA AGT GTG AAG

9301
SER ASP ILE VAL ASN LEU SER LYS HIS ASP GLU LEU ILE ASN GLY TYR GLY LEU LEU ASP
TCA GAT ATC GTG AAT TTA TCT AAA CAT GAC GAA TTA ATA AAT GGA TAC GGG TTG CTT GAT

9361
SER ASN ILE TYR MET SER LYS GLU ILE ALA GLN LYS PHE SER GLU MET VAL ASN ASP ALA
AGT AAT ATT TAT ATG TCA AAA GAA ATA GCA CAA AAA TTT TCA GAG ATG GTC AAT GAT GCT

9421
VAL LYS GLY GLY VAL SER HIS PHE ILE ILE ASN SER GLY TYR ARG ASP PHE ASP GLU GLN
GTA AAG GGT GGC GTT AGT CAT TTT ATT ATT AAT AGT GGC TAT CGA GAC TTT GAT GAG CAA

9481
SER VAL LEU TYR GLN GLU MET GLY ALA GLU TYR ALA LEU PRO ALA GLY TYR SER GLU HIS
AGT GTG CTT TAC CAA GAA ATG GGG GCT GAG TAT GCC TTA CCA GCA GGT TAT AGT GAG CAT
```

```
9541
ASN SER GLY LEU SER LEU ASP VAL GLY SER SER LEU THR LYS MET GLU ARG ALA PRO GLU
AAT TCA GGT TTA TCA CTA GAT GTA GGA TCA AGC TTG ACG AAA ATG GAA CGA GCC CCT GAA

9601
GLY LYS TRP ILE GLU GLU ASN ALA TRP LYS TYR GLY PHE ILE LEU ARG TYR PRO GLU ASP
GGA AAG TGG ATA GAA GAA AAT GCT TGG AAA TAC GGG TTC ATT TTA CGT TAT CCA GAG GAC

9661
LYS THR GLU LEU THR GLY ILE GLN TYR GLU PRO TRP HIS ILE ARG TYR VAL GLY LEU PRO
AAA ACA GAG TTA ACA GGA ATT CAA TAT GAA CCA TGG CAT ATT CGC TAT GTT GGT TTA CCA

9721
HIS SER ALA ILE MET LYS GLU LYS ASN PHE VAL LEU GLU GLU TYR MET ASP TYR LEU LYS
CAT AGT GCG ATT ATG AAA GAA AAG AAT TTC GTT CTC GAG GAA TAT ATG GAT TAC CTA AAA

9781
GLU GLU LYS THR ILE SER VAL SER VAL ASN GLY GLU LYS TYR GLU ILE PHE TYR TYR PRO
GAA GAA AAA ACC ATT TCT GTT AGT GTA AAT GGG GAA AAA TAT GAG ATC TTT TAT TAT CCT

9841
VAL THR LYS ASN THR THR ILE HIS VAL PRO THR ASN LEU ARG TYR GLU ILE SER GLY ASN
GTT ACT AAA AAT ACC ACC ATT CAT GTG CCG ACT AAT CTT CGT TAT GAG ATA TCA GGA AAC

9901
ASN ILE ASP GLY VAL ILE VAL THR VAL PHE PRO GLY SER THR HIS THR ASN SER ARG ARG
AAT ATA GAC GGT GTA ATT GTG ACA GTG TTT CCC GGA TCA ACA CAT ACT AAT TCA AGG AGG

9961
TAA GGA TGG CGG AAT GAA ACC AAC GAA ATT AAT GAA CAG CAT TAT TGT ACT AGC ACT TTT

10021
GGG GTA ACG TTA GCT TTT TAA TTT AAA ACC CAC GTT AAC TAG GAC ATT GCT ATA CTA ATG

10081                                           VanZ     LEU GLY LYS ILE LEU SER ARG GLY LEU
ATA CAA CTT AAA CAA AAG AATTAGAGG AAA TTA TA TTG GGA AAA ATA TTA TCT AGA GGA TTG

10143
LEU ALA LEU TYR LEU VAL THR LEU ILE TRP LEU VAL LEU PHE LYS LEU GLN TYR ASN ILE
CTA GCT TTA TAT TTA GTG ACA CTA ATC TGG TTA GTG TTA TTC AAA TTA CAA TAC AAT ATT

10203
LEU SER VAL PHE ASN TYR HIS GLN ARG SER LEU ASN LEU THR PRO PHE THR ALA THR GLY
TTA TCA GTA TTT AAT TAT CAT CAA AGA AGT CTT AAC TTG ACT CCA TTT ACT GCT ACT GGG

10263
ASN PHE ARG GLU MET ILE ASP ASN VAL ILE ILE PHE ILE PRO PHE GLY LEU LEU LEU ASN
AAT TTC AGA GAG ATG ATA GAT AAT GTT ATA ATC TTT ATT CCA TTT GGC TTG CTT TTG AAT

10323
VAL ASN PHE LYS GLU ILE GLY PHE LEU PRO LYS PHE ALA PHE VAL LEU VAL LEU SER LEU
GTC AAT TTT AAA GAA ATC GGA TTT TTA CCT AAG TTT GCT TTT GTA CTG GTT TTA AGT CTT

10383
THR PHE GLU ILE ILE GLN PHE ILE PHE ALA ILE GLY ALA THR ASP ILE THR ASP VAL ILE
ACT TTT GAA ATA ATT CAA TTT ATC TTC GCT AAT GGA GCG ACA GAC ATA ACA GAT GTA ATT

10433
THR ASN THR VAL GLY GLY PHE LEU GLY LEU LYS LEU TYR GLY LEU SER ASN LYS HIS MET
ACA AAT ACT GTT GGA GGC TTT CTT GGA CTG AAA TTA TAT GGT TTA AGC AAT AAG CAT ATG

10503
ASN GLN LYS LYS LEU ASP ARG VAL ILE ILE PHE VAL GLY ILE LEU LEU LEU VAL LEU LEU
AAT CAA AAA AAA TTA GAC AGA GTT ATT ATT TTT GTA GGT ATA CTT TTG CTC GTA TTA TTG

10563
LEU VAL TYR ARG THR HIS LEU ARG ILE ASN TYR VAL
CTC GTT TAC CGT ACC CAT TTA AGA ATA AAT TAC GTG TAAG ATG TCT AAA TCA AGC AAT

10621
CTG ATC TTT CAT ACA CAT AAA GAT ATT GAA TGA ATT GGA TTA GAT GGA AAA CGG GAT GTG

10681
GGG AAA CTC GCC CGT AGG TGT GAA GTG AGG GGA AAA CCG GTG ATA AAG TAA AAA GCT TAC

10741
CTA ACA CTA TAG TAA CAA AGA AAG CCC AAT TAT CAA TTT TAG TGC TGA GGA ATT GGT CTC

10801
TTT AAT AAA TTT CCT TAA CGT TGT AAA TCC GCA TTT TCC TGA CGG TAC CCC
```

Ib (−) Strand
(corresponds to the sequence of the strand complementary to the (+) strand from 1 to 3189.

```
1
CAA AAT ATC ACC TTA TTT TTG AGA CAA GTC TTA TGA GAC GCT CTT AAC TAT GAT TTT ATC

61
AGT CTA CTA CAT TTG TAT CAA TAG AGT ACA CTC TAT TGA TAT ATA ATT GAA CTA ATA AAT

121             Transposase              MET LYS ILE ALA ARG GLY ARG GLU LEU LEU THR
TGA AAA TAC AGA AAT GGA ATGATACTG AA ATG AAA ATT GCG AGA GGT AGA GAA TTG CTT ACA 182
PRO GLU GLN ARG GLN ALA PHE MET GLN ILE PRO GLU ASP GLU TRP ILE LEU GLY THR TYR
CCG GAA CAG AGA CAG GCT TTT ATG CAA ATC CCT GAA GAT GAA TGG ATA CTG GGG ACC TAC 242
PHE THR PHE SER LYS ARG ASP LEU GLU ILE VAL ASN LYS ARG ARG ARG GLU GLU ASN ARG
TTC ACT TTT TCC AAA CGG GAT TTA GAA ATA GTT AAT AAG CGA AGG AGG GAA GAA AAC CGT 302
LEU GLY PHE ALA VAL GLN LEU ALA VAL LEU ARG TYR PRO GLY TRP PRO TYR THR HIS ILE
TTA GGA TTT GCT GTT CAA TTA GCT GTT CTT CGG TAT CCC GGT TGG CCA TAC ACT CAT ATC 362
LYS SER ILE PRO ASP SER VAL ILE GLN TYR ILE SER LYS GLN ILE GLY VAL SER PRO SER
AAA AGC ATC CCA GAT TCG GTC ATA CAA TAT ATA TCG AAA CAG ATT GGT GTT AGT CCA TCC 422
SER LEU ASP HIS TYR PRO GLN ARG GLU ASN THR LEU TRP ASP HIS LEU LYS GLU ILE ARG
TCG CTT GAT CAT TAT CCT CAA AGG GAA AAT ACA CTT TGG GAT CAT TTG AAA GAA ATT CGA 482
SER GLU TYR ASP PHE VAL THR PHE THR LEU SER GLU TYR ARG MET THR PHE LYS TYR LEU
AGT GAA TAC GAC TTT GTA ACT TTT ACC CTG AGT GAA TAT CGA ATG ACA TTT AAG TAC CTT 542
HIS GLN LEU ALA LEU GLU ASN GLY ASP ALA ILE HIS LEU LEU HIS GLU CYS ILE ASP PHE
CAT CAA TTA GCT TTG GAA AAT GGT GAT GCC ATT CAT CTA CTG CAT GAA TGC ATA GAT TTT 602
LEU ARG LYS ASN LYS ILE ILE LEU PRO ALA ILE THR THR LEU GLU ARG MET VAL TRP GLU
CTA AGA AAA AAC AAA ATT ATA CTG CCT GCT ATC ACT ACA CTT GAA AGA ATG GTG TGG GAA 662
ALA ARG ALA MET ALA GLU LYS LYS LEU PHE ASN THR VAL SER LYS SER LEU THR ASN GLU
GCA AGG GCA ATG GCT GAA AAG AAG CTA TTT AAT ACG GTT AGT AAA TCT CTA ACA AAT GAG 722
GLN LYS GLU LYS LEU GLU GLY ILE ILE THR SER GLN HIS PRO SER GLU SER ASN LYS THR
CAA AAA GAA AAG CTT GAA GGG ATT ATT ACC TCG CAG CAT CCA TCC GAA TCC AAT AAA ACG 782
ILE LEU GLY TRP LEU LYS GLU PRO PRO GLY HIS PRO SER PRO GLU THR PHE LEU LYS ILE
ATA TTG GGT TGG TTA AAA GAG CCA CCG GGT CAT CCT TCA CCC GAA ACT TTT CTA AAA ATA 842
ILE GLU ARG LEU GLU TYR ILE ARG GLY MET ASP LEU GLU THR VAL GLN ILE SER HIS LEU
ATA GAA CGA CTC GAA TAC ATA CGA GGA ATG GAT TTA GAA ACA GTG CAA ATT AGT CAT TTG 902
HIS ARG ASN ARG LEU LEU GLN LEU SER ARG LEU GLY SER ARG TYR GLU PRO TYR ALA PHE
CAC CGT AAC CGC CTG TTG CAG CTG TCT CGC TTA GGC TCA AGA TAC GAG CCG TAT GCA TTC 962
ARG ASP PHE GLN GLU ASN LYS ARG TYR SER ILE LEU THR ILE TYR LEU LEU GLN LEU THR
CGT GAC TTT CAA GAA AAT AAA CGT TAT TCG ATA TTA ACC ATC TAT TTA TTA CAA CTT ACT 1022
GLN GLU LEU THR ASP LYS ALA PHE GLU ILE HIS ASP ARG GLN ILE LEU SER LEU LEU SER
CAG GAG CTA ACG GAT AAA GCG TTT GAA ATT CAT GAT AGG CAA ATA CTT AGT TTG TTA TCA 1082
LYS GLY ARG LYS ALA GLN GLU GLU ILE GLN LYS GLN ASN GLY LYS LYS LEU ASN GLU LYS
AAA GGT CGT AAG GCT CAA GAG GAA ATC CAG AAA CAA AAC GGT AAA AAG CTA AAT GAG AAA 1142
VAL ILE HIS PHE THR ASN ILE GLY GLN ALA LEU ILE LYS ALA ARG GLU GLU LYS LEU ASP
GTT ATA CAC TTT ACG AAC ATC GGA CAA GCA TTA ATT AAA GCA AGA GAG GAA AAA TTA GAC 1202
VAL PHE LYS VAL LEU GLU SER VAL ILE GLU TRP ASN THR PHE VAL SER SER VAL GLU GLU
GTT TTT AAG GTT TTA GAA TCG GTT ATT GAA TGG AAT ACC TTT GTC TCT TCA GTA GAA GAG
```

```
1262
ALA  GLN  GLU  LEU  ALA  ARG  PRO  ALA  ASP  TYR  ASP  TYR  LEU  ASP  LEU  LEU  GLN  LYS  ARG  PHE
GCT  CAG  GAA  CTT  GCA  CGT  CCT  GCC  GAC  TAT  GAT  TAT  TTA  GAC  TTA  CTG  CAA  AAA  CGG  TTT

1322
TYR  SER  LEU  ARG  LYS  TYR  THR  PRO  THR  LEU  LEU  ARG  VAL  LEU  GLU  PHE  HIS  SER  THR  LYS
TAT  TCA  CTA  AGA  AAA  TAT  ACG  CCA  ACG  CTA  TTA  AGA  GTA  TTG  GAA  TTT  CAT  TCT  ACA  AAG

1382
ALA  ASN  GLU  PRO  LEU  LEU  GLN  ALA  VAL  GLU  ILE  ILE  ARG  GLY  MET  ASN  GLU  SER  GLY  LYS
GCA  AAT  GAG  CCA  CTT  TTA  CAA  GCT  GTT  GAG  ATT  ATC  CGA  GGA  ATG  AAC  GAA  TCT  GGA  AAG

1442
ARG  LYS  VAL  PRO  ASP  ASP  SER  PRO  VAL  ASP  PHE  ILE  SER  LYS  ARG  TRP  LYS  ARG  HIS  LEU
CGA  AAA  GTG  CCT  GAT  GAC  TCA  CCT  GTG  GAT  TTT  ATT  TCA  AAA  CGA  TGG  AAA  AGA  CAT  TTA

1502
TYR  GLU  ASP  ASP  GLY  THR  THR  ILE  ASN  ARG  HIS  TYR  TYR  GLU  MET  ALA  VAL  LEU  THR  GLU
TAC  GAG  GAT  GAT  GGT  ACA  ACA  ATT  AAT  CGT  CAT  TAC  TAT  GAA  ATG  GCT  GTT  TTA  ACA  GAA

1562
LEU  ARG  GLU  HIS  VAL  ARG  ALA  GLY  ASP  VAL  SER  ILE  VAL  GLY  SER  ARG  GLN  TYR  ARG  ASP
CTT  CGG  GAG  CAT  GTT  CGG  GCA  GGA  GAT  GTT  TCC  ATT  GTT  GGC  AGC  AGA  CAA  TAT  AGG  GAT

1622
PHE  GLU  GLU  TYR  LEU  PHE  SER  GLU  ASP  THR  TRP  ASN  GLN  SER  LYS  GLY  ASN  THR  ARG  LEU
TTT  GAG  GAA  TAT  TTG  TTT  TCG  GAA  GAT  ACA  TGG  AAT  CAA  TCG  AAG  GGG  AAT  ACG  AGA  TTA

1682
SER  VAL  SER  LEU  SER  PHE  GLU  ASP  TYR  ILE  THR  GLU  ARG  THR  SER  SER  PHE  ASN  GLU  ARG
TCA  GTT  AGT  TTA  TCA  TTC  GAA  GAT  TAT  ATA  ACG  GAG  AGA  ACC  AGC  AGC  TTT  AAT  GAA  AGG

1742
LEU  LYS  TRP  LEU  ALA  ALA  ASN  SER  ASN  LYS  LEU  ASP  GLY  VAL  SER  LEU  GLU  LYS  GLY  LYS
TTA  AAG  TGG  TTA  GCT  GCC  AAT  TCC  AAT  AAG  TTA  GAT  GGG  GTT  TCT  CTT  GAA  AAA  GGA  AAG

1802
LEU  SER  LEU  ALA  ARG  LEU  GLU  LYS  ASP  VAL  PRO  GLU  GLU  ALA  LYS  LYS  PHE  SER  ALA  SER
CTA  TCA  CTT  GCA  CGC  TTA  GAA  AAA  GAT  GTT  CCA  GAA  GAA  GCA  AAA  AAA  TTT  AGT  GCA  AGC

1862
LEU  TYR  GLN  MET  LEU  PRO  ARG  ILE  LYS  LEU  THR  ASP  LEU  LEU  MET  ASP  VAL  ALA  HIS  ILE
CTT  TAT  CAG  ATG  CTA  CCA  AGA  ATA  AAA  TTA  ACT  GAT  TTA  CTC  ATG  GAT  GTG  GCC  CAT  ATA

1922
THR  GLY  PHE  HIS  GLU  GLN  PHE  THR  HIS  ALA  SER  ASN  ASN  ARG  LYS  PRO  ASP  LYS  GLU  GLU
ACA  GGA  TTT  CAT  GAG  CAA  TTC  ACT  CAT  GCT  TCC  AAT  AAT  CGA  AAA  CCA  GAT  AAG  GAA  GAA

1982
THR  ILE  ILE  ILE  MET  ALA  ALA  LEU  LEU  GLY  MET  GLY  MET  ASN  ILE  GLY  LEU  SER  LYS  MET
ACA  ATC  ATT  ATC  ATG  GCT  GCC  CTT  TTA  GGA  ATG  GGA  ATG  AAT  ATT  GGC  TTG  AGC  AAG  ATG

2042
ALA  GLU  ALA  THR  PRO  GLY  LEU  THR  TYR  LYS  GLN  LEU  ALA  ASN  VAL  SER  GLN  TRP  ARG  MET
GCC  GAA  GCC  ACA  CCC  GGA  CTT  ACA  TAT  AAG  CAA  CTA  GCC  AAT  GTA  TCT  CAA  TGG  CGC  ATG

2102
TYR  GLU  ASP  ALA  MET  ASN  LYS  ALA  GLN  ALA  ILE  LEU  VAL  ASN  PHE  HIS  HIS  LYS  LEU  GLN
TAT  GAA  GAT  GCC  ATG  AAT  AAA  GCC  CAA  GCC  ATA  TTA  GTA  AAC  TTT  CAT  CAT  AAA  TTA  CAA

2162
LEU  PRO  PHE  TYR  TRP  GLY  ASP  GLY  THR  THR  SER  SER  SER  ASP  GLY  MET  ARG  MET  GLN  LEU
TTG  CCT  TTC  TAT  TGG  GGC  GAC  GGT  ACA  ACA  TCT  TCG  TCA  GAT  GGT  ATG  AGA  ATG  CAG  CTA

2222
GLY  VAL  SER  SER  LEU  HIS  ALA  ASP  ALA  ASN  PRO  HIS  TYR  GLY  THR  GLY  LYS  GLY  ALA  THR
GGT  GTT  TCA  TCA  CTA  CAT  GCA  GAT  GCA  AAT  CCA  CAT  TAT  GGA  ACT  GGA  AAA  GGA  GCC  ACC

2282
ILE  TYR  ARG  PHE  THR  SER  ASP  GLN  PHE  SER  SER  TYR  TYR  THR  LYS  ILE  ILE  HIS  THR  ASN
ATC  TAC  CGA  TTT  ACA  AGT  GAT  CAA  TTC  TCT  TCT  TAC  TAC  ACA  AAG  ATT  ATT  CAT  ACT  AAT

2342
SER  ARG  ASP  ALA  ILE  HIS  VAL  LEU  ASP  GLY  LEU  LEU  HIS  HIS  GLU  THR  ASP  LEU  ASN  ILE
TCA  AGA  GAT  GCG  ATT  CAT  GTT  TTG  GAT  GGT  TTG  TTA  CAT  CAT  GAG  ACG  GAT  CTA  AAC  ATA

2402
GLU  HIS  TYR  THR  ASP  THR  ALA  GLY  TYR  THR  ASP  GLN  ILE  PHE  GLY  LEU  THR  HIS  LEU
GAG  GAA  CAT  TAT  ACA  GAC  ACT  GCC  GGT  TAC  ACT  GAC  CAA  ATA  TTC  GGA  CTG  ACT  CAT  TTA

2462
LEU  GLY  PHE  LYS  PHE  ALA  PRO  ARG  ILE  ARG  ASP  LEU  SER  ASP  SER  LYS  LEU  PHE  THR  ILE
TTA  GGA  TTT  AAA  TTT  GCC  CCA  AGA  ATA  AGG  GAT  TTA  TCG  GAC  TCA  AAA  TTA  TTT  ACG  ATA
```

```
2522
ASP  LYS  ALA  SER  GLU  TYR  PRO  LYS  LEU  GLU  ALA  ILE  LEU  ARG  GLY  GLN  ILE  ASN  THR  LYS
GAT  AAA  GCA  AGT  GAG  TAT  CCA  AAA  CTA  GAA  GCC  ATT  TTA  CGT  GGA  CAA  ATA  AAT  ACA  AAG

2582
VAL  ILE  LYS  GLU  ASN  TYR  GLU  ASP  VAL  LEU  ARG  LEU  ALA  HIS  SER  ILE  ARG  GLU  GLY  THR
GTC  ATT  AAA  GAA  AAT  TAT  GAG  GAT  GTT  TTG  CGA  TTA  GCT  CAT  TCT  ATA  AGG  GAG  GGA  ACA

2642
AGT  TTC  AGC  ATC  CCT  TAT  TAT  GGG  GAA  GCT  AGG  TTC  CTA  TTC  AAG  ACA  AAA  CAG  CTT  AGC
VAL  SER  ALA  SER  LEU  ILE  MET  GLY  LYS  LEU  GLY  SER  TYR  SER  ARG  GLN  ASN  SER  LEU  ALA
GTT  TCA  GCA  TCC  CTT  ATT  ATG  GGG  AAG  CTA  GGT  TCC  TAT  TCA  AGA  CAA  AAC  AGC  TTA  GCT

2702
THR  ALA  LEU  ARG  GLU  MET  GLY  ARG  ILE  GLU  LYS  THR  ILE  PHE  ILE  LEU  ASN  TYR  ILE  SER
ACA  GCC  TTA  CGT  GAG  ATG  GGC  CGA  ATA  GAA  AAA  ACG  ATC  TTT  ATT  TTG  AAT  TAT  ATA  TCG

2762
ASP  GLU  SER  LEU  ARG  ARG  LYS  ILE  GLN  ARG  GLY  LEU  ASN  LYS  GLY  GLU  ALA  MET  ASN  GLY
GAT  GAA  TCA  TTA  AGA  AGA  AAA  ATA  CAA  AGA  GGA  TTG  AAT  AAA  GGA  GAA  GCC  ATG  AAT  GGA

2822
LEU  ALA  ARG  ALA  ILE  PHE  PHE  GLY  LYS  GLN  GLY  GLU  LEU  ARG  GLU  ARG  THR  ILE  GLN  HIS
TTG  GCA  AGA  GCT  ATT  TTC  TTC  GGA  AAA  CAA  GGT  GAG  CTT  AGA  GAA  CGC  ACC  ATA  CAG  CAT

2882
GLN  LEU  GLN  ARG  ALA  SER  ALA  LEU  ASN  ILE  ILE  ILE  ASN  ALA  ILE  SER  ILE  TRP  ASN  THR
CAA  TTG  CAA  AGA  GCC  AGT  GCT  TTA  AAC  ATA  ATT  ATC  AAT  GCT  ATA  AGT  ATT  TGG  AAT  ACT

2942
TCT  CCA  CCT  AAC  AAC  AGC  AGT  TGA  ATA  TAA  AAA  ACG  GAC  AGG  TAG  CTT  TAA  TGA  AGA  TTT
LEU  HIS  LEU  THR  THR  ALA  VAL  GLU  TYR  LYS  LYS  ARG  THR  GLY  SER  PHE  ASN  GLU  ASP  LEU
CTC  CAC  CTA  ACA  ACA  GCA  GTT  GAA  TAT  AAA  AAA  CGG  ACA  GGT  AGC  TTT  AAT  GAA  GAT  TTG

3002
LEU  HIS  HIS  MET  SER  PRO  LEU  GLY  TRP  GLU  HIS  ILE  ASN  LEU  LEU  GLY  GLU  TYR  HIS  PHE
TTA  CAC  CAT  ATG  TCG  CCC  TTA  GGT  TGG  GAA  CAT  ATT  AAT  TTA  CTA  GGA  GAA  TAC  CAT  TTT

3062
ASN  SER  GLU  LYS  VAL  VAL  SER  LEU  ASN  SER  LEU  ARG  PRO  LEU  LYS  LEU  SER
AAC  TCA  GAG  AAA  GTA  GTC  TCA  TTA  AAT  TCT  TTA  AGA  CCA  CTA  AAA  CTT  TCT  TAA  CGT  TG

3121
TTA  AAA  ACG  AGG  GAT  TCG  TCA  GGA  AAA  TAG  GCT  TAG  CGT  TGT  AAA  TCC  GCA  TTT  TCC  TGA

3181
CGC  TAC  CCC
```

LIST OF SEQUENCES: ii

```
                               SacI
                               GAGCTCTTCCTTCAACGCACTTCTGTACCAAGAGTTGTTGTC    42

CATTTGATCACTAACAATAGCTTCCCCTGCTTTCTTCAAGCCCTTTGTCATAAAATCGTTAGATTTTCA          111

TCATAAAAATACGAGAAAGACAACAGGAAGACCGCAAATTTTCTTTTCTTTTCCTAGGTACACTGAATG          180

RBS              M   K   K   I   A   V   L   F   G   G
TAACCTTAAAAGAAAAAAGGAAAGGAAGAAAATGATGAAAAAATTGCCGTTTTATTTGGAGGG                 244

N   S   D   E   Y   S   V   S   L   T   S   A   A   S   V   I   Q   A   I   D
AATTCTCCAGAATACTCAGTGTCACTAACCTCAGCAGCAAGTGTGATCCAAGCTATTGAC                    304

P   L   K   Y   E   V   M   T   I   G   I   A   P   T   M   D   W   Y   W   Y
CCGCTGAAATATGAAGTAATGACCATTGGCATCGCACCAACAATGGATTGGTATTGGTAT                    364

Q   G   N   L   A   N   V   R   N   D   T   W   L   E   D   H   K   N   C   H
CAAGGAAACCTCGCGAATGTTCGCAATGATACTTGGCTAGAAGATCACAAAAACTGTCAC                    424

Q   L   T   F   S   S   Q   G   F   I   L   G   E   K   R   I   V   P   D   V
CAGCTGACTTTTTCTAGCCAAGGATTTATATTAGGAGAAAAACGAATCGTCCCTGATGTC                    484

L   F   P   V   L   H   G   K   Y   G   E   D   G   C   I   Q   G   L   L   E
CTCTTTCCAGTCTTGCATGGGAAGTATGGCGAGGATGGCTGTATCCAAGGACTGCTTGAA                    544

L   M   N   L   P   Y   V   G   C   H   V   A   A   S   A   L   C   M   N   K
CTAATGAACCTGCCTTATGTTGGTTGCCATGTCGCTGCCTCCGCATTATGTATGAACAAA                    604

W   L   L   H   Q   L   A   D   T   M   G   I   A   S   A   P   T   L   L   L
TGGCTCTTGCATCAACTTGCTGATACCATGGGAATCGCTAGTGCTCCCACTTTGCTTTTA                    664
```

```
         S   R   Y   E   N   D   P   A   T   I   D   R   F   I   Q   D   H   G   F   P
         TCCCGCTATGAAAACGATCCTGCCACAATCGATCGTTTTATTCAAGACCATGGATTCCCG                724

I   F   I   K   P   N   E   A   G   S   S   K   G   I   T   K   V   T   D   K
         ATCTTTATCAAGCCGAATGAAGCCGGTTCTTCAAAAGGGATCACAAAAGTAACTGACAAA                784

T   A   L   Q   S   A   L   T   T   A   F   A   Y   G   S   T   V   L   I   Q
         ACAGCGCTCCAATCTGCATTAACGACTGCTTTTGCTTACGGTTCTACTGTGTTGATCCAA                844

K   A   I   A   G   I   E   I   G   C   G   I   L   G   N   E   Q   L   T   I
         AAGGCGATAGCGGGTATTGAAATTGGCTGCGGCATCTTAGGAAATGAGCAATTGACGATT                904

G   A   C   D   A   I   S   L   V   D   G   F   F   D   F   E   E   K   Y   Q
         GGTGCTTGTGATGCGATTTCTCTTGTCGACGGTTTTTTTGATTTTGAAGAGAAATACCAA                964

L   I   S   A   T   I   T   V   P   A   P   L   P   L   A   L   E   S   Q   I
         TTAATCAGCGCCACGATCACTGTCCCAGCACCATTGCCTCTCGCGCTTGAATCACAGATC                1024

K   E   Q   A   Q   L   L   Y   R   N   L   G   L   T   G   L   A   R   I   D
         AAGGAGCAGGCACAGCTGCTTTATCGAAACTTGGGATTGACGGGTCTGGCTCGAATCGAT                1084

F   F   V   T   N   Q   G   A   I   Y   L   N   E   I   N   T   M   P   G   F
         TTTTTCGTCACCAATCAAGGAGCGATTTATTTAAACGAAATCAACACCATGCCGGGATTT                1144

T   G   H   S   R   Y   P   A   M   M   A   E   V   G   L   S   Y   E   I   L
         ACTGGGCACTCCCGCTACCCAGCTATGATGGCGGAAGTCGGGTTATCCTACGAAATATTA                1204

V   E   Q   L   E   A   L   A   E   E   D   K   R   *
         GTAGAGCAATTGATTGCACTGGCAGAGGAGGACAAACGATGAACACATTACAATTGATCAATA             1267

AAACCATCCATTGAAAAAAAATCAAGAGCCCCCGCACTTAGTGCTAGCTCCTTTTAGCGATCACGATG         1336

TTTACCTGCAG                                                                 1347
            PstI
```

---

We claim:

1. An isolated polynucleotide consisting of SEQ ID NO:9 or SEQ ID NO:10.

2. An isolated polynucleotide probe, which is optionally labelled and which hybridizes under the following conditions:

a reaction temperature of 65° C. overnight in a solution containing 0.1% SDS, 0.7% skimmed milk powder and 6×SSC followed by washing at 65° C. in 2×SSC and 0.1% SDS; or a reaction temperature of 60° C. overnight in a solution containing 0.1% SDS, 0.7% skimmed milk powder, 6×SSC followed by washing at 45° C. in 2×SSC and 0.1% SDS;

with the following:
(a) a polynucleotide encoding the protein of SEQ ID NO:2 (VanH), SEQ ID NO:6 (VanX), SEQ ID NO:8 (VanC), SEQ ID NO:12 (VanR), SEQ ID NO:14 (VanS), SEQ ID NO:19 (transposase), SEQ ID NO:21 (resolvase), SEQ ID NO:23 (VanY) or SEQ ID NO:25 (VanZ) or a combination thereof; or
(b) a polynucleotide from the plasmid pIP816, selected from the group consisting of a HindIII-EcoRI restriction fragment of about 7.3 kb in length, an EcoRI-XbaI restriction fragment of about 3.4 kb in length, and EcoRV-SacII restriction fragment of about 1.7 kb in length or a HindIII-EcoRI restriction fragment of about 3.3 kb in length, wherein said polynucleotide probe hybridizes specifically to a polynucleotide in a gram-positive bacterium having a sequence encoding a protein for resistance to vancomycin, teicoplanin, or both vancomycin and teicoplanin.

3. An isolated polynucleotide probe consisting essentially of a polynucleotide consisting of SEQ ID NO:9 or SEQ ID NO:10.

4. The probe of claim 2, wherein said gram-positive bacterium is a strain of enterococcus.

5. The probe of claim 4, wherein said strain of enterococcus is E. faecium 4147.

6. A process for detecting in a strain of bacteria the presence of a gene encoding a D-Ala-D-Ala ligase or a related enzyme involved in resistance to vancomycin, teicoplanin, or both vancomycin and teicoplanin, comprising:

(a) contacting a biological sample containing said strain of bacteria with a primer consisting essentially of the polynucleotide of claim 1,
(b) hybridizing said primer to nucleic acids from said strain of bacteria,
(c) extending said primer in the presence of a polymerase and dATP, dCTP, dTTP and dGTP to produce a double stranded polynucleotide,
(d) denaturing the polymerized double stranded polynucleotide,
(e) repeating steps (a)–(c) sufficiently to produce a detectable amount of amplified polynucleotide, and
(f) detecting said amplified polynucleotide,
wherein detection of an amplified product is indicative of the presence in said stain of bacteria of a gene encoding a D-Ala-D-Ala ligase or a related enzyme involved in resistance to vancomycin, teicoplanin, or both vancomycin and teicoplanin.

7. The process of claim 6, wherein the amplified product is obtained from a strain of bacteria resistant to vancomycin, teicoplanin, or both vancomycin and teicoplanin.

8. An isolated polynucleotide probe, which is optionally labelled and is selected from the group consisting of:
(a) a polynucleotide encoding the protein of SEQ ID NO:2 (VanH), SEQ ID NO:6 (VanX), SEQ ID NO:8 (VanC), SEQ ID NO:12 (VanR), SEQ ID NO:14 (VanS), SEQ ID NO:19 (transposase), SEQ ID NO:21 (resolvase), SEQ ID NO:23 (VanY) or SEQ ID NO:25 (VanZ) or a combination thereof;
(b) a polynucleotide from the plasmid pIP816, selected from the group consisting of a HindIII-EcoRI restriction fragment of about 7.3 kb in length, an EcoRI-XbaI restriction fragment of about 3.4 kb in length, and EcoRV-SacII restriction fragment of about 1.7 kb in length or a HindIII-EcoRI restriction fragment of about 3.3 kb in length;
(c) a polynucleotide complementary to the polynucleotide of (a) or (b); and
(d) mixtures thereof;
wherein said polynucleotide probe hybridizes specifically to a polynucleotide in a gram-positive bacterium having a sequence encoding a protein for resistance to vancomycin, teicoplanin, or both vancomycin and teicoplanin.

* * * * *

SEQUENCE LISTING ( 1 ) GENERAL INFORMATION:

( i i i ) NUMBER OF SEQUENCES: 54

( 2 ) INFORMATION FOR SEQ ID NO:1:

( i ) SEQUENCE CHARACTERISTICS:
        ( A ) LENGTH: 966 base pairs
        ( B ) TYPE: nucleic acid
        ( C ) STRANDEDNESS: unknown
        ( D ) TOPOLOGY: linear ( i i ) MOLECULE TYPE: DNA (genomic)

( i x ) FEATURE:
        ( A ) NAME/KEY: CDS
        ( B ) LOCATION: 1..966

( x i ) SEQUENCE DESCRIPTION: SEQ ID NO:1:

```
ATG  AAT  AAC  ATC  GGC  ATT  ACT  GTT  TAT  GGA  TGT  GAG  CAG  GAT  GAG  GCA         48
Met  Asn  Asn  Ile  Gly  Ile  Thr  Val  Tyr  Gly  Cys  Glu  Gln  Asp  Glu  Ala
 1                   5                   10                  15

GAT  GCA  TTC  CAT  GCT  CTT  TCG  CCT  CGC  TTT  GGC  GTT  ATG  GCA  ACG  ATA         96
Asp  Ala  Phe  His  Ala  Leu  Ser  Pro  Arg  Phe  Gly  Val  Met  Ala  Thr  Ile
                      20                  25                  30

ATT  AAC  GCC  AAC  GTG  TCG  GAA  TCC  AAC  GCC  AAA  TCC  GCG  CCT  TTC  AAT         144
Ile  Asn  Ala  Asn  Val  Ser  Glu  Ser  Asn  Ala  Lys  Ser  Ala  Pro  Phe  Asn
              35                  40                  45

CAA  TGT  ATC  AGT  GTG  GGA  CAT  AAA  TCA  GAG  ATT  TCC  GCC  TCT  ATT  CTT         192
Gln  Cys  Ile  Ser  Val  Gly  His  Lys  Ser  Glu  Ile  Ser  Ala  Ser  Ile  Leu
      50                  55                  60

CTT  GCG  CTG  AAG  AGA  GCC  GGT  GTG  AAA  TAT  ATT  TCT  ACC  CGA  AGC  ATC         240
Leu  Ala  Leu  Lys  Arg  Ala  Gly  Val  Lys  Tyr  Ile  Ser  Thr  Arg  Ser  Ile
 65                  70                  75                  80
```

```
GGC  TGC  AAT  CAT  ATA  GAT  ACA  ACT  GCT  GCT  AAG  AGA  ATG  GGC  ATC  ACT      288
Gly  Cys  Asn  His  Ile  Asp  Thr  Thr  Ala  Ala  Lys  Arg  Met  Gly  Ile  Thr
               85                          90                           95

GTC  GAC  AAT  GTG  GCG  TAC  TCG  CCG  GAT  AGC  GTT  GCC  GAT  TAT  ACT  ATG      336
Val  Asp  Asn  Val  Ala  Tyr  Ser  Pro  Asp  Ser  Val  Ala  Asp  Tyr  Thr  Met
              100                         105                         110

ATG  CTA  ATT  CTT  ATG  GCA  GTA  CGC  AAC  GTA  AAA  TCG  ATT  GTG  CGC  TCT      384
Met  Leu  Ile  Leu  Met  Ala  Val  Arg  Asn  Val  Lys  Ser  Ile  Val  Arg  Ser
              115                         120                         125

GTG  GAA  AAA  CAT  GAT  TTC  AGG  TTG  GAC  AGC  GAC  CGT  GGC  AAG  GTA  CTC      432
Val  Glu  Lys  His  Asp  Phe  Arg  Leu  Asp  Ser  Asp  Arg  Gly  Lys  Val  Leu
     130                         135                         140

AGC  GAC  ATG  ACA  GTT  GGT  GTG  GTG  GGA  ACG  GGC  CAG  ATA  GGC  AAA  GCG      480
Ser  Asp  Met  Thr  Val  Gly  Val  Val  Gly  Thr  Gly  Gln  Ile  Gly  Lys  Ala
145                         150                         155                    160

GTT  ATT  GAG  CGG  CTG  CGA  GGA  TTT  GGA  TGT  AAA  GTG  TTG  GCT  TAT  AGT      528
Val  Ile  Glu  Arg  Leu  Arg  Gly  Phe  Gly  Cys  Lys  Val  Leu  Ala  Tyr  Ser
                    165                         170                         175

CGC  AGC  CGA  AGT  ATA  GAG  GTA  AAC  TAT  GTA  CCG  TTT  GAT  GAG  TTG  CTG      576
Arg  Ser  Arg  Ser  Ile  Glu  Val  Asn  Tyr  Val  Pro  Phe  Asp  Glu  Leu  Leu
               180                         185                         190

CAA  AAT  AGC  GAT  ATC  GTT  ACG  CTT  CAT  GTG  CCG  CTC  AAT  ACG  GAT  ACG      624
Gln  Asn  Ser  Asp  Ile  Val  Thr  Leu  His  Val  Pro  Leu  Asn  Thr  Asp  Thr
          195                         200                         205

CAC  TAT  ATT  ATC  AGC  CAC  GAA  CAA  ATA  CAG  AGA  ATG  AAG  CAA  GGA  GCA      672
His  Tyr  Ile  Ile  Ser  His  Glu  Gln  Ile  Gln  Arg  Met  Lys  Gln  Gly  Ala
     210                         215                         220

TTT  CTT  ATC  AAT  ACT  GGG  CGC  GGT  CCA  CTT  GTA  GAT  ACC  TAT  GAG  TTG      720
Phe  Leu  Ile  Asn  Thr  Gly  Arg  Gly  Pro  Leu  Val  Asp  Thr  Tyr  Glu  Leu
225                         230                         235                    240

GTT  AAA  GCA  TTA  GAA  AAC  GGG  AAA  CTG  GGC  GGT  GCC  GCA  TTG  GAT  GTA      768
Val  Lys  Ala  Leu  Glu  Asn  Gly  Lys  Leu  Gly  Gly  Ala  Ala  Leu  Asp  Val
               245                         250                         255

TTG  GAA  GGA  GAG  GAA  GAG  TTT  TTC  TAC  TCT  GAT  TGC  ACC  CAA  AAA  CCA      816
Leu  Glu  Gly  Glu  Glu  Glu  Phe  Phe  Tyr  Ser  Asp  Cys  Thr  Gln  Lys  Pro
          260                         265                         270

ATT  GAT  AAT  CAA  TTT  TTA  CTT  AAA  CTT  CAA  AGA  ATG  CCT  AAC  GTG  ATA      864
Ile  Asp  Asn  Gln  Phe  Leu  Leu  Lys  Leu  Gln  Arg  Met  Pro  Asn  Val  Ile
     275                         280                         285

ATC  ACA  CCG  CAT  ACG  GCC  TAT  TAT  ACC  GAG  CAA  GCG  TTG  CGT  GAT  ACC      912
Ile  Thr  Pro  His  Thr  Ala  Tyr  Tyr  Thr  Glu  Gln  Ala  Leu  Arg  Asp  Thr
290                         295                         300

GTT  GAA  AAA  ACC  ATT  AAA  AAC  TGT  TTG  GAT  TTT  GAA  AGG  AGA  CAG  GAG      960
Val  Glu  Lys  Thr  Ile  Lys  Asn  Cys  Leu  Asp  Phe  Glu  Arg  Arg  Gln  Glu
305                         310                         315                    320

CAT  GAA                                                                             966
His  Glu
```

( 2 ) INFORMATION FOR SEQ ID NO:2:

( i ) SEQUENCE CHARACTERISTICS:
        ( A ) LENGTH: 322 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met  Asn  Asn  Ile  Gly  Ile  Thr  Val  Tyr  Gly  Cys  Glu  Gln  Asp  Glu  Ala
 1                    5                         10                          15

Asp  Ala  Phe  His  Ala  Leu  Ser  Pro  Arg  Phe  Gly  Val  Met  Ala  Thr  Ile
```

|  |  |  | 20 |  |  |  |  | 25 |  |  |  |  | 30 |  |
|---|---|---|---|---|---|---|---|---|---|---|---|---|---|---|

Ile Asn Ala Asn Val Ser Glu Ser Asn Ala Lys Ser Ala Pro Phe Asn
            35                      40                  45

Gln Cys Ile Ser Val Gly His Lys Ser Glu Ile Ser Ala Ser Ile Leu
        50                  55                  60

Leu Ala Leu Lys Arg Ala Gly Val Lys Tyr Ile Ser Thr Arg Ser Ile
65                  70                  75                      80

Gly Cys Asn His Ile Asp Thr Thr Ala Ala Lys Arg Met Gly Ile Thr
                85                      90                  95

Val Asp Asn Val Ala Tyr Ser Pro Asp Ser Val Ala Asp Tyr Thr Met
            100                 105                 110

Met Leu Ile Leu Met Ala Val Arg Asn Val Lys Ser Ile Val Arg Ser
        115                 120                 125

Val Glu Lys His Asp Phe Arg Leu Asp Ser Asp Arg Gly Lys Val Leu
    130                 135                 140

Ser Asp Met Thr Val Gly Val Val Gly Thr Gly Gln Ile Gly Lys Ala
145                 150                 155                 160

Val Ile Glu Arg Leu Arg Gly Phe Gly Cys Lys Val Leu Ala Tyr Ser
                165                 170                 175

Arg Ser Arg Ser Ile Glu Val Asn Tyr Val Pro Phe Asp Glu Leu Leu
            180                 185                 190

Gln Asn Ser Asp Ile Val Thr Leu His Val Pro Leu Asn Thr Asp Thr
        195                 200                 205

His Tyr Ile Ile Ser His Glu Gln Ile Gln Arg Met Lys Gln Gly Ala
    210                 215                 220

Phe Leu Ile Asn Thr Gly Arg Gly Pro Leu Val Asp Thr Tyr Glu Leu
225                 230                 235                 240

Val Lys Ala Leu Glu Asn Gly Lys Leu Gly Gly Ala Ala Leu Asp Val
                245                 250                 255

Leu Glu Gly Glu Glu Glu Phe Phe Tyr Ser Asp Cys Thr Gln Lys Pro
            260                 265                 270

Ile Asp Asn Gln Phe Leu Leu Lys Leu Gln Arg Met Pro Asn Val Ile
        275                 280                 285

Ile Thr Pro His Thr Ala Tyr Tyr Thr Glu Gln Ala Leu Arg Asp Thr
    290                 295                 300

Val Glu Lys Thr Ile Lys Asn Cys Leu Asp Phe Glu Arg Arg Gln Glu
305                 310                 315                 320

His Glu ( 2 ) INFORMATION FOR SEQ ID NO:3:

( i ) SEQUENCE CHARACTERISTICS:
        ( A ) LENGTH: 1029 base pairs
        ( B ) TYPE: nucleic acid
        ( C ) STRANDEDNESS: unknown
        ( D ) TOPOLOGY: linear ( i i ) MOLECULE TYPE: DNA (genomic)

( i x ) FEATURE:
        ( A ) NAME/KEY: CDS
        ( B ) LOCATION: 1..1029

( x i ) SEQUENCE DESCRIPTION: SEQ ID NO:3:

ATG AAT AGA ATA AAA GTT GCA ATA CTG TTT GGG GGT TGC TCA GAG GAG     48
Met Asn Arg Ile Lys Val Ala Ile Leu Phe Gly Gly Cys Ser Glu Glu
 1               5                  10                  15

CAT GAC GTA TCG GTA AAA TCT GCA ATA GAG ATA GCC GCT AAC ATT AAT     96

|     |     |     |     |     |     |     |     |     |     |     |     |     |     |      |
| --- | --- | --- | --- | --- | --- | --- | --- | --- | --- | --- | --- | --- | --- | ---- |
| His | Asp | Val | Ser | Val | Lys | Ser | Ala | Ile | Glu | Ile | Ala | Ala | Asn | Ile Asn |
|     |     |     | 20  |     |     |     | 25  |     |     |     | 30  |     |     |      |
| AAA | GAA | AAA | TAC | GAG | CCG | TTA | TAC | ATT | GGA | ATT | ACG | AAA | TCT | GGT GTA | 144 |
| Lys | Glu | Lys | Tyr | Glu | Pro | Leu | Tyr | Ile | Gly | Ile | Thr | Lys | Ser | Gly Val |
|     |     | 35  |     |     |     | 40  |     |     |     | 45  |     |     |     |      |
| TGG | AAA | ATG | TGC | GAA | AAA | CCT | TGC | GCG | GAA | TGG | GAA | AAC | GAC | AAT TGC | 192 |
| Trp | Lys | Met | Cys | Glu | Lys | Pro | Cys | Ala | Glu | Trp | Glu | Asn | Asp | Asn Cys |
|     | 50  |     |     |     | 55  |     |     |     | 60  |     |     |     |     |      |
| TAT | TCA | GCT | GTA | CTC | TCG | CCG | GAT | AAA | AAA | ATG | CAC | GGA | TTA | CTT GTT | 240 |
| Tyr | Ser | Ala | Val | Leu | Ser | Pro | Asp | Lys | Lys | Met | His | Gly | Leu | Leu Val |
| 65  |     |     |     | 70  |     |     |     | 75  |     |     |     |     |     | 80   |
| AAA | AAG | AAC | CAT | GAA | TAT | GAA | ATC | AAC | CAT | GTT | GAT | GTA | GCA | TTT TCA | 288 |
| Lys | Lys | Asn | His | Glu | Tyr | Glu | Ile | Asn | His | Val | Asp | Val | Ala | Phe Ser |
|     |     |     |     | 85  |     |     |     |     | 90  |     |     |     |     | 95   |
| GCT | TTG | CAT | GGC | AAG | TCA | GGT | GAA | GAT | GGA | TCC | ATA | CAA | GGT | CTG TTT | 336 |
| Ala | Leu | His | Gly | Lys | Ser | Gly | Glu | Asp | Gly | Ser | Ile | Gln | Gly | Leu Phe |
|     |     |     | 100 |     |     |     |     | 105 |     |     |     |     | 110 |      |
| GAA | TTG | TCC | GGT | ATC | CCT | TTT | GTA | GGC | TGC | GAT | ATT | CAA | AGC | TCA GCA | 384 |
| Glu | Leu | Ser | Gly | Ile | Pro | Phe | Val | Gly | Cys | Asp | Ile | Gln | Ser | Ser Ala |
|     |     | 115 |     |     |     |     | 120 |     |     |     |     | 125 |     |      |
| ATT | TGT | ATG | GAC | AAA | TCG | TTG | ACA | TAC | ATC | GTT | GCG | AAA | AAT | GCT GGG | 432 |
| Ile | Cys | Met | Asp | Lys | Ser | Leu | Thr | Tyr | Ile | Val | Ala | Lys | Asn | Ala Gly |
|     | 130 |     |     |     |     | 135 |     |     |     |     | 140 |     |     |      |
| ATA | GCT | ACT | CCC | GCC | TTT | TGG | GTT | ATT | AAT | AAA | GAT | GAT | AGG | CCG GTG | 480 |
| Ile | Ala | Thr | Pro | Ala | Phe | Trp | Val | Ile | Asn | Lys | Asp | Asp | Arg | Pro Val |
| 145 |     |     |     |     | 150 |     |     |     |     | 155 |     |     |     | 160  |
| GCA | GCT | ACG | TTT | ACC | TAT | CCT | GTT | TTT | GTT | AAG | CCG | GCG | CGT | TCA GGC | 528 |
| Ala | Ala | Thr | Phe | Thr | Tyr | Pro | Val | Phe | Val | Lys | Pro | Ala | Arg | Ser Gly |
|     |     |     |     | 165 |     |     |     |     | 170 |     |     |     |     | 175  |
| TCA | TCC | TTC | GGT | GTG | AAA | AAA | GTC | AAT | AGC | GCG | GAC | GAA | TTG | GAC TAC | 576 |
| Ser | Ser | Phe | Gly | Val | Lys | Lys | Val | Asn | Ser | Ala | Asp | Glu | Leu | Asp Tyr |
|     |     |     | 180 |     |     |     |     | 185 |     |     |     |     | 190 |      |
| GCA | ATT | GAA | TCG | GCA | AGA | CAA | TAT | GAC | AGC | AAA | ATC | TTA | ATT | GAG CAG | 624 |
| Ala | Ile | Glu | Ser | Ala | Arg | Gln | Tyr | Asp | Ser | Lys | Ile | Leu | Ile | Glu Gln |
|     |     | 195 |     |     |     |     | 200 |     |     |     |     | 205 |     |      |
| GCT | GTT | TCG | GGC | TGT | GAG | GTC | GGT | TGT | GCG | GTA | TTG | GGA | AAC | AGT GCC | 672 |
| Ala | Val | Ser | Gly | Cys | Glu | Val | Gly | Cys | Ala | Val | Leu | Gly | Asn | Ser Ala |
|     | 210 |     |     |     |     | 215 |     |     |     |     | 220 |     |     |      |
| GCG | TTA | GTT | GTT | GGC | GAG | GTG | GAC | CAA | ATC | AGG | CTG | CAG | TAC | GGA ATC | 720 |
| Ala | Leu | Val | Val | Gly | Glu | Val | Asp | Gln | Ile | Arg | Leu | Gln | Tyr | Gly Ile |
| 225 |     |     |     |     | 230 |     |     |     |     | 235 |     |     |     | 240  |
| TTT | CGT | ATT | CAT | CAG | GAA | GTC | GAG | CCG | GAA | AAA | GGC | TCT | GAA | AAC GCA | 768 |
| Phe | Arg | Ile | His | Gln | Glu | Val | Glu | Pro | Glu | Lys | Gly | Ser | Glu | Asn Ala |
|     |     |     |     | 245 |     |     |     |     | 250 |     |     |     |     | 255  |
| GTT | ATA | ACC | GTT | CCC | GCA | GAC | CTT | TCA | GCA | GAG | GAG | CGA | GGA | CGG ATA | 816 |
| Val | Ile | Thr | Val | Pro | Ala | Asp | Leu | Ser | Ala | Glu | Glu | Arg | Gly | Arg Ile |
|     |     |     | 260 |     |     |     |     | 265 |     |     |     |     | 270 |      |
| CAG | GAA | ACG | GCA | AAA | AAA | ATA | TAT | AAA | GCG | CTC | GGC | TGT | AGA | GGT CTA | 864 |
| Gln | Glu | Thr | Ala | Lys | Lys | Ile | Tyr | Lys | Ala | Leu | Gly | Cys | Arg | Gly Leu |
|     |     | 275 |     |     |     |     | 280 |     |     |     |     | 285 |     |      |
| GCC | CGT | GTG | GAT | ATG | TTT | TTA | CAA | GAT | AAC | GGC | CGC | ATT | GTA | CTG AAC | 912 |
| Ala | Arg | Val | Asp | Met | Phe | Leu | Gln | Asp | Asn | Gly | Arg | Ile | Val | Leu Asn |
|     | 290 |     |     |     |     | 295 |     |     |     |     | 300 |     |     |      |
| GAA | GTC | AAT | ACT | CTG | CCC | GGT | TTC | ACG | TCA | TAC | AGT | CGT | TAT | CCC CGT | 960 |
| Glu | Val | Asn | Thr | Leu | Pro | Gly | Phe | Thr | Ser | Tyr | Ser | Arg | Tyr | Pro Arg |
| 305 |     |     |     |     | 310 |     |     |     |     | 315 |     |     |     | 320  |
| ATG | ATG | GCC | GCT | GCA | GGT | ATT | GCA | CTT | CCC | GAA | CTG | ATT | GAC | CGC TTG | 1008 |
| Met | Met | Ala | Ala | Ala | Gly | Ile | Ala | Leu | Pro | Glu | Leu | Ile | Asp | Arg Leu |
|     |     |     |     | 325 |     |     |     |     | 330 |     |     |     |     | 335  |
| ATC | GTA | TTA | GCG | TTA | AAG | GGG |     |     |     |     |     |     |     |      | 1029 |

Ile Val Leu Ala Leu Lys Gly
340

(2) INFORMATION FOR SEQ ID NO:4:

(i) SEQUENCE CHARACTERISTICS:
        (A) LENGTH: 343 amino acids
        (B) TYPE: amino acid
        (D) TOPOLOGY: linear (ii) MOLECULE TYPE: protein (xi) SEQUENCE DESCRIPTION: SEQ ID NO:4:

Met Asn Arg Ile Lys Val Ala Ile Leu Phe Gly Gly Cys Ser Glu
1               5                   10                  15

His Asp Val Ser Val Lys Ser Ala Ile Glu Ile Ala Ala Asn Ile Asn
            20                  25                  30

Lys Glu Lys Tyr Glu Pro Leu Tyr Ile Gly Ile Thr Lys Ser Gly Val
            35                  40                  45

Trp Lys Met Cys Glu Lys Pro Cys Ala Glu Trp Glu Asn Asp Asn Cys
        50              55                  60

Tyr Ser Ala Val Leu Ser Pro Asp Lys Lys Met His Gly Leu Leu Val
65              70                  75                          80

Lys Lys Asn His Glu Tyr Glu Ile Asn His Val Asp Val Ala Phe Ser
                85                  90                  95

Ala Leu His Gly Lys Ser Gly Glu Asp Gly Ser Ile Gln Gly Leu Phe
                100                 105                 110

Glu Leu Ser Gly Ile Pro Phe Val Gly Cys Asp Ile Gln Ser Ser Ala
            115                 120                 125

Ile Cys Met Asp Lys Ser Leu Thr Tyr Ile Val Ala Lys Asn Ala Gly
    130                 135                 140

Ile Ala Thr Pro Ala Phe Trp Val Ile Asn Lys Asp Asp Arg Pro Val
145                 150                 155                 160

Ala Ala Thr Phe Thr Tyr Pro Val Phe Val Lys Pro Ala Arg Ser Gly
                165                 170                 175

Ser Ser Phe Gly Val Lys Lys Val Asn Ser Ala Asp Glu Leu Asp Tyr
            180                 185                 190

Ala Ile Glu Ser Ala Arg Gln Tyr Asp Ser Lys Ile Leu Ile Glu Gln
        195                 200                 205

Ala Val Ser Gly Cys Glu Val Gly Cys Ala Val Leu Gly Asn Ser Ala
210                 215                 220

Ala Leu Val Val Gly Glu Val Asp Gln Ile Arg Leu Gln Tyr Gly Ile
225                 230                 235                 240

Phe Arg Ile His Gln Glu Val Glu Pro Glu Lys Gly Ser Glu Asn Ala
                245                 250                 255

Val Ile Thr Val Pro Ala Asp Leu Ser Ala Glu Glu Arg Gly Arg Ile
            260                 265                 270

Gln Glu Thr Ala Lys Lys Ile Tyr Lys Ala Leu Gly Cys Arg Gly Leu
        275                 280                 285

Ala Arg Val Asp Met Phe Leu Gln Asp Asn Gly Arg Ile Val Leu Asn
    290                 295                 300

Glu Val Asn Thr Leu Pro Gly Phe Thr Ser Tyr Ser Arg Tyr Pro Arg
305                 310                 315                 320

Met Met Ala Ala Ala Gly Ile Ala Leu Pro Glu Leu Ile Asp Arg Leu
                325                 330                 335

Ile Val Leu Ala Leu Lys Gly
            340

( 2 ) INFORMATION FOR SEQ ID NO:5:

( i ) SEQUENCE CHARACTERISTICS:
        ( A ) LENGTH: 606 base pairs
        ( B ) TYPE: nucleic acid
        ( C ) STRANDEDNESS: unknown
        ( D ) TOPOLOGY: linear ( i i ) MOLECULE TYPE: DNA (genomic)

( i x ) FEATURE:
        ( A ) NAME/KEY: CDS
        ( B ) LOCATION: 1..606

( x i ) SEQUENCE DESCRIPTION: SEQ ID NO:5:

```
ATG GAA ATA GGA TTT ACT TTT TTA GAT GAA ATA GTA CAC GGT GTT CGT        48
Met Glu Ile Gly Phe Thr Phe Leu Asp Glu Ile Val His Gly Val Arg
 1               5                  10                  15

TGG GAC GCT AAA TAT GCC ACT TGG GAT AAT TTC ACC GGA AAA CCG GTT        96
Trp Asp Ala Lys Tyr Ala Thr Trp Asp Asn Phe Thr Gly Lys Pro Val
             20                  25                  30

GAC GGT TAT GAA GTA AAT CGC ATT GTA GGG ACA TAC GAG TTG GCT GAA       144
Asp Gly Tyr Glu Val Asn Arg Ile Val Gly Thr Tyr Glu Leu Ala Glu
         35                  40                  45

TCG CTT TTG AAG GCA AAA GAA CTG GCT GCT ACC CAA GGG TAC GGA TTG       192
Ser Leu Leu Lys Ala Lys Glu Leu Ala Ala Thr Gln Gly Tyr Gly Leu
 50                  55                  60

CTT CTA TGG GAC GGT TAC CGT CCT AAG CGT GCT GTA AAC TGT TTT ATG       240
Leu Leu Trp Asp Gly Tyr Arg Pro Lys Arg Ala Val Asn Cys Phe Met
 65                  70                  75                  80

CAA TGG GCT GCA CAG CCG GAA AAT AAC CTG ACA AAG GAA AGT TAT TAT       288
Gln Trp Ala Ala Gln Pro Glu Asn Asn Leu Thr Lys Glu Ser Tyr Tyr
                 85                  90                  95

CCC AAT ATT GAC CGA ACT GAG ATG ATT TCA AAA GGA TAC GTG GCT TCA       336
Pro Asn Ile Asp Arg Thr Glu Met Ile Ser Lys Gly Tyr Val Ala Ser
             100                 105                 110

AAA TCA AGC CAT AGC CGC GGC AGT GCC ATT GAT CTT ACG CTT TAT CGA       384
Lys Ser Ser His Ser Arg Gly Ser Ala Ile Asp Leu Thr Leu Tyr Arg
         115                 120                 125

TTA GAC ACG GGT GAG CTT GTA CCA ATG GGG AGC CGA TTT GAT TTT ATG       432
Leu Asp Thr Gly Glu Leu Val Pro Met Gly Ser Arg Phe Asp Phe Met
 130                 135                 140

GAT GAA CGC TCT CAT CAT GCG GCA AAT GGA ATA TCA TGC AAT GAA GCG       480
Asp Glu Arg Ser His His Ala Ala Asn Gly Ile Ser Cys Asn Glu Ala
 145                 150                 155                 160

CAA AAT CGC AGA CGT TTG CGC TCC ATC ATG GAA AAC AGT GGG TTT GAA       528
Gln Asn Arg Arg Arg Leu Arg Ser Ile Met Glu Asn Ser Gly Phe Glu
                 165                 170                 175

GCA TAT AGC CTC GAA TGG TGG CAC TAT GTA TTA AGA GAC GAA CCA TAC       576
Ala Tyr Ser Leu Glu Trp Trp His Tyr Val Leu Arg Asp Glu Pro Tyr
             180                 185                 190

CCC AAT AGC TAT TTT GAT TTC CCC GTT AAA                               606
Pro Asn Ser Tyr Phe Asp Phe Pro Val Lys
         195                 200
```

( 2 ) INFORMATION FOR SEQ ID NO:6:

( i ) SEQUENCE CHARACTERISTICS:
        ( A ) LENGTH: 202 amino acids
        ( B ) TYPE: amino acid
        ( D ) TOPOLOGY: linear ( i i ) MOLECULE TYPE: protein ( x i ) SEQUENCE DESCRIPTION: SEQ ID NO:6:

| | | | | | | | | | | | | | | |
|---|---|---|---|---|---|---|---|---|---|---|---|---|---|---|
| Met | Glu | Ile | Gly | Phe | Thr | Phe | Leu | Asp | Glu | Ile | Val | His | Gly | Val | Arg |
| 1 | | | | 5 | | | | | 10 | | | | | 15 | |

| Trp | Asp | Ala | Lys | Tyr | Ala | Thr | Trp | Asp | Asn | Phe | Thr | Gly | Lys | Pro | Val |
|---|---|---|---|---|---|---|---|---|---|---|---|---|---|---|---|
| | | | 20 | | | | | 25 | | | | | 30 | | |

| Asp | Gly | Tyr | Glu | Val | Asn | Arg | Ile | Val | Gly | Thr | Tyr | Glu | Leu | Ala | Glu |
|---|---|---|---|---|---|---|---|---|---|---|---|---|---|---|---|
| | | | 35 | | | | | 40 | | | | | 45 | | |

| Ser | Leu | Leu | Lys | Ala | Lys | Glu | Leu | Ala | Ala | Thr | Gln | Gly | Tyr | Gly | Leu |
|---|---|---|---|---|---|---|---|---|---|---|---|---|---|---|---|
| | 50 | | | | | 55 | | | | | 60 | | | | |

| Leu | Leu | Trp | Asp | Gly | Tyr | Arg | Pro | Lys | Arg | Ala | Val | Asn | Cys | Phe | Met |
|---|---|---|---|---|---|---|---|---|---|---|---|---|---|---|---|
| 65 | | | | | 70 | | | | | 75 | | | | | 80 |

| Gln | Trp | Ala | Ala | Gln | Pro | Glu | Asn | Asn | Leu | Thr | Lys | Glu | Ser | Tyr | Tyr |
|---|---|---|---|---|---|---|---|---|---|---|---|---|---|---|---|
| | | | | 85 | | | | | 90 | | | | | 95 | |

| Pro | Asn | Ile | Asp | Arg | Thr | Glu | Met | Ile | Ser | Lys | Gly | Tyr | Val | Ala | Ser |
|---|---|---|---|---|---|---|---|---|---|---|---|---|---|---|---|
| | | | 100 | | | | | 105 | | | | | 110 | | |

| Lys | Ser | Ser | His | Ser | Arg | Gly | Ser | Ala | Ile | Asp | Leu | Thr | Leu | Tyr | Arg |
|---|---|---|---|---|---|---|---|---|---|---|---|---|---|---|---|
| | | | 115 | | | | | 120 | | | | | 125 | | |

| Leu | Asp | Thr | Gly | Glu | Leu | Val | Pro | Met | Gly | Ser | Arg | Phe | Asp | Phe | Met |
|---|---|---|---|---|---|---|---|---|---|---|---|---|---|---|---|
| | | | 130 | | | | | 135 | | | | | 140 | | |

| Asp | Glu | Arg | Ser | His | His | Ala | Ala | Asn | Gly | Ile | Ser | Cys | Asn | Glu | Ala |
|---|---|---|---|---|---|---|---|---|---|---|---|---|---|---|---|
| 145 | | | | | 150 | | | | | 155 | | | | | 160 |

| Gln | Asn | Arg | Arg | Arg | Leu | Arg | Ser | Ile | Met | Glu | Asn | Ser | Gly | Phe | Glu |
|---|---|---|---|---|---|---|---|---|---|---|---|---|---|---|---|
| | | | | 165 | | | | | 170 | | | | | 175 | |

| Ala | Tyr | Ser | Leu | Glu | Trp | Trp | His | Tyr | Val | Leu | Arg | Asp | Glu | Pro | Tyr |
|---|---|---|---|---|---|---|---|---|---|---|---|---|---|---|---|
| | | | 180 | | | | | 185 | | | | | 190 | | |

| Pro | Asn | Ser | Tyr | Phe | Asp | Phe | Pro | Val | Lys |
|---|---|---|---|---|---|---|---|---|---|
| | | 195 | | | | | 200 | | |

( 2 ) INFORMATION FOR SEQ ID NO:7:

( i ) SEQUENCE CHARACTERISTICS:
        ( A ) LENGTH: 1347 base pairs
        ( B ) TYPE: nucleic acid
        ( C ) STRANDEDNESS: unknown
        ( D ) TOPOLOGY: unknown ( i i ) MOLECULE TYPE: DNA (genomic)

( i x ) FEATURE:
        ( A ) NAME/KEY: CDS
        ( B ) LOCATION: 215..1243

( x i ) SEQUENCE DESCRIPTION: SEQ ID NO:7:

```
GAGCTCTTCC TTCAACGCAC TTCTGTACCA AGAGTTGTTG TCCATTTGAT CACTAACAAT      60

AGCTTCCCCT GCTTTCTTCA AGCCCTTTGT CATAAAATCG TTAGATTTTC ATCATAAAAA     120

TACGAGAAAG ACAACAGGAA GACCGCAAAT TTTCTTTTCT TTTCCTAGGT ACACTGAATG     180

TAACCTTAAA AGAAAAAAGG AAAGGAAGAA AATG ATG AAA AAA ATT GCC GTT         232
                                    Met Lys Lys Ile Ala Val
                                      1               5
```

| TTA | TTT | GGA | GGG | AAT | TCT | CCA | GAA | TAC | TCA | GTG | TCA | CTA | ACC | TCA | GCA | 280 |
|---|---|---|---|---|---|---|---|---|---|---|---|---|---|---|---|---|
| Leu | Phe | Gly | Gly | Asn | Ser | Pro | Glu | Tyr | Ser | Val | Ser | Leu | Thr | Ser | Ala | |
| | | | 10 | | | | | 15 | | | | | 20 | | | |

| GCA | AGT | GTG | ATC | CAA | GCT | ATT | GAC | CCG | CTG | AAA | TAT | GAA | GTA | ATG | ACC | 328 |
|---|---|---|---|---|---|---|---|---|---|---|---|---|---|---|---|---|
| Ala | Ser | Val | Ile | Gln | Ala | Ile | Asp | Pro | Leu | Lys | Tyr | Glu | Val | Met | Thr | |
| | | | 25 | | | | | 30 | | | | | 35 | | | |

| ATT | GGC | ATC | GCA | CCA | ACA | ATG | GAT | TGG | TAT | TGG | TAT | CAA | GGA | AAC | CTC | 376 |
|---|---|---|---|---|---|---|---|---|---|---|---|---|---|---|---|---|
| Ile | Gly | Ile | Ala | Pro | Thr | Met | Asp | Trp | Tyr | Trp | Tyr | Gln | Gly | Asn | Leu | |
| | | | 40 | | | | | 45 | | | | | 50 | | | |

| | | | | | | | | | | | | | | | | |
|---|---|---|---|---|---|---|---|---|---|---|---|---|---|---|---|---|
| GCG | AAT | GTT | CGC | AAT | GAT | ACT | TGG | CTA | GAA | GAT | CAC | AAA | AAC | TGT | CAC | 424 |
| Ala | Asn | Val | Arg | Asn | Asp | Thr | Trp | Leu | Glu | Asp | His | Lys | Asn | Cys | His | |
| 55 | | | | 60 | | | | | 65 | | | | | | 70 | |
| CAG | CTG | ACT | TTT | TCT | AGC | CAA | GGA | TTT | ATA | TTA | GGA | GAA | AAA | CGA | ATC | 472 |
| Gln | Leu | Thr | Phe | Ser | Ser | Gln | Gly | Phe | Ile | Leu | Gly | Glu | Lys | Arg | Ile | |
| | | | | 75 | | | | | 80 | | | | | 85 | | |
| GTC | CCT | GAT | GTC | CTC | TTT | CCA | GTC | TTG | CAT | GGG | AAG | TAT | GGC | GAG | GAT | 520 |
| Val | Pro | Asp | Val | Leu | Phe | Pro | Val | Leu | His | Gly | Lys | Tyr | Gly | Glu | Asp | |
| | | | 90 | | | | | 95 | | | | | 100 | | | |
| GGC | TGT | ATC | CAA | GGA | CTG | CTT | GAA | CTA | ATG | AAC | CTG | CCT | TAT | GTT | GGT | 568 |
| Gly | Cys | Ile | Gln | Gly | Leu | Leu | Glu | Leu | Met | Asn | Leu | Pro | Tyr | Val | Gly | |
| | | 105 | | | | | 110 | | | | | 115 | | | | |
| TGC | CAT | GTC | GCT | GCC | TCC | GCA | TTA | TGT | ATG | AAC | AAA | TGG | CTC | TTG | CAT | 616 |
| Cys | His | Val | Ala | Ala | Ser | Ala | Leu | Cys | Met | Asn | Lys | Trp | Leu | Leu | His | |
| | 120 | | | | | 125 | | | | | 130 | | | | | |
| CAA | CTT | GCT | GAT | ACC | ATG | GGA | ATC | GCT | AGT | GCT | CCC | ACT | TTG | CTT | TTA | 664 |
| Gln | Leu | Ala | Asp | Thr | Met | Gly | Ile | Ala | Ser | Ala | Pro | Thr | Leu | Leu | Leu | |
| 135 | | | | | 140 | | | | | 145 | | | | | 150 | |
| TCC | CGC | TAT | GAA | AAC | GAT | CCT | GCC | ACA | ATC | GAT | CGT | TTT | ATT | CAA | GAC | 712 |
| Ser | Arg | Tyr | Glu | Asn | Asp | Pro | Ala | Thr | Ile | Asp | Arg | Phe | Ile | Gln | Asp | |
| | | | | 155 | | | | | 160 | | | | | 165 | | |
| CAT | GGA | TTC | CCG | ATC | TTT | ATC | AAG | CCG | AAT | GAA | GCC | GGT | TCT | TCA | AAA | 760 |
| His | Gly | Phe | Pro | Ile | Phe | Ile | Lys | Pro | Asn | Glu | Ala | Gly | Ser | Ser | Lys | |
| | | | 170 | | | | | 175 | | | | | 180 | | | |
| GGG | ATC | ACA | AAA | GTA | ACT | GAC | AAA | ACA | GCG | CTC | CAA | TCT | GCA | TTA | ACG | 808 |
| Gly | Ile | Thr | Lys | Val | Thr | Asp | Lys | Thr | Ala | Leu | Gln | Ser | Ala | Leu | Thr | |
| | | 185 | | | | | 190 | | | | | 195 | | | | |
| ACT | GCT | TTT | GCT | TAC | GGT | TCT | ACT | GTG | TTG | ATC | CAA | AAG | GCG | ATA | GCG | 856 |
| Thr | Ala | Phe | Ala | Tyr | Gly | Ser | Thr | Val | Leu | Ile | Gln | Lys | Ala | Ile | Ala | |
| | 200 | | | | | 205 | | | | | 210 | | | | | |
| GGT | ATT | GAA | ATT | GGC | TGC | GGC | ATC | TTA | GGA | AAT | GAG | CAA | TTG | ACG | ATT | 904 |
| Gly | Ile | Glu | Ile | Gly | Cys | Gly | Ile | Leu | Gly | Asn | Glu | Gln | Leu | Thr | Ile | |
| 215 | | | | | 220 | | | | | 225 | | | | | 230 | |
| GGT | GCT | TGT | GAT | GCG | ATT | TCT | CTT | GTC | GAC | GGT | TTT | TTT | GAT | TTT | GAA | 952 |
| Gly | Ala | Cys | Asp | Ala | Ile | Ser | Leu | Val | Asp | Gly | Phe | Phe | Asp | Phe | Glu | |
| | | | | 235 | | | | | 240 | | | | | 245 | | |
| GAG | AAA | TAC | CAA | TTA | ATC | AGC | GCC | ACG | ATC | ACT | GTC | CCA | GCA | CCA | TTG | 1000 |
| Glu | Lys | Tyr | Gln | Leu | Ile | Ser | Ala | Thr | Ile | Thr | Val | Pro | Ala | Pro | Leu | |
| | | | 250 | | | | | 255 | | | | | 260 | | | |
| CCT | CTC | GCG | CTT | GAA | TCA | CAG | ATC | AAG | GAG | CAG | GCA | CAG | CTG | CTT | TAT | 1048 |
| Pro | Leu | Ala | Leu | Glu | Ser | Gln | Ile | Lys | Glu | Gln | Ala | Gln | Leu | Leu | Tyr | |
| | | 265 | | | | | 270 | | | | | 275 | | | | |
| CGA | AAC | TTG | GGA | TTG | ACG | GGT | CTG | GCT | CGA | ATC | GAT | TTT | TTC | GTC | ACC | 1096 |
| Arg | Asn | Leu | Gly | Leu | Thr | Gly | Leu | Ala | Arg | Ile | Asp | Phe | Phe | Val | Thr | |
| | | 280 | | | | | 285 | | | | | 290 | | | | |
| AAT | CAA | GGA | GCG | ATT | TAT | TTA | AAC | GAA | ATC | AAC | ACC | ATG | CCG | GGA | TTT | 1144 |
| Asn | Gln | Gly | Ala | Ile | Tyr | Leu | Asn | Glu | Ile | Asn | Thr | Met | Pro | Gly | Phe | |
| 295 | | | | | 300 | | | | | 305 | | | | | 310 | |
| ACT | GGG | CAC | TCC | CGC | TAC | CCA | GCT | ATG | ATG | GCG | GAA | GTC | GGG | TTA | TCC | 1192 |
| Thr | Gly | His | Ser | Arg | Tyr | Pro | Ala | Met | Met | Ala | Glu | Val | Gly | Leu | Ser | |
| | | | | 315 | | | | | 320 | | | | | 325 | | |
| TAC | GAA | ATA | TTA | GTA | GAG | CAA | TTG | ATT | GCA | CTG | GCA | GAG | GAG | GAC | AAA | 1240 |
| Tyr | Glu | Ile | Leu | Val | Glu | Gln | Leu | Ile | Ala | Leu | Ala | Glu | Glu | Asp | Lys | |
| | | | 330 | | | | | 335 | | | | | 340 | | | |

```
CGA  TGAACACATT  ACAATTGATC  AATAAAAACC  ATCCATTGAA  AAAAAATCAA        1293
Arg

GAGCCCCCGC  ACTTAGTGCT  AGCTCCTTTT  AGCGATCACG  ATGTTACCT  GCAG         1347
```

( 2 ) INFORMATION FOR SEQ ID NO:8:

(i) SEQUENCE CHARACTERISTICS:
(A) LENGTH: 343 amino acids
(B) TYPE: amino acid
(D) TOPOLOGY: linear (ii) MOLECULE TYPE: protein (xi) SEQUENCE DESCRIPTION: SEQ ID NO:8:

| Met | Lys | Lys | Ile | Ala | Val | Leu | Phe | Gly | Gly | Asn | Ser | Pro | Glu | Tyr | Ser |
|---|---|---|---|---|---|---|---|---|---|---|---|---|---|---|---|
| 1 | | | | 5 | | | | | 10 | | | | | 15 | |

| Val | Ser | Leu | Thr | Ser | Ala | Ala | Ser | Val | Ile | Gln | Ala | Ile | Asp | Pro | Leu |
|---|---|---|---|---|---|---|---|---|---|---|---|---|---|---|---|
| | | | 20 | | | | 25 | | | | | 30 | | | |

| Lys | Tyr | Glu | Val | Met | Thr | Ile | Gly | Ile | Ala | Pro | Thr | Met | Asp | Trp | Tyr |
|---|---|---|---|---|---|---|---|---|---|---|---|---|---|---|---|
| | | 35 | | | | 40 | | | | | 45 | | | | |

| Trp | Tyr | Gln | Gly | Asn | Leu | Ala | Asn | Val | Arg | Asn | Asp | Thr | Trp | Leu | Glu |
|---|---|---|---|---|---|---|---|---|---|---|---|---|---|---|---|
| | 50 | | | | 55 | | | | | 60 | | | | | |

| Asp | His | Lys | Asn | Cys | His | Gln | Leu | Thr | Phe | Ser | Ser | Gln | Gly | Phe | Ile |
|---|---|---|---|---|---|---|---|---|---|---|---|---|---|---|---|
| 65 | | | | | 70 | | | | 75 | | | | | | 80 |

| Leu | Gly | Glu | Lys | Arg | Ile | Val | Pro | Asp | Val | Leu | Phe | Pro | Val | Leu | His |
|---|---|---|---|---|---|---|---|---|---|---|---|---|---|---|---|
| | | | | 85 | | | | | 90 | | | | | 95 | |

| Gly | Lys | Tyr | Gly | Glu | Asp | Gly | Cys | Ile | Gln | Gly | Leu | Leu | Glu | Leu | Met |
|---|---|---|---|---|---|---|---|---|---|---|---|---|---|---|---|
| | | | 100 | | | | | 105 | | | | | 110 | | |

| Asn | Leu | Pro | Tyr | Val | Gly | Cys | His | Val | Ala | Ala | Ser | Ala | Leu | Cys | Met |
|---|---|---|---|---|---|---|---|---|---|---|---|---|---|---|---|
| | | 115 | | | | | 120 | | | | | 125 | | | |

| Asn | Lys | Trp | Leu | Leu | His | Gln | Leu | Ala | Asp | Thr | Met | Gly | Ile | Ala | Ser |
|---|---|---|---|---|---|---|---|---|---|---|---|---|---|---|---|
| | 130 | | | | | 135 | | | | | 140 | | | | |

| Ala | Pro | Thr | Leu | Leu | Leu | Ser | Arg | Tyr | Glu | Asn | Asp | Pro | Ala | Thr | Ile |
|---|---|---|---|---|---|---|---|---|---|---|---|---|---|---|---|
| 145 | | | | | 150 | | | | | 155 | | | | | 160 |

| Asp | Arg | Phe | Ile | Gln | Asp | His | Gly | Phe | Pro | Ile | Phe | Ile | Lys | Pro | Asn |
|---|---|---|---|---|---|---|---|---|---|---|---|---|---|---|---|
| | | | | 165 | | | | | 170 | | | | | 175 | |

| Glu | Ala | Gly | Ser | Ser | Lys | Gly | Ile | Thr | Lys | Val | Thr | Asp | Lys | Thr | Ala |
|---|---|---|---|---|---|---|---|---|---|---|---|---|---|---|---|
| | | | 180 | | | | | 185 | | | | | 190 | | |

| Leu | Gln | Ser | Ala | Leu | Thr | Thr | Ala | Phe | Ala | Tyr | Gly | Ser | Thr | Val | Leu |
|---|---|---|---|---|---|---|---|---|---|---|---|---|---|---|---|
| | | 195 | | | | | 200 | | | | | 205 | | | |

| Ile | Gln | Lys | Ala | Ile | Ala | Gly | Ile | Glu | Ile | Gly | Cys | Gly | Ile | Leu | Gly |
|---|---|---|---|---|---|---|---|---|---|---|---|---|---|---|---|
| | 210 | | | | | 215 | | | | | 220 | | | | |

| Asn | Glu | Gln | Leu | Thr | Ile | Gly | Ala | Cys | Asp | Ala | Ile | Ser | Leu | Val | Asp |
|---|---|---|---|---|---|---|---|---|---|---|---|---|---|---|---|
| 225 | | | | | 230 | | | | | 235 | | | | | 240 |

| Gly | Phe | Phe | Asp | Phe | Glu | Glu | Lys | Tyr | Gln | Leu | Ile | Ser | Ala | Thr | Ile |
|---|---|---|---|---|---|---|---|---|---|---|---|---|---|---|---|
| | | | | 245 | | | | | 250 | | | | | 255 | |

| Thr | Val | Pro | Ala | Pro | Leu | Pro | Leu | Ala | Leu | Glu | Ser | Gln | Ile | Lys | Glu |
|---|---|---|---|---|---|---|---|---|---|---|---|---|---|---|---|
| | | | 260 | | | | | 265 | | | | | 270 | | |

| Gln | Ala | Gln | Leu | Leu | Tyr | Arg | Asn | Leu | Gly | Leu | Thr | Gly | Leu | Ala | Arg |
|---|---|---|---|---|---|---|---|---|---|---|---|---|---|---|---|
| | | 275 | | | | | 280 | | | | | 285 | | | |

| Ile | Asp | Phe | Phe | Val | Thr | Asn | Gln | Gly | Ala | Ile | Tyr | Leu | Asn | Glu | Ile |
|---|---|---|---|---|---|---|---|---|---|---|---|---|---|---|---|
| | 290 | | | | | 295 | | | | | 300 | | | | |

| Asn | Thr | Met | Pro | Gly | Phe | Thr | Gly | His | Ser | Arg | Tyr | Pro | Ala | Met | Met |
|---|---|---|---|---|---|---|---|---|---|---|---|---|---|---|---|
| 305 | | | | | 310 | | | | | 315 | | | | | 320 |

| Ala | Glu | Val | Gly | Leu | Ser | Tyr | Glu | Ile | Leu | Val | Glu | Gln | Leu | Ile | Ala |
|---|---|---|---|---|---|---|---|---|---|---|---|---|---|---|---|
| | | | | 325 | | | | | 330 | | | | | 335 | |

| Leu | Ala | Glu | Glu | Asp | Lys | Arg |
|---|---|---|---|---|---|---|
| | | | 340 | | | |

(2) INFORMATION FOR SEQ ID NO:9:

(i) SEQUENCE CHARACTERISTICS:
(A) LENGTH: 24 base pairs (B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:9:

```
GGNGARGAYG GNWSNHTNCA RGGN                                              24
```

(2) INFORMATION FOR SEQ ID NO:10:

(i) SEQUENCE CHARACTERISTICS:
(A) LENGTH: 20 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:10:

```
AAYACNHTNC CNGGNTTYAC                                                   20
```

(2) INFORMATION FOR SEQ ID NO:11:

(i) SEQUENCE CHARACTERISTICS:
(A) LENGTH: 693 base pairs
(B) TYPE: nucleic acid
(C) STRANDEDNESS: unknown
(D) TOPOLOGY: linear (ii) MOLECULE TYPE: DNA (genomic)

(ix) FEATURE:
(A) NAME/KEY: CDS
(B) LOCATION: 1..693

(xi) SEQUENCE DESCRIPTION: SEQ ID NO:11:

```
ATG AGC GAT AAA ATA CTT ATT GTG GAT GAT GAA CAT GAA ATT GCC GAT         48
Met Ser Asp Lys Ile Leu Ile Val Asp Asp Glu His Glu Ile Ala Asp
 1               5                  10                  15

TTG GTT GAA TTA TAC TTA AAA AAC GAG AAT TAT ACG GTT TTC AAA TAC         96
Leu Val Glu Leu Tyr Leu Lys Asn Glu Asn Tyr Thr Val Phe Lys Tyr
            20                  25                  30

TAT ACC GCC AAA GAA GCA TTG GAA TGT ATA GAC AAG TCT GAG ATT GAC        144
Tyr Thr Ala Lys Glu Ala Leu Glu Cys Ile Asp Lys Ser Glu Ile Asp
        35                  40                  45

CTT GCC ATA TTG GAC ATC ATG CTT CCC GGC ACA AGC GGC CTT ACT ATC        192
Leu Ala Ile Leu Asp Ile Met Leu Pro Gly Thr Ser Gly Leu Thr Ile
    50                  55                  60

TGT CAA AAA ATA AGG GAC AAG CAC ACC TAT CCG ATT ATC ATG CTG ACC        240
Cys Gln Lys Ile Arg Asp Lys His Thr Tyr Pro Ile Ile Met Leu Thr
65                  70                  75                  80

GGG AAA GAT ACA GAG GTA GAT AAA ATT ACA GGG TTA ACA ATC GGC GCG        288
Gly Lys Asp Thr Glu Val Asp Lys Ile Thr Gly Leu Thr Ile Gly Ala
                85                  90                  95

GAT GAT TAT ATA ACG AAG CCC TTT CGC CCA CTG GAG TTA ATT GCT CGG        336
Asp Asp Tyr Ile Thr Lys Pro Phe Arg Pro Leu Glu Leu Ile Ala Arg
            100                 105                 110

GTA AAG GCC CAG TTG CGC CGA TAC AAA AAA TTC AGT GGA GTA AAG GAG        384
Val Lys Ala Gln Leu Arg Arg Tyr Lys Lys Phe Ser Gly Val Lys Glu
        115                 120                 125

CAG AAC GAA AAT GTT ATC GTC CAC TCC GGC CTT GTC ATT AAT GTT AAC        432
Gln Asn Glu Asn Val Ile Val His Ser Gly Leu Val Ile Asn Val Asn
    130                 135                 140

ACC CAT GAG TGT TAT CTG AAC GAG AAG CAG TTA TCC CTT ACT CCC ACC        480
Thr His Glu Cys Tyr Leu Asn Glu Lys Gln Leu Ser Leu Thr Pro Thr
```

```
                                                        145                                   150                                   155                                   160
GAG  TTT  TCA  ATA  CTG  CGA  ATC  CTC  TGT  GAA  AAC  AAG  GGG  AAT  GTG  GTT                      528
Glu  Phe  Ser  Ile  Leu  Arg  Ile  Leu  Cys  Glu  Asn  Lys  Gly  Asn  Val  Val
                         165                        170                             175

AGC  TCC  GAG  CTG  CTA  TTT  CAT  GAG  ATA  TGG  GGC  GAC  GAA  TAT  TTC  AGC                      576
Ser  Ser  Glu  Leu  Leu  Phe  His  Glu  Ile  Trp  Gly  Asp  Glu  Tyr  Phe  Ser
               180                        185                             190

AAG  AGC  AAC  AAC  ACC  ATC  ACC  GTG  CAT  ATC  CGG  CAT  TTG  CGC  GAA  AAA                      624
Lys  Ser  Asn  Asn  Thr  Ile  Thr  Val  His  Ile  Arg  His  Leu  Arg  Glu  Lys
               195                        200                             205

ATG  AAC  GAC  ACC  ATT  GAT  AAT  CCG  AAA  TAT  ATA  AAA  ACG  GTA  TGG  GGG                      672
Met  Asn  Asp  Thr  Ile  Asp  Asn  Pro  Lys  Tyr  Ile  Lys  Thr  Val  Trp  Gly
     210                        215                             220

GTT  GGT  TAT  AAA  ATT  GAA  AAA                                                                   693
Val  Gly  Tyr  Lys  Ile  Glu  Lys
225                        230
```

( 2 ) INFORMATION FOR SEQ ID NO:12:

( i ) SEQUENCE CHARACTERISTICS:
        ( A ) LENGTH: 231 amino acids
        ( B ) TYPE: amino acid
        ( D ) TOPOLOGY: linear ( i i ) MOLECULE TYPE: protein ( x i ) SEQUENCE DESCRIPTION: SEQ ID NO:12:

```
Met  Ser  Asp  Lys  Ile  Leu  Ile  Val  Asp  Asp  Glu  His  Glu  Ile  Ala  Asp
  1                 5                        10                            15

Leu  Val  Glu  Leu  Tyr  Leu  Lys  Asn  Glu  Asn  Tyr  Thr  Val  Phe  Lys  Tyr
               20                        25                            30

Tyr  Thr  Ala  Lys  Glu  Ala  Leu  Glu  Cys  Ile  Asp  Lys  Ser  Glu  Ile  Asp
               35                        40                            45

Leu  Ala  Ile  Leu  Asp  Ile  Met  Leu  Pro  Gly  Thr  Ser  Gly  Leu  Thr  Ile
          50                        55                        60

Cys  Gln  Lys  Ile  Arg  Asp  Lys  His  Thr  Tyr  Pro  Ile  Ile  Met  Leu  Thr
 65                      70                        75                            80

Gly  Lys  Asp  Thr  Glu  Val  Asp  Lys  Ile  Thr  Gly  Leu  Thr  Ile  Gly  Ala
                    85                        90                            95

Asp  Asp  Tyr  Ile  Thr  Lys  Pro  Phe  Arg  Pro  Leu  Glu  Leu  Ile  Ala  Arg
               100                       105                           110

Val  Lys  Ala  Gln  Leu  Arg  Arg  Tyr  Lys  Lys  Phe  Ser  Gly  Val  Lys  Glu
               115                       120                           125

Gln  Asn  Glu  Asn  Val  Ile  Val  His  Ser  Gly  Leu  Val  Ile  Asn  Val  Asn
     130                       135                           140

Thr  His  Glu  Cys  Tyr  Leu  Asn  Glu  Lys  Gln  Leu  Ser  Leu  Thr  Pro  Thr
145                      150                       155                           160

Glu  Phe  Ser  Ile  Leu  Arg  Ile  Leu  Cys  Glu  Asn  Lys  Gly  Asn  Val  Val
                    165                       170                           175

Ser  Ser  Glu  Leu  Leu  Phe  His  Glu  Ile  Trp  Gly  Asp  Glu  Tyr  Phe  Ser
               180                       185                           190

Lys  Ser  Asn  Asn  Thr  Ile  Thr  Val  His  Ile  Arg  His  Leu  Arg  Glu  Lys
               195                       200                           205

Met  Asn  Asp  Thr  Ile  Asp  Asn  Pro  Lys  Tyr  Ile  Lys  Thr  Val  Trp  Gly
     210                       215                           220

Val  Gly  Tyr  Lys  Ile  Glu  Lys
225                      230
```

( 2 ) INFORMATION FOR SEQ ID NO:13:

( i ) SEQUENCE CHARACTERISTICS:
    ( A ) LENGTH: 1152 base pairs
    ( B ) TYPE: nucleic acid
    ( C ) STRANDEDNESS: unknown
    ( D ) TOPOLOGY: linear ( i i ) MOLECULE TYPE: DNA (genomic)

( i x ) FEATURE:
    ( A ) NAME/KEY: CDS
    ( B ) LOCATION: 1..1152

( x i ) SEQUENCE DESCRIPTION: SEQ ID NO:13:

```
TTG  GTT  ATA  AAA  TTG  AAA  AAT  AAA  AAA  AAC  GAC  TAT  TCC  AAA  CTA  GAA         48
Leu  Val  Ile  Lys  Leu  Lys  Asn  Lys  Lys  Asn  Asp  Tyr  Ser  Lys  Leu  Glu
  1              5                        10                       15

CGA  AAA  CTT  TAC  ATG  TAT  ATC  GTT  GCA  ATT  GTT  GTG  GTA  GCA  ATT  GTA         96
Arg  Lys  Leu  Tyr  Met  Tyr  Ile  Val  Ala  Ile  Val  Val  Val  Ala  Ile  Val
              20                       25                       30

TTC  GTG  TTG  TAT  ATT  CGT  TCA  ATG  ATC  CGA  GGG  AAA  CTT  GGG  GAT  TGG        144
Phe  Val  Leu  Tyr  Ile  Arg  Ser  Met  Ile  Arg  Gly  Lys  Leu  Gly  Asp  Trp
         35                       40                       45

ATC  TTA  AGT  ATT  TTG  GAA  AAC  AAA  TAT  GAC  TTA  AAT  CAC  CTG  GAC  GCG        192
Ile  Leu  Ser  Ile  Leu  Glu  Asn  Lys  Tyr  Asp  Leu  Asn  His  Leu  Asp  Ala
     50                       55                       60

ATG  AAA  TTA  TAT  CAA  TAT  TCC  ATA  CGG  AAC  AAT  ATA  GAT  ATC  TTT  ATT        240
Met  Lys  Leu  Tyr  Gln  Tyr  Ser  Ile  Arg  Asn  Asn  Ile  Asp  Ile  Phe  Ile
 65                       70                       75                       80

TAT  GTG  GCG  ATT  GTC  ATT  AGT  ATT  CTT  ATT  CTA  TGT  CGC  GTC  ATG  CTT        288
Tyr  Val  Ala  Ile  Val  Ile  Ser  Ile  Leu  Ile  Leu  Cys  Arg  Val  Met  Leu
                         85                       90                       95

TCA  AAA  TTC  GCA  AAA  TAC  TTT  GAC  GAG  ATA  AAT  ACC  GGC  ATT  GAT  GTA        336
Ser  Lys  Phe  Ala  Lys  Tyr  Phe  Asp  Glu  Ile  Asn  Thr  Gly  Ile  Asp  Val
                    100                      105                      110

CTT  ATT  CAG  AAC  GAA  GAT  AAA  CAA  ATT  GAG  CTT  TCT  GCG  GAA  ATG  GAT        384
Leu  Ile  Gln  Asn  Glu  Asp  Lys  Gln  Ile  Glu  Leu  Ser  Ala  Glu  Met  Asp
               115                      120                      125

GTT  ATG  GAA  CAA  AAG  CTC  AAC  ACA  TTA  AAA  CGG  ACT  CTG  GAA  AAG  CGA        432
Val  Met  Glu  Gln  Lys  Leu  Asn  Thr  Leu  Lys  Arg  Thr  Leu  Glu  Lys  Arg
     130                      135                      140

GAG  CAG  GAT  GCA  AAG  CTG  GCC  GAA  CAA  AGA  AAA  AAT  GAC  GTT  GTT  ATG        480
Glu  Gln  Asp  Ala  Lys  Leu  Ala  Glu  Gln  Arg  Lys  Asn  Asp  Val  Val  Met
145                      150                      155                      160

TAC  TTG  GCG  CAC  GAT  ATT  AAA  ACG  CCC  CTT  ACA  TCC  ATT  ATC  GGT  TAT        528
Tyr  Leu  Ala  His  Asp  Ile  Lys  Thr  Pro  Leu  Thr  Ser  Ile  Ile  Gly  Tyr
                    165                      170                      175

TTG  AGC  CTG  CTT  GAC  GAG  GCT  CCA  GAC  ATG  CCG  GTA  GAT  CAA  AAG  GCA        576
Leu  Ser  Leu  Leu  Asp  Glu  Ala  Pro  Asp  Met  Pro  Val  Asp  Gln  Lys  Ala
               180                      185                      190

AAG  TAT  GTG  CAT  ATC  ACG  TTG  GAC  AAA  GCG  TAT  CGA  CTC  GAA  CAG  CTA        624
Lys  Tyr  Val  His  Ile  Thr  Leu  Asp  Lys  Ala  Tyr  Arg  Leu  Glu  Gln  Leu
     195                      200                      205

ATC  GAC  GAG  TTT  TTT  GAG  ATT  ACA  CGG  TAT  AAC  CTA  CAA  ACG  ATA  ACG        672
Ile  Asp  Glu  Phe  Phe  Glu  Ile  Thr  Arg  Tyr  Asn  Leu  Gln  Thr  Ile  Thr
210                      215                      220

CTA  ACA  AAA  ACG  CAC  ATA  GAC  CTA  TAC  TAT  ATG  CTG  GTG  CAG  ATG  ACC        720
Leu  Thr  Lys  Thr  His  Ile  Asp  Leu  Tyr  Tyr  Met  Leu  Val  Gln  Met  Thr
225                      230                      235                      240

GAT  GAA  TTT  TAT  CCT  CAG  CTT  TCC  GCA  CAT  GGA  AAA  CAG  GCG  GTT  ATT        768
Asp  Glu  Phe  Tyr  Pro  Gln  Leu  Ser  Ala  His  Gly  Lys  Gln  Ala  Val  Ile
               245                      250                      255
```

```
CAC  GCC  CCC  GAG  GAT  CTG  ACC  GTG  TCC  GGC  GAC  CCT  GAT  AAA  CTC  GCG      816
His  Ala  Pro  Glu  Asp  Leu  Thr  Val  Ser  Gly  Asp  Pro  Asp  Lys  Leu  Ala
          260                      265                      270

AGA  GTC  TTT  AAC  AAC  ATT  TTG  AAA  AAC  GCC  GCT  GCA  TAC  AGT  GAG  GAT      864
Arg  Val  Phe  Asn  Asn  Ile  Leu  Lys  Asn  Ala  Ala  Ala  Tyr  Ser  Glu  Asp
          275                      280                      285

AAC  AGC  ATC  ATT  GAC  ATT  ACC  GCG  GGC  CTC  TCC  GGG  GAT  GTG  GTG  TCA      912
Asn  Ser  Ile  Ile  Asp  Ile  Thr  Ala  Gly  Leu  Ser  Gly  Asp  Val  Val  Ser
          290                      295                      300

ATC  GAA  TTC  AAG  AAC  ACT  GGA  AGC  ATC  CCA  AAA  GAT  AAG  CTA  GCT  GCC      960
Ile  Glu  Phe  Lys  Asn  Thr  Gly  Ser  Ile  Pro  Lys  Asp  Lys  Leu  Ala  Ala
305                      310                      315                      320

ATA  TTT  GAA  AAG  TTC  TAT  AGG  CTG  GAC  AAT  GCT  CGT  TCT  TCC  GAT  ACG     1008
Ile  Phe  Glu  Lys  Phe  Tyr  Arg  Leu  Asp  Asn  Ala  Arg  Ser  Ser  Asp  Thr
          325                      330                      335

GGT  GGC  GCG  GGA  CTT  GGA  TTG  GCG  ATT  GCA  AAA  GAA  ATT  ATT  GTT  CAG     1056
Gly  Gly  Ala  Gly  Leu  Gly  Leu  Ala  Ile  Ala  Lys  Glu  Ile  Ile  Val  Gln
          340                      345                      350

CAT  GGA  GGG  CAG  ATT  TAC  GCG  GAA  AGC  AAT  GAT  AAC  TAT  ACG  ACG  TTT     1104
His  Gly  Gly  Gln  Ile  Tyr  Ala  Glu  Ser  Asn  Asp  Asn  Tyr  Thr  Thr  Phe
          355                      360                      365

AGG  GTA  GAG  CTT  CCA  GCG  ATG  CCA  GAC  TTG  GTT  GAT  AAA  AGG  AGG  TCC     1152
Arg  Val  Glu  Leu  Pro  Ala  Met  Pro  Asp  Leu  Val  Asp  Lys  Arg  Arg  Ser
          370                      375                      380
```

( 2 ) INFORMATION FOR SEQ ID NO:14:

( i ) SEQUENCE CHARACTERISTICS:
        ( A ) LENGTH: 384 amino acids
        ( B ) TYPE: amino acid
        ( D ) TOPOLOGY: linear ( i i ) MOLECULE TYPE: protein ( x i ) SEQUENCE DESCRIPTION: SEQ ID NO:14:

```
Leu  Val  Ile  Lys  Leu  Lys  Asn  Lys  Lys  Asn  Asp  Tyr  Ser  Lys  Leu  Glu
 1              5                        10                      15

Arg  Lys  Leu  Tyr  Met  Tyr  Ile  Val  Ala  Ile  Val  Val  Ala  Ile  Val
              20                        25                      30

Phe  Val  Leu  Tyr  Ile  Arg  Ser  Met  Ile  Arg  Gly  Lys  Leu  Gly  Asp  Trp
              35                        40                      45

Ile  Leu  Ser  Ile  Leu  Glu  Asn  Lys  Tyr  Asp  Leu  Asn  His  Leu  Asp  Ala
           50                        55                      60

Met  Lys  Leu  Tyr  Gln  Tyr  Ser  Ile  Arg  Asn  Asn  Ile  Asp  Ile  Phe  Ile
65                        70                      75                      80

Tyr  Val  Ala  Ile  Val  Ile  Ser  Ile  Leu  Ile  Leu  Cys  Arg  Val  Met  Leu
                     85                        90                      95

Ser  Lys  Phe  Ala  Lys  Tyr  Phe  Asp  Glu  Ile  Asn  Thr  Gly  Ile  Asp  Val
              100                      105                      110

Leu  Ile  Gln  Asn  Glu  Asp  Lys  Gln  Ile  Glu  Leu  Ser  Ala  Glu  Met  Asp
              115                      120                      125

Val  Met  Glu  Gln  Lys  Leu  Asn  Thr  Leu  Lys  Arg  Thr  Leu  Glu  Lys  Arg
              130                      135                      140

Glu  Gln  Asp  Ala  Lys  Leu  Ala  Glu  Gln  Arg  Lys  Asn  Asp  Val  Val  Met
145                      150                      155                      160

Tyr  Leu  Ala  His  Asp  Ile  Lys  Thr  Pro  Leu  Thr  Ser  Ile  Ile  Gly  Tyr
                    165                      170                      175

Leu  Ser  Leu  Leu  Asp  Glu  Ala  Pro  Asp  Met  Pro  Val  Asp  Gln  Lys  Ala
              180                      185                      190
```

-continued

| | | | | | | | | | | | | | |
|---|---|---|---|---|---|---|---|---|---|---|---|---|---|
| Lys | Tyr | Val<br>195 | His | Ile | Thr | Leu | Asp<br>200 | Lys | Ala | Tyr | Arg | Leu<br>205 | Glu | Gln | Leu |
| Ile | Asp<br>210 | Glu | Phe | Phe | Glu | Ile<br>215 | Thr | Arg | Tyr | Asn | Leu<br>220 | Gln | Thr | Ile | Thr |
| Leu<br>225 | Thr | Lys | Thr | His | Ile<br>230 | Asp | Leu | Tyr | Tyr | Met<br>235 | Leu | Val | Gln | Met | Thr<br>240 |
| Asp | Glu | Phe | Tyr | Pro<br>245 | Gln | Leu | Ser | Ala | His<br>250 | Gly | Lys | Gln | Ala | Val<br>255 | Ile |
| His | Ala | Pro | Glu<br>260 | Asp | Leu | Thr | Val | Ser<br>265 | Gly | Asp | Pro | Asp | Lys<br>270 | Leu | Ala |
| Arg | Val | Phe<br>275 | Asn | Asn | Ile | Leu | Lys<br>280 | Asn | Ala | Ala | Ala | Tyr<br>285 | Ser | Glu | Asp |
| Asn | Ser<br>290 | Ile | Ile | Asp | Ile | Thr<br>295 | Ala | Gly | Leu | Ser | Gly<br>300 | Asp | Val | Val | Ser |
| Ile<br>305 | Glu | Phe | Lys | Asn | Thr<br>310 | Gly | Ser | Ile | Pro | Lys<br>315 | Asp | Lys | Leu | Ala | Ala<br>320 |
| Ile | Phe | Glu | Lys | Phe<br>325 | Tyr | Arg | Leu | Asp | Asn<br>330 | Ala | Arg | Ser | Ser | Asp<br>335 | Thr |
| Gly | Gly | Ala | Gly<br>340 | Leu | Gly | Leu | Ala | Ile<br>345 | Ala | Lys | Glu | Ile | Ile<br>350 | Val | Gln |
| His | Gly | Gly<br>355 | Gln | Ile | Tyr | Ala | Glu<br>360 | Ser | Asn | Asp | Asn | Tyr<br>365 | Thr | Thr | Phe |
| Arg | Val<br>370 | Glu | Leu | Pro | Ala | Met<br>375 | Pro | Asp | Leu | Val | Asp<br>380 | Lys | Arg | Arg | Ser |

(2) INFORMATION FOR SEQ ID NO:15:

(i) SEQUENCE CHARACTERISTICS:
        (A) LENGTH: 7225 base pairs
        (B) TYPE: nucleic acid
        (C) STRANDEDNESS: unknown
        (D) TOPOLOGY: linear (ii) MOLECULE TYPE: DNA (genomic)

(xi) SEQUENCE DESCRIPTION: SEQ ID NO:15:

| | | | | | |
|---|---|---|---|---|---|
| AAGCTTTTCT | TTTTGCTCAT | TTGTTAGAGA | TTTACTAACC | GTATTAAATA | GCTTCTTTTC | 60 |
| AGCCATTGCC | CTTGCTTCCC | ACACCATTCT | TTCAAGTGTA | GTGATAGCAG | GCAGTATAAT | 120 |
| TTTGTTTTTT | CTTAGAAAAT | CTATGCATTC | ATGCAGTAGA | TGAATGGCAT | CACCATTTTC | 180 |
| CAAAGCTAAT | TGATGAAGGT | ACTTAAATGT | CATTCGATAT | TCACTCAGGG | TAAAAGTTAC | 240 |
| AAAGTCGTAT | TCACTTCGAA | TTTCTTTCAA | ATGATCCCAA | AGTGTATTTT | CCCTTTGAGG | 300 |
| ATAATGATCA | AGCGAGGATG | GACTAACACC | AATCTGTTTC | GATATATATT | GTATGACCGA | 360 |
| ATCTGGGATG | CTTTTGATAT | GAGTGTATGG | CCAACCGGGA | TACCGAAGAA | CAGCTAATTG | 420 |
| AACAGCAAAT | CCTAAACGGT | TTCTTCCCT | CCTTCGCTTA | TTAACTATTT | CTAAATCCCG | 480 |
| TTTGGAAAAA | GTGAAGTAGG | TCCCCAGTAT | CCATTCATCT | TCAGGGATTT | GCATAAAAGC | 540 |
| CTGTCTCTGT | TCCGGTGTAA | GCAATTCTCT | ACCTCTCGCA | ATTTTCATTC | AGTATCATTC | 600 |
| CATTTCTGTA | TTTTCAATTT | ATTAGTTCAA | TTATATATCA | ATAGAGTGTA | CTCTATTGAT | 660 |
| ACAAATGTAG | TAGACTGATA | AAATCATAGT | TAAGAGCGTC | TCATAAGACT | TGTCTCAAAA | 720 |
| ATGAGGTGAT | ATTTTGCGGA | AAATCGGTTA | TATTCGTGTC | AGTTCGACTA | ACCAGAATCC | 780 |
| TTCAAGACAA | TTTCAGCAGT | TGAACGAGAT | CGGAATGGAT | ATTATATAAA | GAGAAAGTTT | 840 |
| CAGGAGCAAC | AAAGGATCGC | GAGCAACTTC | AAAAAGTGTT | AGACGATTTA | CAGGAAGATG | 900 |
| ACATCATTTA | TGTTACAGAC | TTAACTCGAA | TCACTCGTAG | TACACAAGAT | CTATTTGAAT | 960 |

```
TAATCGATAA  CATACGAGAT  AAAAAGGCAA  GTTTAAAATC  ACTAAAAGAT  ACATGGCTTG    1020

ATTTATCAGA  AGATAATCCA  TACAGCCAAT  TCTTAATTAC  TGTAATGGCT  GGTGTTAACC    1080

AATTAGAGCG  AGATCTTATT  CGGATGAGAC  AACGTGAAGG  GATTGAATTG  CTAAGAAAG     1140

AAGGAAAGTT  TAAAGGTCGA  TTAAGAAGT   ATCATAAAAA  TCACGCAGGA  ATGAATTATG    1200

CGGAAAGCTA  TATAAAGAAG  GAAATATGAC  TGTAAATCAA  ATTTGTGAAA  TTACTAATGT    1260

ATCTAGGGCT  TCATTATACA  GGAAATTATC  AGAAGTGAAT  AATTAGCCAT  TCTGTATTCC    1320

GCTAATGGGC  AATATTTTA   AAGAAGAAAA  GGAAACTATA  AATATTAAC   AGCCTCCTAG    1380

CGATGCCGAA  AAGCCCTTTG  ATAAAAAAG   AATCATCATC  TTAAGAAATT  CTTAGTCATT    1440

TATTATGTAA  ATGCTTATAA  ATTCGGCCCT  ATAATCTGAT  AAATTATTAA  GGGCAAACTT    1500

ATGTGAAAGG  GTGATAACTA  TGAGCGATAA  ATACTTATT   GTGGATGATG  AACATGAAAT    1560

TGCCGATTTG  GTTGAATTAT  ACTTAAAAAA  CGAGAATTAT  ACGGTTTCA   AATACTATAC    1620

CGCCAAAGAA  GCATTGGAAT  GTATAGACAA  GTCTGAGATT  GACCTTGCCA  TATTGGACAT    1680

CATGCTTCCC  GGCACAAGCG  GCCTTACTAT  CTGTCAAAAA  ATAAGGGACA  AGCACACCTA    1740

TCCGATTATC  ATGCTGACCG  GGAAAGATAC  AGAGGTAGAT  AAAATTACAG  GGTTAACAAT    1800

CGGCGCGGAT  GATTATATAA  CGAAGCCCTT  TCGCCCACTG  GAGTTAATTG  CTCGGGTAAA    1860

GGCCCAGTTG  CGCCGATACA  AAAAATTCAG  TGGAGTAAAG  GAGCAGAACG  AAAATGTTAT    1920

CGTCCACTCC  GGCCTTGTCA  TTAATGTTAA  CACCCATGAG  TGTTATCTGA  ACGAGAAGCA    1980

GTTATCCCTT  ACTCCCACCG  AGTTTTCAAT  ACTGCGAATC  CTCTGTGAAA  ACAAGGGGAA    2040

TGTGGTTAGC  TCCGAGCTGC  TATTTCATGA  GATATGGGGC  GACGAATATT  TCAGCAAGAG    2100

CAACAACACC  ATCACCGTGC  ATATCCGGCA  TTTGCGCGAA  AAAATGAACG  ACACCATTGA    2160

TAATCCGAAA  TATATAAAAA  CGGTATGGGG  GGTTGGTTAT  AAAATTGAAA  AATAAAAAAA    2220

ACGACTATTC  CAAACTAGAA  CGAAAACTTT  ACATGTATAT  CGTTGCAATT  GTTGTGGTAG    2280

CAATTGTATT  CGTGTTGTAT  ATTCGTTCAA  TGATCCGAGG  GAAACTTGGG  GATTGGATCT    2340

TAAGTATTTT  GGAAAACAAA  TATGACTTAA  ATCACCTGGA  CGCGATGAAA  TTATATCAAT    2400

ATTCCATACG  GAACAATATA  GATATCTTTA  TTTATGTGGC  GATTGTCATT  AGTATTCTTA    2460

TTCTATGTCG  CGTCATGCTT  TCAAAATTCG  CAAAATACTT  TGACGAGATA  AATACCGGCA    2520

TTGATGTACT  TATTCAGAAC  GAAGATAAAC  AAATTGAGCT  TTCTGCGGAA  ATGGATGTTA    2580

TGGAACAAAA  GCTCAACACA  TTAAAACGGA  CTCTGGAAAA  GCGAGAGCAG  GATGCAAAGC    2640

TGGCCGAACA  AAGAAAAAAT  GACGTTGTTA  TGTACTTGGC  GCACGATATT  AAAACGCCCC    2700

TTACATCCAT  TATCGGTTAT  TTGAGCCTGC  TTGACGAGGC  TCCAGACATG  CCGGTAGATC    2760

AAAAGGCAAA  GTATGTGCAT  ATCACGTTGG  ACAAAGCGTA  TCGACTCGAA  CAGCTAATCG    2820

ACGAGTTTTT  TGAGATTACA  CGGTATAACC  TACAAACGAT  AACGCTAACA  AAAACGCACA    2880

TAGACCTATA  CTATATGCTG  GTGCAGATGA  CCGATGAATT  TTATCCTCAG  CTTTCCGCAC    2940

ATGGAAAACA  GGCGGTTATT  CACGCCCCG   AGGATCTGAC  CGTGTCCGGC  GACCCTGATA    3000

AACTCGCGAG  AGTCTTTAAC  AACATTTTGA  AAAACGCCGC  TGCATACAGT  GAGGATAACA    3060

GCATCATTGA  CATTACCGCG  GGCCTCTCCG  GGATGTGGT   GTCAATCGAA  TTCAAGAACA    3120

CTGGAAGCAT  CCCAAAAGAT  AAGCTAGCTG  CCATATTTGA  AAAGTTCTAT  AGGCTGGACA    3180

ATTCTCGTTC  TTCCGATACG  GGTGGCGCGG  GACTTGGATT  GGCGATTGCA  AAAGAAATTA    3240

TTGTTCAGCA  TGGAGGGCAG  ATTTACGCGG  AAAGCTATGA  TAACTATACG  ACGTTTAGGG    3300

TAGAGCTTCC  AGCGATGCCA  GACTTGGTTG  ATAAAAGGAG  GTCCTAAGAG  ATGTATATAA    3360
```

```
TTTTTTAGGA  AAATCTCAAG  GTTATCTTTA  CTTTTTCTTA  GGAAATTAAC  AATTTAATAT   3420
TAAGAAACGG  CTCGTTCTTA  CACGGTAGAC  TTAATACCGT  AAGAACGAGC  CGTTTTCGTT   3480
CTTCAGAGAA  AGATTTGACA  AGATTACCAT  TGGCATCCCC  GTTTTATTTG  GTGCCTTTCA   3540
CAGAAAGGGT  TGGTCTTAAT  TATGAATAAC  ATCGGCATTA  CTGTTTATGG  ATGTGAGCAG   3600
GATGAGGCAG  ATGCATTCCA  TGCTCTTTCG  CCTCGCTTTG  GCGTTATGGC  AACGATAATT   3660
AACGCCAACG  TGTCGGAATC  CAACGCCAAA  TCCGCGCCTT  TCAATCAATG  TATCAGTGTG   3720
GGACATAAAT  CAGAGATTTC  CGCCTCTATT  CTTCTTGCGC  TGAAGAGAGC  CGGTGTGAAA   3780
TATATTTCTA  CCCGAAGCAT  CGGCTGCAAT  CATATAGATA  CAACTGCTGC  TAAGAGAATG   3840
GGCATCACTG  TCGACAATGT  GGCGTACTCG  CCGGATAGCG  TTGCCGATTA  TACTATGATG   3900
CTAATTCTTA  TGGCAGTACG  CAACGTAAAA  TCGATTGTGC  GCTCTGTGGA  AAAACATGAT   3960
TTCAGGTTGG  ACAGCGACCG  TGGCAAGGTA  CTCAGCGACA  TGACAGTTGG  TGTGGTGGGA   4020
ACGGGCCAGA  TAGGCAAAGC  GGTTATTGAG  CGGCTGCGAG  GATTTGGATG  TAAAGTGTTG   4080
GCTTATAGTC  GCAGCCGAAG  TATAGAGGTA  AACTATGTAC  CGTTTGATGA  GTTGATGCAA   4140
AATAGCGATA  TCGTTACGCT  TCATGTGCCG  CTCAATACGG  ATACGCACTA  TATTATCAGC   4200
CACGAACAAA  TACAGAGAAT  GAAGCAAGGA  GCATTTCTTA  TCAATACTGG  GCGCGGTCCA   4260
CTTGTAGATA  CCTATGAGTT  GGTTAAAGCA  TTAGAAAACG  GAAACTGGG   CGGTGCCGCA   4320
TTGGATGTAT  TGGAAGGAGA  GGAAGAGTTT  TTCTACTCTG  ATTGCACCCA  AAAACCAATT   4380
GATAATCAAT  TTTTACTTAA  ACTTCAAAGA  ATGCCTAACG  TGATAATCAC  ACCGCATACG   4440
GCCTATTATA  CCGAGCAAGC  GTTGCGTGAT  ACCGTTGAAA  AAACCATTAA  AAACTGTTTG   4500
GATTTTGAAA  GGAGACAGGA  GCATGAATAG  AATAAAAGTT  GCAATACTGT  TTGGGGGTTG   4560
CTCAGAGGAG  CATGACGTAT  CGGTAAAATC  TGCAATAGAG  ATAGCCGCTA  ACATTAATAA   4620
AGAAAAATAC  GAGCCGTTAT  ACATTGGAAT  TACGAAATCT  GGTGTATGGA  AAATGTGCGA   4680
AAAACCTTGC  GCGGAATGGG  AAAACGACAA  TTGCTATTCA  GCTGTACTCT  CGCCGGATAA   4740
AAAAATGCAC  GGATTACTTG  TTAAAAAGAA  CCATGAATAT  GAAATCAACC  ATGTTGATGT   4800
AGCATTTTCA  GCTTTGCATG  GCAAGTCAGG  TGAAGATGGA  TCCATACAAG  GTCTGTTTGA   4860
ATTGTCCGGT  ATCCCTTTTG  TAGGCTGCGA  TATTCAAAGC  TCAGCAATTT  GTATGGACAA   4920
ATCGTTGACA  TACATCGTTG  CGAAAAATGC  TGGGATAGCT  ACTCCCGCCT  TTGGGTTAT    4980
TAATAAAGAT  GATAGGCCGG  TGGCAGCTAC  GTTACCTAT   CCTGTTTTTG  TTAAGCCGGC   5040
GCGTTCAGGC  TCATCCTTCG  GTGTGAAAAA  AGTCAATAGC  GCGGACGAAT  TGGACTACGC   5100
AATTGAATCG  GCAAGACAAT  ATGACAGCAA  AATCTTAATT  GAGCAGGCTG  TTTCGGGCTG   5160
TGAGGTCGGT  TGTGCGGTAT  TGGGAAACAG  TGCCGCGTTA  GTTGTTGGCG  AGGTGGACCA   5220
AATCAGGCTG  CAGTACGGAA  TCTTTCGTAT  TCATCAGGAA  GTCGAGCCGG  AAAAAGGCTC   5280
TGAAAACGCA  GTTATAACCG  TTCCCGCAGA  CCTTTCAGCA  GAGGAGCGAG  GACGGATACA   5340
GGAAACGGCA  AAAAAAATAT  ATAAAGCGCT  CGGCTGTAGA  GGTCTAGCCC  GTGTGGATAT   5400
GTTTTTACAA  GATAACGGCC  GCATTGTACT  GAACGAAGTC  AATACTCTGC  CCGGTTTCAC   5460
GTCATACAGT  CGTTATCCCC  GTATGATGGC  CGCTGCAGGT  ATTGCACTTC  CCGAACTGAT   5520
TGACCGCTTG  ATCGTATTAG  CGTTAAAGGG  GTGATAAGCA  TGGAAATAGG  ATTTACTTTT   5580
TTAGATGAAA  TAGTACACGG  TGTTCGTTGG  GACGCTAAAT  ATGCCACTTG  GATAATTTC    5640
ACCGGAAAAC  CGGTTGACGG  TTATGAAGTA  AATCGCATTG  TAGGGACATA  CGAGTTGGCT   5700
GAATCGCTTT  TGAAGGCAAA  AGAACTGGCT  GCTACCCAAG  GGTACGGATT  GCTTCTATGG   5760
```

```
GACGGTTACC GTCCTAAGCG TGCTGTAAAC TGTTTTATGC AATGGGCTGC ACAGCCGGAA      5820

AATAACCTGA CAAAGGAAAG TTATTATCCC AATATTGACC GAACTGAGAT GATTTCAAAA      5880

GGATACGTGG CTTCAAAATC AAGCCATAGC CGCGGCAGTG CCATTGATCT TACGCTTTAT      5940

CGATTAGACA CGGGTGAGCT TGTACCAATG GGGAGCCGAT TTGATTTTAT GGATGAACGC      6000

TCTCATCATG CGGCAAATGG AATATCATGC AATGAAGCGC AAAATCGCAG ACGTTTGCGC      6060

TCCATCATGG AAAACAGTGG GTTTGAAGCA TATAGCCTCG AATGGTGGCA CTATGTATTA      6120

AGAGACGAAC CATACCCCAA TAGCTATTTT GATTTCCCCG TTAAATAAAC TTTTAACCGT      6180

TGCACGGACA AACTATATAA GCTAACTCTT TCGGCAGGAA ACCCGACGTA TGTAACTGGT      6240

TCTTAGGGAA TTTATATATA GTAGATAGTA TTGAAGATGT AAGGCAGAGC GATATTGCGG      6300

TCATTATCTG CGTGCGCTGC GGCAAGATAG CCTGATAATA AGACTGATCG CATAGAGGGG      6360

TGGTATTTCA CACCGCCCAT TGTCAACAGG CAGTTCAGCC TCGTTAAATT CAGCATGGGT      6420

ATCACTTATG AAAATTCATC TACATTGGTG ATAATAGTAA ATCCAGTAGG GCGAAATAAT      6480

TGACTGTAAT TTACGGGGCA AAACGGCACA ATCTCAAACG AGATTGTGCC GTTTAAGGGG      6540

AAGATTCTAG AAATATTTCA TACTTCCAAC TATATAGTTA AGGAGGAGAC TGAAAATGAA      6600

GAAGTTGTTT TTTTTATTGT TATTGTTATT CTTAATATAC TTAGGTTATG ACTACGTTAA      6660

TGAAGCACTG TTTTCTCAGG AAAAAGTCGA ATTTCAAAAT TATGATCAAA ATCCCAAAGA      6720

ACATTTAGAA AATAGTGGGA CTTCTGAAAA TACCCAAGAG AAAACAATTA CAGAAGAACA      6780

GGTTTATCAA GGAAATCTGC TATTAATCAA TAGTAAATAT CCTGTTCGCC AAGAAGTGTG      6840

AAGTCAGATA TCGTGAATTT ATCTAAACAT GACGAATTAA TAAATGGATA CGGGTTGCTT      6900

GATAGTAATA TTTATATGTC AAAAGAAATA GCACAAAAAT TTTCAGAGAT GGTCAATGAT      6960

GCTGTAAAGG GTGGCGTTAG TCATTTTATT ATTAATAGTG GCTATCGAGA CTTTGATGAG      7020

CAAAGTGTGC TTTACCAAGA AATGGGGGCT GAGTATGCCT TACCAGCAGG TTATAGTGAG      7080

CATAATTCAG GTTTATCACT AGATGTAGGA TCAAGCTTGA CGAAAATGGA ACGAGCCCCT      7140

GAAGGAAAGT GGATAGAAGA AAATGCTTGG AAATACGGGT TCATTTTACG TTATCCAGAG      7200

GACAAAACAG AGTTAACAGG AATTC                                          7225
```

( 2 ) INFORMATION FOR SEQ ID NO:16:

( i ) SEQUENCE CHARACTERISTICS:
        ( A ) LENGTH: 10851 base pairs
        ( B ) TYPE: nucleic acid
        ( C ) STRANDEDNESS: double
        ( D ) TOPOLOGY: unknown ( i i ) MOLECULE TYPE: DNA (genomic)

( x i ) SEQUENCE DESCRIPTION: SEQ ID NO:16:

```
GGGGTAGCGT CAGGAAAATG CGGATTTACA ACGCTAAGCC TATTTTCCTG ACGAATCCCT        60

CGTTTTTAAC AACGTTAAGA AAGTTTTAGT GGTCTTAAAG AATTTAATGA GACTACTTTC       120

TCTGAGTTAA AATGGTATTC TCCTAGTAAA TTAATATGTT CCCAACCTAA GGGCGACATA       180

TGGTGTAACA AATCTTCATT AAAGCTACCT GTCCGTTTTT TATATTCAAC TGCTGTTGTT       240

AGGTGGAGAG TATTCCAAAT ACTTATAGCA TTGATAATTA TGTTAAAGC ACTGGCTCTT        300

TGCAATTGAT GCTGTATGGT GCGTTCTCTA AGCTCACCTT GTTTTCCGAA GAAAATAGCT       360

CTTGCCAATC CATTCATGGC TTCTCCTTTA TTCAATCCTC TTTGTATTTT TCTTCTTAAT       420

GATTCATCCG ATATATAATT CAAAATAAAG ATCGTTTTTT CTATTCGGCC CATCTCACGT       480
```

-continued

| | | | | | | |
|---|---|---|---|---|---|---|
| AAGGCTGTAG | CTAAGCTGTT | TTGTCTTGAA | TAGGAACCTA | GCTTCCCCAT | AATAAGGGAT | 540 |
| GCTGAAACTG | TTCCCTCCCT | TATAGAATGA | GCTAATCGCA | AAACATCCTC | ATAATTTTCT | 600 |
| TTAATGACCT | TTGTATTTAT | TTGTCCACGT | AAAATGGCTT | CTAGTTTTGG | ATACTCACTT | 660 |
| GCTTTATCTA | TCGTAAATAA | TTTTGAGTCC | GATAAATCCC | TTATTCTTGG | GGCAAATTTA | 720 |
| AATCCTAATA | AATGAGTCAG | TCCGAATATT | TGGTCAGTGT | AACCGGCAGT | GTCTGTATAA | 780 |
| TGTTCCTCTA | TGTTTAGATC | CGTCTCATGA | TGTAACAAAC | CATCCAAAAC | ATGAATCGCA | 840 |
| TCTCTTGAAT | TAGTATGAAT | AATCTTTGTG | TAGTAAGAAG | AGAATTGATC | ACTTGTAAAT | 900 |
| CGGTAGATGG | TGGCTCCTTT | TCCAGTTCCA | TAATGTGGAT | TTGCATCTGC | ATGTAGTGAT | 960 |
| GAAACACCTA | GCTGCATTCT | CATACCATCT | GACGAAGATG | TTGTACCGTC | GCCCCAATAG | 1020 |
| AAAGGCAATT | GTAATTTATG | ATGAAAGTTT | ACTAATATGG | CTTGGGCTTT | ATTCATGGCA | 1080 |
| TCTTCATACA | TGCGCCATTG | AGATACATTG | GCTAGTTGCT | TATATGTAAG | TCCGGGTGTG | 1140 |
| GCTTCGGCCA | TCTTGCTCAA | GCCAATATTC | ATTCCATTC | CTAAAAGGGC | AGCCATGATA | 1200 |
| ATGATTGTTT | CTTCCTTATC | TGGTTTTCGA | TTATTGGAAG | CATGAGTGAA | TTGCTCATGA | 1260 |
| AATCCTGTTA | TATGGGCCAC | ATCCATGAGT | AAATCAGTTA | ATTTATTCT | TGGTAGCATC | 1320 |
| TGATAAAGGC | TTGCACTAAA | TTTTTTTGCT | TCTTCTGGAA | CATCTTTTC | TAAGCGTGCA | 1380 |
| AGTGATAGCT | TTCCTTTTTC | AAGAGAAACC | CCATCTAACT | TATTGGAATT | GGCAGCTAAC | 1440 |
| CACTTTAACC | TTTCATTAAA | GCTGCTGGTT | CTCTCCGTTA | TATAATCTTC | GAATGATAAA | 1500 |
| CTAACTGATA | ATCTCGTATT | CCCCTTCGAT | TGATTCCATG | TATCTTCCGA | AAACAAATAT | 1560 |
| TCCTCAAAAT | CCCTATATTG | TCTGCTGCCA | ACAATGGAAA | CATCTCCTGC | CCGAACATGC | 1620 |
| TCCGAAGTT | CTGTTAAAAC | AGCCATTTCA | TAGTAATGAC | GATTAATTGT | TGTACCATCA | 1680 |
| TCCTCGTATA | AATGTCTTTT | CCATCGTTTT | GAAATAAAAT | CCACAGGTGA | GTCATCAGGC | 1740 |
| ACTTTTCGCT | TTCCAGATTC | GTTCATTCCT | CGGATAATCT | CAACAGCTTG | TAAAAGTGGC | 1800 |
| TCATTTGCCT | TTGTAGAATG | AAATTCCAAT | ACTCTTAATA | GCGTTGGCGT | ATATTTCTT | 1860 |
| AGTGAATAAA | ACCGTTTTG | CAGTAAGTCT | AAATAATCAT | AGTCGGCAGG | ACGTGCAAGT | 1920 |
| TCCTGAGCCT | CTTCTACTGA | AGAGACAAAG | GTATTCCATT | CAATAACCGA | TTCTAAAACC | 1980 |
| TTAAAAACGT | CTAATTTTC | CTCTCTTGCT | TTAATTAATG | CTTGTCCGAT | GTTCGTAAAG | 2040 |
| TGTATAACTT | TCTCATTTAG | CTTTTTACCG | TTTTGTTTCT | GGATTTCCTC | TTGAGCCTTA | 2100 |
| CGACCTTTTG | ATAACAAACT | AAGTATTTGC | CTATCATGAA | TTTCAAACGC | TTTATCCGTT | 2160 |
| AGCTCCTGAG | TAAGTTGTAA | TAAATAGATG | GTTAATATCG | AATAACGTTT | ATTTTCTTGA | 2220 |
| AAGTCACGGA | ATGCATACGG | CTCGTATCTT | GAGCCTAAGC | GAGACAGCTG | CAACAGGCGG | 2280 |
| TTACGGTGCA | AATGACTAAT | TTGCACTGTT | TCTAAATCCA | TTCCTCGTAT | GTATTCGAGT | 2340 |
| CGTTCTATTA | TTTTTAGAAA | AGTTTCGGGT | GAAGGATGAC | CCGGTGGCTC | TTTTAACCAA | 2400 |
| CCCAATATCG | TTTTATTGGA | TTCGGATGGA | TGCTGCGAGG | TAATAATCCC | TTCAAGCTTT | 2460 |
| TCTTTTTGCT | CATTGTTAG | AGATTACTA | ACCGTATTAA | ATAGCTTCTT | TTCAGCCATT | 2520 |
| GCCCTTGCTT | CCCACACCAT | TCTTTCAAGT | GTAGTGATAG | CAGGCAGTAT | AATTTTGTTT | 2580 |
| TTTCTTAGAA | AATCTATGCA | TTCATGCAGT | AGATGAATGG | CATCACCATT | TTCCAAAGCT | 2640 |
| AATTGATGAA | GGTACTTAAA | TGTCATTCGA | TATTCACTCA | GGGTAAAAGT | TACAAAGTCG | 2700 |
| TATTCACTTC | GAATTTCTTT | CAAATGATCC | CAAAGTGTAT | TTTCCCTTTG | AGGATAATGA | 2760 |
| TCAAGCGAGG | ATGGACTAAC | ACCAATCTGT | TTCGATATAT | ATTGTATGAC | CGAATCTGGG | 2820 |
| ATGCTTTTGA | TATGAGTGTA | TGGCCAACCG | GGATACCGAA | GAACAGCTAA | TTGAACAGCA | 2880 |

| | | | | | | |
|---|---|---|---|---|---|---|
| AATCCTAAAC | GGTTTTCTTC | CCTCCTTCGC | TTATTAACTA | TTTCTAAATC | CCGTTTGGAA | 2940 |
| AAAGTGAAGT | AGGTCCCCAG | TATCCATTCA | TCTTCAGGGA | TTTGCATAAA | AGCCTGTCTC | 3000 |
| TGTTCCGGTG | TAAGCAATTC | TCTACCTCTC | GCAATTTTCA | TTCAGTATCA | TTCCATTTCT | 3060 |
| GTATTTTCAA | TTTATTAGTT | CAATTATATA | TCAATAGAGT | GTACTCTATT | GATACAAATG | 3120 |
| TAGTAGACTG | ATAAAATCAT | AGTTAAGAGC | GTCTCATAAG | ACTTGTCTCA | AAAATGAGGT | 3180 |
| GATATTTTGC | GGAAAATCGG | TTATATTCGT | GTCAGTTCGA | CTAACCAGAA | TCCTTCAAGA | 3240 |
| CAATTTCAGC | AGTTGAACGA | GATCGGAATG | GATATTATAT | ATGAAGAGAA | AGTTTCAGGA | 3300 |
| GCAACAAAGG | ATCGCGAGCA | ACTTCAAAAA | GTGTTAGACG | ATTTACAGGA | AGATGACATC | 3360 |
| ATTTATGTTA | CAGACTTAAC | TCGAATCACT | CGTAGTACAC | AAGATCTATT | TGAATTAATC | 3420 |
| GATAACATAC | GAGATAAAAA | GGCAAGTTTA | AAATCACTAA | AAGATACATG | GCTTGATTTA | 3480 |
| TCAGAAGATA | ATCCATACAG | CCAATTCTTA | ATTACTGTAA | TGGCTGGTGT | TAACCAATTA | 3540 |
| GAGCGAGATC | TTATTCGGAT | GAGACAACGT | GAAGGGATTG | AATTGGCTAA | GAAAGAAGGA | 3600 |
| AAGTTTAAAG | GTCGATTAAA | GAAGTATCAT | AAAAATCACG | CAGGAATGAA | TTATGCGGTA | 3660 |
| AAGCTATATA | AGAAGGAAA | TATGACTGTA | AATCAAATTT | GTGAAATTAC | TAATGTATCT | 3720 |
| AGGGCTTCAT | TATACAGGAA | ATTATCAGAA | GTGAATAATT | AGCCATTCTG | TATTCCGCTA | 3780 |
| ATGGGCAATA | TTTTTAAAGA | AGAAAAGGAA | ACTATAAAAT | ATTAACAGCC | TCCTAGCGAT | 3840 |
| GCCGAAAAGC | CCTTTGATAA | AAAAAGAATC | ATCATCTTAA | GAAATTCTTA | GTCATTTATT | 3900 |
| ATGTAAATGC | TTATAAATTC | GGCCCTATAA | TCTGATAAAT | TATTAAGGGC | AAACTTATGT | 3960 |
| GAAAGGGTGA | TAACTATGAG | CGATAAAATA | CTTATTGTGG | ATGATGAACA | TGAAATTGCC | 4020 |
| GATTGGTTG | AATTATACTT | AAAAAACGAG | AATTATACGG | TTTTCAAATA | CTATACCGCC | 4080 |
| AAAGAAGCAT | TGGAATGTAT | AGACAAGTCT | GAGATTGACC | TTGCCATATT | GGACATCATG | 4140 |
| CTTCCCGGCA | CAAGCGGCCT | TACTATCTGT | CAAAAAATAA | GGGACAAGCA | CACCTATCCG | 4200 |
| ATTATCATGC | TGACCGGGAA | AGATACAGAG | GTAGATAAAA | TTACAGGGTT | AACAATCGGC | 4260 |
| GCGGATGATT | ATATAACGAA | GCCCTTTCGC | CCACTGGAGT | TAATTGCTCG | GGTAAAGGCC | 4320 |
| CAGTTGCGCC | GATACAAAAA | ATTCAGTGGA | GTAAAGGAGC | AGAACGAAAA | TGTTATCGTC | 4380 |
| CACTCCGGCC | TTGTCATTAA | TGTTAACACC | CATGAGTGTT | ATCTGAACGA | GAAGCAGTTA | 4440 |
| TCCCTTACTC | CCACCGAGTT | TTCAATACTG | CGAATCCTCT | GTGAAAACAA | GGGGAATGTG | 4500 |
| GTTAGCTCCG | AGCTGCTATT | TCATGAGATA | TGGGGCGACG | AATATTTCAG | CAAGAGCAAC | 4560 |
| AACACCATCA | CCGTGCATAT | CCGGCATTTG | CGCGAAAAAA | TGAACGACAC | CATTGATAAT | 4620 |
| CCGAAATATA | TAAAAACGGT | ATGGGGGGTT | GGTTATAAAA | TTGAAAAATA | AAAAAAACGA | 4680 |
| CTATTCCAAA | CTAGAACGAA | AACTTTACAT | GTATATCGTT | GCAATTGTTG | TGGTAGCAAT | 4740 |
| TGTATTCGTG | TTGTATATTC | GTTCAATGAT | CCGAGGGAAA | CTTGGGGATT | GGATCTTAAG | 4800 |
| TATTTTGGAA | AACAAATATG | ACTTAAATCA | CCTGGACGCG | ATGAAATTAT | ATCAATATTC | 4860 |
| CATACGGAAC | AATATAGATA | TCTTTATTTA | TGTGGCGATT | GTCATTAGTA | TTCTTATTCT | 4920 |
| ATGTCGCGTC | ATGCTTTCAA | AATTCGCAAA | ATACTTTGAC | GAGATAAATA | CCGGCATTGA | 4980 |
| TGTACTTATT | CAGAACGAAG | ATAAACAAAT | TGAGCTTTCT | GCGGAAATGG | ATGTTATGGA | 5040 |
| ACAAAGCTC | AACACATTAA | AACGGACTCT | GGAAAAGCGA | GAGCAGGATG | CAAAGCTGGC | 5100 |
| CGAACAAAGA | AAAAATGACG | TTGTTATGTA | CTTGGCGCAC | GATATTAAAA | CGCCCCTTAC | 5160 |
| ATCCATTATC | GGTTATTTGA | GCCTGCTTGA | CGAGGCTCCA | GACATGCCGG | TAGATCAAAA | 5220 |
| GGCAAAGTAT | GTGCATATCA | CGTTGGACAA | AGCGTATCGA | CTCGAACAGC | TAATCGACGA | 5280 |

| | | | | | | |
|---|---|---|---|---|---|---|
| GTTTTTTGAG | ATTACACGGT | ATAACCTACA | AACGATAACG | CTAACAAAAA | CGCACATAGA | 5340 |
| CCTATACTAT | ATGCTGGTGC | AGATGACCGA | TGAATTTTAT | CCTCAGCTTT | CCGCACATGG | 5400 |
| AAAACAGGCG | GTTATTCACG | CCCCCGAGGA | TCTGACCGTG | TCCGGCGACC | CTGATAAACT | 5460 |
| CGCGAGAGTC | TTTAACAACA | TTTTGAAAAA | CGCCGCTGCA | TACAGTGAGG | ATAACAGCAT | 5520 |
| CATTGACATT | ACCGCGGGCC | TCTCCGGGGA | TGTGGTGTCA | ATCGAATTCA | AGAACACTGG | 5580 |
| AAGCATCCCA | AAAGATAAGC | TAGCTGCCAT | ATTTGAAAAG | TTCTATAGGC | TGGACAATGC | 5640 |
| TCGTTCTTCC | GATACGGGTG | GCGCGGGACT | TGGATTGGCG | ATTGCAAAAG | AAATTATTGT | 5700 |
| TCAGCATGGA | GGGCAGATTT | ACGCGGAAAG | CAATGATAAC | TATACGACGT | TTAGGGTAGA | 5760 |
| GCTTCCAGCG | ATGCCAGACT | TGGTTGATAA | AAGGAGGTCC | TAAGAGATGT | ATATAATTTT | 5820 |
| TTAGGAAAAT | CTCAAGGTTA | TCTTTACTTT | TTCTTAGGAA | ATTAACAATT | TAATATTAAG | 5880 |
| AAACGGCTCG | TTCTTACACG | GTAGACTTAA | TACCGTAAGA | ACGAGCCGTT | TTCGTTCTTC | 5940 |
| AGAGAAAGAT | TTGACAAGAT | TACCATTGGC | ATCCCGTTT | TATTTGGTGC | CTTTCACAGA | 6000 |
| AAGGGTTGGT | CTTAATTATG | AATAACATCG | GCATTACTGT | TTATGGATGT | GAGCAGGATG | 6060 |
| AGGCAGATGC | ATTCCATGCT | CTTTCGCCTC | GCTTTGGCGT | TATGGCAACG | ATAATTAACG | 6120 |
| CCAACGTGTC | GGAATCCAAC | GCCAAATCCG | CGCCTTTCAA | TCAATGTATC | AGTGTGGGAC | 6180 |
| ATAAATCAGA | GATTTCCGCC | TCTATTCTTC | TTGCGCTGAA | GAGAGCCGGT | GTGAAATATA | 6240 |
| TTTCTACCCG | AAGCATCGGC | TGCAATCATA | TAGATACAAC | TGCTGCTAAG | AGAATGGGCA | 6300 |
| TCACTGTCGA | CAATGTGGCG | TACTCGCCGG | ATAGCGTTGC | CGATTATACT | ATGATGCTAA | 6360 |
| TTCTTATGGC | AGTACGCAAC | GTAAAATCGA | TTGTGCGCTC | TGTGGAAAAA | CATGATTTCA | 6420 |
| GGTTGGACAG | CGACCGTGGC | AAGGTACTCA | GCGACATGAC | AGTTGGTGTG | GTGGGAACGG | 6480 |
| GCCAGATAGG | CAAAGCGGTT | ATTGAGCGGC | TGCGAGGATT | TGGATGTAAA | GTGTTGGCTT | 6540 |
| ATAGTCGCAG | CCGAAGTATA | GAGGTAAACT | ATGTACCGTT | TGATGAGTTG | CTGCAAAATA | 6600 |
| GCGATATCGT | TACGCTTCAT | GTGCCGCTCA | ATACGGATAC | GCACTATATT | ATCAGCCACG | 6660 |
| AACAAATACA | GAGAATGAAG | CAAGGAGCAT | TTCTTATCAA | TACTGGGCGC | GGTCCACTTG | 6720 |
| TAGATACCTA | TGAGTTGGTT | AAAGCATTAG | AAAACGGGAA | ACTGGGCGGT | GCCGCATTGG | 6780 |
| ATGTATTGGA | AGGAGAGGAA | GAGTTTTCT | ACTCTGATTG | CACCCAAAAA | CCAATTGATA | 6840 |
| ATCAATTTTT | ACTTAAACTT | CAAAGAATGC | CTAACGTGAT | AATCACACCG | CATACGGCCT | 6900 |
| ATTATACCGA | GCAAGCGTTG | CGTGATACCG | TTGAAAAAAC | CATTAAAAAC | TGTTTGGATT | 6960 |
| TTGAAAGGAG | ACAGGAGCAT | GAATAGAATA | AAAGTTGCAA | TACTGTTTGG | GGGTTGCTCA | 7020 |
| GAGGAGCATG | ACGTATCGGT | AAAATCTGCA | ATAGAGATAG | CCGCTAACAT | TAATAAAGAA | 7080 |
| AAATACGAGC | CGTTATACAT | TGGAATTACG | AAATCTGGTG | TATGGAAAAT | GTGCGAAAAA | 7140 |
| CCTTGCGCGG | AATGGGAAAA | CGACAATTGC | TATTCAGCTG | TACTCTCGCC | GGATAAAAAA | 7200 |
| ATGCACGGAT | TACTTGTTAA | AAAGAACCAT | GAATATGAAA | TCAACCATGT | TGATGTAGCA | 7260 |
| TTTTCAGCTT | TGCATGGCAA | GTCAGGTGAA | GATGGATCCA | TACAAGGTCT | GTTTGAATTG | 7320 |
| TCCGGTATCC | CTTTTGTAGG | CTGCGATATT | CAAAGCTCAG | CAATTTGTAT | GGACAAATCG | 7380 |
| TTGACATACA | TCGTTGCGAA | AAATGCTGGG | ATAGCTACTC | CCGCCTTTTG | GGTTATTAAT | 7440 |
| AAAGATGATA | GGCCGGTGGC | AGCTACGTTT | ACCTATCCTG | TTTTTGTTAA | GCCGGCGCGT | 7500 |
| TCAGGCTCAT | CCTTCGGTGT | GAAAAAGTC | AATAGCGCGG | ACGAATTGGA | CTACGCAATT | 7560 |
| GAATCGGCAA | GACAATATGA | CAGCAAAATC | TTAATTGAGC | AGGCTGTTTC | GGGCTGTGAG | 7620 |
| GTCGGTTGTG | CGGTATTGGG | AAACAGTGCC | GCGTTAGTTG | TTGGCGAGGT | GGACCAAATC | 7680 |

| | | | | | | |
|---|---|---|---|---|---|---|
| AGGCTGCAGT | ACGGAATCTT | TCGTATTCAT | CAGGAAGTCG | AGCCGGAAAA | AGGCTCTGAA | 7740 |
| AACGCAGTTA | TAACCGTTCC | CGCAGACCTT | TCAGCAGAGG | AGCGAGGACG | GATACAGGAA | 7800 |
| ACGGCAAAAA | AAATATATAA | AGCGCTCGGC | TGTAGAGGTC | TAGCCCGTGT | GGATATGTTT | 7860 |
| TTACAAGATA | ACGGCCGCAT | TGTACTGAAC | GAAGTCAATA | CTCTGCCCGG | TTTCACGTCA | 7920 |
| TACAGTCGTT | ATCCCCGTAT | GATGGCCGCT | GCAGGTATTG | CACTTCCCGA | ACTGATTGAC | 7980 |
| CGCTTGATCG | TATTAGCGTT | AAAGGGGTGA | TAAGCATGGA | AATAGGATTT | ACTTTTTTAG | 8040 |
| ATGAAATAGT | ACACGGTGTT | CGTTGGGACG | CTAAATATGC | CACTTGGGAT | AATTTCACCG | 8100 |
| GAAAACCGGT | TGACGGTTAT | GAAGTAAATC | GCATTGTAGG | GACATACGAG | TTGGCTGAAT | 8160 |
| CGCTTTTGAA | GGCAAAGAA | CTGGCTGCTA | CCCAAGGGTA | CGGATTGCTT | CTATGGGACG | 8220 |
| GTTACCGTCC | TAAGCGTGCT | GTAAACTGTT | TTATGCAATG | GGCTGCACAG | CCGGAAAATA | 8280 |
| ACCTGACAAA | GGAAAGTTAT | TATCCCAATA | TTGACCGAAC | TGAGATGATT | TCAAAGGAT | 8340 |
| ACGTGGCTTC | AAAATCAAGC | CATAGCCGCG | GCAGTGCCAT | TGATCTTACG | CTTTATCGAT | 8400 |
| TAGACACGGG | TGAGCTTGTA | CCAATGGGGA | GCCGATTTGA | TTTTATGGAT | GAACGCTCTC | 8460 |
| ATCATGCGGC | AAATGGAATA | TCATGCAATG | AAGCGCAAAA | TCGCAGACGT | TTGCGCTCCA | 8520 |
| TCATGGAAAA | CAGTGGGTTT | GAAGCATATA | GCCTCGAATG | GTGGCACTAT | GTATTAAGAG | 8580 |
| ACGAACCATA | CCCCAATAGC | TATTTGATT | TCCCCGTTAA | ATAAACTTTT | AACCGTTGCA | 8640 |
| CGGACAAACT | ATATAAGCTA | ACTCTTTCGG | CAGGAAACCC | GACGTATGTA | ACTGGTTCTT | 8700 |
| AGGGAATTTA | TATATAGTAG | ATAGTATTGA | AGATGTAAGG | CAGAGCGATA | TTGCGGTCAT | 8760 |
| TATCTGCGTG | CGCTGCGGCA | AGATAGCCTG | ATAATAAGAC | TGATCGCATA | GAGGGGTGGT | 8820 |
| ATTTCACACC | GCCCATTGTC | AACAGGCAGT | TCAGCCTCGT | TAAATTCAGC | ATGGGTATCA | 8880 |
| CTTATGAAAA | TTCATCTACA | TTGGTGATAA | TAGTAAATCC | AGTAGGGCGA | ATAATTGAC | 8940 |
| TGTAATTTAC | GGGGCAAAAC | GGCACAATCT | CAAACGAGAT | TGTGCCGTTT | AAGGGGAAGA | 9000 |
| TTCTAGAAAT | ATTTCATACT | TCCAACTATA | TAGTTAAGGA | GGAGACTGAA | AATGAAGAAG | 9060 |
| TTGTTTTTTT | TATTGTTATT | GTTATTCTTA | ATATACTTAG | GTTATGACTA | CGTTAATGAA | 9120 |
| GCACTGTTTT | CTCAGGAAAA | AGTCGAATTT | CAAAATTATG | ATCAAAATCC | CAAAGAACAT | 9180 |
| TTAGAAAATA | GTGGGACTTC | TGAAAATACC | CAAGAGAAAA | CAATTACAGA | AGAACAGGTT | 9240 |
| TATCAAGGAA | ATCTGCTATT | AATCAATAGT | AAATATCCTG | TTCGCCAAGA | AAGTGTGAAG | 9300 |
| TCAGATATCG | TGAATTTATC | TAAACATGAC | GAATTAATAA | ATGGATACGG | TTGCTTGAT | 9360 |
| AGTAATATTT | ATATGTCAAA | AGAAATAGCA | CAAAAATTTT | CAGAGATGGT | CAATGATGCT | 9420 |
| GTAAAGGGTG | GCGTTAGTCA | TTTTATTATT | AATAGTGGCT | ATCGAGACTT | TGATGAGCAA | 9480 |
| AGTGTGCTTT | ACCAAGAAAT | GGGGGCTGAG | TATGCCTTAC | CAGCAGGTTA | TAGTGAGCAT | 9540 |
| AATTCAGGTT | TATCACTAGA | TGTAGGATCA | AGCTTGACGA | AAATGGAACG | AGCCCCTGAA | 9600 |
| GGAAAGTGGA | TAGAAGAAAA | TGCTTGGAAA | TACGGGTTCA | TTTTACGTTA | TCCAGAGGAC | 9660 |
| AAAACAGAGT | TAACAGGAAT | TCAATATGAA | CCATGGCATA | TTCGCTATGT | TGGTTTACCA | 9720 |
| CATAGTGCGA | TTATGAAAGA | AAAGAATTTC | GTTCTCGAGG | AATATATGGA | TTACCTAAAA | 9780 |
| GAAGAAAAAA | CCATTTCTGT | TAGTGTAAAT | GGGGAAAAAT | ATGAGATCTT | TTATTATCCT | 9840 |
| GTTACTAAAA | ATACCACCAT | TCATGTGCCG | ACTAATCTTC | GTTATGAGAT | ATCAGGAAAC | 9900 |
| AATATAGACG | GTGTAATTGT | GACAGTGTTT | CCCGGATCAA | CACATACTAA | TTCAAGGAGG | 9960 |
| TAAGGATGGC | GGAATGAAAC | CAACGAAATT | AATGAACAGC | ATTATTGTAC | TAGCACTTTT | 10020 |
| GGGGTAACGT | TAGCTTTTTA | ATTTAAAACC | CACGTTAACT | AGGACATTGC | TATACTAATG | 10080 |

-continued

| | | | | | | |
|---|---|---|---|---|---|---|
| ATACAACTTA | AACAAAAGAA | TTAGAGGAAA | TTATATTGGG | AAAAATATTA | TCTAGAGGAT | 10140 |
| TGCTAGCTTT | ATATTTAGTG | ACACTAATCT | GGTTAGTGTT | ATTCAAATTA | CAATACAATA | 10200 |
| TTTTATCAGT | ATTTAATTAT | CATCAAAGAA | GTCTTAACTT | GACTCCATTT | ACTGCTACTG | 10260 |
| GGAATTTCAG | AGAGATGATA | GATAATGTTA | TAATCTTTAT | TCCATTTGGC | TTGCTTTTGA | 10320 |
| ATGTCAATTT | TAAAGAAATC | GGATTTTAC | CTAAGTTTGC | TTTTGTACTG | GTTTTAAGTC | 10380 |
| TTACTTTTGA | AATAATTCAA | TTTATCTTCG | CTATTGGAGC | GACAGACATA | ACAGATGTAA | 10440 |
| TTACAAATAC | TGTTGGAGGC | TTTCTTGGAC | TGAAATTATA | TGGTTTAAGC | AATAAGCATA | 10500 |
| TGAATCAAAA | AAAATTAGAC | AGAGTTATTA | TTTTTGTAGG | TATACTTTTG | CTCGTATTAT | 10560 |
| TGCTCGTTTA | CCGTACCCAT | TTAAGAATAA | ATTACGTGTA | AGATGTCTAA | ATCAAGCAAT | 10620 |
| CTGATCTTTC | ATACACATAA | AGATATTGAA | TGAATTGGAT | TAGATGGAAA | ACGGGATGTG | 10680 |
| GGGAAACTCG | CCCGTAGGTG | TGAAGTGAGG | GGAAAACCGG | TGATAAAGTA | AAAAGCTTAC | 10740 |
| CTAACACTAT | AGTAACAAAG | AAAGCCCAAT | TATCAATTTT | AGTGCTGAGG | AATTGGTCTC | 10800 |
| TTTAATAAAT | TTCCTTAACG | TTGTAAATCC | GCATTTTCCT | GACGGTACCC | C | 10851 |

( 2 ) INFORMATION FOR SEQ ID NO:17:

( i ) SEQUENCE CHARACTERISTICS:
        ( A ) LENGTH: 2667 base pairs
        ( B ) TYPE: nucleic acid
        ( C ) STRANDEDNESS: unknown
        ( D ) TOPOLOGY: linear ( i i ) MOLECULE TYPE: DNA (genomic)

( x i ) SEQUENCE DESCRIPTION: SEQ ID NO:17:

| | | | | | | |
|---|---|---|---|---|---|---|
| CAAGATTACC | ATTGGCATCC | CCGTTTTATT | TGGTGCCTTT | CACAGAAAGG | GTTGGTCTTA | 60 |
| ATTATGAATA | ACATCGGCAT | TACTGTTTAT | GGATGTGAGC | AGGATGAGGC | AGATGCATTC | 120 |
| CATGCTCTTT | CGCCTCGCTT | TGGCGTTATG | GCAACGATAA | TTAACGCCAA | CGTGTCGGAA | 180 |
| TCCAACGCCA | AATCCGCGCC | TTTCAATCAA | TGTATCAGTG | TGGGACATAA | ATCAGAGATT | 240 |
| TCCGCCTCTA | TTCTTCTTGC | GCTGAAGAGA | GCCGGTGTGA | AATATATTTC | TACCCGAAGC | 300 |
| ATCGGCTGCA | ATCATATAGA | TACAACTGCT | GCTAAGAGAA | TGGGCATCAC | TGTCGACAAT | 360 |
| GTGGCGTACT | CGCCGGATAG | CGTTGCCGAT | TATACTATGA | TGCTAATTCT | TATGGCAGTA | 420 |
| CGCAACGTAA | AATCGATTGT | GCGCTCTGTG | GAAAAACATG | ATTTCAGGTT | GGACAGCGAC | 480 |
| CGTGGCAAGG | TACTCAGCGA | CATGACAGTT | GGTGTGGTGG | GAACGGGCCA | GATAGGCAAA | 540 |
| GCGGTTATTG | AGCGGCTGCG | AGGATTTGGA | TGTAAAGTGT | TGGCTTATAG | TCGCAGCCGA | 600 |
| AGTATAGAGG | TAAACTATGT | ACCGTTTGAT | GAGTTGATGC | AAAATAGCGA | TATCGTTACG | 660 |
| CTTCATGTGC | CGCTCAATAC | GGATACGCAC | TATATTATCA | GCCACGAACA | AATACAGAGA | 720 |
| ATGAAGCAAG | GAGCATTTCT | TATCAATACT | GGGCGCGGTC | CACTTGTAGA | TACCTATGAG | 780 |
| TTGGTTAAAG | CATTAGAAAA | CGGGAAACTG | GGCGGTGCCG | CATTGGATGT | ATTGGAAGGA | 840 |
| GAGGAAGAGT | TTTTCTACTC | TGATTGCACC | CAAAAACCAA | TTGATAATCA | ATTTTTACTT | 900 |
| AAACTTCAAA | GAATGCCTAA | CGTGATAATC | ACACCGCATA | CGGCCTATTA | TACCGAGCAA | 960 |
| GCGTTGCGTG | ATACCGTTGA | AAAAACCATT | AAAAACTGTT | TGGATTTTGA | AAGGAGACAG | 1020 |
| GAGCATGAAT | AGAATAAAAG | TTGCAATACT | GTTTGGGGGT | TGCTCAGAGG | AGCATGACGT | 1080 |
| ATCGGTAAAA | TCTGCAATAG | AGATAGCCGC | TAACATTAAT | AAAGAAAAAT | ACGAGCCGTT | 1140 |
| ATACATTGGA | ATTACGAAAT | CTGGTGTATG | GAAAATGTGC | GAAAAACCTT | GCGCGGAATG | 1200 |
| GGAAAACGAC | AATTGCTATT | CAGCTGTACT | CTCGCCGGAT | AAAAAAATGC | ACGGATTACT | 1260 |

-continued

| | | | | | |
|---|---|---|---|---|---|
|TGTTAAAAAG|AACCATGAAT|ATGAAATCAA|CCATGTTGAT|GTAGCATTTT|CAGCTTTGCA|1320|
|TGGCAAGTCA|GGTGAAGATG|GATCCATACA|AGGTCTGTTT|GAATTGTCCG|GTATCCCTTT|1380|
|TGTAGGCTGC|GATATTCAAA|GCTCAGCAAT|TTGTATGGAC|AAATCGTTGA|CATACATCGT|1440|
|TGCGAAAAAT|GCTGGGATAG|CTACTCCCGC|CTTTTGGGTT|ATTAATAAAG|ATGATAGGCC|1500|
|GGTGGCAGCT|ACGTTTACCT|ATCCTGTTTT|TGTTAAGCCG|GCGCGTTCAG|GCTCATCCTT|1560|
|CGGTGTGAAA|AAAGTCAATA|GCGCGGACGA|ATTGGACTAC|GCAATTGAAT|CGGCAAGACA|1620|
|ATATGACAGC|AAAATCTTAA|TTGAGCAGGC|TGTTTCGGGC|TGTGAGGTCG|GTTGTGCGGT|1680|
|ATTGGGAAAC|AGTGCCGCGT|TAGTTGTTGG|CGAGGTGGAC|CAAATCAGGC|TGCAGTACGG|1740|
|AATCTTTCGT|ATTCATCAGG|AAGTCGAGCC|GGAAAAAGGC|TCTGAAAACG|CAGTTATAAC|1800|
|CGTTCCCGCA|GACCTTTCAG|CAGAGGAGCG|AGGACGGATA|CAGGAAACGG|CAAAAAAAT|1860|
|ATATAAAGCG|CTCGGCTGTA|GAGGTCTAGC|CCGTGTGGAT|ATGTTTTTAC|AAGATAACGG|1920|
|CCGCATTGTA|CTGAACGAAG|TCAATACTCT|GCCCGGTTTC|ACGTCATACA|GTCGTTATCC|1980|
|CCGTATGATG|GCCGCTGCAG|GTATTGCACT|TCCCGAACTG|ATTGACCGCT|TGATCGTATT|2040|
|AGCGTTAAAG|GGGTGATAAG|CATGGAAATA|GGATTTACTT|TTTTAGATGA|AATAGTACAC|2100|
|GGTGTTCGTT|GGGACGCTAA|ATATGCCACT|TGGGATAATT|TCACCGGAAA|ACCGGTTGAC|2160|
|GGTTATGAAG|TAAATCGCAT|TGTAGGGACA|TACGAGTTGG|CTGAATCGCT|TTTGAAGGCA|2220|
|AAAGAACTGG|CTGCTACCCA|AGGGTACGGA|TTGCTTCTAT|GGGACGGTTA|CCGTCCTAAG|2280|
|CGTGCTGTAA|ACTGTTTTAT|GCAATGGGCT|GCACAGCCGG|AAAATAACCT|GACAAAGGAA|2340|
|AGTTATTATC|CCAATATTGA|CCGAACTGAG|ATGATTTCAA|AAGGATACGT|GGCTTCAAAA|2400|
|TCAAGCCATA|GCCGCGGCAG|TGCCATTGAT|CTTACGCTTT|ATCGATTAGA|CACGGGTGAG|2460|
|CTTGTACCAA|TGGGGAGCCG|ATTTGATTTT|ATGGATGAAC|GCTCTCATCA|TGCGGCAAAT|2520|
|GGAATATCAT|GCAATGAAGC|GCAAAATCGC|AGACGTTTGC|GCTCCATCAT|GGAAAACAGT|2580|
|GGGTTTGAAG|CATATAGCCT|CGAATGGTGG|CACTATGTAT|TAAGAGACGA|ACCATACCCC|2640|
|AATAGCTATT|TTGATTTCCC|CGTTAAA| | |2667|

( 2 ) INFORMATION FOR SEQ ID NO:18:

( i ) SEQUENCE CHARACTERISTICS:
        ( A ) LENGTH: 2964 base pairs
        ( B ) TYPE: nucleic acid
        ( C ) STRANDEDNESS: unknown
        ( D ) TOPOLOGY: linear ( i i ) MOLECULE TYPE: DNA (genomic)

( i x ) FEATURE:
        ( A ) NAME/KEY: CDS
        ( B ) LOCATION: 1..2964

( x i ) SEQUENCE DESCRIPTION: SEQ ID NO:18:

```
ATG  AAA  ATT  GCG  AGA  GGT  AGA  GAA  TTG  CTT  ACA  CCG  GAA  CAG  AGA  CAG        48
Met  Lys  Ile  Ala  Arg  Gly  Arg  Glu  Leu  Leu  Thr  Pro  Glu  Gln  Arg  Gln
 1                 5                        10                       15

GCT  TTT  ATG  CAA  ATC  CCT  GAA  GAT  GAA  TGG  ATA  CTG  GGG  ACC  TAC  TTC        96
Ala  Phe  Met  Gln  Ile  Pro  Glu  Asp  Glu  Trp  Ile  Leu  Gly  Thr  Tyr  Phe
             20                       25                       30

ACT  TTT  TCC  AAA  CGG  GAT  TTA  GAA  ATA  GTT  AAT  AAG  CGA  AGG  AGG  GAA       144
Thr  Phe  Ser  Lys  Arg  Asp  Leu  Glu  Ile  Val  Asn  Lys  Arg  Arg  Arg  Glu
         35                       40                       45

GAA  AAC  CGT  TTA  GGA  TTT  GCT  GTT  CAA  TTA  GCT  GTT  CTT  CGG  TAT  CCC       192
Glu  Asn  Arg  Leu  Gly  Phe  Ala  Val  Gln  Leu  Ala  Val  Leu  Arg  Tyr  Pro
```

```
                50                              55                              60
GGT TGG CCA TAC ACT CAT ATC AAA AGC ATC CCA GAT TCG GTC ATA CAA        240
Gly Trp Pro Tyr Thr His Ile Lys Ser Ile Pro Asp Ser Val Ile Gln
 65              70                  75                      80

TAT ATA TCG AAA CAG ATT GGT GTT AGT CCA TCC TCG CTT GAT CAT TAT        288
Tyr Ile Ser Lys Gln Ile Gly Val Ser Pro Ser Ser Leu Asp His Tyr
             85                  90                      95

CCT CAA AGG GAA AAT ACA CTT TGG GAT CAT TTG AAA GAA ATT CGA AGT        336
Pro Gln Arg Glu Asn Thr Leu Trp Asp His Leu Lys Glu Ile Arg Ser
            100                 105                     110

GAA TAC GAC TTT GTA ACT TTT ACC CTG AGT GAA TAT CGA ATG ACA TTT        384
Glu Tyr Asp Phe Val Thr Phe Thr Leu Ser Glu Tyr Arg Met Thr Phe
        115                 120                     125

AAG TAC CTT CAT CAA TTA GCT TTG GAA AAT GGT GAT GCC ATT CAT CTA        432
Lys Tyr Leu His Gln Leu Ala Leu Glu Asn Gly Asp Ala Ile His Leu
    130                 135                     140

CTG CAT GAA TGC ATA GAT TTT CTA AGA AAA AAC AAA ATT ATA CTG CCT        480
Leu His Glu Cys Ile Asp Phe Leu Arg Lys Asn Lys Ile Ile Leu Pro
145                 150                     155                 160

GCT ATC ACT ACA CTT GAA AGA ATG GTG TGG GAA GCA AGG GCA ATG GCT        528
Ala Ile Thr Thr Leu Glu Arg Met Val Trp Glu Ala Arg Ala Met Ala
                165                     170                 175

GAA AAG AAG CTA TTT AAT ACG GTT AGT AAA TCT CTA ACA AAT GAG CAA        576
Glu Lys Lys Leu Phe Asn Thr Val Ser Lys Ser Leu Thr Asn Glu Gln
            180                     185                 190

AAA GAA AAG CTT GAA GGG ATT ATT ACC TCG CAG CAT CCA TCC GAA TCC        624
Lys Glu Lys Leu Glu Gly Ile Ile Thr Ser Gln His Pro Ser Glu Ser
        195                     200                 205

AAT AAA ACG ATA TTG GGT TGG TTA AAA GAG CCA CCG GGT CAT CCT TCA        672
Asn Lys Thr Ile Leu Gly Trp Leu Lys Glu Pro Pro Gly His Pro Ser
210                     215                 220

CCC GAA ACT TTT CTA AAA ATA ATA GAA CGA CTC GAA TAC ATA CGA GGA        720
Pro Glu Thr Phe Leu Lys Ile Ile Glu Arg Leu Glu Tyr Ile Arg Gly
225                 230                     235                 240

ATG GAT TTA GAA ACA GTG CAA ATT AGT CAT TTG CAC CGT AAC CGC CTG        768
Met Asp Leu Glu Thr Val Gln Ile Ser His Leu His Arg Asn Arg Leu
                245                     250                 255

TTG CAG CTG TCT CGC TTA GGC TCA AGA TAC GAG CCG TAT GCA TTC CGT        816
Leu Gln Leu Ser Arg Leu Gly Ser Arg Tyr Glu Pro Tyr Ala Phe Arg
            260                     265                 270

GAC TTT CAA GAA AAT AAA CGT TAT TCG ATA TTA ACC ATC TAT TTA TTA        864
Asp Phe Gln Glu Asn Lys Arg Tyr Ser Ile Leu Thr Ile Tyr Leu Leu
        275                     280                 285

CAA CTT ACT CAG GAG CTA ACG GAT AAA GCG TTT GAA ATT CAT GAT AGG        912
Gln Leu Thr Gln Glu Leu Thr Asp Lys Ala Phe Glu Ile His Asp Arg
    290                     295                 300

CAA ATA CTT AGT TTG TTA TCA AAA GGT CGT AAG GCT CAA GAG GAA ATC        960
Gln Ile Leu Ser Leu Leu Ser Lys Gly Arg Lys Ala Gln Glu Glu Ile
305                     310                 315                 320

CAG AAA CAA AAC GGT AAA AAG CTA AAT GAG AAA GTT ATA CAC TTT ACG       1008
Gln Lys Gln Asn Gly Lys Lys Leu Asn Glu Lys Val Ile His Phe Thr
                325                 330                     335

AAC ATC GGA CAA GCA TTA ATT AAA GCA AGA GAG GAA AAA TTA GAC GTT       1056
Asn Ile Gly Gln Ala Leu Ile Lys Ala Arg Glu Glu Lys Leu Asp Val
            340                 345                     350

TTT AAG GTT TTA GAA TCG GTT ATT GAA TGG AAT ACC TTT GTC TCT TCA       1104
Phe Lys Val Leu Glu Ser Val Ile Glu Trp Asn Thr Phe Val Ser Ser
        355                 360                     365

GTA GAA GAG GCT CAG GAA CTT GCA CGT CCT GCC GAC TAT GAT TAT TTA       1152
Val Glu Glu Ala Gln Glu Leu Ala Arg Pro Ala Asp Tyr Asp Tyr Leu
```

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
|     |     | 370 |     |     |     |     |     | 375 |     |     |     |     |     | 380 |     |      |
| GAC | TTA | CTG | CAA | AAA | CGG | TTT | TAT | TCA | CTA | AGA | AAA | TAT | ACG | CCA | ACG | 1200 |
| Asp | Leu | Leu | Gln | Lys | Arg | Phe | Tyr | Ser | Leu | Arg | Lys | Tyr | Thr | Pro | Thr |      |
| 385 |     |     |     | 390 |     |     |     |     | 395 |     |     |     |     |     | 400 |      |
| CTA | TTA | AGA | GTA | TTG | GAA | TTT | CAT | TCT | ACA | AAG | GCA | AAT | GAG | CCA | CTT | 1248 |
| Leu | Leu | Arg | Val | Leu | Glu | Phe | His | Ser | Thr | Lys | Ala | Asn | Glu | Pro | Leu |      |
|     |     |     |     | 405 |     |     |     |     | 410 |     |     |     |     | 415 |     |      |
| TTA | CAA | GCT | GTT | GAG | ATT | ATC | CGA | GGA | ATG | AAC | GAA | TCT | GGA | AAG | CGA | 1296 |
| Leu | Gln | Ala | Val | Glu | Ile | Ile | Arg | Gly | Met | Asn | Glu | Ser | Gly | Lys | Arg |      |
|     |     |     | 420 |     |     |     |     | 425 |     |     |     |     | 430 |     |     |      |
| AAA | GTG | CCT | GAT | GAC | TCA | CCT | GTG | GAT | TTT | ATT | TCA | AAA | CGA | TGG | AAA | 1344 |
| Lys | Val | Pro | Asp | Asp | Ser | Pro | Val | Asp | Phe | Ile | Ser | Lys | Arg | Trp | Lys |      |
|     |     | 435 |     |     |     |     | 440 |     |     |     |     | 445 |     |     |     |      |
| AGA | CAT | TTA | TAC | GAG | GAT | GAT | GGT | ACA | ACA | ATT | AAT | CGT | CAT | TAC | TAT | 1392 |
| Arg | His | Leu | Tyr | Glu | Asp | Asp | Gly | Thr | Thr | Ile | Asn | Arg | His | Tyr | Tyr |      |
|     | 450 |     |     |     |     | 455 |     |     |     |     | 460 |     |     |     |     |      |
| GAA | ATG | GCT | GTT | TTA | ACA | GAA | CTT | CGG | GAG | CAT | GTT | CGG | GCA | GGA | GAT | 1440 |
| Glu | Met | Ala | Val | Leu | Thr | Glu | Leu | Arg | Glu | His | Val | Arg | Ala | Gly | Asp |      |
| 465 |     |     |     |     | 470 |     |     |     |     | 475 |     |     |     |     | 480 |      |
| GTT | TCC | ATT | GTT | GGC | AGC | AGA | CAA | TAT | AGG | GAT | TTT | GAG | GAA | TAT | TTG | 1488 |
| Val | Ser | Ile | Val | Gly | Ser | Arg | Gln | Tyr | Arg | Asp | Phe | Glu | Glu | Tyr | Leu |      |
|     |     |     |     | 485 |     |     |     |     | 490 |     |     |     |     | 495 |     |      |
| TTT | TCG | GAA | GAT | ACA | TGG | AAT | CAA | TCG | AAG | GGG | AAT | ACG | AGA | TTA | TCA | 1536 |
| Phe | Ser | Glu | Asp | Thr | Trp | Asn | Gln | Ser | Lys | Gly | Asn | Thr | Arg | Leu | Ser |      |
|     |     |     | 500 |     |     |     |     | 505 |     |     |     |     | 510 |     |     |      |
| GTT | AGT | TTA | TCA | TTC | GAA | GAT | TAT | ATA | ACG | GAG | AGA | ACC | AGC | AGC | TTT | 1584 |
| Val | Ser | Leu | Ser | Phe | Glu | Asp | Tyr | Ile | Thr | Glu | Arg | Thr | Ser | Ser | Phe |      |
|     |     | 515 |     |     |     |     | 520 |     |     |     |     | 525 |     |     |     |      |
| AAT | GAA | AGG | TTA | AAG | TGG | TTA | GCT | GCC | AAT | TCC | AAT | AAG | TTA | GAT | GGG | 1632 |
| Asn | Glu | Arg | Leu | Lys | Trp | Leu | Ala | Ala | Asn | Ser | Asn | Lys | Leu | Asp | Gly |      |
|     | 530 |     |     |     |     | 535 |     |     |     |     | 540 |     |     |     |     |      |
| GTT | TCT | CTT | GAA | AAA | GGA | AAG | CTA | TCA | CTT | GCA | CGC | TTA | GAA | AAA | GAT | 1680 |
| Val | Ser | Leu | Glu | Lys | Gly | Lys | Leu | Ser | Leu | Ala | Arg | Leu | Glu | Lys | Asp |      |
| 545 |     |     |     |     | 550 |     |     |     |     | 555 |     |     |     |     | 560 |      |
| GTT | CCA | GAA | GAA | GCA | AAA | AAA | TTT | AGT | GCA | AGC | CTT | TAT | CAG | ATG | CTA | 1728 |
| Val | Pro | Glu | Glu | Ala | Lys | Lys | Phe | Ser | Ala | Ser | Leu | Tyr | Gln | Met | Leu |      |
|     |     |     |     | 565 |     |     |     |     | 570 |     |     |     |     | 575 |     |      |
| CCA | AGA | ATA | AAA | TTA | ACT | GAT | TTA | CTC | ATG | GAT | GTG | GCC | CAT | ATA | ACA | 1776 |
| Pro | Arg | Ile | Lys | Leu | Thr | Asp | Leu | Leu | Met | Asp | Val | Ala | His | Ile | Thr |      |
|     |     |     | 580 |     |     |     |     | 585 |     |     |     |     | 590 |     |     |      |
| GGA | TTT | CAT | GAG | CAA | TTC | ACT | CAT | GCT | TCC | AAT | AAT | CGA | AAA | CCA | GAT | 1824 |
| Gly | Phe | His | Glu | Gln | Phe | Thr | His | Ala | Ser | Asn | Asn | Arg | Lys | Pro | Asp |      |
|     |     | 595 |     |     |     |     | 600 |     |     |     |     | 605 |     |     |     |      |
| AAG | GAA | GAA | ACA | ATC | ATT | ATC | ATG | GCT | GCC | CTT | TTA | GGA | ATG | GGA | ATG | 1872 |
| Lys | Glu | Glu | Thr | Ile | Ile | Ile | Met | Ala | Ala | Leu | Leu | Gly | Met | Gly | Met |      |
|     | 610 |     |     |     |     | 615 |     |     |     |     | 620 |     |     |     |     |      |
| AAT | ATT | GGC | TTG | AGC | AAG | ATG | GCC | GAA | GCC | ACA | CCC | GGA | CTT | ACA | TAT | 1920 |
| Asn | Ile | Gly | Leu | Ser | Lys | Met | Ala | Glu | Ala | Thr | Pro | Gly | Leu | Thr | Tyr |      |
| 625 |     |     |     |     | 630 |     |     |     |     | 635 |     |     |     |     | 640 |      |
| AAG | CAA | CTA | GCC | AAT | GTA | TCT | CAA | TGG | CGC | ATG | TAT | GAA | GAT | GCC | ATG | 1968 |
| Lys | Gln | Leu | Ala | Asn | Val | Ser | Gln | Trp | Arg | Met | Tyr | Glu | Asp | Ala | Met |      |
|     |     |     |     | 645 |     |     |     |     | 650 |     |     |     |     | 655 |     |      |
| AAT | AAA | GCC | CAA | GCC | ATA | TTA | GTA | AAC | TTT | CAT | CAT | AAA | TTA | CAA | TTG | 2016 |
| Asn | Lys | Ala | Gln | Ala | Ile | Leu | Val | Asn | Phe | His | His | Lys | Leu | Gln | Leu |      |
|     |     |     | 660 |     |     |     |     | 665 |     |     |     |     | 670 |     |     |      |
| CCT | TTC | TAT | TGG | GGC | GAC | GGT | ACA | ACA | TCT | TCG | TCA | GAT | GGT | ATG | AGA | 2064 |
| Pro | Phe | Tyr | Trp | Gly | Asp | Gly | Thr | Thr | Ser | Ser | Ser | Asp | Gly | Met | Arg |      |
|     |     | 675 |     |     |     |     | 680 |     |     |     |     | 685 |     |     |     |      |
| ATG | CAG | CTA | GGT | GTT | TCA | TCA | CTA | CAT | GCA | GAT | GCA | AAT | CCA | CAT | TAT | 2112 |
| Met | Gln | Leu | Gly | Val | Ser | Ser | Leu | His | Ala | Asp | Ala | Asn | Pro | His | Tyr |      |

```
                   690                             695                              700
GGA  ACT  GGA  AAA  GGA  GCC  ACC  ATC  TAC  CGA  TTT  ACA  AGT  GAT  CAA  TTC        2160
Gly  Thr  Gly  Lys  Gly  Ala  Thr  Ile  Tyr  Arg  Phe  Thr  Ser  Asp  Gln  Phe
705                      710                      715                      720

TCT  TCT  TAC  TAC  ACA  AAG  ATT  ATT  CAT  ACT  AAT  TCA  AGA  GAT  GCG  ATT        2208
Ser  Ser  Tyr  Tyr  Thr  Lys  Ile  Ile  His  Thr  Asn  Ser  Arg  Asp  Ala  Ile
                    725                      730                      735

CAT  GTT  TTG  GAT  GGT  TTG  TTA  CAT  CAT  GAG  ACG  GAT  CTA  AAC  ATA  GAG        2256
His  Val  Leu  Asp  Gly  Leu  Leu  His  His  Glu  Thr  Asp  Leu  Asn  Ile  Glu
               740                      745                      750

GAA  CAT  TAT  ACA  GAC  ACT  GCC  GGT  TAC  ACT  GAC  CAA  ATA  TTC  GGA  CTG        2304
Glu  His  Tyr  Thr  Asp  Thr  Ala  Gly  Tyr  Thr  Asp  Gln  Ile  Phe  Gly  Leu
          755                      760                      765

ACT  CAT  TTA  TTA  GGA  TTT  AAA  TTT  GCC  CCA  AGA  ATA  AGG  GAT  TTA  TCG        2352
Thr  His  Leu  Leu  Gly  Phe  Lys  Phe  Ala  Pro  Arg  Ile  Arg  Asp  Leu  Ser
     770                      775                      780

GAC  TCA  AAA  TTA  TTT  ACG  ATA  GAT  AAA  GCA  AGT  GAG  TAT  CCA  AAA  CTA        2400
Asp  Ser  Lys  Leu  Phe  Thr  Ile  Asp  Lys  Ala  Ser  Glu  Tyr  Pro  Lys  Leu
785                      790                      795                      800

GAA  GCC  ATT  TTA  CGT  GGA  CAA  ATA  AAT  ACA  AAG  GTC  ATT  AAA  GAA  AAT        2448
Glu  Ala  Ile  Leu  Arg  Gly  Gln  Ile  Asn  Thr  Lys  Val  Ile  Lys  Glu  Asn
                    805                      810                      815

TAT  GAG  GAT  GTT  TTG  CGA  TTA  GCT  CAT  TCT  ATA  AGG  GAG  GGA  ACA  GTT        2496
Tyr  Glu  Asp  Val  Leu  Arg  Leu  Ala  His  Ser  Ile  Arg  Glu  Gly  Thr  Val
               820                      825                      830

TCA  GCA  TCC  CTT  ATT  ATG  GGG  AAG  CTA  GGT  TCC  TAT  TCA  AGA  CAA  AAC        2544
Ser  Ala  Ser  Leu  Ile  Met  Gly  Lys  Leu  Gly  Ser  Tyr  Ser  Arg  Gln  Asn
          835                      840                      845

AGC  TTA  GCT  ACA  GCC  TTA  CGT  GAG  ATG  GGC  CGA  ATA  GAA  AAA  ACG  ATC        2592
Ser  Leu  Ala  Thr  Ala  Leu  Arg  Glu  Met  Gly  Arg  Ile  Glu  Lys  Thr  Ile
     850                      855                      860

TTT  ATT  TTG  AAT  TAT  ATA  TCG  GAT  GAA  TCA  TTA  AGA  AGA  AAA  ATA  CAA        2640
Phe  Ile  Leu  Asn  Tyr  Ile  Ser  Asp  Glu  Ser  Leu  Arg  Arg  Lys  Ile  Gln
865                      870                      875                      880

AGA  GGA  TTG  AAT  AAA  GGA  GAA  GCC  ATG  AAT  GGA  TTG  GCA  AGA  GCT  ATT        2688
Arg  Gly  Leu  Asn  Lys  Gly  Glu  Ala  Met  Asn  Gly  Leu  Ala  Arg  Ala  Ile
                    885                      890                      895

TTC  TTC  GGA  AAA  CAA  GGT  GAG  CTT  AGA  GAA  CGC  ACC  ATA  CAG  CAT  CAA        2736
Phe  Phe  Gly  Lys  Gln  Gly  Glu  Leu  Arg  Glu  Arg  Thr  Ile  Gln  His  Gln
               900                      905                      910

TTG  CAA  AGA  GCC  AGT  GCT  TTA  AAC  ATA  ATT  ATC  AAT  GCT  ATA  AGT  ATT        2784
Leu  Gln  Arg  Ala  Ser  Ala  Leu  Asn  Ile  Ile  Ile  Asn  Ala  Ile  Ser  Ile
          915                      920                      925

TGG  AAT  ACT  CTC  CAC  CTA  ACA  ACA  GCA  GTT  GAA  TAT  AAA  AAA  CGG  ACA        2832
Trp  Asn  Thr  Leu  His  Leu  Thr  Thr  Ala  Val  Glu  Tyr  Lys  Lys  Arg  Thr
     930                      935                      940

GGT  AGC  TTT  AAT  GAA  GAT  TTG  TTA  CAC  CAT  ATG  TCG  CCC  TTA  GGT  TGG        2880
Gly  Ser  Phe  Asn  Glu  Asp  Leu  Leu  His  His  Met  Ser  Pro  Leu  Gly  Trp
945                      950                      955                      960

GAA  CAT  ATT  AAT  TTA  CTA  GGA  GAA  TAC  CAT  TTT  AAC  TCA  GAG  AAA  GTA        2928
Glu  His  Ile  Asn  Leu  Leu  Gly  Glu  Tyr  His  Phe  Asn  Ser  Glu  Lys  Val
                    965                      970                      975

GTC  TCA  TTA  AAT  TCT  TTA  AGA  CCA  CTA  AAA  CTT  TCT                            2964
Val  Ser  Leu  Asn  Ser  Leu  Arg  Pro  Leu  Lys  Leu  Ser
               980                      985
```

( 2 ) INFORMATION FOR SEQ ID NO:19:

( i ) SEQUENCE CHARACTERISTICS:
        ( A ) LENGTH: 988 amino acids
        ( B ) TYPE: amino acid ( D ) TOPOLOGY: linear ( i i ) MOLECULE TYPE: protein ( x i ) SEQUENCE DESCRIPTION: SEQ ID NO:19:

| Met | Lys | Ile | Ala | Arg | Gly | Arg | Glu | Leu | Leu | Thr | Pro | Glu | Gln | Arg | Gln |
| 1 | | | | 5 | | | | | 10 | | | | | 15 | |

| Ala | Phe | Met | Gln | Ile | Pro | Glu | Asp | Glu | Trp | Ile | Leu | Gly | Thr | Tyr | Phe |
| | | | 20 | | | | 25 | | | | | | 30 | | |

| Thr | Phe | Ser | Lys | Arg | Asp | Leu | Glu | Ile | Val | Asn | Lys | Arg | Arg | Arg | Glu |
| | | | 35 | | | | | 40 | | | | | 45 | | |

| Glu | Asn | Arg | Leu | Gly | Phe | Ala | Val | Gln | Leu | Ala | Val | Leu | Arg | Tyr | Pro |
| | | 50 | | | | | 55 | | | | | 60 | | | |

| Gly | Trp | Pro | Tyr | Thr | His | Ile | Lys | Ser | Ile | Pro | Asp | Ser | Val | Ile | Gln |
| 65 | | | | | 70 | | | | | 75 | | | | | 80 |

| Tyr | Ile | Ser | Lys | Gln | Ile | Gly | Val | Ser | Pro | Ser | Ser | Leu | Asp | His | Tyr |
| | | | | 85 | | | | | 90 | | | | | 95 | |

| Pro | Gln | Arg | Glu | Asn | Thr | Leu | Trp | Asp | His | Leu | Lys | Glu | Ile | Arg | Ser |
| | | | | 100 | | | | | 105 | | | | | 110 | |

| Glu | Tyr | Asp | Phe | Val | Thr | Phe | Thr | Leu | Ser | Glu | Tyr | Arg | Met | Thr | Phe |
| | | | 115 | | | | | 120 | | | | | 125 | | |

| Lys | Tyr | Leu | His | Gln | Leu | Ala | Leu | Glu | Asn | Gly | Asp | Ala | Ile | His | Leu |
| | | | 130 | | | | | 135 | | | | | 140 | | |

| Leu | His | Glu | Cys | Ile | Asp | Phe | Leu | Arg | Lys | Asn | Lys | Ile | Ile | Leu | Pro |
| 145 | | | | | 150 | | | | | 155 | | | | | 160 |

| Ala | Ile | Thr | Thr | Leu | Glu | Arg | Met | Val | Trp | Glu | Ala | Arg | Ala | Met | Ala |
| | | | | 165 | | | | | 170 | | | | | 175 | |

| Glu | Lys | Lys | Leu | Phe | Asn | Thr | Val | Ser | Lys | Ser | Leu | Thr | Asn | Glu | Gln |
| | | | | 180 | | | | | 185 | | | | | 190 | |

| Lys | Glu | Lys | Leu | Glu | Gly | Ile | Ile | Thr | Ser | Gln | His | Pro | Ser | Glu | Ser |
| | | | 195 | | | | | 200 | | | | | 205 | | |

| Asn | Lys | Thr | Ile | Leu | Gly | Trp | Leu | Lys | Glu | Pro | Pro | Gly | His | Pro | Ser |
| | | 210 | | | | | 215 | | | | | 220 | | | |

| Pro | Glu | Thr | Phe | Leu | Lys | Ile | Ile | Glu | Arg | Leu | Glu | Tyr | Ile | Arg | Gly |
| 225 | | | | | 230 | | | | | 235 | | | | | 240 |

| Met | Asp | Leu | Glu | Thr | Val | Gln | Ile | Ser | His | Leu | His | Arg | Asn | Arg | Leu |
| | | | | 245 | | | | | 250 | | | | | 255 | |

| Leu | Gln | Leu | Ser | Arg | Leu | Gly | Ser | Arg | Tyr | Glu | Pro | Tyr | Ala | Phe | Arg |
| | | | | 260 | | | | | 265 | | | | | 270 | |

| Asp | Phe | Gln | Glu | Asn | Lys | Arg | Tyr | Ser | Ile | Leu | Thr | Ile | Tyr | Leu | Leu |
| | | | 275 | | | | | 280 | | | | | 285 | | |

| Gln | Leu | Thr | Gln | Glu | Leu | Thr | Asp | Lys | Ala | Phe | Glu | Ile | His | Asp | Arg |
| | | 290 | | | | | 295 | | | | | 300 | | | |

| Gln | Ile | Leu | Ser | Leu | Leu | Ser | Lys | Gly | Arg | Lys | Ala | Gln | Glu | Glu | Ile |
| 305 | | | | | 310 | | | | | 315 | | | | | 320 |

| Gln | Lys | Gln | Asn | Gly | Lys | Lys | Leu | Asn | Glu | Lys | Val | Ile | His | Phe | Thr |
| | | | | 325 | | | | | 330 | | | | | 335 | |

| Asn | Ile | Gly | Gln | Ala | Leu | Ile | Lys | Ala | Arg | Glu | Glu | Lys | Leu | Asp | Val |
| | | | 340 | | | | | 345 | | | | | 350 | | |

| Phe | Lys | Val | Leu | Glu | Ser | Val | Ile | Glu | Trp | Asn | Thr | Phe | Val | Ser | Ser |
| | | 355 | | | | | 360 | | | | | 365 | | | |

| Val | Glu | Glu | Ala | Gln | Glu | Leu | Ala | Arg | Pro | Ala | Asp | Tyr | Asp | Tyr | Leu |
| | 370 | | | | | 375 | | | | | 380 | | | | |

| Asp | Leu | Leu | Gln | Lys | Arg | Phe | Tyr | Ser | Leu | Arg | Lys | Tyr | Thr | Pro | Thr |
| 385 | | | | | 390 | | | | | 395 | | | | | 400 |

-continued

| | | | | | | | | | | | | | |
|---|---|---|---|---|---|---|---|---|---|---|---|---|---|
| Leu | Leu | Arg | Val | Leu | Glu | Phe | His | Ser | Thr | Lys | Ala | Asn | Glu | Pro | Leu |
| | | | | 405 | | | | | 410 | | | | | | 415 |
| Leu | Gln | Ala | Val | Glu | Ile | Ile | Arg | Gly | Met | Asn | Glu | Ser | Gly | Lys | Arg |
| | | | 420 | | | | | 425 | | | | | 430 | | |
| Lys | Val | Pro | Asp | Asp | Ser | Pro | Val | Asp | Phe | Ile | Ser | Lys | Arg | Trp | Lys |
| | | | 435 | | | | 440 | | | | | 445 | | | |
| Arg | His | Leu | Tyr | Glu | Asp | Asp | Gly | Thr | Thr | Ile | Asn | Arg | His | Tyr | Tyr |
| | 450 | | | | | 455 | | | | | 460 | | | | |
| Glu | Met | Ala | Val | Leu | Thr | Glu | Leu | Arg | Glu | His | Val | Arg | Ala | Gly | Asp |
| 465 | | | | | 470 | | | | | 475 | | | | | 480 |
| Val | Ser | Ile | Val | Gly | Ser | Arg | Gln | Tyr | Arg | Asp | Phe | Glu | Glu | Tyr | Leu |
| | | | | 485 | | | | | 490 | | | | | | 495 |
| Phe | Ser | Glu | Asp | Thr | Trp | Asn | Gln | Ser | Lys | Gly | Asn | Thr | Arg | Leu | Ser |
| | | | 500 | | | | | 505 | | | | | 510 | | |
| Val | Ser | Leu | Ser | Phe | Glu | Asp | Tyr | Ile | Thr | Glu | Arg | Thr | Ser | Ser | Phe |
| | | | 515 | | | | | 520 | | | | | 525 | | |
| Asn | Glu | Arg | Leu | Lys | Trp | Leu | Ala | Ala | Asn | Ser | Asn | Lys | Leu | Asp | Gly |
| | | 530 | | | | | 535 | | | | | 540 | | | |
| Val | Ser | Leu | Glu | Lys | Gly | Lys | Leu | Ser | Leu | Ala | Arg | Leu | Glu | Lys | Asp |
| 545 | | | | | 550 | | | | | 555 | | | | | 560 |
| Val | Pro | Glu | Glu | Ala | Lys | Lys | Phe | Ser | Ala | Ser | Leu | Tyr | Gln | Met | Leu |
| | | | | 565 | | | | | 570 | | | | | 575 | |
| Pro | Arg | Ile | Lys | Leu | Thr | Asp | Leu | Leu | Met | Asp | Val | Ala | His | Ile | Thr |
| | | | 580 | | | | | 585 | | | | | 590 | | |
| Gly | Phe | His | Glu | Gln | Phe | Thr | His | Ala | Ser | Asn | Asn | Arg | Lys | Pro | Asp |
| | | 595 | | | | | 600 | | | | | 605 | | | |
| Lys | Glu | Glu | Thr | Ile | Ile | Ile | Met | Ala | Ala | Leu | Leu | Gly | Met | Gly | Met |
| | | | 610 | | | | 615 | | | | | 620 | | | |
| Asn | Ile | Gly | Leu | Ser | Lys | Met | Ala | Glu | Ala | Thr | Pro | Gly | Leu | Thr | Tyr |
| 625 | | | | | 630 | | | | | 635 | | | | | 640 |
| Lys | Gln | Leu | Ala | Asn | Val | Ser | Gln | Trp | Arg | Met | Tyr | Glu | Asp | Ala | Met |
| | | | | 645 | | | | | 650 | | | | | 655 | |
| Asn | Lys | Ala | Gln | Ala | Ile | Leu | Val | Asn | Phe | His | His | Lys | Leu | Gln | Leu |
| | | | 660 | | | | | 665 | | | | | 670 | | |
| Pro | Phe | Tyr | Trp | Gly | Asp | Gly | Thr | Ser | Ser | Ser | Asp | Gly | Met | Arg |
| | | 675 | | | | | 680 | | | | | 685 | | | |
| Met | Gln | Leu | Gly | Val | Ser | Ser | Leu | His | Ala | Asp | Ala | Asn | Pro | His | Tyr |
| | 690 | | | | | 695 | | | | | 700 | | | | |
| Gly | Thr | Gly | Lys | Gly | Ala | Thr | Ile | Tyr | Arg | Phe | Thr | Ser | Asp | Gln | Phe |
| 705 | | | | | 710 | | | | | 715 | | | | | 720 |
| Ser | Ser | Tyr | Tyr | Thr | Lys | Ile | Ile | His | Thr | Asn | Ser | Arg | Asp | Ala | Ile |
| | | | | 725 | | | | | 730 | | | | | 735 | |
| His | Val | Leu | Asp | Gly | Leu | Leu | His | His | Glu | Thr | Asp | Leu | Asn | Ile | Glu |
| | | | 740 | | | | | 745 | | | | | 750 | | |
| Glu | His | Tyr | Thr | Asp | Thr | Ala | Gly | Tyr | Thr | Asp | Gln | Ile | Phe | Gly | Leu |
| | | 755 | | | | | 760 | | | | | 765 | | | |
| Thr | His | Leu | Leu | Gly | Phe | Lys | Phe | Ala | Pro | Arg | Ile | Arg | Asp | Leu | Ser |
| | | 770 | | | | | 775 | | | | | 780 | | | |
| Asp | Ser | Lys | Leu | Phe | Thr | Ile | Asp | Lys | Ala | Ser | Glu | Tyr | Pro | Lys | Leu |
| 785 | | | | | 790 | | | | | 795 | | | | | 800 |
| Glu | Ala | Ile | Leu | Arg | Gly | Gln | Ile | Asn | Thr | Lys | Val | Ile | Lys | Glu | Asn |
| | | | | 805 | | | | | 810 | | | | | 815 | |
| Tyr | Glu | Asp | Val | Leu | Arg | Leu | Ala | His | Ser | Ile | Arg | Glu | Gly | Thr | Val |

|     |     |     |     |     |     | 820 |     |     |     |     |     | 825 |     |     |     |     |     | 830 |     |     |
|---|---|---|---|---|---|---|---|---|---|---|---|---|---|---|---|---|---|---|---|---|

Ser Ala Ser Leu Ile Met Gly Lys Leu Gly Ser Tyr Ser Arg Gln Asn
        835                     840                 845

Ser Leu Ala Thr Ala Leu Arg Glu Met Gly Arg Ile Glu Lys Thr Ile
    850                     855                 860

Phe Ile Leu Asn Tyr Ile Ser Asp Glu Ser Leu Arg Arg Lys Ile Gln
865                 870                 875                 880

Arg Gly Leu Asn Lys Gly Glu Ala Met Asn Gly Leu Ala Arg Ala Ile
            885                 890                 895

Phe Phe Gly Lys Gln Gly Glu Leu Arg Glu Arg Thr Ile Gln His Gln
            900                 905                 910

Leu Gln Arg Ala Ser Ala Leu Asn Ile Ile Ile Asn Ala Ile Ser Ile
        915                 920                 925

Trp Asn Thr Leu His Leu Thr Thr Ala Val Glu Tyr Lys Lys Arg Thr
    930                 935                 940

Gly Ser Phe Asn Glu Asp Leu Leu His His Met Ser Pro Leu Gly Trp
945                 950                 955                 960

Glu His Ile Asn Leu Leu Gly Glu Tyr His Phe Asn Ser Glu Lys Val
                965                 970                 975

Val Ser Leu Asn Ser Leu Arg Pro Leu Lys Leu Ser
            980                 985

( 2 ) INFORMATION FOR SEQ ID NO:20:

( i ) SEQUENCE CHARACTERISTICS:
        ( A ) LENGTH: 573 base pairs
        ( B ) TYPE: nucleic acid
        ( C ) STRANDEDNESS: double
        ( D ) TOPOLOGY: linear ( i i ) MOLECULE TYPE: DNA (genomic)

( i x ) FEATURE:
        ( A ) NAME/KEY: CDS
        ( B ) LOCATION: 1..573

( x i ) SEQUENCE DESCRIPTION: SEQ ID NO:20:

```
TTG  CGG  AAA  ATC  GGT  TAT  ATT  CGT  GTC  AGT  TCG  ACT  AAC  CAG  AAT  CCT        48
Leu  Arg  Lys  Ile  Gly  Tyr  Ile  Arg  Val  Ser  Ser  Thr  Asn  Gln  Asn  Pro
  1              5                      10                     15

TCA  AGA  CAA  TTT  CAG  CAG  TTG  AAC  GAG  ATC  GGA  ATG  GAT  ATT  ATA  TAT        96
Ser  Arg  Gln  Phe  Gln  Gln  Leu  Asn  Glu  Ile  Gly  Met  Asp  Ile  Ile  Tyr
                  20                      25                     30

GAA  GAG  AAA  GTT  TCA  GGA  GCA  ACA  AAG  GAT  CGC  GAG  CAA  CTT  CAA  AAA       144
Glu  Glu  Lys  Val  Ser  Gly  Ala  Thr  Lys  Asp  Arg  Glu  Gln  Leu  Gln  Lys
              35                      40                     45

GTG  TTA  GAC  GAT  TTA  CAG  GAA  GAT  GAC  ATC  ATT  TAT  GTT  ACA  GAC  TTA       192
Val  Leu  Asp  Asp  Leu  Gln  Glu  Asp  Asp  Ile  Ile  Tyr  Val  Thr  Asp  Leu
      50                      55                      60

ACT  CGA  ATC  ACT  CGT  AGT  ACA  CAA  GAT  CTA  TTT  GAA  TTA  ATC  GAT  AAC       240
Thr  Arg  Ile  Thr  Arg  Ser  Thr  Gln  Asp  Leu  Phe  Glu  Leu  Ile  Asp  Asn
 65                      70                      75                     80

ATA  CGA  GAT  AAA  AAG  GCA  AGT  TTA  AAA  TCA  CTA  AAA  GAT  ACA  TGG  CTT       288
Ile  Arg  Asp  Lys  Lys  Ala  Ser  Leu  Lys  Ser  Leu  Lys  Asp  Thr  Trp  Leu
                  85                      90                     95

GAT  TTA  TCA  GAA  GAT  AAT  CCA  TAC  AGC  CAA  TTC  TTA  ATT  ACT  GTA  ATG       336
Asp  Leu  Ser  Glu  Asp  Asn  Pro  Tyr  Ser  Gln  Phe  Leu  Ile  Thr  Val  Met
             100                     105                    110

GCT  GGT  GTT  AAC  CAA  TTA  GAG  CGA  GAT  CTT  ATT  CGG  ATG  AGA  CAA  CGT       384
Ala  Gly  Val  Asn  Gln  Leu  Glu  Arg  Asp  Leu  Ile  Arg  Met  Arg  Gln  Arg
         115                     120                    125
```

| GAA | GGG | ATT | GAA | TTG | GCT | AAG | AAA | GAA | GGA | AAG | TTT | AAA | GGT | CGA | TTA | 432 |
| Glu | Gly | Ile | Glu | Leu | Ala | Lys | Lys | Glu | Gly | Lys | Phe | Lys | Gly | Arg | Leu | |
| | 130 | | | | | 135 | | | | | 140 | | | | | |

| AAG | AAG | TAT | CAT | AAA | AAT | CAC | GCA | GGA | ATG | AAT | TAT | GCG | GTA | AAG | CTA | 480 |
| Lys | Lys | Tyr | His | Lys | Asn | His | Ala | Gly | Met | Asn | Tyr | Ala | Val | Lys | Leu | |
| 145 | | | | | 150 | | | | 155 | | | | | | 160 | |

| TAT | AAA | GAA | GGA | AAT | ATG | ACT | GTA | AAT | CAA | ATT | TGT | GAA | ATT | ACT | AAT | 528 |
| Tyr | Lys | Glu | Gly | Asn | Met | Thr | Val | Asn | Gln | Ile | Cys | Glu | Ile | Thr | Asn | |
| | | | | 165 | | | | | 170 | | | | | 175 | | |

| GTA | TCT | AGG | GCT | TCA | TTA | TAC | AGG | AAA | TTA | TCA | GAA | GTG | AAT | AAT | | 573 |
| Val | Ser | Arg | Ala | Ser | Leu | Tyr | Arg | Lys | Leu | Ser | Glu | Val | Asn | Asn | | |
| | | | 180 | | | | | 185 | | | | | 190 | | | |

( 2 ) INFORMATION FOR SEQ ID NO:21:

( i ) SEQUENCE CHARACTERISTICS:
        ( A ) LENGTH: 191 amino acids
        ( B ) TYPE: amino acid
        ( D ) TOPOLOGY: linear ( i i ) MOLECULE TYPE: protein ( x i ) SEQUENCE DESCRIPTION: SEQ ID NO:21:

| Leu | Arg | Lys | Ile | Gly | Tyr | Ile | Arg | Val | Ser | Ser | Thr | Asn | Gln | Asn | Pro |
| 1 | | | | 5 | | | | | 10 | | | | | 15 | |

| Ser | Arg | Gln | Phe | Gln | Gln | Leu | Asn | Glu | Ile | Gly | Met | Asp | Ile | Ile | Tyr |
| | | | 20 | | | | | 25 | | | | | 30 | | |

| Glu | Glu | Lys | Val | Ser | Gly | Ala | Thr | Lys | Asp | Arg | Glu | Gln | Leu | Gln | Lys |
| | | 35 | | | | | 40 | | | | | 45 | | | |

| Val | Leu | Asp | Asp | Leu | Gln | Glu | Asp | Asp | Ile | Ile | Tyr | Val | Thr | Asp | Leu |
| | 50 | | | | | 55 | | | | 60 | | | | | |

| Thr | Arg | Ile | Thr | Arg | Ser | Thr | Gln | Asp | Leu | Phe | Glu | Leu | Ile | Asp | Asn |
| 65 | | | | | 70 | | | | | 75 | | | | | 80 |

| Ile | Arg | Asp | Lys | Lys | Ala | Ser | Leu | Lys | Ser | Leu | Lys | Asp | Thr | Trp | Leu |
| | | | | 85 | | | | | 90 | | | | | 95 | |

| Asp | Leu | Ser | Glu | Asp | Asn | Pro | Tyr | Ser | Gln | Phe | Leu | Ile | Thr | Val | Met |
| | | | 100 | | | | | 105 | | | | | 110 | | |

| Ala | Gly | Val | Asn | Gln | Leu | Glu | Arg | Asp | Leu | Ile | Arg | Met | Arg | Gln | Arg |
| | | 115 | | | | | 120 | | | | | 125 | | | |

| Glu | Gly | Ile | Glu | Leu | Ala | Lys | Lys | Glu | Gly | Lys | Phe | Lys | Gly | Arg | Leu |
| | 130 | | | | | 135 | | | | | 140 | | | | |

| Lys | Lys | Tyr | His | Lys | Asn | His | Ala | Gly | Met | Asn | Tyr | Ala | Val | Lys | Leu |
| 145 | | | | | 150 | | | | 155 | | | | | | 160 |

| Tyr | Lys | Glu | Gly | Asn | Met | Thr | Val | Asn | Gln | Ile | Cys | Glu | Ile | Thr | Asn |
| | | | | 165 | | | | | 170 | | | | | 175 | |

| Val | Ser | Arg | Ala | Ser | Leu | Tyr | Arg | Lys | Leu | Ser | Glu | Val | Asn | Asn | |
| | | | 180 | | | | | 185 | | | | | 190 | | |

( 2 ) INFORMATION FOR SEQ ID NO:22:

( i ) SEQUENCE CHARACTERISTICS:
        ( A ) LENGTH: 909 base pairs
        ( B ) TYPE: nucleic acid
        ( C ) STRANDEDNESS: unknown
        ( D ) TOPOLOGY: linear ( i i ) MOLECULE TYPE: DNA (genomic)

( i x ) FEATURE:
        ( A ) NAME/KEY: CDS
        ( B ) LOCATION: 1..909

( x i ) SEQUENCE DESCRIPTION: SEQ ID NO:22:

| | | | | | | | | | | | | | | | | |
|---|---|---|---|---|---|---|---|---|---|---|---|---|---|---|---|---|
| ATG | AAG | AAG | TTG | TTT | TTT | TTA | TTG | TTA | TTG | TTA | TTC | TTA | ATA | TAC | TTA | 48 |
| Met | Lys | Lys | Leu | Phe | Phe | Leu | Leu | Leu | Leu | Leu | Phe | Leu | Ile | Tyr | Leu | |
| 1 | | | | 5 | | | | | 10 | | | | | 15 | | |
| GGT | TAT | GAC | TAC | GTT | AAT | GAA | GCA | CTG | TTT | TCT | CAG | GAA | AAA | GTC | GAA | 96 |
| Gly | Tyr | Asp | Tyr | Val | Asn | Glu | Ala | Leu | Phe | Ser | Gln | Glu | Lys | Val | Glu | |
| | | | 20 | | | | | 25 | | | | | 30 | | | |
| TTT | CAA | AAT | TAT | GAT | CAA | AAT | CCC | AAA | GAA | CAT | TTA | GAA | AAT | AGT | GGG | 144 |
| Phe | Gln | Asn | Tyr | Asp | Gln | Asn | Pro | Lys | Glu | His | Leu | Glu | Asn | Ser | Gly | |
| | | 35 | | | | | 40 | | | | | 45 | | | | |
| ACT | TCT | GAA | AAT | ACC | CAA | GAG | AAA | ACA | ATT | ACA | GAA | GAA | CAG | GTT | TAT | 192 |
| Thr | Ser | Glu | Asn | Thr | Gln | Glu | Lys | Thr | Ile | Thr | Glu | Glu | Gln | Val | Tyr | |
| | 50 | | | | | 55 | | | | | 60 | | | | | |
| CAA | GGA | AAT | CTG | CTA | TTA | ATC | AAT | AGT | AAA | TAT | CCT | GTT | CGC | CAA | GAA | 240 |
| Gln | Gly | Asn | Leu | Leu | Leu | Ile | Asn | Ser | Lys | Tyr | Pro | Val | Arg | Gln | Glu | |
| 65 | | | | | 70 | | | | | 75 | | | | | 80 | |
| AGT | GTG | AAG | TCA | GAT | ATC | GTG | AAT | TTA | TCT | AAA | CAT | GAC | GAA | TTA | ATA | 288 |
| Ser | Val | Lys | Ser | Asp | Ile | Val | Asn | Leu | Ser | Lys | His | Asp | Glu | Leu | Ile | |
| | | | | 85 | | | | | 90 | | | | | 95 | | |
| AAT | GGA | TAC | GGG | TTG | CTT | GAT | AGT | AAT | ATT | TAT | ATG | TCA | AAA | GAA | ATA | 336 |
| Asn | Gly | Tyr | Gly | Leu | Leu | Asp | Ser | Asn | Ile | Tyr | Met | Ser | Lys | Glu | Ile | |
| | | | 100 | | | | | 105 | | | | | 110 | | | |
| GCA | CAA | AAA | TTT | TCA | GAG | ATG | GTC | AAT | GAT | GCT | GTA | AAG | GGT | GGC | GTT | 384 |
| Ala | Gln | Lys | Phe | Ser | Glu | Met | Val | Asn | Asp | Ala | Val | Lys | Gly | Gly | Val | |
| | | 115 | | | | | 120 | | | | | 125 | | | | |
| AGT | CAT | TTT | ATT | ATT | AAT | AGT | GGC | TAT | CGA | GAC | TTT | GAT | GAG | CAA | AGT | 432 |
| Ser | His | Phe | Ile | Ile | Asn | Ser | Gly | Tyr | Arg | Asp | Phe | Asp | Glu | Gln | Ser | |
| | 130 | | | | | 135 | | | | | 140 | | | | | |
| GTG | CTT | TAC | CAA | GAA | ATG | GGG | GCT | GAG | TAT | GCC | TTA | CCA | GCA | GGT | TAT | 480 |
| Val | Leu | Tyr | Gln | Glu | Met | Gly | Ala | Glu | Tyr | Ala | Leu | Pro | Ala | Gly | Tyr | |
| 145 | | | | | 150 | | | | | 155 | | | | | 160 | |
| AGT | GAG | CAT | AAT | TCA | GGT | TTA | TCA | CTA | GAT | GTA | GGA | TCA | AGC | TTG | ACG | 528 |
| Ser | Glu | His | Asn | Ser | Gly | Leu | Ser | Leu | Asp | Val | Gly | Ser | Ser | Leu | Thr | |
| | | | | 165 | | | | | 170 | | | | | 175 | | |
| AAA | ATG | GAA | CGA | GCC | CCT | GAA | GGA | AAG | TGG | ATA | GAA | GAA | AAT | GCT | TGG | 576 |
| Lys | Met | Glu | Arg | Ala | Pro | Glu | Gly | Lys | Trp | Ile | Glu | Glu | Asn | Ala | Trp | |
| | | | 180 | | | | | 185 | | | | | 190 | | | |
| AAA | TAC | GGG | TTC | ATT | TTA | CGT | TAT | CCA | GAG | GAC | AAA | ACA | GAG | TTA | ACA | 624 |
| Lys | Tyr | Gly | Phe | Ile | Leu | Arg | Tyr | Pro | Glu | Asp | Lys | Thr | Glu | Leu | Thr | |
| | | 195 | | | | | 200 | | | | | 205 | | | | |
| GGA | ATT | CAA | TAT | GAA | CCA | TGG | CAT | ATT | CGC | TAT | GTT | GGT | TTA | CCA | CAT | 672 |
| Gly | Ile | Gln | Tyr | Glu | Pro | Trp | His | Ile | Arg | Tyr | Val | Gly | Leu | Pro | His | |
| | 210 | | | | | 215 | | | | | 220 | | | | | |
| AGT | GCG | ATT | ATG | AAA | GAA | AAG | AAT | TTC | GTT | CTC | GAG | GAA | TAT | ATG | GAT | 720 |
| Ser | Ala | Ile | Met | Lys | Glu | Lys | Asn | Phe | Val | Leu | Glu | Glu | Tyr | Met | Asp | |
| 225 | | | | | 230 | | | | | 235 | | | | | 240 | |
| TAC | CTA | AAA | GAA | GAA | AAA | ACC | ATT | TCT | GTT | AGT | GTA | AAT | GGG | GAA | AAA | 768 |
| Tyr | Leu | Lys | Glu | Glu | Lys | Thr | Ile | Ser | Val | Ser | Val | Asn | Gly | Glu | Lys | |
| | | | | 245 | | | | | 250 | | | | | 255 | | |
| TAT | GAG | ATC | TTT | TAT | TAT | CCT | GTT | ACT | AAA | AAT | ACC | ACC | ATT | CAT | GTG | 816 |
| Tyr | Glu | Ile | Phe | Tyr | Tyr | Pro | Val | Thr | Lys | Asn | Thr | Thr | Ile | His | Val | |
| | | | 260 | | | | | 265 | | | | | 270 | | | |
| CCG | ACT | AAT | CTT | CGT | TAT | GAG | ATA | TCA | GGA | AAC | AAT | ATA | GAC | GGT | GTA | 864 |
| Pro | Thr | Asn | Leu | Arg | Tyr | Glu | Ile | Ser | Gly | Asn | Asn | Ile | Asp | Gly | Val | |
| | | 275 | | | | | 280 | | | | | 285 | | | | |
| ATT | GTG | ACA | GTG | TTT | CCC | GGA | TCA | ACA | CAT | ACT | AAT | TCA | AGG | AGG | | 909 |
| Ile | Val | Thr | Val | Phe | Pro | Gly | Ser | Thr | His | Thr | Asn | Ser | Arg | Arg | | |
| | 290 | | | | | 295 | | | | | 300 | | | | | |

( 2 ) INFORMATION FOR SEQ ID NO:23:

(i) SEQUENCE CHARACTERISTICS:
    (A) LENGTH: 303 amino acids
    (B) TYPE: amino acid
    (D) TOPOLOGY: linear (ii) MOLECULE TYPE: protein (xi) SEQUENCE DESCRIPTION: SEQ ID NO:23:

| Met | Lys | Lys | Leu | Phe | Phe | Leu | Leu | Leu | Leu | Phe | Leu | Ile | Tyr | Leu |
|---|---|---|---|---|---|---|---|---|---|---|---|---|---|---|
| 1 | | | | 5 | | | | | 10 | | | | | 15 |
| Gly | Tyr | Asp | Tyr | Val | Asn | Glu | Ala | Leu | Phe | Ser | Gln | Glu | Lys | Val | Glu |
| | | | 20 | | | | | 25 | | | | | 30 | | |
| Phe | Gln | Asn | Tyr | Asp | Gln | Asn | Pro | Lys | Glu | His | Leu | Glu | Asn | Ser | Gly |
| | | | 35 | | | | 40 | | | | | 45 | | | |
| Thr | Ser | Glu | Asn | Thr | Gln | Glu | Lys | Thr | Ile | Thr | Glu | Gln | Val | Tyr |
| | | 50 | | | | 55 | | | | | 60 | | | |
| Gln | Gly | Asn | Leu | Leu | Leu | Ile | Asn | Ser | Lys | Tyr | Pro | Val | Arg | Gln | Glu |
| 65 | | | | | 70 | | | | | 75 | | | | | 80 |
| Ser | Val | Lys | Ser | Asp | Ile | Val | Asn | Leu | Ser | Lys | His | Asp | Glu | Leu | Ile |
| | | | | 85 | | | | | 90 | | | | | 95 | |
| Asn | Gly | Tyr | Gly | Leu | Leu | Asp | Ser | Asn | Ile | Tyr | Met | Ser | Lys | Glu | Ile |
| | | | 100 | | | | | 105 | | | | | 110 | | |
| Ala | Gln | Lys | Phe | Ser | Glu | Met | Val | Asn | Asp | Ala | Val | Lys | Gly | Gly | Val |
| | | 115 | | | | | 120 | | | | | 125 | | | |
| Ser | His | Phe | Ile | Ile | Asn | Ser | Gly | Tyr | Arg | Asp | Phe | Asp | Glu | Gln | Ser |
| | 130 | | | | | 135 | | | | | 140 | | | | |
| Val | Leu | Tyr | Gln | Glu | Met | Gly | Ala | Glu | Tyr | Ala | Leu | Pro | Ala | Gly | Tyr |
| 145 | | | | | 150 | | | | 155 | | | | | | 160 |
| Ser | Glu | His | Asn | Ser | Gly | Leu | Ser | Leu | Asp | Val | Gly | Ser | Ser | Leu | Thr |
| | | | | 165 | | | | | 170 | | | | | 175 | |
| Lys | Met | Glu | Arg | Ala | Pro | Glu | Gly | Lys | Trp | Ile | Glu | Glu | Asn | Ala | Trp |
| | | | 180 | | | | | 185 | | | | | 190 | | |
| Lys | Tyr | Gly | Phe | Ile | Leu | Arg | Tyr | Pro | Glu | Asp | Lys | Thr | Glu | Leu | Thr |
| | | 195 | | | | | 200 | | | | 205 | | | | |
| Gly | Ile | Gln | Tyr | Glu | Pro | Trp | His | Ile | Arg | Tyr | Val | Gly | Leu | Pro | His |
| | 210 | | | | | 215 | | | | | 220 | | | | |
| Ser | Ala | Ile | Met | Lys | Glu | Lys | Asn | Phe | Val | Leu | Glu | Glu | Tyr | Met | Asp |
| 225 | | | | | 230 | | | | | 235 | | | | | 240 |
| Tyr | Leu | Lys | Glu | Glu | Lys | Thr | Ile | Ser | Val | Ser | Val | Asn | Gly | Glu | Lys |
| | | | | 245 | | | | | 250 | | | | | 255 | |
| Tyr | Glu | Ile | Phe | Tyr | Tyr | Pro | Val | Thr | Lys | Asn | Thr | Thr | Ile | His | Val |
| | | | 260 | | | | | 265 | | | | | 270 | | |
| Pro | Thr | Asn | Leu | Arg | Tyr | Glu | Ile | Ser | Gly | Asn | Asn | Ile | Asp | Gly | Val |
| | | 275 | | | | | 280 | | | | | 285 | | | |
| Ile | Val | Thr | Val | Phe | Pro | Gly | Ser | Thr | His | Thr | Asn | Ser | Arg | Arg |
| | 290 | | | | | 295 | | | | | 300 | | | |

(2) INFORMATION FOR SEQ ID NO:24:

(i) SEQUENCE CHARACTERISTICS:
    (A) LENGTH: 483 base pairs
    (B) TYPE: nucleic acid
    (C) STRANDEDNESS: unknown
    (D) TOPOLOGY: linear (ii) MOLECULE TYPE: DNA (genomic)

(ix) FEATURE:
    (A) NAME/KEY: CDS ( B ) LOCATION: 1..483

( x i ) SEQUENCE DESCRIPTION: SEQ ID NO:24:

| TTG | GGA | AAA | ATA | TTA | TCT | AGA | GGA | TTG | CTA | GCT | TTA | TAT | TTA | GTG | ACA | 48 |
|---|---|---|---|---|---|---|---|---|---|---|---|---|---|---|---|---|
| Leu | Gly | Lys | Ile | Leu | Ser | Arg | Gly | Leu | Leu | Ala | Leu | Tyr | Leu | Val | Thr | |
| 1 | | | | 5 | | | | | 10 | | | | | 15 | | |

| CTA | ATC | TGG | TTA | GTG | TTA | TTC | AAA | TTA | CAA | TAC | AAT | ATT | TTA | TCA | GTA | 96 |
|---|---|---|---|---|---|---|---|---|---|---|---|---|---|---|---|---|
| Leu | Ile | Trp | Leu | Val | Leu | Phe | Lys | Leu | Gln | Tyr | Asn | Ile | Leu | Ser | Val | |
| | | | 20 | | | | | 25 | | | | | 30 | | | |

| TTT | AAT | TAT | CAT | CAA | AGA | AGT | CTT | AAC | TTG | ACT | CCA | TTT | ACT | GCT | ACT | 144 |
|---|---|---|---|---|---|---|---|---|---|---|---|---|---|---|---|---|
| Phe | Asn | Tyr | His | Gln | Arg | Ser | Leu | Asn | Leu | Thr | Pro | Phe | Thr | Ala | Thr | |
| | | 35 | | | | | 40 | | | | | 45 | | | | |

| GGG | AAT | TTC | AGA | GAG | ATG | ATA | GAT | AAT | GTT | ATA | ATC | TTT | ATT | CCA | TTT | 192 |
|---|---|---|---|---|---|---|---|---|---|---|---|---|---|---|---|---|
| Gly | Asn | Phe | Arg | Glu | Met | Ile | Asp | Asn | Val | Ile | Ile | Phe | Ile | Pro | Phe | |
| | 50 | | | | | 55 | | | | | 60 | | | | | |

| GGC | TTG | CTT | TTG | AAT | GTC | AAT | TTT | AAA | GAA | ATC | GGA | TTT | TTA | CCT | AAG | 240 |
|---|---|---|---|---|---|---|---|---|---|---|---|---|---|---|---|---|
| Gly | Leu | Leu | Leu | Asn | Val | Asn | Phe | Lys | Glu | Ile | Gly | Phe | Leu | Pro | Lys | |
| 65 | | | | | 70 | | | | | 75 | | | | | 80 | |

| TTT | GCT | TTT | GTA | CTG | GTT | TTA | AGT | CTT | ACT | TTT | GAA | ATA | ATT | CAA | TTT | 288 |
|---|---|---|---|---|---|---|---|---|---|---|---|---|---|---|---|---|
| Phe | Ala | Phe | Val | Leu | Val | Leu | Ser | Leu | Thr | Phe | Glu | Ile | Ile | Gln | Phe | |
| | | | | 85 | | | | | 90 | | | | | 95 | | |

| ATC | TTC | GCT | ATT | GGA | GCG | ACA | GAC | ATA | ACA | GAT | GTA | ATT | ACA | AAT | ACT | 336 |
|---|---|---|---|---|---|---|---|---|---|---|---|---|---|---|---|---|
| Ile | Phe | Ala | Ile | Gly | Ala | Thr | Asp | Ile | Thr | Asp | Val | Ile | Thr | Asn | Thr | |
| | | | 100 | | | | | 105 | | | | | 110 | | | |

| GTT | GGA | GGC | TTT | CTT | GGA | CTG | AAA | TTA | TAT | GGT | TTA | AGC | AAT | AAG | CAT | 384 |
|---|---|---|---|---|---|---|---|---|---|---|---|---|---|---|---|---|
| Val | Gly | Gly | Phe | Leu | Gly | Leu | Lys | Leu | Tyr | Gly | Leu | Ser | Asn | Lys | His | |
| | | 115 | | | | | 120 | | | | | 125 | | | | |

| ATG | AAT | CAA | AAA | AAA | TTA | GAC | AGA | GTT | ATT | ATT | TTT | GTA | GGT | ATA | CTT | 432 |
|---|---|---|---|---|---|---|---|---|---|---|---|---|---|---|---|---|
| Met | Asn | Gln | Lys | Lys | Leu | Asp | Arg | Val | Ile | Ile | Phe | Val | Gly | Ile | Leu | |
| | 130 | | | | | 135 | | | | | 140 | | | | | |

| TTG | CTC | GTA | TTA | TTG | CTC | GTT | TAC | CGT | ACC | CAT | TTA | AGA | ATA | AAT | TAC | 480 |
|---|---|---|---|---|---|---|---|---|---|---|---|---|---|---|---|---|
| Leu | Leu | Val | Leu | Leu | Leu | Val | Tyr | Arg | Thr | His | Leu | Arg | Ile | Asn | Tyr | |
| 145 | | | | | 150 | | | | | 155 | | | | | 160 | |

| GTG | | | | | | | | | | | | | | | | 483 |
|---|---|---|---|---|---|---|---|---|---|---|---|---|---|---|---|---|
| Val | | | | | | | | | | | | | | | | |

( 2 ) INFORMATION FOR SEQ ID NO:25:

( i ) SEQUENCE CHARACTERISTICS:
        ( A ) LENGTH: 161 amino acids
        ( B ) TYPE: amino acid
        ( D ) TOPOLOGY: linear ( i i ) MOLECULE TYPE: protein ( x i ) SEQUENCE DESCRIPTION: SEQ ID NO:25:

| Leu | Gly | Lys | Ile | Leu | Ser | Arg | Gly | Leu | Leu | Ala | Leu | Tyr | Leu | Val | Thr |
|---|---|---|---|---|---|---|---|---|---|---|---|---|---|---|---|
| 1 | | | | 5 | | | | | 10 | | | | | 15 | |

| Leu | Ile | Trp | Leu | Val | Leu | Phe | Lys | Leu | Gln | Tyr | Asn | Ile | Leu | Ser | Val |
|---|---|---|---|---|---|---|---|---|---|---|---|---|---|---|---|
| | | | 20 | | | | | 25 | | | | | 30 | | |

| Phe | Asn | Tyr | His | Gln | Arg | Ser | Leu | Asn | Leu | Thr | Pro | Phe | Thr | Ala | Thr |
|---|---|---|---|---|---|---|---|---|---|---|---|---|---|---|---|
| | | 35 | | | | | 40 | | | | | 45 | | | |

| Gly | Asn | Phe | Arg | Glu | Met | Ile | Asp | Asn | Val | Ile | Ile | Phe | Ile | Pro | Phe |
|---|---|---|---|---|---|---|---|---|---|---|---|---|---|---|---|
| | 50 | | | | | 55 | | | | | 60 | | | | |

| Gly | Leu | Leu | Leu | Asn | Val | Asn | Phe | Lys | Glu | Ile | Gly | Phe | Leu | Pro | Lys |
|---|---|---|---|---|---|---|---|---|---|---|---|---|---|---|---|
| 65 | | | | | 70 | | | | | 75 | | | | | 80 |

| Phe | Ala | Phe | Val | Leu | Val | Leu | Ser | Leu | Thr | Phe | Glu | Ile | Ile | Gln | Phe |
|---|---|---|---|---|---|---|---|---|---|---|---|---|---|---|---|
| | | | | 85 | | | | | 90 | | | | | 95 | |

| Ile | Phe | Ala | Ile | Gly | Ala | Thr | Asp | Ile | Thr | Asp | Val | Ile | Thr | Asn | Thr |
|---|---|---|---|---|---|---|---|---|---|---|---|---|---|---|---|
| | | | 100 | | | | | 105 | | | | | 110 | | |

5,871,910

-continued

| Val | Gly | Gly | Phe | Leu | Gly | Leu | Lys | Leu | Tyr | Gly | Leu | Ser | Asn | Lys | His |
|     |     | 115 |     |     |     | 120 |     |     |     |     | 125 |     |     |     |     |

| Met | Asn | Gln | Lys | Lys | Leu | Asp | Arg | Val | Ile | Ile | Phe | Val | Gly | Ile | Leu |
|     | 130 |     |     |     |     | 135 |     |     |     |     | 140 |     |     |     |     |

| Leu | Leu | Val | Leu | Leu | Leu | Val | Tyr | Arg | Thr | His | Leu | Arg | Ile | Asn | Tyr |
| 145 |     |     |     |     | 150 |     |     |     |     | 155 |     |     |     |     | 160 |

Val ( 2 ) INFORMATION FOR SEQ ID NO:26:

( i ) SEQUENCE CHARACTERISTICS:
        ( A ) LENGTH: 18 base pairs
        ( B ) TYPE: nucleic acid
        ( C ) STRANDEDNESS: unknown
        ( D ) TOPOLOGY: linear ( i i ) MOLECULE TYPE: DNA (genomic)

( x i ) SEQUENCE DESCRIPTION: SEQ ID NO:26:

ATGCTCCTGT CTCCTTTC                                          18

( 2 ) INFORMATION FOR SEQ ID NO:27:

( i ) SEQUENCE CHARACTERISTICS:
        ( A ) LENGTH: 2296 amino acids
        ( B ) TYPE: amino acid
        ( D ) TOPOLOGY: linear ( i i ) MOLECULE TYPE: protein ( x i ) SEQUENCE DESCRIPTION: SEQ ID NO:27:

| Lys | Leu | Phe | Phe | Leu | Leu | Ile | Cys | Arg | Phe | Thr | Asn | Arg | Ile | Lys | Leu |
| 1   |     |     |     | 5   |     |     |     |     | 10  |     |     |     |     | 15  |     |

| Leu | Phe | Ser | His | Cys | Pro | Cys | Phe | Pro | His | His | Ser | Phe | Lys | Cys | Ser |
|     |     |     | 20  |     |     |     |     | 25  |     |     |     |     | 30  |     |     |

| Asp | Ser | Arg | Gln | Tyr | Asn | Phe | Val | Phe | Ser | Lys | Ile | Tyr | Ala | Phe | Met |
|     |     | 35  |     |     |     |     | 40  |     |     |     |     | 45  |     |     |     |

| Gln | Met | Asn | Gly | Ile | Thr | Ile | Phe | Gln | Ser | Leu | Met | Lys | Val | Leu | Lys |
|     | 50  |     |     |     |     | 55  |     |     |     |     | 60  |     |     |     |     |

| Cys | His | Ser | Ile | Phe | Thr | Gln | Gly | Lys | Ser | Tyr | Lys | Val | Val | Phe | Thr |
| 65  |     |     |     |     | 70  |     |     |     |     | 75  |     |     |     |     | 80  |

| Ser | Asn | Phe | Phe | Gln | Met | Ile | Pro | Lys | Cys | Ile | Phe | Pro | Leu | Arg | Ile |
|     |     |     |     | 85  |     |     |     |     | 90  |     |     |     |     | 95  |     |

| Met | Ile | Lys | Arg | Gly | Trp | Thr | Asn | Thr | Asn | Leu | Phe | Arg | Tyr | Ile | Leu |
|     |     |     | 100 |     |     |     |     | 105 |     |     |     |     | 110 |     |     |

| Tyr | Asp | Arg | Ile | Trp | Asp | Ala | Phe | Asp | Met | Ser | Val | Trp | Pro | Thr | Gly |
|     |     | 115 |     |     |     |     | 120 |     |     |     |     | 125 |     |     |     |

| Ile | Pro | Lys | Asn | Ser | Leu | Asn | Ser | Lys | Ser | Thr | Val | Phe | Phe | Pro | Pro |
|     | 130 |     |     |     |     | 135 |     |     |     |     | 140 |     |     |     |     |

| Ser | Leu | Ile | Asn | Tyr | Phe | Ile | Pro | Phe | Gly | Lys | Ser | Glu | Val | Gly | Pro |
| 145 |     |     |     |     | 150 |     |     |     |     | 155 |     |     |     |     | 160 |

| Gln | Tyr | Pro | Phe | Ile | Phe | Arg | Asp | Leu | His | Lys | Ser | Leu | Ser | Leu | Phe |
|     |     |     |     | 165 |     |     |     |     | 170 |     |     |     |     | 175 |     |

| Arg | Cys | Lys | Gln | Phe | Ser | Thr | Ser | Arg | Asn | Phe | His | Ser | Val | Ser | Phe |
|     |     |     | 180 |     |     |     |     | 185 |     |     |     |     | 190 |     |     |

| His | Phe | Cys | Ile | Phe | Asn | Leu | Leu | Val | Gln | Leu | Tyr | Ile | Asn | Arg | Val |
|     |     | 195 |     |     |     |     | 200 |     |     |     |     | 205 |     |     |     |

| Tyr | Ser | Ile | Asp | Thr | Asn | Val | Val | Asp | Asn | His | Ser | Glu | Arg | Leu | Ile |
|     |     | 210 |     |     |     |     | 215 |     |     |     |     | 220 |     |     |     |

```
Arg  Leu  Val  Ser  Lys  Met  Arg  Tyr  Phe  Ala  Glu  Asn  Arg  Leu  Tyr  Ser
225            230                 235                           240

Cys  Gln  Phe  Asp  Pro  Glu  Ser  Phe  Lys  Thr  Ile  Ser  Ala  Val  Glu  Arg
               245                      250                          255

Asp  Arg  Asn  Gly  Tyr  Tyr  Ile  Lys  Arg  Lys  Phe  Gln  Glu  Gln  Gln  Arg
               260                 265                      270

Ile  Ala  Ser  Asn  Phe  Lys  Lys  Cys  Thr  Ile  Tyr  Arg  Lys  Met  Thr  Ser
          275                      280                      285

Phe  Met  Leu  Gln  Thr  Leu  Glu  Ser  Leu  Val  Val  His  Lys  Ile  Tyr  Leu
     290                 295                      300

Asn  Ser  Ile  Thr  Tyr  Glu  Ile  Lys  Arg  Gln  Val  Asn  His  Lys  Ile  His
305                      310                 315                           320

Gly  Leu  Ile  Tyr  Gln  Lys  Ile  Ile  His  Thr  Ala  Asn  Ser  Leu  Leu  Trp
                    325                 330                           335

Leu  Val  Leu  Thr  Asn  Ser  Glu  Ile  Leu  Phe  Gly  Asp  Asn  Val  Lys  Gly
               340                      345                      350

Leu  Asn  Trp  Leu  Arg  Lys  Lys  Glu  Ser  Leu  Lys  Val  Asp  Arg  Ser  Ile
               355                 360                      365

Ile  Lys  Ile  Thr  Gln  Glu  Ile  Met  Arg  Arg  Lys  Leu  Tyr  Lys  Glu  Gly
     370                      375                      380

Asn  Met  Thr  Val  Asn  Gln  Ile  Cys  Glu  Ile  Thr  Asn  Val  Ser  Arg  Ala
385                      390                      395                      400

Ser  Leu  Tyr  Arg  Lys  Leu  Ser  Glu  Val  Asn  Asn  Pro  Phe  Cys  Ile  Pro
               405                      410                      415

Leu  Met  Gly  Asn  Ile  Phe  Lys  Glu  Glu  Lys  Glu  Thr  Ile  Lys  Tyr  Gln
               420                 425                      430

Pro  Pro  Ser  Asp  Ala  Glu  Lys  Pro  Phe  Asp  Lys  Lys  Arg  Ile  Ile  Ile
               435                 440                      445

Leu  Arg  Asn  Ser  Ser  Phe  Ile  Met  Met  Leu  Ile  Asn  Ser  Ala  Leu  Ser
     450                      455                      460

Asp  Lys  Leu  Leu  Arg  Ala  Asn  Leu  Cys  Glu  Arg  Val  Ile  Thr  Met  Ser
465                 470                      475                           480

Asp  Lys  Ile  Leu  Ile  Val  Asp  Asp  Glu  His  Glu  Ile  Ala  Asp  Leu  Val
               485                      490                           495

Glu  Leu  Tyr  Leu  Lys  Asn  Glu  Asn  Tyr  Thr  Val  Phe  Lys  Tyr  Tyr  Thr
               500                      505                      510

Ala  Lys  Glu  Ala  Leu  Glu  Cys  Ile  Asp  Lys  Ser  Glu  Ile  Asp  Leu  Ala
          515                      520                      525

Ile  Leu  Asp  Ile  Met  Leu  Pro  Gly  Thr  Ser  Gly  Leu  Thr  Ile  Cys  Gln
     530                      535                      540

Lys  Ile  Arg  Asp  Lys  His  Thr  Tyr  Pro  Ile  Ile  Met  Leu  Thr  Gly  Lys
545                      550                      555                      560

Asp  Thr  Glu  Val  Asp  Lys  Ile  Thr  Gly  Leu  Thr  Ile  Gly  Ala  Asp  Asp
               565                      570                           575

Tyr  Ile  Thr  Lys  Pro  Phe  Arg  Pro  Leu  Glu  Leu  Ile  Ala  Arg  Val  Lys
               580                      585                           590

Ala  Gln  Leu  Arg  Arg  Tyr  Lys  Lys  Phe  Ser  Gly  Val  Lys  Glu  Gln  Asn
          595                      600                      605

Glu  Asn  Val  Ile  Val  His  Ser  Gly  Leu  Val  Ile  Asn  Val  Asn  Thr  His
     610                      615                      620

Glu  Cys  Tyr  Leu  Asn  Glu  Lys  Gln  Leu  Ser  Leu  Thr  Pro  Thr  Glu  Phe
625                      630                      635                      640

Ser  Ile  Leu  Arg  Ile  Leu  Cys  Glu  Asn  Lys  Gly  Asn  Val  Val  Ser  Ser
               645                      650                      655
```

| | | | | | | | | | | | | | | |
|---|---|---|---|---|---|---|---|---|---|---|---|---|---|---|
|Glu|Leu|Leu|Phe|His|Glu|Ile|Trp|Gly|Asp|Glu|Tyr|Phe|Ser|Lys|Ser|
| | | |660| | |665| | | | |670| | | |
|Asn|Asn|Thr|Ile|Thr|Val|His|Ile|Arg|His|Leu|Arg|Glu|Lys|Met|Asn|
| | |675| | | |680| | | |685| | | | |
|Asp|Thr|Ile|Asp|Asn|Pro|Lys|Tyr|Ile|Lys|Thr|Val|Trp|Gly|Val|Gly|
| |690| | | |695| | | |700| | | | | |
|Tyr|Lys|Ile|Glu|Lys|Lys|Arg|Leu|Phe|Gln|Thr|Arg|Thr|Lys|Thr|
|705| | | |710| | | |715| | | | |720|
|Leu|His|Val|Tyr|Arg|Cys|Asn|Cys|Gly|Ser|Asn|Cys|Ile|Arg|Val|
| | | |725| | | |730| | | |735| | |
|Val|Tyr|Ser|Phe|Asn|Asp|Pro|Arg|Glu|Thr|Trp|Gly|Leu|Asp|Leu|Lys|
| | |740| | | |745| | | |750| | | |
|Tyr|Phe|Gly|Lys|Gln|Ile|Leu|Lys|Ser|Pro|Gly|Arg|Asp|Glu|Ile|Ile|
| |755| | | |760| | | |765| | | | |
|Ser|Ile|Phe|His|Thr|Glu|Gln|Tyr|Arg|Tyr|Leu|Tyr|Leu|Cys|Gly|Asp|
|770| | | |775| | | |780| | | | | |
|Cys|His|Tyr|Ser|Tyr|Ser|Met|Ser|Arg|His|Ala|Phe|Lys|Ile|Arg|Lys|
|785| | | |790| | | |795| | | |800| |
|Ile|Leu|Arg|Asp|Lys|Tyr|Arg|His|Cys|Thr|Tyr|Ser|Glu|Arg|Arg|Thr|
| | | |805| | | |810| | | |815| | |
|Asn|Ala|Phe|Cys|Gly|Asn|Gly|Cys|Tyr|Gly|Thr|Lys|Ala|Gln|His|Ile|
| | |820| | | |825| | | |830| | | |
|Lys|Thr|Asp|Ser|Gly|Lys|Ala|Arg|Ala|Gly|Cys|Lys|Ala|Gly|Arg|Thr|
| |835| | | |840| | | |845| | | | |
|Lys|Lys|Lys|Arg|Cys|Tyr|Val|Leu|Gly|Ala|Arg|Tyr|Asn|Ala|Pro|Tyr|
|850| | | |855| | | |860| | | | | |
|Ile|His|Tyr|Arg|Leu|Phe|Glu|Pro|Ala|Arg|Gly|Ser|Arg|His|Ala|Gly|
|865| | | |870| | | |875| | | | |880|
|Arg|Ser|Lys|Gly|Lys|Val|Cys|Ala|Tyr|His|Val|Gly|Gln|Ser|Val|Ser|
| | | |885| | | |890| | | |895| | |
|Thr|Arg|Thr|Ala|Asn|Arg|Arg|Val|Phe|Asp|Tyr|Thr|Val|Pro|Thr|Asn|
| | |900| | | |905| | | |910| | | |
|Asp|Asn|Ala|Asn|Lys|Asn|Ala|His|Arg|Pro|Ile|Leu|Tyr|Ala|Gly|Ala|
| | |915| | | |920| | | |925| | | |
|Asp|Asp|Arg|Ile|Leu|Ser|Ser|Ala|Phe|Arg|Thr|Trp|Lys|Thr|Gly|Gly|
|930| | | |935| | | |940| | | | | |
|Tyr|Ser|Arg|Pro|Arg|Gly|Ser|Asp|Arg|Val|Arg|Arg|Pro|Thr|Arg|Glu|
|945| | | |950| | | |955| | | | |960|
|Ser|Leu|Gln|His|Phe|Glu|Lys|Arg|Arg|Cys|Ile|Gln|Gly|Gln|His|His|
| | | |965| | | |970| | | |975| | |
|His|Tyr|Arg|Gly|Pro|Leu|Arg|Gly|Cys|Gly|Val|Asn|Arg|Ile|Gln|Glu|
| | |980| | | |985| | | |990| | | |
|His|Trp|Lys|His|Pro|Lys|Arg|Ala|Ser|Cys|His|Ile|Lys|Val|Leu|Ala|
| |995| | | |1000| | | |1005| | | | |
|Gly|Gln|Phe|Ser|Phe|Phe|Arg|Tyr|Gly|Trp|Arg|Gly|Thr|Trp|Ile|Gly|
| |1010| | | |1015| | | |1020| | | | |
|Asp|Cys|Lys|Arg|Asn|Tyr|Cys|Ser|Ala|Trp|Arg|Ala|Asp|Leu|Arg|Gly|
|1025| | | |1030| | | |1035| | | |1040|
|Lys|Leu|Leu|Tyr|Asp|Val|Gly|Arg|Ala|Ser|Ser|Asp|Ala|Arg|Leu|Gly|
| | | |1045| | | |1050| | | |1055| |
|Lys|Glu|Val|Leu|Arg|Asp|Val|Tyr|Asn|Phe|Leu|Gly|Lys|Ser|Gln|Gly|
| | | |1060| | | |1065| | | |1070| |
|Tyr|Leu|Tyr|Phe|Phe|Leu|Gly|Asn|Gln|Phe|Asn|Ile|Lys|Lys|Arg|Leu|

-continued

```
                    1075                      1080                          1085
Val Leu Thr Arg Thr Tyr Arg Lys Asn Glu Pro Phe Ser Phe Arg
        1090                      1095                  1100
Glu Arg Phe Asp Lys Ile Thr Ile Gly Ile Pro Val Leu Phe Gly Ala
1105                  1110                      1115                      1120
Phe His Arg Lys Gly Trp Ser Leu Ile Thr Ser Ala Leu Leu Phe Met
                    1125                      1130                      1135
Asp Val Ser Arg Met Arg Gln Met His Ser Met Leu Phe Arg Leu Ala
                1140                      1145                      1150
Leu Ala Leu Trp Gln Arg Leu Thr Pro Thr Cys Arg Asn Pro Thr Pro
        1155                      1160                      1165
Asn Pro Arg Leu Ser Ile Asn Val Ser Val Trp Asp Ile Asn Gln Arg
1170                      1175                      1180
Phe Pro Pro Leu Phe Phe Leu Arg Arg Glu Pro Val Asn Ile Phe Leu
1185                  1190                      1195                      1200
Pro Glu Ala Ser Ala Ala Ile Ile Ile Gln Leu Leu Leu Arg Glu Trp
                    1205                      1210                  1215
Ala Ser Leu Ser Thr Met Trp Arg Thr Arg Arg Ile Ala Leu Pro Ile
                1220                      1225                  1230
Ile Leu Cys Phe Leu Trp Gln Tyr Ala Thr Asn Arg Leu Cys Ala Leu
            1235                      1240                  1245
Trp Lys Asn Met Ile Ser Gly Trp Thr Ala Thr Val Ala Arg Tyr Ser
1250                      1255                      1260
Ala Thr Gln Leu Val Trp Trp Glu Arg Ala Arg Ala Lys Arg Leu Leu
1265                      1270                      1275                  1280
Ser Gly Cys Glu Asp Leu Asp Val Lys Cys Trp Leu Ile Val Ala Ala
                    1285                      1290                  1295
Glu Val Arg Thr Met Tyr Arg Leu Met Ser Cys Cys Lys Ile Ala Ile
                1300                      1305                  1310
Ser Leu Arg Phe Met Cys Arg Ser Ile Arg Ile Arg Thr Ile Leu Ser
            1315                      1320                  1325
Ala Thr Asn Lys Tyr Arg Glu Ser Lys Glu His Phe Leu Ser Ile Leu
        1330                      1335                  1340
Gly Ala Val His Leu Ile Pro Met Ser Trp Leu Lys His Lys Thr Gly
1345                      1350                      1355                  1360
Asn Trp Ala Val Pro His Trp Met Tyr Trp Lys Glu Arg Lys Ser Phe
                    1365                      1370                  1375
Ser Thr Leu Ile Ala Pro Lys Asn Gln Leu Ile Ile Asn Phe Tyr Leu
            1380                      1385                  1390
Asn Phe Lys Glu Cys Leu Thr Ser His Arg Ile Arg Pro Ile Ile Pro
        1395                      1400                  1405
Ser Lys Arg Cys Val Ile Pro Leu Lys Lys Pro Leu Lys Thr Val Trp
    1410                      1415                  1420
Ile Leu Lys Gly Asp Arg Ser Met Asn Arg Ile Lys Val Ala Ile Leu
1425                      1430                      1435                  1440
Phe Gly Gly Cys Ser Glu Glu His Asp Val Ser Val Lys Ser Ala Ile
                    1445                      1450                  1455
Glu Ile Ala Ala Asn Ile Asn Lys Glu Lys Tyr Glu Pro Leu Tyr Ile
                1460                      1465                  1470
Gly Ile Thr Lys Ser Gly Val Trp Lys Met Cys Glu Lys Pro Cys Ala
            1475                      1480                  1485
Glu Trp Glu Asn Asp Asn Cys Tyr Ser Ala Val Leu Ser Pro Asp Lys
        1490                      1495                  1500
```

-continued

```
Lys  Met  His  Gly  Leu  Leu  Val  Lys  Lys  Asn  His  Glu  Tyr  Glu  Ile  Asn
1505                1510                1515                          1520

His  Val  Asp  Val  Ala  Phe  Ser  Ala  Leu  His  Gly  Lys  Ser  Gly  Glu  Asp
                         1525                1530                     1535

Gly  Ser  Ile  Gln  Gly  Leu  Phe  Glu  Leu  Ser  Gly  Ile  Pro  Phe  Val  Gly
                    1540                1545                     1550

Cys  Asp  Ile  Gln  Ser  Ser  Ala  Ile  Cys  Met  Asp  Lys  Ser  Leu  Thr  Tyr
               1555                1560                1565

Ile  Val  Ala  Lys  Asn  Ala  Gly  Ile  Ala  Thr  Pro  Ala  Phe  Trp  Val  Ile
                    1570                1575                     1580

Asn  Lys  Asp  Asp  Arg  Pro  Val  Ala  Ala  Thr  Phe  Thr  Tyr  Pro  Val  Phe
1585                1590                1595                          1600

Val  Lys  Pro  Ala  Arg  Ser  Gly  Ser  Ser  Phe  Gly  Val  Lys  Lys  Val  Asn
                         1605                1610                     1615

Ser  Ala  Asp  Glu  Leu  Asp  Tyr  Ala  Ile  Glu  Ser  Ala  Arg  Gln  Tyr  Asp
                    1620                1625                     1630

Ser  Lys  Ile  Leu  Ile  Glu  Gln  Ala  Val  Ser  Gly  Cys  Glu  Val  Gly  Cys
               1635                1640                1645

Ala  Val  Leu  Gly  Asn  Ser  Ala  Ala  Leu  Val  Val  Gly  Glu  Val  Asp  Gln
          1650                1655                1660

Ile  Arg  Leu  Gln  Tyr  Gly  Ile  Phe  Arg  Ile  His  Gln  Glu  Val  Glu  Pro
1665                1670                1675                          1680

Glu  Lys  Gly  Ser  Glu  Asn  Ala  Val  Ile  Thr  Val  Pro  Ala  Asp  Leu  Ser
                    1685                1690                     1695

Ala  Glu  Glu  Arg  Gly  Arg  Ile  Gln  Glu  Thr  Ala  Lys  Lys  Ile  Tyr  Lys
                    1700                1705                     1710

Ala  Leu  Gly  Cys  Arg  Gly  Leu  Ala  Arg  Val  Asp  Met  Phe  Leu  Gln  Asp
               1715                1720                1725

Asn  Gly  Arg  Ile  Val  Leu  Asn  Glu  Val  Asn  Thr  Leu  Pro  Gly  Phe  Thr
          1730                1735                1740

Ser  Tyr  Ser  Arg  Tyr  Pro  Arg  Met  Met  Ala  Ala  Ala  Gly  Ile  Ala  Leu
1745                1750                1755                          1760

Pro  Glu  Leu  Ile  Asp  Arg  Leu  Ile  Val  Leu  Ala  Leu  Lys  Gly  Ala  Trp
                    1765                1770                     1775

Lys  Asp  Leu  Leu  Phe  Met  Lys  Tyr  Thr  Val  Phe  Val  Gly  Thr  Leu  Asn
               1780                1785                1790

Met  Pro  Leu  Gly  Ile  Ile  Ser  Pro  Glu  Asn  Arg  Leu  Thr  Val  Met  Lys
               1795                1800                1805

Ile  Ala  Leu  Gly  His  Thr  Ser  Trp  Leu  Asn  Arg  Phe  Arg  Gln  Lys  Asn
          1810                1815                1820

Trp  Leu  Leu  Pro  Lys  Gly  Thr  Asp  Cys  Phe  Tyr  Gly  Thr  Val  Thr  Val
1825                1830                1835                          1840

Leu  Ser  Val  Leu  Thr  Val  Leu  Cys  Asn  Gly  Leu  His  Ser  Arg  Lys  Ile
                    1845                1850                     1855

Thr  Gln  Arg  Lys  Val  Ile  Ile  Pro  Ile  Leu  Thr  Glu  Leu  Arg  Phe  Gln
                    1860                1865                     1870

Lys  Asp  Thr  Trp  Leu  Gln  Asn  Gln  Ala  Ile  Ala  Ala  Ala  Val  Pro  Leu
               1875                1880                1885

Ile  Leu  Arg  Phe  Ile  Asp  Thr  Arg  Val  Ser  Leu  Tyr  Gln  Trp  Gly  Ala
          1890                1895                1900

Asp  Leu  Ile  Leu  Trp  Met  Asn  Ala  Leu  Ile  Met  Arg  Gln  Met  Glu  Tyr
1905                1910                1915                          1920

His  Ala  Met  Lys  Arg  Lys  Ile  Ala  Asp  Val  Cys  Ala  Pro  Ser  Trp  Lys
                    1925                1930                     1935
```

Thr Val Gly Leu Lys His Ile Ala Ser Asn Gly Gly Thr Met Tyr Glu
            1940                    1945                    1950

Thr Asn His Thr Pro Ile Ala Ile Leu Ile Ser Pro Leu Asn Lys Leu
            1955                    1960                    1965

Leu Thr Val Ala Arg Thr Asn Tyr Ile Ser Leu Phe Arg Gln Glu Thr
            1970                    1975                    1980

Arg Arg Met Leu Val Leu Arg Glu Phe Ile Tyr Ser Arg Tyr Arg Cys
1985                    1990                    1995                    2000

Lys Ala Glu Arg Tyr Cys Gly His Tyr Leu Arg Ala Leu Arg Gln Asp
                        2005                    2010                    2015

Ser Leu Ile Ile Arg Leu Ile Ala Arg Gly Gly Ile Ser His Arg Pro
                        2020                    2025                    2030

Leu Ser Thr Gly Ser Ser Ala Ser Leu Asn Ser Ala Trp Val Ser Leu
                        2035                    2040                    2045

Met Lys Ile His Leu His Trp Ile Gln Gly Glu Ile Ile Asp Cys Asn
                        2050                    2055                    2060

Leu Arg Gly Lys Thr Ala Gln Ser Gln Thr Arg Leu Cys Arg Leu Arg
2065                    2070                    2075                    2080

Gly Arg Phe Lys Tyr Phe Ile Leu Pro Thr Ile Leu Arg Arg Arg Leu
                        2085                    2090                    2095

Lys Met Lys Lys Leu Phe Phe Leu Leu Leu Leu Leu Phe Leu Ile Tyr
                        2100                    2105                    2110

Leu Gly Tyr Asp Tyr Val Asn Glu Ala Leu Phe Ser Gln Glu Lys Val
                        2115                    2120                    2125

Glu Phe Gln Asn Tyr Asp Gln Asn Pro Lys Glu His Leu Glu Asn Ser
                        2130                    2135                    2140

Gly Thr Ser Glu Asn Thr Gln Glu Lys Thr Ile Thr Glu Glu Gln Val
2145                    2150                    2155                    2160

Tyr Gln Gly Asn Leu Leu Leu Ile Asn Ser Lys Tyr Pro Val Arg Gln
                        2165                    2170                    2175

Glu Val Ser Gln Ile Ser Ile Tyr Leu Asn Met Thr Asn Met Asp Thr
                        2180                    2185                    2190

Gly Cys Leu Ile Val Ile Phe Ile Cys Gln Lys Lys His Lys Asn Phe
                        2195                    2200                    2205

Gln Arg Trp Ser Met Met Leu Arg Val Ala Leu Val Ile Leu Leu Leu
                        2210                    2215                    2220

Ile Val Ala Ile Glu Thr Leu Met Ser Lys Val Cys Phe Thr Lys Lys
2225                    2230                    2235                    2240

Trp Gly Leu Ser Met Pro Tyr Gln Gln Val Ile Val Ser Ile Ile Gln
                        2245                    2250                    2255

Val Tyr His Met Asp Gln Ala Arg Lys Trp Asn Glu Pro Leu Lys Glu
                        2260                    2265                    2270

Ser Gly Lys Lys Met Leu Gly Asn Thr Gly Ser Phe Tyr Val Ile Gln
                        2275                    2280                    2285

Arg Thr Lys Gln Ser Gln Glu Phe
            2290                    2295

( 2 ) INFORMATION FOR SEQ ID NO:28:

( i ) SEQUENCE CHARACTERISTICS:
        ( A ) LENGTH: 2254 amino acids
        ( B ) TYPE: amino acid
        ( D ) TOPOLOGY: linear ( i i ) MOLECULE TYPE: protein ( x i ) SEQUENCE DESCRIPTION: SEQ ID NO:28:

| | | | | | | | | | | | | | | |
|---|---|---|---|---|---|---|---|---|---|---|---|---|---|---|
| Ser 1 | Phe | Ser | Phe | Cys 5 | Ser | Phe | Val | Arg | Asp 10 | Leu | Leu | Thr | Val | Leu Asn 15 |
| Ser | Phe | Phe | Ser 20 | Ala | Ile | Ala | Leu | Ala 25 | Ser | His | Thr | Ile | Leu 30 | Ser Ser |
| Val | Val | Ile 35 | Ala | Gly | Ser | Ile | Ile 40 | Leu | Phe | Phe | Leu | Arg 45 | Lys | Ser Met |
| His | Ser 50 | Cys | Ser | Arg | Met | Ala 55 | Ser | Pro | Phe | Ser | Lys 60 | Ala | Asn | Arg Tyr |
| Leu 65 | Asn | Val | Ile | Arg | Tyr 70 | Ser | Leu | Arg | Val | Lys 75 | Val | Thr | Lys | Ser Tyr 80 |
| Ser | Leu | Arg | Ile | Ser 85 | Phe | Lys | Ser | Gln | Ser 90 | Val | Phe | Ser | Leu | Gly Ser 95 |
| Ser | Glu | Asp | Gly 100 | Leu | Thr | Pro | Ile | Cys 105 | Phe | Asp | Ile | Tyr | Cys 110 | Met Thr |
| Glu | Ser | Gly 115 | Met | Leu | Leu | Ile | Val 120 | Tyr | Gly | Gln | Pro | Gly 125 | Tyr | Arg Arg |
| Thr | Ala | Asn 130 | Thr | Ala | Asn | Pro 135 | Lys | Arg | Phe | Ser | Ser 140 | Leu | Leu | Arg Leu |
| Leu 145 | Thr | Ile | Ser | Lys | Ser 150 | Arg | Leu | Glu | Lys | Val 155 | Lys | Val | Pro | Ser Ile 160 |
| His | Ser | Ser | Ser | Gly 165 | Ile | Cys | Ile | Lys | Ala 170 | Cys | Leu | Cys | Ser | Gly Val 175 |
| Ser | Asn | Ser | Leu 180 | Pro | Leu | Ala | Ile | Phe 185 | Ile | Gln | Tyr | His | Ser 190 | Ile Ser |
| Val | Phe | Ser 195 | Ile | Tyr | Phe | Asn | Tyr 200 | Ile | Ser | Ile | Glu | Cys 205 | Thr | Leu Leu |
| Ile | Gln | Met 210 | Thr | Asp | Lys | Ile 215 | Ile | Val | Lys | Ser | Val 220 | Ser | Asp | Leu Ser |
| Gln 225 | Lys | Gly | Asp | Ile | Leu 230 | Arg | Lys | Ile | Gly | Tyr 235 | Ile | Arg | Val | Ser Ser 240 |
| Thr | Asn | Gln | Asn | Pro 245 | Ser | Arg | Gln | Phe | Gln 250 | Gln | Leu | Asn | Glu | Ile Gly 255 |
| Met | Asp | Ile | Ile 260 | Arg | Glu | Ser | Phe | Arg 265 | Ser | Asn | Lys | Gly | Ser 270 | Arg Ala |
| Thr | Ser | Lys 275 | Ser | Val | Arg | Arg | Phe 280 | Thr | Gly | Arg | His | His 285 | Leu | Cys Tyr |
| Arg | Leu | Asn 290 | Ser | Asn | His | Ser 295 | Tyr | Thr | Arg | Ser | Ile 300 | Ile | Asn | Arg His |
| Thr 305 | Arg | Lys | Gly | Lys | Phe 310 | Lys | Ile | Thr | Lys | Arg 315 | Tyr | Met | Ala | Phe Ile 320 |
| Arg | Arg | Ser | Ile | Gln 325 | Pro | Ile | Leu | Asn | Tyr 330 | Cys | Asn | Gly | Trp | Cys Pro 335 |
| Ile | Arg | Ala | Arg 340 | Ser | Tyr | Ser | Asp | Glu 345 | Thr | Thr | Arg | Asp | Ile 350 | Gly Glu |
| Arg | Arg | Lys 355 | Val | Arg | Ser | Ile | Lys 360 | Glu | Val | Ser | Lys | Ser 365 | Arg | Arg Asn |
| Glu | Leu | Cys 370 | Gly | Glu | Ser | Tyr | Ile 375 | Lys | Lys | Glu | Ile 380 | Leu | Ile | Lys Phe |
| Val 385 | Lys | Leu | Leu | Met | Tyr 390 | Leu | Gly | Leu | His | Tyr 395 | Thr | Gly | Asn | Tyr Gln 400 |
| Lys | Ile | Ile | Ser | His 405 | Ser | Val | Phe | Arg | Trp 410 | Ala | Ile | Phe | Leu | Lys Lys 415 |

```
Lys  Arg  Lys  Leu  Asn  Ile  Asn  Ser  Leu  Leu  Ala  Met  Pro  Lys  Ser  Pro
               420                 425                      430

Leu  Ile  Lys  Lys  Glu  Ser  Ser  Ser  Glu  Ile  Leu  Ser  His  Leu  Leu  Cys
          435                 440                      445

Lys  Cys  Leu  Ile  Arg  Pro  Tyr  Asn  Leu  Ile  Asn  Tyr  Gly  Gln  Thr  Tyr
     450                 455                      460

Val  Lys  Gly  Leu  Ala  Ile  Lys  Tyr  Leu  Leu  Trp  Met  Met  Asn  Met  Lys
465                      470                 475                           480

Leu  Pro  Ile  Trp  Leu  Asn  Tyr  Thr  Lys  Thr  Arg  Ile  Ile  Arg  Phe  Ser
               485                      490                           495

Asn  Thr  Ile  Pro  Pro  Lys  Lys  His  Trp  Asn  Val  Thr  Ser  Leu  Arg  Leu
               500                 505                      510

Thr  Leu  Pro  Tyr  Trp  Thr  Ser  Cys  Phe  Pro  Ala  Gln  Ala  Ala  Leu  Leu
          515                 520                      525

Ser  Val  Lys  Lys  Gly  Thr  Ser  Thr  Pro  Ile  Arg  Leu  Ser  Cys  Pro  Gly
     530                 535                      540

Lys  Ile  Gln  Arg  Ile  Lys  Leu  Gln  Gly  Gln  Ser  Ala  Arg  Met  Ile  Ile
545                      550                 555                           560

Arg  Ser  Pro  Phe  Ala  His  Trp  Ser  Leu  Leu  Gly  Arg  Pro  Ser  Cys  Ala
               565                      570                           575

Asp  Thr  Lys  Asn  Ser  Val  Glu  Arg  Ser  Arg  Thr  Lys  Met  Leu  Ser  Ser
               580                 585                      590

Thr  Pro  Ala  Leu  Ser  Leu  Met  Leu  Thr  Pro  Met  Ser  Val  Ile  Thr  Arg
          595                 600                      605

Ser  Ser  Tyr  Pro  Leu  Leu  Pro  Pro  Ser  Phe  Gln  Tyr  Cys  Glu  Ser  Ser
     610                 615                      620

Val  Lys  Thr  Arg  Gly  Met  Trp  Leu  Ala  Pro  Ser  Cys  Tyr  Phe  Met  Arg
625                      630                 635                           640

Tyr  Gly  Ala  Thr  Asn  Ile  Ser  Ala  Arg  Ala  Thr  Thr  Pro  Ser  Pro  Cys
               645                      650                           655

Ile  Ser  Gly  Ile  Cys  Ala  Lys  Lys  Thr  Thr  Pro  Leu  Ile  Ile  Arg  Asn
               660                 665                      670

Ile  Lys  Arg  Tyr  Gly  Gly  Leu  Val  Ile  Lys  Leu  Lys  Asn  Lys  Lys  Asn
          675                 680                      685

Asp  Tyr  Ser  Lys  Leu  Glu  Arg  Lys  Leu  Tyr  Met  Tyr  Ile  Val  Ala  Ile
     690                 695                      700

Val  Val  Val  Ala  Ile  Val  Phe  Val  Leu  Tyr  Ile  Arg  Ser  Met  Ile  Arg
705                      710                 715                           720

Gly  Lys  Leu  Gly  Asp  Trp  Ile  Leu  Ser  Ile  Leu  Glu  Asn  Lys  Tyr  Asp
               725                      730                           735

Leu  Asn  His  Leu  Asp  Ala  Met  Lys  Leu  Tyr  Gln  Tyr  Ser  Ile  Arg  Asn
               740                      745                           750

Asn  Ile  Asp  Ile  Phe  Ile  Tyr  Val  Ala  Ile  Val  Ile  Ser  Ile  Leu  Ile
          755                      760                      765

Leu  Cys  Arg  Val  Met  Leu  Ser  Lys  Phe  Ala  Lys  Tyr  Phe  Asp  Glu  Ile
     770                 775                      780

Asn  Thr  Gly  Ile  Asp  Val  Leu  Ile  Gln  Asn  Glu  Asp  Lys  Gln  Ile  Glu
785                 790                      795                           800

Leu  Ser  Ala  Glu  Met  Asp  Val  Met  Glu  Gln  Lys  Leu  Asn  Thr  Leu  Lys
               805                      810                           815

Arg  Thr  Leu  Glu  Lys  Arg  Glu  Gln  Asp  Ala  Lys  Leu  Ala  Glu  Gln  Arg
               820                 825                      830

Lys  Asn  Asp  Val  Val  Met  Tyr  Leu  Ala  His  Asp  Ile  Lys  Thr  Pro  Leu
               835                      840                      845
```

-continued

| | | | | | | | | | | | | | | |
|---|---|---|---|---|---|---|---|---|---|---|---|---|---|---|
|Thr|Ser|Ile|Ile|Gly|Tyr|Leu|Ser|Leu|Leu|Asp|Glu|Ala|Pro|Asp|Met|
| | |850| | | |855| | | |860| | | | |
|Pro|Val|Asp|Gln|Lys|Ala|Lys|Tyr|Val|His|Ile|Thr|Leu|Asp|Lys|Ala|
|865| | | | |870| | | | |875| | | | |880|
|Tyr|Arg|Leu|Glu|Gln|Leu|Ile|Asp|Glu|Phe|Phe|Glu|Ile|Thr|Arg|Tyr|
| | | | |885| | | | |890| | | | |895| |
|Asn|Leu|Gln|Thr|Ile|Thr|Leu|Thr|Lys|Thr|His|Ile|Asp|Leu|Tyr|Tyr|
| | | |900| | | | |905| | | | |910| | |
|Met|Leu|Val|Gln|Met|Thr|Asp|Glu|Phe|Tyr|Pro|Gln|Leu|Ser|Ala|His|
| | |915| | | |920| | | |925| | | | | |
|Gly|Lys|Gln|Ala|Val|Ile|His|Ala|Pro|Glu|Asp|Leu|Thr|Val|Ser|Gly|
| |930| | | | |935| | | |940| | | | | |
|Asp|Pro|Asp|Lys|Leu|Ala|Arg|Val|Phe|Asn|Asn|Ile|Leu|Lys|Asn|Ala|
|945| | | | |950| | | | |955| | | | |960|
|Ala|Ala|Tyr|Ser|Glu|Asp|Asn|Ser|Ile|Ile|Asp|Ile|Thr|Ala|Gly|Leu|
| | | | |965| | | | |970| | | | |975| |
|Ser|Gly|Asp|Val|Val|Ser|Ile|Glu|Phe|Lys|Asn|Thr|Gly|Ser|Ile|Pro|
| | | |980| | | | |985| | | | |990| | |
|Lys|Asp|Lys|Leu|Ala|Ala|Ile|Phe|Glu|Lys|Phe|Tyr|Arg|Leu|Asp|Asn|
| | |995| | | | |1000| | | | |1005| | | |
|Ser|Arg|Ser|Ser|Asp|Thr|Gly|Gly|Ala|Gly|Leu|Gly|Leu|Ala|Ile|Ala|
| | |1010| | | | |1015| | | | |1020| | | |
|Lys|Glu|Ile|Ile|Val|Gln|His|Gly|Gly|Gln|Ile|Tyr|Ala|Glu|Ser|Tyr|
|1025| | | | |1030| | | | |1035| | | | |1040|
|Asp|Asn|Tyr|Thr|Thr|Phe|Arg|Val|Glu|Leu|Pro|Ala|Met|Pro|Asp|Leu|
| | | | |1045| | | | |1050| | | | |1055| |
|Val|Asp|Lys|Arg|Arg|Ser|Glu|Met|Tyr|Ile|Ile|Phe|Glu|Asn|Leu|Lys|
| | | |1060| | | | |1065| | | | |1070| | |
|Val|Ile|Phe|Thr|Phe|Ser|Glu|Ile|Asn|Asn|Leu|Ile|Leu|Arg|Asn|Gly|
| | | |1075| | | | |1080| | | | |1085| | |
|Ser|Phe|Leu|His|Gly|Arg|Leu|Asn|Thr|Val|Arg|Thr|Ser|Arg|Phe|Arg|
| | |1090| | | | |1095| | | | |1100| | | |
|Ser|Ser|Glu|Lys|Asp|Leu|Thr|Arg|Leu|Pro|Leu|Ala|Ser|Pro|Phe|Tyr|
|1105| | | | |1110| | | | |1115| | | | |1120|
|Leu|Val|Pro|Phe|Thr|Glu|Arg|Val|Gly|Leu|Asn|Tyr|Glu|His|Arg|His|
| | | | |1125| | | | |1130| | | | |1135| |
|Tyr|Cys|Leu|Trp|Met|Ala|Gly|Gly|Arg|Cys|Ile|Pro|Cys|Ser|Phe|Ala|
| | | | |1140| | | | |1145| | | | |1150| |
|Ser|Leu|Trp|Arg|Tyr|Gly|Asn|Asp|Asn|Arg|Gln|Arg|Val|Gly|Ile|Gln|
| | | |1155| | | | |1160| | | | |1165| | |
|Arg|Gln|Ile|Arg|Ala|Phe|Gln|Ser|Met|Tyr|Gln|Cys|Gly|Thr|Ile|Arg|
| | |1170| | | | |1175| | | | |1180| | | |
|Asp|Phe|Arg|Leu|Tyr|Ser|Ser|Cys|Ala|Glu|Glu|Ser|Arg|Cys|Glu|Ile|
|1185| | | | |1190| | | | |1195| | | | |1200|
|Tyr|Phe|Tyr|Pro|Lys|His|Arg|Leu|Gln|Ser|Tyr|Arg|Tyr|Asn|Cys|Cys|
| | | | |1205| | | | |1210| | | | |1215| |
|Glu|Asn|Gly|His|His|Cys|Arg|Gln|Cys|Gly|Val|Leu|Ala|Gly|Arg|Cys|
| | | |1220| | | | |1225| | | | |1230| | |
|Arg|Leu|Tyr|Tyr|Asp|Ala|Asn|Ser|Tyr|Gly|Ser|Thr|Gln|Arg|Lys|Ile|
| | | |1235| | | | |1240| | | | |1245| | |
|Asp|Cys|Ala|Leu|Cys|Gly|Lys|Thr|Phe|Gln|Val|Gly|Gln|Arg|Pro|Trp|
| | |1250| | | | |1255| | | | |1260| | | |
|Gln|Gly|Thr|Gln|Arg|His|Asp|Ser|Trp|Cys|Gly|Gly|Asn|Gly|Pro|Asp|

-continued

```
1265                1270                1275                1280
Arg Gln Ser Gly Tyr Ala Ala Ala Arg Ile Trp Met Ser Val Gly Leu
                1285                1290                1295
Ser Gln Pro Lys Tyr Arg Gly Lys Leu Cys Thr Val Val Ala Ala Lys
                1300            1305                    1310
Arg Tyr Arg Tyr Ala Ser Cys Ala Ala Gln Tyr Gly Tyr Ala Leu Tyr
            1315                1320                1325
Tyr Gln Pro Arg Thr Asn Thr Glu Asn Glu Ala Arg Ser Ile Ser Tyr
        1330            1335                1340
Gln Tyr Trp Ala Arg Ser Thr Cys Arg Tyr Leu Val Gly Ser Ile Arg
1345                1350                1355                1360
Lys Arg Glu Thr Gly Arg Cys Arg Ile Gly Cys Ile Gly Arg Arg Gly
                1365                1370                1375
Arg Val Phe Leu Leu Leu His Pro Lys Thr Asn Ser Ile Phe Thr Thr
                1380                1385                1390
Ser Lys Asn Ala Arg Asp Asn His Thr Ala Tyr Gly Leu Leu Tyr Arg
                1395                1400            1405
Ala Ser Val Ala Tyr Arg Lys Asn His Lys Leu Phe Gly Phe Lys Glu
                1410                1415                1420
Thr Gly Ala Ile Glu Lys Leu Gln Tyr Cys Leu Gly Val Ala Gln Arg
1425                1430                1435                1440
Ser Met Thr Tyr Arg Asn Leu Gln Arg Pro Leu Thr Leu Ile Lys Lys
                1445                1450                1455
Asn Thr Ser Arg Tyr Thr Leu Glu Leu Arg Asn Leu Val Tyr Gly Lys
                1460                1465                1470
Cys Ala Lys Asn Leu Ala Arg Asn Gly Lys Thr Thr Ile Ala Ile Gln
            1475                1480                1485
Leu Tyr Ser Arg Arg Ile Lys Lys Cys Thr Asp Tyr Leu Leu Lys Arg
            1490                1495                1500
Thr Met Asn Met Lys Ser Thr Met Leu Met His Phe Gln Leu Cys Met
1505                1510                1515                1520
Ala Ser Gln Val Lys Met Asp Pro Tyr Lys Val Cys Leu Asn Cys Pro
                1525                1530                1535
Val Ser Leu Leu Ala Ala Ile Phe Lys Ala Gln Gln Phe Val Trp Thr
                1540                1545                1550
Asn Arg His Thr Ser Leu Arg Lys Met Leu Gly Leu Leu Pro Pro Phe
                1555                1560                1565
Gly Leu Leu Ile Lys Met Ile Gly Arg Trp Gln Leu Arg Leu Pro Ile
            1570                1575                1580
Leu Phe Leu Leu Ser Arg Arg Val Gln Ala His Pro Ser Val Lys Lys
1585                1590                1595                1600
Ser Ile Ala Arg Thr Asn Trp Thr Thr Gln Leu Asn Arg Gln Asp Asn
                1605                1610                1615
Met Thr Ala Lys Ser Leu Ser Arg Leu Phe Arg Ala Val Arg Ser Val
                1620                1625                1630
Val Arg Tyr Trp Glu Thr Val Pro Arg Leu Leu Ala Arg Trp Thr Lys
            1635                1640                1645
Ser Gly Cys Ser Thr Glu Ser Phe Val Phe Ile Arg Lys Ser Ser Arg
            1650                1655                1660
Lys Lys Ala Leu Lys Thr Gln Leu Pro Phe Pro Gln Thr Phe Gln Gln
1665                1670                1675                1680
Arg Ser Glu Asp Gly Tyr Arg Lys Arg Gln Lys Lys Tyr Ile Lys Arg
                1685                1690                1695
```

```
Ser Ala Val Glu Val Pro Val Trp Ile Cys Phe Tyr Lys Ile Thr Ala
                1700                1705                1710

Ala Leu Tyr Thr Lys Ser Ile Leu Cys Pro Val Ser Arg His Thr Val
                1715                1720                1725

Val Ile Pro Val Trp Pro Leu Gln Val Leu His Phe Pro Asn Leu Thr
            1730                1735                1740

Ala Ser Tyr Arg Arg Gly Asp Lys His Gly Asn Arg Ile Tyr Phe Phe
1745                1750                1755                1760

Arg Asn Ser Thr Arg Cys Ser Leu Gly Arg Ile Cys His Leu Gly Phe
                    1765                1770                1775

His Arg Lys Thr Gly Arg Leu Ser Lys Ser His Cys Arg Asp Ile Arg
                1780                1785                1790

Val Gly Ile Ala Phe Glu Gly Lys Arg Thr Gly Cys Tyr Pro Arg Val
                1795                1800                1805

Arg Ile Ala Ser Met Gly Arg Leu Pro Ser Ala Cys Cys Lys Leu Phe
            1810                1815                1820

Tyr Ala Met Gly Cys Thr Ala Gly Lys Pro Asp Lys Gly Lys Leu Leu
1825                1830                1835                1840

Ser Gln Tyr Pro Asn Asp Asp Phe Lys Arg Ile Arg Gly Phe Lys Ile
                1845                1850                1855

Lys Pro Pro Arg Gln Cys His Ser Tyr Ala Leu Ser Ile Arg His Gly
                1860                1865                1870

Ala Cys Thr Asn Gly Glu Pro Ile Phe Tyr Gly Thr Leu Ser Ser Cys
                1875                1880                1885

Gly Lys Trp Asn Ile Met Gln Ser Ala Lys Ser Gln Thr Phe Ala Leu
            1890                1895                1900

His His Gly Lys Gln Trp Val Ser Ile Pro Arg Met Val Ala Leu Cys
1905                1910                1915                1920

Ile Lys Arg Arg Thr Ile Pro Gln Leu Phe Phe Pro Arg Ile Asn Phe
                1925                1930                1935

Pro Leu His Gly Gln Thr Ile Ala Asn Ser Phe Gly Arg Lys Pro Asp
                1940                1945                1950

Val Cys Asn Trp Phe Leu Gly Asn Leu Tyr Ile Val Asp Ser Ile Glu
            1955                1960                1965

Asp Val Arg Gln Ser Asp Ile Ala Val Ile Ile Cys Val Arg Cys Gly
        1970                1975                1980

Lys Ile Ala Asp Ser His Arg Gly Val Val Phe His Thr Ala His Cys
1985                1990                1995                2000

Gln Gln Ala Val Gln Pro Arg Ile Gln His Gly Tyr His Leu Lys Phe
                2005                2010                2015

Ile Tyr Ile Gly Asp Asn Ser Lys Ser Ser Arg Ala Lys Leu Thr Val
            2020                2025                2030

Ile Tyr Gly Ala Lys Arg His Asn Leu Lys Arg Asp Cys Ala Val Gly
        2035                2040                2045

Glu Asp Ser Arg Asn Ile Ser Tyr Phe Gln Leu Tyr Ser Gly Gly Asp
    2050                2055                2060

Lys Arg Ser Cys Phe Phe Tyr Cys Tyr Cys Tyr Ser Tyr Thr Val Met
2065                2070                2075                2080

Thr Thr Leu Met Lys His Cys Phe Leu Arg Lys Lys Ser Asn Phe Lys
                2085                2090                2095

Ile Met Ile Lys Ile Pro Lys Asn Ile Lys Ile Val Gly Leu Leu Lys
            2100                2105                2110

Ile Pro Lys Arg Lys Gln Leu Gln Lys Asn Arg Phe Ile Lys Glu Ile
        2115                2120                2125
```

5,871,910

135

136

-continued

| Cys | Tyr | Ser | Ile | Val | Asn | Ile | Leu | Phe | Ala | Lys | Lys | Cys | Glu | Val | Arg |
|  | 2130 |  |  |  |  | 2135 |  |  |  | 2140 |  |  |  |  |  |

| Tyr | Arg | Glu | Phe | Ile | Thr | Arg | Ile | Asn | Lys | Trp | Ile | Arg | Val | Ala | Tyr |
| 2145 |  |  |  |  | 2150 |  |  |  | 2155 |  |  |  |  |  | 2160 |

| Leu | Tyr | Val | Lys | Arg | Asn | Ser | Thr | Lys | Ile | Phe | Arg | Asp | Gly | Gln | Cys |
|  |  |  |  | 2165 |  |  |  |  | 2170 |  |  |  |  | 2175 |  |

| Cys | Lys | Gly | Trp | Arg | Ser | Phe | Tyr | Tyr | Trp | Leu | Ser | Arg | Leu | Ala | Lys |
|  |  |  | 2180 |  |  |  |  | 2185 |  |  |  |  | 2190 |  |  |

| Cys | Ala | Leu | Pro | Arg | Asn | Gly | Gly | Val | Cys | Leu | Thr | Ser | Arg | Leu | Ala |
|  |  | 2195 |  |  |  |  | 2200 |  |  |  |  | 2205 |  |  |  |

| Phe | Arg | Phe | Ile | Thr | Arg | Cys | Arg | Ile | Lys | Leu | Asp | Glu | Asn | Gly | Thr |
|  | 2210 |  |  |  |  | 2215 |  |  |  | 2220 |  |  |  |  |  |

| Ser | Pro | Arg | Lys | Val | Asp | Arg | Arg | Lys | Cys | Leu | Glu | Ile | Arg | Val | His |
| 2225 |  |  |  |  | 2230 |  |  |  | 2235 |  |  |  |  |  | 2240 |

| Phe | Thr | Leu | Ser | Arg | Gly | Gln | Asn | Arg | Val | Asn | Arg | Asn | Ser |
|  |  |  |  | 2245 |  |  |  |  | 2250 |  |  |  |  |

(2) INFORMATION FOR SEQ ID NO:29:

(i) SEQUENCE CHARACTERISTICS:
(A) LENGTH: 2291 amino acids
(B) TYPE: amino acid
(D) TOPOLOGY: linear (ii) MOLECULE TYPE: protein (xi) SEQUENCE DESCRIPTION: SEQ ID NO:29:

| Ala | Phe | Leu | Phe | Ala | His | Leu | Leu | Glu | Ile | Tyr | Pro | Tyr | Ile | Ala | Ser |
| 1 |  |  |  | 5 |  |  |  |  | 10 |  |  |  |  | 15 |  |

| Phe | Gln | Pro | Leu | Pro | Leu | Leu | Pro | Thr | Pro | Phe | Phe | Gln | Val | Gln | Ala |
|  |  |  | 20 |  |  |  |  | 25 |  |  |  |  | 30 |  |  |

| Val | Phe | Cys | Phe | Phe | Leu | Glu | Asn | Leu | Cys | Ile | His | Ala | Val | Asp | Glu |
|  |  | 35 |  |  |  |  | 40 |  |  |  |  | 45 |  |  |  |

| Trp | His | His | His | Phe | Pro | Lys | Leu | Ile | Asp | Glu | Gly | Thr | Met | Ser | Phe |
|  | 50 |  |  |  |  | 55 |  |  |  |  | 60 |  |  |  |  |

| Asp | Ile | His | Ser | Gly | Lys | Leu | Gln | Ser | Arg | Ile | His | Phe | Glu | Phe | Leu |
| 65 |  |  |  |  | 70 |  |  |  |  | 75 |  |  |  |  | 80 |

| Ser | Asn | Asp | Pro | Lys | Val | Tyr | Phe | Pro | Phe | Glu | Asp | Asn | Asp | Gln | Ala |
|  |  |  |  | 85 |  |  |  |  | 90 |  |  |  |  | 95 |  |

| Arg | Met | Asp | His | Gln | Ser | Val | Ser | Ile | Tyr | Ile | Val | Pro | Asn | Leu | Gly |
|  |  |  | 100 |  |  |  |  | 105 |  |  |  |  | 110 |  |  |

| Cys | Phe | Tyr | Glu | Cys | Met | Ala | Asn | Arg | Asp | Thr | Glu | Glu | Gln | Leu | Ile |
|  |  |  | 115 |  |  |  |  | 120 |  |  |  |  | 125 |  |  |

| Glu | Gln | Gln | Ile | Leu | Asn | Gly | Phe | Leu | Pro | Ser | Phe | Ala | Tyr | Leu | Phe |
|  | 130 |  |  |  |  | 135 |  |  |  |  | 140 |  |  |  |  |

| Leu | Asn | Pro | Val | Trp | Lys | Lys | Ser | Arg | Ser | Pro | Val | Ser | Ile | His | Leu |
| 145 |  |  |  |  | 150 |  |  |  |  | 155 |  |  |  |  | 160 |

| Gln | Gly | Phe | Ala | Lys | Pro | Val | Ser | Val | Pro | Val | Ala | Ile | Leu | Tyr | Leu |
|  |  |  |  | 165 |  |  |  |  | 170 |  |  |  |  | 175 |  |

| Ser | Gln | Phe | Ser | Phe | Ser | Ile | Ile | Pro | Phe | Leu | Tyr | Phe | Gln | Phe | Ile |
|  |  |  |  | 180 |  |  |  |  | 185 |  |  |  |  | 190 |  |

| Ser | Ser | Ile | Ile | Tyr | Gln | Ser | Val | Leu | Tyr | Tyr | Lys | Cys | Ser | Arg | Leu |
|  |  |  | 195 |  |  |  |  | 200 |  |  |  |  | 205 |  |  |

| Ile | Lys | Ser | Leu | Arg | Ala | Ser | His | Lys | Thr | Cys | Leu | Lys | Asn | Glu | Val |
|  | 210 |  |  |  |  | 215 |  |  |  |  | 220 |  |  |  |  |

| Ile | Phe | Cys | Gly | Lys | Ser | Val | Ile | Phe | Val | Ser | Val | Arg | Leu | Thr | Arg |

```
             225                 230                 235                 240

Ile Leu Gln Asp Asn Phe Ser Ser Thr Arg Ser Glu Trp Ile Leu Tyr
                     245                 250                 255

Lys Glu Lys Val Ser Gly Ala Thr Lys Asp Arg Glu Gln Leu Gln Lys
                     260                 265                 270

Val Leu Asp Asp Leu Gln Glu Asp Ile Ile Tyr Val Thr Asp Leu
                 275                 280                 285

Thr Arg Ile Thr Arg Ser Thr Gln Asp Leu Phe Glu Leu Ile Asp Asn
         290                 295                 300

Ile Arg Asp Lys Lys Ala Ser Leu Lys Ser Leu Lys Asp Thr Trp Leu
     305                 310                 315                 320

Asp Leu Ser Glu Asp Asn Pro Tyr Ser Gln Phe Leu Ile Thr Val Met
                     325                 330                 335

Ala Gly Val Asn Gln Leu Glu Arg Asp Leu Ile Arg Met Arg Gln Arg
                     340                 345                 350

Glu Gly Ile Glu Leu Ala Lys Lys Glu Gly Lys Phe Lys Gly Arg Leu
                     355                 360                 365

Lys Lys Tyr His Lys Asn His Ala Gly Met Asn Tyr Ala Ala Lys Ala
                 370                 375                 380

Ile Arg Arg Lys Tyr Asp Cys Lys Ser Asn Leu Asn Tyr Cys Ile Gly
     385                 390                 395                 400

Phe Ile Ile Gln Glu Ile Ile Arg Ser Glu Leu Ala Ile Leu Tyr Ser
                     405                 410                 415

Ala Asn Gly Gln Tyr Phe Arg Arg Lys Gly Asn Tyr Lys Ile Leu Thr
                     420                 425                 430

Ala Ser Arg Cys Arg Lys Ala Leu Lys Lys Asn His His Leu Lys Lys
                 435                 440                 445

Phe Leu Val Ile Tyr Tyr Val Asn Ala Tyr Lys Phe Gly Pro Ile Ile
                 450                 455                 460

Ile Ile Lys Gly Lys Leu Met Lys Gly Asp Asn Tyr Glu Arg Asn Thr
     465                 470                 475                 480

Tyr Cys Gly Thr Asn Cys Arg Phe Gly Ile Ile Leu Lys Lys Arg Glu
                     485                 490                 495

Leu Tyr Gly Phe Gln Ile Leu Tyr Arg Gln Arg Ser Ile Gly Met Tyr
                 500                 505                 510

Arg Gln Val Asp Pro Cys His Ile Gly His His Ala Ser Arg His Lys
                 515                 520                 525

Arg Pro Tyr Tyr Leu Ser Lys Asn Lys Gly Gln Ala His Leu Ser Asp
         530                 535                 540

Tyr His Ala Asp Arg Glu Arg Tyr Arg Gly Arg Asn Tyr Arg Val Asn
     545                 550                 555                 560

Asn Arg Arg Gly Leu Tyr Asn Glu Ala Leu Ser Pro Thr Gly Val Asn
                     565                 570                 575

Cys Ser Gly Lys Gly Pro Val Ala Pro Ile Gln Lys Ile Gln Trp Ser
                 580                 585                 590

Lys Gly Ala Glu Arg Lys Cys Tyr Arg Pro Leu Arg Pro Cys His Cys
                 595                 600                 605

His Pro Val Leu Ser Glu Arg Glu Ala Val Ile Pro Tyr Ser His Arg
         610                 615                 620

Val Phe Asn Thr Ala Asn Pro Leu Lys Gln Gly Glu Cys Gly Leu Arg
     625                 630                 635                 640

Ala Ala Ile Ser Asp Met Gly Arg Arg Ile Phe Gln Gln Glu Gln Gln
                     645                 650                 655
```

-continued

```
His  His  His  Arg  Ala  Tyr  Pro  Ala  Phe  Ala  Arg  Lys  Asn  Glu  Arg  His
          660                 665                      670

His  Ser  Glu  Ile  Tyr  Lys  Asn  Gly  Met  Gly  Gly  Trp  Leu  Asn  Lys  Ile
          675                 680                      685

Lys  Lys  Thr  Thr  Ile  Pro  Asn  Glu  Asn  Phe  Thr  Cys  Ile  Ser  Leu
     690                 695                 700

Gln  Leu  Leu  Trp  Gln  Leu  Tyr  Ser  Cys  Cys  Ile  Phe  Val  Gln  Ser  Glu
705            710                 715                                720

Gly  Asn  Leu  Gly  Ile  Gly  Ser  Val  Phe  Trp  Lys  Thr  Asn  Met  Thr  Ile
               725                 730                           735

Thr  Trp  Thr  Arg  Asn  Tyr  Ile  Asn  Ile  Pro  Tyr  Gly  Thr  Ile  Ile  Ser
               740                 745                           750

Leu  Phe  Met  Trp  Arg  Leu  Ser  Leu  Val  Phe  Leu  Phe  Tyr  Val  Ala  Ser
          755                 760                      765

Cys  Phe  Gln  Asn  Ser  Gln  Asn  Thr  Leu  Thr  Arg  Ile  Pro  Ala  Leu  Met
     770                 775                      780

Tyr  Leu  Phe  Arg  Thr  Lys  Ile  Asn  Lys  Leu  Ser  Phe  Leu  Arg  Lys  Trp
785                      790                      795                     800

Met  Leu  Trp  Asn  Lys  Ser  Ser  Thr  His  Asn  Gly  Leu  Trp  Lys  Ser  Glu
               805                      810                     815

Ser  Arg  Met  Gln  Ser  Trp  Pro  Asn  Lys  Glu  Lys  Met  Thr  Leu  Leu  Cys
               820                      825                     830

Thr  Trp  Arg  Thr  Ile  Leu  Lys  Arg  Pro  Leu  His  Pro  Leu  Ser  Val  Ile
               835                      840                     845

Ala  Cys  Leu  Thr  Arg  Leu  Gln  Thr  Cys  Arg  Ile  Lys  Arg  Gln  Ser  Met
     850                 855                      860

Cys  Ile  Ser  Arg  Trp  Thr  Lys  Arg  Ile  Asp  Ser  Asn  Ser  Ser  Thr  Ser
865                      870                      875                     880

Phe  Leu  Arg  Leu  His  Gly  Ile  Thr  Tyr  Lys  Arg  Arg  Gln  Lys  Arg  Thr
               885                      890                     895

Thr  Tyr  Thr  Ile  Cys  Trp  Cys  Arg  Pro  Met  Asn  Phe  Ile  Leu  Ser  Phe
               900                      905                     910

Pro  His  Met  Glu  Asn  Arg  Arg  Leu  Phe  Thr  Pro  Pro  Arg  Ile  Pro  Cys
          915                      920                      925

Pro  Ala  Thr  Leu  Ile  Asn  Ser  Arg  Glu  Ser  Leu  Thr  Thr  Phe  Lys  Thr
     930                      935                      940

Pro  Leu  His  Thr  Val  Arg  Ile  Thr  Ala  Ser  Leu  Thr  Leu  Pro  Arg  Ala
945                      950                      955                     960

Ser  Pro  Gly  Met  Trp  Cys  Gln  Ser  Asn  Ser  Arg  Thr  Leu  Glu  Ala  Ser
               965                      970                     975

Gln  Lys  Ile  Ser  Leu  Pro  Tyr  Leu  Lys  Ser  Ser  Ile  Gly  Trp  Thr  Ile
               980                      985                     990

Leu  Val  Leu  Pro  Ile  Arg  Val  Ala  Arg  Asp  Leu  Asp  Trp  Arg  Leu  Gln
          995                      1000                     1005

Lys  Lys  Leu  Leu  Phe  Ser  Met  Glu  Gly  Arg  Phe  Thr  Arg  Lys  Ala  Met
     1010                     1015                     1020

Ile  Thr  Ile  Arg  Arg  Leu  Gly  Ser  Phe  Gln  Arg  Cys  Gln  Thr  Trp  Leu
1025                     1030                     1035                    1040

Ile  Lys  Gly  Gly  Pro  Lys  Arg  Cys  Ile  Phe  Phe  Arg  Lys  Ile  Ser  Arg
               1045                     1050                    1055

Leu  Ser  Leu  Leu  Phe  Leu  Arg  Lys  Leu  Thr  Ile  Tyr  Glu  Thr  Ala  Arg
               1060                     1065                    1070

Ser  Tyr  Thr  Val  Asp  Leu  Ile  Pro  Glu  Arg  Ala  Val  Phe  Val  Leu  Gln
               1075                     1080                    1085
```

-continued

```
Arg  Lys  Ile  Gln  Asp  Tyr  His  Trp  His  Pro  Arg  Phe  Ile  Trp  Cys  Leu
     1090                1095                1100

Ser  Gln  Lys  Gly  Leu  Val  Leu  Ile  Met  Asn  Asn  Ile  Gly  Ile  Thr  Val
1105                1110                1115                          1120

Tyr  Gly  Cys  Glu  Gln  Asp  Glu  Ala  Asp  Ala  Phe  His  Ala  Leu  Ser  Pro
               1125                1130                     1135

Arg  Phe  Gly  Val  Met  Ala  Thr  Ile  Ile  Asn  Ala  Asn  Val  Ser  Glu  Ser
               1140                1145                     1150

Asn  Ala  Lys  Ser  Ala  Pro  Phe  Asn  Gln  Cys  Ile  Ser  Val  Gly  His  Lys
               1155                1160                     1165

Ser  Glu  Ile  Ser  Ala  Ser  Ile  Leu  Leu  Ala  Leu  Lys  Arg  Ala  Gly  Val
     1170                1175                1180

Lys  Tyr  Ile  Ser  Thr  Arg  Ser  Ile  Gly  Cys  Asn  His  Ile  Asp  Thr  Thr
1185                1190                1195                          1200

Ala  Ala  Lys  Arg  Met  Gly  Ile  Thr  Val  Asp  Asn  Val  Ala  Tyr  Ser  Pro
               1205                1210                     1215

Asp  Ser  Val  Ala  Asp  Tyr  Thr  Met  Met  Leu  Ile  Leu  Met  Ala  Val  Arg
               1220                1225                     1230

Asn  Val  Lys  Ser  Ile  Val  Arg  Ser  Val  Glu  Lys  His  Asp  Phe  Arg  Leu
               1235                1240                     1245

Asp  Ser  Asp  Arg  Gly  Lys  Val  Leu  Ser  Asp  Met  Thr  Val  Gly  Val  Val
     1250                1255                1260

Gly  Thr  Gly  Gln  Ile  Gly  Lys  Ala  Val  Ile  Glu  Arg  Leu  Arg  Gly  Phe
1265                1270                1275                          1280

Gly  Cys  Lys  Val  Leu  Ala  Tyr  Ser  Arg  Ser  Arg  Ser  Ile  Glu  Val  Asn
               1285                1290                     1295

Tyr  Val  Pro  Phe  Asp  Glu  Leu  Leu  Gln  Asn  Ser  Asp  Ile  Val  Thr  Leu
               1300                1305                     1310

His  Val  Pro  Leu  Asn  Thr  Asp  Thr  His  Tyr  Ile  Ile  Ser  His  Glu  Gln
               1315                1320                     1325

Ile  Gln  Arg  Met  Lys  Gln  Gly  Ala  Phe  Leu  Ile  Asn  Thr  Gly  Arg  Gly
     1330                1335                1340

Pro  Leu  Val  Asp  Thr  Tyr  Glu  Leu  Val  Lys  Ala  Leu  Glu  Asn  Gly  Lys
1345                1350                1355                          1360

Leu  Gly  Gly  Ala  Ala  Leu  Asp  Val  Leu  Glu  Gly  Glu  Glu  Glu  Phe  Phe
               1365                1370                     1375

Tyr  Ser  Asp  Cys  Thr  Gln  Lys  Pro  Ile  Asp  Asn  Gln  Phe  Leu  Leu  Lys
               1380                1385                     1390

Leu  Gln  Arg  Met  Pro  Asn  Val  Ile  Ile  Thr  Pro  His  Thr  Ala  Tyr  Tyr
               1395                1400                     1405

Thr  Glu  Gln  Ala  Leu  Arg  Asp  Thr  Val  Glu  Lys  Thr  Ile  Lys  Asn  Cys
               1410                1415                     1420

Leu  Asp  Phe  Glu  Arg  Arg  Gln  Glu  His  Glu  Asn  Lys  Ser  Cys  Asn  Thr
1425                1430                1435                          1440

Val  Trp  Gly  Leu  Leu  Arg  Gly  Ala  Arg  Ile  Gly  Lys  Ile  Cys  Asn  Arg
               1445                1450                     1455

Asp  Ser  Arg  His  Arg  Lys  Ile  Arg  Ala  Val  Ile  His  Trp  Asn  Tyr  Glu
               1460                1465                     1470

Ile  Trp  Cys  Met  Glu  Asn  Val  Arg  Lys  Thr  Leu  Arg  Gly  Met  Gly  Lys
               1475                1480                     1485

Arg  Gln  Leu  Leu  Phe  Ser  Cys  Thr  Leu  Ala  Gly  Lys  Asn  Ala  Arg  Ile
               1490                1495                     1500

Thr  Cys  Lys  Glu  Pro  Ile  Asn  Gln  Pro  Cys  Cys  Ser  Ile  Phe  Ser  Phe
```

```
      1505                1510                1515                1520
Ala  Trp  Gln  Val  Arg  Arg  Trp  Ile  His  Thr  Arg  Ser  Val  Ile  Val  Arg
                    1525                1530                1535
Tyr  Pro  Phe  Cys  Arg  Leu  Arg  Tyr  Ser  Lys  Leu  Ser  Asn  Leu  Tyr  Gly
                    1540                1545                1550
Gln  Ile  Val  Asp  Ile  His  Arg  Cys  Glu  Lys  Cys  Trp  Asp  Ser  Tyr  Ser
                    1555                1560                1565
Arg  Leu  Leu  Gly  Tyr  Arg  Ala  Gly  Gly  Ser  Tyr  Val  Tyr  Leu  Ser  Cys
                    1570                1575                1580
Phe  Cys  Ala  Gly  Ala  Phe  Arg  Leu  Ile  Leu  Arg  Cys  Glu  Lys  Ser  Gln
1585                1590                1595                     1600
Arg  Gly  Arg  Ile  Gly  Leu  Arg  Asn  Ile  Gly  Lys  Thr  Ile  Gln  Gln  Asn
                    1605                1610                1615
Leu  Asn  Ala  Gly  Cys  Phe  Gly  Leu  Gly  Arg  Leu  Cys  Gly  Ile  Gly  Lys
                    1620                1625                1630
Gln  Cys  Arg  Val  Ser  Cys  Trp  Arg  Gly  Gly  Pro  Asn  Gln  Ala  Ala  Val
                    1635                1640                1645
Arg  Asn  Leu  Ser  Tyr  Ser  Ser  Gly  Ser  Arg  Ala  Gly  Lys  Arg  Leu  Lys
                    1650                1655                1660
Arg  Ser  Tyr  Asn  Arg  Ser  Arg  Arg  Pro  Phe  Ser  Arg  Gly  Ala  Arg  Thr
1665                1670                1675                     1680
Asp  Thr  Gly  Asn  Gly  Lys  Lys  Asn  Ile  Ser  Ala  Arg  Leu  Arg  Ser  Ser
                    1685                1690                1695
Pro  Cys  Gly  Tyr  Val  Phe  Thr  Arg  Arg  Pro  His  Cys  Thr  Glu  Arg  Ser
                    1700                1705                1710
Gln  Tyr  Ser  Ala  Arg  Phe  His  Val  Ile  Gln  Ser  Leu  Ser  Pro  Tyr  Asp
                    1715                1720                1725
Gly  Arg  Cys  Arg  Tyr  Cys  Thr  Ser  Arg  Thr  Asp  Pro  Leu  Asp  Arg  Ile
                    1730                1735                1740
Ser  Val  Lys  Gly  Val  Ile  Ser  Met  Glu  Ile  Gly  Phe  Thr  Phe  Leu  Asp
1745                1750                1755                     1760
Glu  Ile  Val  His  Gly  Val  Arg  Trp  Asp  Ala  Lys  Tyr  Ala  Thr  Trp  Asp
                    1765                1770                1775
Asn  Phe  Thr  Gly  Lys  Pro  Val  Asp  Gly  Tyr  Glu  Val  Asn  Arg  Ile  Val
                    1780                1785                1790
Gly  Thr  Tyr  Glu  Leu  Ala  Glu  Ser  Leu  Leu  Lys  Ala  Lys  Glu  Leu  Ala
                    1795                1800                1805
Ala  Thr  Gln  Gly  Tyr  Gly  Leu  Leu  Leu  Trp  Asp  Gly  Tyr  Arg  Pro  Lys
                    1810                1815                1820
Arg  Ala  Val  Asn  Cys  Phe  Met  Gln  Trp  Ala  Ala  Gln  Pro  Glu  Asn  Asn
1825                1830                1835                     1840
Leu  Thr  Lys  Glu  Ser  Tyr  Tyr  Pro  Asn  Ile  Asp  Arg  Thr  Glu  Met  Ile
                    1845                1850                1855
Ser  Lys  Gly  Tyr  Val  Ala  Ser  Lys  Ser  Ser  His  Ser  Arg  Gly  Ser  Ala
                    1860                1865                1870
Ile  Asp  Leu  Thr  Leu  Tyr  Arg  Leu  Asp  Thr  Gly  Glu  Leu  Val  Pro  Met
                    1875                1880                1885
Gly  Ser  Arg  Phe  Asp  Phe  Met  Asp  Glu  Arg  Ser  His  His  Ala  Ala  Asn
                    1890                1895                1900
Gly  Ile  Ser  Cys  Asn  Glu  Ala  Gln  Asn  Arg  Arg  Arg  Leu  Arg  Ser  Ile
1905                1910                1915                     1920
Met  Glu  Asn  Ser  Gly  Phe  Glu  Ala  Tyr  Ser  Leu  Glu  Trp  Trp  His  Tyr
                    1925                1930                1935
```

```
Val  Leu  Arg  Asp  Glu  Pro  Tyr  Pro  Asn  Ser  Tyr  Phe  Asp  Phe  Pro  Val
          1940                1945                          1950

Lys  Thr  Phe  Asn  Arg  Cys  Thr  Asp  Lys  Leu  Tyr  Lys  Leu  Thr  Leu  Ser
          1955                1960                          1965

Ala  Gly  Asn  Pro  Thr  Tyr  Val  Thr  Gly  Ser  Gly  Ile  Tyr  Ile  Ile  Val
          1970                1975                          1980

Leu  Lys  Met  Gly  Arg  Ala  Ile  Leu  Arg  Ser  Leu  Ser  Ala  Cys  Ala  Ala
1985                     1990                     1995                     2000

Ala  Arg  Pro  Asp  Asn  Lys  Thr  Asp  Arg  Ile  Glu  Gly  Trp  Tyr  Phe  Thr
               2005                2010                          2015

Pro  Pro  Ile  Val  Asn  Arg  Gln  Phe  Ser  Leu  Val  Lys  Phe  Ser  Met  Gly
               2020                2025                          2030

Ile  Thr  Tyr  Glu  Asn  Ser  Ser  Thr  Leu  Val  Ile  Ile  Val  Asn  Pro  Val
               2035                2040                          2045

Gly  Arg  Asn  Asn  Leu  Phe  Thr  Gly  Gln  Asn  Gly  Thr  Ile  Ser  Asn  Glu
               2050                2055                          2060

Ile  Val  Pro  Phe  Lys  Gly  Lys  Ile  Leu  Glu  Ile  Phe  His  Thr  Ser  Asn
2065                     2070                     2075                     2080

Tyr  Ile  Val  Lys  Glu  Glu  Thr  Asn  Glu  Glu  Val  Val  Phe  Phe  Ile
               2085                2090                          2095

Val  Ile  Val  Ile  Leu  Asn  Ile  Leu  Arg  Leu  Leu  Arg  Ser  Thr  Val  Phe
               2100                2105                          2110

Ser  Gly  Lys  Ser  Arg  Ile  Ser  Lys  Leu  Ser  Lys  Ser  Gln  Arg  Thr  Phe
               2115                2120                          2125

Arg  Lys  Trp  Asp  Phe  Lys  Tyr  Pro  Arg  Glu  Asn  Asn  Tyr  Arg  Arg  Thr
          2130                2135                          2140

Gly  Leu  Ser  Arg  Lys  Ser  Ala  Ile  Asn  Gln  Ile  Ser  Cys  Ser  Pro  Arg
2145                     2150                     2155                     2160

Ser  Val  Lys  Ser  Asp  Ile  Val  Asn  Leu  Ser  Lys  His  Asp  Glu  Leu  Ile
               2165                2170                          2175

Asn  Gly  Tyr  Gly  Leu  Leu  Asp  Ser  Asn  Ile  Tyr  Met  Ser  Lys  Glu  Ile
               2180                2185                          2190

Ala  Gln  Lys  Phe  Ser  Glu  Met  Val  Asn  Asp  Ala  Val  Lys  Gly  Gly  Val
          2195                2200                          2205

Ser  His  Phe  Ile  Ile  Asn  Ser  Gly  Tyr  Arg  Asp  Phe  Asp  Glu  Gln  Ser
          2210                2215                          2220

Val  Leu  Tyr  Gln  Glu  Met  Gly  Ala  Glu  Tyr  Ala  Leu  Pro  Ala  Gly  Tyr
2225                     2230                     2235                     2240

Ser  Glu  His  Asn  Ser  Gly  Leu  Ser  Leu  Asp  Val  Gly  Ser  Ser  Leu  Thr
               2245                2250                          2255

Lys  Met  Glu  Arg  Ala  Pro  Glu  Gly  Lys  Trp  Ile  Glu  Glu  Asn  Ala  Trp
               2260                2265                          2270

Lys  Tyr  Gly  Phe  Ile  Leu  Arg  Tyr  Pro  Glu  Asp  Lys  Thr  Glu  Leu  Thr
               2275                2280                          2285

Gly  Ile  Gln
          2290
```

(2) INFORMATION FOR SEQ ID NO:30:

(i) SEQUENCE CHARACTERISTICS:
        (A) LENGTH: 3190 base pairs
        (B) TYPE: nucleic acid
        (C) STRANDEDNESS: double
        (D) TOPOLOGY: linear (ii) MOLECULE TYPE: DNA (genomic)

( x i ) SEQUENCE DESCRIPTION: SEQ ID NO:30:

```
CAAAATATCA CCTCATTTTT GAGACAAGTC TTATGAGACG CTCTTAACTA TGATTTTATC      60
AGTCTACTAC ATTTGTATCA ATAGAGTACA CTCTATTGAT ATATAATTGA ACTAATAAAT     120
TGAAAATACA GAAATGGAAT GATACTGAAA TGAAAATTGC GAGAGGTAGA GAATTGCTTA     180
CACCGGAACA GAGACAGGCT TTTATGCAAA TCCCTGAAGA TGAATGGATA CTGGGGACCT     240
ACTTCACTTT TTCCAAACGG GATTTAGAAA TAGTTAATAA GCGAAGGAGG GAAGAAAACC     300
GTTTAGGATT TGCTGTTCAA TTAGCTGTTC TTCGGTATCC CGGTTGGCCA TACACTCATA     360
TCAAAAGCAT CCCAGATTCG GTCATACAAT ATATATCGAA ACAGATTGGT GTTAGTCCAT     420
CCTCGCTTGA TCATTATCCT CAAAGGGAAA ATACACTTTG GGATCATTTG AAAGAAATTC     480
GAAGTGAATA CGACTTTGTA ACTTTTACCC TGAGTGAATA TCGAATGACA TTTAAGTACC     540
TTCATCAATT AGCTTTGGAA AATGGTGATG CCATTCATCT ACTGCATGAA TGCATAGATT     600
TTCTAAGAAA AAACAAAATT ATACTGCCTG CTATCACTAC ACTTGAAAGA ATGGTGTGGG     660
AAGCAAGGGC AATGGCTGAA AAGAAGCTAT TTAATACGGT TAGTAAATCT CTAACAAATG     720
AGCAAAAAGA AAAGCTTGAA GGGATTATTA CCTCGCAGCA TCCATCCGAA TCCAATAAAA     780
CGATATTGGG TTGGTTAAAA GAGCCACCGG GTCATCCTTC ACCCGAAACT TTTCTAAAAA     840
TAATAGAACG ACTCGAATAC ATACGAGGAA TGGATTTAGA AACAGTGCAA ATTAGTCATT     900
TGCACCGTAA CCGCCTGTTG CAGCTGTCTC GCTTAGGCTC AAGATACGAG CCGTATGCAT     960
TCCGTGACTT TCAAGAAAAT AAACGTTATT CGATATTAAC CATCTATTTA TTACAACTTA    1020
CTCAGGAGCT AACGGATAAA GCGTTTGAAA TTCATGATAG GCAAATACTT AGTTTGTTAT    1080
CAAAAGGTCG TAAGGCTCAA GAGGAAATCC AGAAACAAAA CGGTAAAAAG CTAAATGAGA    1140
AAGTTATACA CTTTACGAAC ATCGGACAAG CATTAATTAA AGCAAGAGAG GAAAAATTAG    1200
ACGTTTTTAA GGTTTTAGAA TCGGTTATTG AATGGAATAC CTTTGTCTCT TCAGTAGAAG    1260
AGGCTCAGGA ACTTGCACGT CCTGCCGACT ATGATTATTT AGACTTACTG CAAAAACGGT    1320
TTTATTCACT AAGAAAATAT ACGCCAACGC TATTAAGAGT ATTGGAATTT CATTCTACAA    1380
AGGCAAATGA GCCACTTTTA CAAGCTGTTG AGATTATCCG AGGAATGAAC GAATCTGGAA    1440
AGCGAAAAGT GCCTGATGAC TCACCTGTGG ATTTTATTTC AAAACGATGG AAAAGACATT    1500
TATACGAGGA TGATGGTACA ACAATTAATC GTCATTACTA TGAAATGGCT GTTTTAACAG    1560
AACTTCGGGA GCATGTTCGG GCAGGAGATG TTTCCATTGT TGGCAGCAGA CAATATAGGG    1620
ATTTTGAGGA ATATTTGTTT TCGGAAGATA CATGGAATCA ATCGAAGGGG AATACGAGAT    1680
TATCAGTTAG TTTATCATTC GAAGATTATA TAACGGAGAG AACCAGCAGC TTTAATGAAA    1740
GGTTAAAGTG GTTAGCTGCC AATTCCAATA AGTTAGATGG GGTTTCTCTT GAAAAAGGAA    1800
AGCTATCACT TGCACGCTTA GAAAAAGATG TTCCAGAAGA AGCAAAAAAA TTTAGTGCAA    1860
GCCTTTATCA GATGCTACCA AGAATAAAAT TAACTGATTT ACTCATGGAT GTGGCCCATA    1920
TAACAGGATT TCATGAGCAA TTCACTCATG CTTCCAATAA TCGAAACCA GATAAGGAAG    1980
AAACAATCAT TATCATGGCT GCCCTTTTAG GAATGGGAAT GAATATTGGC TTGAGCAAGA    2040
TGGCCGAAGC CACACCCGGA CTTACATATA AGCAACTAGC CAATGTATCT CAATGGCGCA    2100
TGTATGAAGA TGCCATGAAT AAAGCCCAAG CCATATTAGT AAACTTTCAT CATAAATTAC    2160
AATTGCCTTT CTATTGGGGC GACGGTACAA CATCTTCGTC AGATGGTATG AGAATGCAGC    2220
TAGGTGTTTC ATCACTACAT GCAGATGCAA ATCCACATTA TGGAACTGGA AAAGGAGCCA    2280
CCATCTACCG ATTTACAAGT GATCAATTCT CTTCTTACTA CACAAAGATT ATTCATACTA    2340
```

| | | | | | | |
|---|---|---|---|---|---|---|
| ATTCAAGAGA | TGCGATTCAT | GTTTTGGATG | GTTTGTTACA | TCATGAGACG | GATCTAAACA | 2400 |
| TAGAGGAACA | TTATACAGAC | ACTGCCGGTT | ACACTGACCA | AATATTCGGA | CTGACTCATT | 2460 |
| TATTAGGATT | TAAATTTGCC | CCAAGAATAA | GGGATTTATC | GGACTCAAAA | TTATTTACGA | 2520 |
| TAGATAAAGC | AAGTGAGTAT | CCAAAACTAG | AAGCCATTTT | ACGTGGACAA | ATAAATACAA | 2580 |
| AGGTCATTAA | AGAAAATTAT | GAGGATGTTT | TGCGATTAGC | TCATTCTATA | AGGGAGGGAA | 2640 |
| CAGTTTCAGC | ATCCCTTATT | ATGGGGAAGC | TAGGTTCCTA | TTCAAGACAA | AACAGCTTAG | 2700 |
| CTACAGCCTT | ACGTGAGATG | GGCCGAATAG | AAAAAACGAT | CTTTATTTTG | AATTATATAT | 2760 |
| CGGATGAATC | ATTAAGAAGA | AAAATACAAA | GAGGATTGAA | TAAAGGAGAA | GCCATGAATG | 2820 |
| GATTGGCAAG | AGCTATTTTC | TTCGGAAAAC | AAGGTGAGCT | TAGAGAACGC | ACCATACAGC | 2880 |
| ATCAATTGCA | AAGAGCCAGT | GCTTTAAACA | TAATTATCAA | TGCTATAAGT | ATTTGGAATA | 2940 |
| CTCTCCACCT | AACAACAGCA | GTTGAATATA | AAAACGGAC | AGGTAGCTTT | AATGAAGATT | 3000 |
| TGTTACACCA | TATGTCGCCC | TTAGGTTGGG | AACATATTAA | TTTACTAGGA | GAATACCATT | 3060 |
| TTAACTCAGA | GAAAGTAGTC | TCATTAAATT | CTTTAAGACC | ACTAAAACTT | TCTTAACGTT | 3120 |
| GTTAAAAACG | AGGGATTCGT | CAGGAAAATA | GGCTTAGCGT | TGTAAATCCG | CATTTTCCTG | 3180 |
| ACGCTACCCC | | | | | | 3190 |

(2) INFORMATION FOR SEQ ID NO:31:

(i) SEQUENCE CHARACTERISTICS:
        (A) LENGTH: 1347 base pairs
        (B) TYPE: nucleic acid
        (C) STRANDEDNESS: unknown
        (D) TOPOLOGY: linear (ii) MOLECULE TYPE: DNA (genomic)

(xi) SEQUENCE DESCRIPTION: SEQ ID NO:31:

| | | | | | | |
|---|---|---|---|---|---|---|
| GAGCTCTTCC | TTCAACGCAC | TTCTGTACCA | AGAGTTGTTG | TCCATTTGAT | CACTAACAAT | 60 |
| AGCTTCCCCT | GCTTTCTTCA | AGCCCTTTGT | CATAAATCG | TTAGATTTTC | ATCATAAAAA | 120 |
| TACGAGAAAG | ACAACAGGAA | GACCGCAAAT | TTTCTTTTCT | TTTCCTAGGT | ACACTGAATG | 180 |
| TAACCTTAAA | AGAAAAAAGG | AAAGGAAGAA | AATGATGAAA | AAATTGCCG | TTTTATTTGG | 240 |
| AGGGAATTCT | CCAGAATACT | CAGTGTCACT | AACCTCAGCA | GCAAGTGTGA | TCCAAGCTAT | 300 |
| TGACCCGCTG | AAATATGAAG | TAATGACCAT | TGGCATCGCA | CCAACAATGG | ATTGGTATTG | 360 |
| GTATCAAGGA | AACCTCGCGA | ATGTTCGCAA | TGATACTTGG | CTAGAAGATC | ACAAAAACTG | 420 |
| TCACCAGCTG | ACTTTTTCTA | GCCAAGGATT | TATATTAGGA | GAAAACGAA | TCGTCCCTGA | 480 |
| TGTCCTCTTT | CCAGTCTTGC | ATGGGAAGTA | TGGCGAGGAT | GGCTGTATCC | AAGGACTGCT | 540 |
| TGAACTAATG | AACCTGCCTT | ATGTTGGTTG | CCATGTCGCT | GCCTCCGCAT | TATGTATGAA | 600 |
| CAAATGGCTC | TTGCATCAAC | TTGCTGATAC | CATGGGAATC | GCTAGTGCTC | CCACTTTGCT | 660 |
| TTTATCCCGC | TATGAAAACG | ATCCTGCCAC | AATCGATCGT | TTTATTCAAG | ACCATGGATT | 720 |
| CCCGATCTTT | ATCAAGCCGA | ATGAAGCCGG | TTCTTCAAAA | GGGATCACAA | AAGTAACTGA | 780 |
| CAAAACAGCG | CTCCAATCTG | CATTAACGAC | TGCTTTTGCT | TACGGTTCTA | CTGTGTTGAT | 840 |
| CCAAAAGGCG | ATAGCGGGTA | TTGAAATTGG | CTGCGGCATC | TTAGGAAATG | AGCAATTGAC | 900 |
| GATTGGTGCT | TGTGATGCGA | TTTCTCTTGT | CGACGGTTTT | TTTGATTTTG | AAGAGAAATA | 960 |
| CCAATTAATC | AGCGCCACGA | TCACTGTCCC | AGCACCATTG | CCTCTCGCGC | TTGAATCACA | 1020 |
| GATCAAGGAG | CAGGCACAGC | TGCTTTATCG | AAACTTGGGA | TTGACGGGTC | TGGCTCGAAT | 1080 |
| CGATTTTTTC | GTCACCAATC | AAGGAGCGAT | TTATTTAAAC | GAAATCAACA | CCATGCCGGG | 1140 |

```
ATTTACTGGG  CACTCCCGCT  ACCCAGCTAT  GATGGCGGAA  GTCGGGTTAT  CCTACGAAAT    1200

ATTAGTAGAG  CAATTGATTG  CACTGGCAGA  GGAGGACAAA  CGATGAACAC  ATTACAATTG    1260

ATCAATAAAA  ACCATCCATT  GAAAAAAAAT  CAAGAGCCCC  CGCACTTAGT  GCTAGCTCCT    1320

TTTAGCGATC  ACGATGTTTA  CCTGCAG                                           1347
```

(2) INFORMATION FOR SEQ ID NO:32:

(i) SEQUENCE CHARACTERISTICS:
        (A) LENGTH: 364 amino acids
        (B) TYPE: amino acid
        (D) TOPOLOGY: linear (ii) MOLECULE TYPE: protein (xi) SEQUENCE DESCRIPTION: SEQ ID NO:32:

```
Met  Glu  Lys  Leu  Arg  Val  Gly  Ile  Val  Gly  Gly  Gly  Lys  Ser  Ala  Glu
1                  5                      10                      15

His  Glu  Val  Ser  Leu  Gln  Ser  Ala  Lys  Asn  Ile  Val  Asp  Ala  Ile  Asp
                20                      25                      30

Lys  Ser  Arg  Phe  Asp  Val  Val  Leu  Leu  Gly  Ile  Asp  Lys  Gln  Gly  Gln
            35                      40                      45

Trp  His  Val  Ser  Asp  Ala  Ser  Asn  Tyr  Leu  Leu  Asn  Ala  Asp  Asp  Pro
        50                      55                      60

Ala  His  Ile  Ala  Leu  Arg  Pro  Ser  Ala  Thr  Ser  Leu  Ala  Gln  Val  Pro
65                      70                      75                      80

Gly  Lys  His  Glu  His  Gln  Leu  Ile  Asp  Ala  Gln  Asn  Gly  Gln  Pro  Leu
                    85                      90                      95

Pro  Thr  Val  Asp  Val  Ile  Phe  Pro  Ile  Val  His  Gly  Thr  Leu  Gly  Glu
               100                     105                     110

Asp  Gly  Ser  Leu  Gln  Gly  Met  Leu  Arg  Val  Ala  Asn  Leu  Pro  Phe  Val
           115                     120                     125

Gly  Ser  Asp  Val  Leu  Ala  Ser  Ala  Ala  Cys  Met  Asp  Lys  Asp  Val  Thr
       130                     135                     140

Lys  Arg  Leu  Leu  Arg  Asp  Ala  Gly  Leu  Asn  Ile  Ala  Pro  Phe  Ile  Thr
145                     150                     155                     160

Leu  Thr  Arg  Ala  Asn  Arg  His  Asn  Ile  Ser  Phe  Ala  Glu  Val  Glu  Ser
                    165                     170                     175

Lys  Leu  Gly  Leu  Pro  Leu  Phe  Val  Lys  Pro  Ala  Asn  Gln  Gly  Ser  Ser
               180                     185                     190

Val  Gly  Val  Ser  Lys  Val  Thr  Ser  Glu  Glu  Gln  Tyr  Ala  Thr  Ala  Val
           195                     200                     205

Ala  Leu  Ala  Phe  Glu  Phe  Asp  His  Lys  Val  Ile  Val  Glu  Gln  Gly  Ile
       210                     215                     220

Lys  Gly  Arg  Glu  Ile  Glu  Cys  Ala  Val  Leu  Gly  Asn  Asp  Asn  Pro  Gln
225                     230                     235                     240

Ala  Ser  Thr  Cys  Gly  Glu  Ile  Val  Leu  Thr  Ser  Asp  Phe  Tyr  Ala  Tyr
                    245                     250                     255

Asp  Thr  Lys  Tyr  Ile  Asp  Glu  Asp  Gly  Ala  Lys  Val  Val  Pro  Ala
               260                     265                     270

Ala  Ile  Ala  Pro  Glu  Ile  Asn  Asp  Lys  Ile  Arg  Ala  Ile  Ala  Val  Gln
           275                     280                     285

Ala  Tyr  Gln  Thr  Leu  Gly  Cys  Ala  Gly  Met  Ala  Arg  Val  Asp  Val  Phe
       290                     295                     300

Leu  Thr  Pro  Glu  Asn  Glu  Val  Val  Ile  Asn  Glu  Ile  Asn  Thr  Leu  Pro
305                     310                     315                     320
```

-continued

```
        Gly Phe Thr Asn Ile Ser Met Tyr Pro Lys Leu Trp Gln Ala Ser Gly
                        325                 330                 335

Leu Gly Tyr Thr Asp Leu Ile Thr Arg Leu Ile Glu Leu Ala Leu Glu
                        340                 345                 350

Arg His Ala Ala Asn Asn Ala Leu Lys Thr Thr Met
                        355                 360
```

( 2 ) INFORMATION FOR SEQ ID NO:33:

( i ) SEQUENCE CHARACTERISTICS:
        ( A ) LENGTH: 306 amino acids
        ( B ) TYPE: amino acid
        ( D ) TOPOLOGY: linear ( i i ) MOLECULE TYPE: protein ( x i ) SEQUENCE DESCRIPTION: SEQ ID NO:33:

```
        Met Thr Asp Lys Ile Ala Val Leu Leu Gly Gly Thr Ser Ala Glu Arg
        1               5                   10                  15

Glu Val Ser Leu Asn Ser Gly Ala Ala Val Leu Ala Gly Leu Arg Glu
                        20                  25                  30

Gly Gly Ile Asp Ala Tyr Pro Val Asp Pro Lys Glu Val Asp Val Thr
                        35                  40                  45

Gln Leu Lys Ser Met Gly Phe Gln Lys Val Phe Ile Ala Leu His Gly
                        50                  55                  60

Arg Gly Gly Glu Asp Gly Thr Leu Gln Gly Met Leu Glu Leu Met Gly
        65                  70                  75                  80

Leu Pro Tyr Thr Gly Ser Gly Val Met Ala Ser Ala Leu Ser Met Asp
                        85                  90                  95

Lys Leu Arg Ser Lys Leu Leu Trp Gln Gly Ala Gly Leu Pro Val Ala
                        100                 105                 110

Pro Trp Val Ala Leu Thr Arg Ala Glu Phe Glu Lys Gly Leu Ser Asp
                        115                 120                 125

Lys Gln Leu Ala Glu Ile Ser Ala Leu Gly Leu Pro Val Ile Val Lys
                        130                 135                 140

Pro Ser Arg Glu Gly Ser Ser Val Gly Met Ser Lys Val Val Ala Glu
        145                 150                 155                 160

Asn Ala Leu Gln Asp Ala Leu Arg Leu Ala Phe Gln His Asp Glu Glu
                        165                 170                 175

Val Leu Ile Glu Lys Trp Leu Ser Gly Pro Glu Phe Thr Val Ala Ile
                        180                 185                 190

Leu Gly Glu Glu Ile Leu Pro Ser Ile Arg Ile Gln Pro Ser Gly Thr
                        195                 200                 205

Phe Tyr Asp Tyr Glu Ala Lys Tyr Leu Ser Asp Glu Thr Gln Tyr Phe
                        210                 215                 220

Cys Pro Ala Gly Leu Glu Ala Ser Gln Glu Ala Asn Leu Gln Ala Leu
        225                 230                 235                 240

Val Leu Lys Ala Trp Thr Thr Leu Gly Cys Lys Gly Trp Gly Arg Ile
                        245                 250                 255

Asp Val Met Leu Asp Ser Asp Gly Gln Phe Tyr Leu Leu Glu Ala Asn
                        260                 265                 270

Thr Ser Pro Gly Met Thr Ser His Ser Leu Val Pro Met Ala Ala Arg
                        275                 280                 285

Gln Ala Gly Met Ser Phe Ser Gln Leu Val Val Arg Ile Leu Glu Leu
                        290                 295                 300

Ala Asp
```

3 0 5

( 2 ) INFORMATION FOR SEQ ID NO:34:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:34:

```
Leu  Phe  Pro  Met  Val  Ile
1                   5
```

( 2 ) INFORMATION FOR SEQ ID NO:35:

( i ) SEQUENCE CHARACTERISTICS:
        ( A ) LENGTH: 5 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:35:

```
Ser  Thr  Gln  Asn  Cys
1                   5
```

( 2 ) INFORMATION FOR SEQ ID NO:36:

( i ) SEQUENCE CHARACTERISTICS:
        ( A ) LENGTH: 8 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:36:

```
Gly  Glu  Asp  Gly  Ser  Ile  Gln  Gly
1                   5
```

( 2 ) INFORMATION FOR SEQ ID NO:37:

( i ) SEQUENCE CHARACTERISTICS:
        ( A ) LENGTH: 7 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:37:

```
Asn  Thr  Leu  Pro  Gly  Phe  Thr
1                   5
```

( 2 ) INFORMATION FOR SEQ ID NO:38:

( i ) SEQUENCE CHARACTERISTICS:
        ( A ) LENGTH: 8 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:38:

```
Gly  Glu  Asp  Gly  Thr  Leu  Gln  Gly
1                   5
```

( 2 ) INFORMATION FOR SEQ ID NO:39:

(i) SEQUENCE CHARACTERISTICS:
    (A) LENGTH: 7 amino acids
    (B) TYPE: amino acid
    (D) TOPOLOGY: linear (ii) MOLECULE TYPE: peptide (xi) SEQUENCE DESCRIPTION: SEQ ID NO:39:

```
Asn  Thr  Ser  Pro  Gly  Met  Thr
1                   5
```

(2) INFORMATION FOR SEQ ID NO:40:

(i) SEQUENCE CHARACTERISTICS:
    (A) LENGTH: 259 amino acids
    (B) TYPE: amino acid
    (D) TOPOLOGY: linear (ii) MOLECULE TYPE: protein (v) FRAGMENT TYPE: internal (vi) ORIGINAL SOURCE:
    (A) ORGANISM: E. faecium
    (B) STRAIN: BM4147

(xi) SEQUENCE DESCRIPTION: SEQ ID NO:40:

```
Glu  Met  Asp  Val  Met  Glu  Gln  Lys  Leu  Asn  Thr  Leu  Lys  Arg  Thr  Leu
1                   5                        10                       15

Glu  Lys  Arg  Glu  Gln  Asp  Ala  Lys  Leu  Ala  Glu  Gln  Arg  Lys  Asn  Asp
                20                       25                       30

Val  Val  Met  Tyr  Leu  Ala  His  Asp  Ile  Lys  Thr  Pro  Leu  Thr  Ser  Ile
                35                       40                       45

Ile  Gly  Tyr  Leu  Ser  Leu  Leu  Asp  Glu  Ala  Pro  Asp  Met  Pro  Val  Asp
     50                       55                       60

Gln  Lys  Ala  Lys  Tyr  Val  His  Ile  Thr  Leu  Asp  Lys  Ala  Tyr  Arg  Leu
65                            70                       75                       80

Glu  Gln  Leu  Ile  Asp  Glu  Phe  Phe  Glu  Ile  Thr  Arg  Tyr  Asn  Leu  Gln
                    85                       90                       95

Thr  Ile  Thr  Leu  Thr  Lys  Thr  His  Ile  Asp  Leu  Tyr  Tyr  Met  Leu  Val
               100                      105                      110

Gln  Met  Thr  Asp  Glu  Phe  Tyr  Pro  Gln  Leu  Ser  Ala  His  Gly  Lys  Gln
               115                      120                      125

Ala  Val  Ile  His  Ala  Pro  Glu  Asp  Leu  Thr  Val  Ser  Gly  Asp  Pro  Asp
     130                      135                      140

Lys  Leu  Ala  Arg  Val  Phe  Asn  Asn  Ile  Leu  Lys  Asn  Ala  Ala  Ala  Tyr
145                           150                      155                      160

Ser  Glu  Asp  Asn  Ser  Ile  Ile  Asp  Ile  Thr  Ala  Gly  Leu  Ser  Gly  Asp
                    165                      170                      175

Val  Val  Ser  Ile  Glu  Phe  Lys  Asn  Thr  Gly  Ser  Ile  Pro  Lys  Asp  Lys
               180                      185                      190

Leu  Ala  Ala  Ile  Phe  Glu  Lys  Phe  Tyr  Arg  Leu  Asp  Asn  Ala  Arg  Ser
          195                      200                      205

Ser  Asp  Thr  Gly  Gly  Ala  Gly  Leu  Gly  Leu  Ala  Ile  Ala  Lys  Glu  Ile
     210                      215                      220

Ile  Val  Gln  His  Gly  Gly  Gln  Ile  Tyr  Ala  Glu  Ser  Asn  Asp  Asn  Tyr
225                      230                      235                      240

Thr  Thr  Phe  Arg  Val  Glu  Leu  Pro  Ala  Met  Pro  Asp  Leu  Val  Asp  Lys
               245                      250                      255

Arg  Arg  Ser
```

(2) INFORMATION FOR SEQ ID NO:41:

(i) SEQUENCE CHARACTERISTICS:
        (A) LENGTH: 256 amino acids
        (B) TYPE: amino acid
        (D) TOPOLOGY: linear (ii) MOLECULE TYPE: protein (v) FRAGMENT TYPE: internal (vi) ORIGINAL SOURCE:
        (A) ORGANISM: Escherichia coli (xi) SEQUENCE DESCRIPTION: SEQ ID NO:41:

| | | | | | | | | | | | | | | |
|---|---|---|---|---|---|---|---|---|---|---|---|---|---|---|
| Glu | Ile | Arg | Val | Met | Pro | Tyr | Thr | His | Lys | Gln | Leu | Leu | Met | Val | Ala |
| 1 | | | | 5 | | | | | 10 | | | | | 15 | |
| Arg | Asp | Val | Thr | Gln | Met | His | Gln | Leu | Glu | Gly | Ala | Arg | Arg | Asn | Phe |
| | | | 20 | | | | 25 | | | | | 30 | | | |
| Phe | Ala | Asn | Val | Ser | His | Glu | Leu | Arg | Thr | Pro | Leu | Thr | Val | Leu | Gln |
| | | 35 | | | | | 40 | | | | | 45 | | | |
| Gly | Tyr | Leu | Glu | Met | Met | Asn | Glu | Gln | Pro | Leu | Glu | Gly | Ala | Val | Arg |
| | | 50 | | | | | 55 | | | | | 60 | | | |
| Glu | Lys | Ala | Leu | His | Thr | Met | Arg | Glu | Gln | Thr | Gln | Arg | Met | Glu | Gly |
| 65 | | | | | 70 | | | | 75 | | | | | | 80 |
| Leu | Val | Lys | Gln | Leu | Leu | Thr | Leu | Ser | Lys | Ile | Glu | Ala | Ala | Pro | Thr |
| | | | | 85 | | | | | 90 | | | | | 95 | |
| His | Leu | Leu | Asn | Glu | Lys | Val | Asp | Val | Pro | Met | Met | Leu | Arg | Val | Val |
| | | | 100 | | | | | 105 | | | | | 110 | | |
| Glu | Arg | Glu | Ala | Gln | Thr | Leu | Ser | Gln | Lys | Lys | Gln | Thr | Phe | Thr | Phe |
| | | 115 | | | | | 120 | | | | | 125 | | | |
| Glu | Ile | Asp | Asn | Gly | Leu | Lys | Val | Ser | Gly | Asn | Glu | Asp | Gln | Leu | Arg |
| | 130 | | | | | 135 | | | | | 140 | | | | |
| Ser | Ala | Ile | Ser | Asn | Leu | Val | Tyr | Asn | Ala | Val | Asn | His | Thr | Pro | Glu |
| 145 | | | | | 150 | | | | | 155 | | | | | 160 |
| Gly | Thr | His | Ile | Thr | Val | Arg | Trp | Gln | Arg | Val | Pro | His | Gly | Ala | Glu |
| | | | | 165 | | | | | 170 | | | | | 175 | |
| Phe | Ser | Val | Glu | Asp | Asn | Gly | Pro | Gly | Ile | Ala | Pro | Glu | His | Ile | Pro |
| | | | 180 | | | | | 185 | | | | | 190 | | |
| Arg | Leu | Thr | Glu | Arg | Phe | Tyr | Arg | Val | Asp | Lys | Ala | Arg | Ser | Arg | Gln |
| | | 195 | | | | | 200 | | | | | 205 | | | |
| Thr | Gly | Gly | Ser | Gly | Leu | Gly | Leu | Ala | Ile | Val | Lys | His | Ala | Val | Asn |
| | 210 | | | | | 215 | | | | | 220 | | | | |
| His | His | Glu | Ser | Arg | Leu | Asn | Ile | Glu | Ser | Thr | Val | Gly | Lys | Gly | Thr |
| 225 | | | | | 230 | | | | | 235 | | | | | 240 |
| Arg | Phe | Ser | Phe | Val | Ile | Pro | Glu | Arg | Leu | Ile | Ala | Lys | Asn | Ser | Asp |
| | | | | 245 | | | | | 250 | | | | | 255 | |

(2) INFORMATION FOR SEQ ID NO:42:

(i) SEQUENCE CHARACTERISTICS:
        (A) LENGTH: 241 amino acids
        (B) TYPE: amino acid
        (D) TOPOLOGY: linear (ii) MOLECULE TYPE: protein (v) FRAGMENT TYPE: internal (vi) ORIGINAL SOURCE:
        (A) ORGANISM: Escherichia coli ( x i ) SEQUENCE DESCRIPTION: SEQ ID NO:42:

| Ala<br>1 | Ser | Glu | Val | Arg<br>5 | Ser | Val | Thr | Arg | Ala<br>10 | Phe | Asn | His | Met | Ala<br>15 | Ala |
|---|---|---|---|---|---|---|---|---|---|---|---|---|---|---|---|
| Gly | Val | Lys | Gln<br>20 | Leu | Ala | Asp | Asp | Arg<br>25 | Thr | Leu | Leu | Met | Ala<br>30 | Gly | Val |
| Ser | His | Asp<br>35 | Leu | Arg | Thr | Pro | Leu<br>40 | Thr | Arg | Ile | Arg | Leu<br>45 | Ala | Thr | Glu |
| Met | Met<br>50 | Ser | Glu | Gln | Asp | Gly<br>55 | Tyr | Leu | Ala | Glu | Ser<br>60 | Ile | Asn | Lys | Asp |
| Ile<br>65 | Glu | Glu | Cys | Asn | Ala<br>70 | Ile | Ile | Glu | Gln | Phe<br>75 | Ile | Asp | Tyr | Leu | Arg<br>80 |
| Thr | Gly | Gln | Glu | Met<br>85 | Pro | Met | Glu | Met | Ala<br>90 | Asp | Leu | Asn | Ala | Val<br>95 | Leu |
| Gly | Glu | Val | Ile<br>100 | Ala | Ala | Glu | Ser | Gly<br>105 | Tyr | Glu | Arg | Glu | Ile<br>110 | Glu | Thr |
| Ala | Leu | Tyr<br>115 | Pro | Gly | Ser | Ile | Glu<br>120 | Val | Lys | Met | His | Pro<br>125 | Leu | Ser | Ile |
| Lys | Arg<br>130 | Ala | Val | Ala | Asn | Met<br>135 | Val | Val | Asn | Ala | Ala<br>140 | Arg | Tyr | Gly | Asn |
| Gly<br>145 | Trp | Ile | Lys | Val | Ser<br>150 | Ser | Gly | Thr | Glu | Pro<br>155 | Asn | Arg | Ala | Trp | Phe<br>160 |
| Gln | Val | Glu | Asp | Asp<br>165 | Gly | Pro | Gly | Ile | Ala<br>170 | Pro | Glu | Gln | Arg | Lys<br>175 | His |
| Leu | Phe | Gln | Pro<br>180 | Phe | Val | Arg | Gly | Asp<br>185 | Ser | Ala | Arg | Thr | Ile<br>190 | Ser | Gly |
| Thr | Gly | Leu<br>195 | Gly | Leu | Ala | Ile | Val<br>200 | Gln | Arg | Ile | Val | Asp<br>205 | Asn | His | Asn |
| Gly | Met<br>210 | Leu | Glu | Leu | Gly | Thr<br>215 | Ser | Glu | Arg | Gly | Gly<br>220 | Leu | Ser | Ile | Arg |
| Ala<br>225 | Trp | Leu | Pro | Val | Pro<br>230 | Val | Thr | Arg | Ala | Gln<br>235 | Gly | Thr | Thr | Lys | Glu<br>240 |
| Gly |  |  |  |  |  |  |  |  |  |  |  |  |  |  |  |

( 2 ) INFORMATION FOR SEQ ID NO:43:

( i ) SEQUENCE CHARACTERISTICS:
        ( A ) LENGTH: 231 amino acids
        ( B ) TYPE: amino acid
        ( D ) TOPOLOGY: linear ( i i ) MOLECULE TYPE: protein ( v i ) ORIGINAL SOURCE:
        ( A ) ORGANISM: E. faecium
        ( B ) STRAIN: BM4147

( x i ) SEQUENCE DESCRIPTION: SEQ ID NO:43:

| Met<br>1 | Ser | Asp | Lys | Ile<br>5 | Leu | Ile | Val | Asp | Asp<br>10 | Glu | His | Glu | Ile | Ala<br>15 | Asp |
|---|---|---|---|---|---|---|---|---|---|---|---|---|---|---|---|
| Leu | Val | Glu | Leu<br>20 | Tyr | Leu | Lys | Asn | Glu<br>25 | Asn | Tyr | Thr | Val | Phe<br>30 | Lys | Tyr |
| Tyr | Thr | Ala<br>35 | Lys | Glu | Ala | Leu | Glu<br>40 | Cys | Ile | Asp | Lys | Ser<br>45 | Glu | Ile | Asp |
| Leu | Ala<br>50 | Ile | Leu | Asp | Ile | Met<br>55 | Leu | Pro | Gly | Thr | Ser<br>60 | Gly | Leu | Thr | Ile |
| Cys<br>65 | Gln | Lys | Ile | Arg | Asp<br>70 | Lys | His | Thr | Tyr | Pro<br>75 | Ile | Ile | Met | Leu | Thr<br>80 |

```
Gly Lys Asp Thr Glu Val Asp Lys Ile Thr Gly Leu Thr Ile Gly Ala
                85                  90                  95

Asp Asp Tyr Ile Thr Lys Pro Phe Arg Pro Leu Glu Leu Ile Ala Arg
            100                 105                 110

Val Lys Ala Gln Leu Arg Arg Tyr Lys Lys Phe Ser Gly Val Lys Glu
        115                 120                 125

Gln Asn Glu Asn Val Ile Val His Ser Gly Leu Val Ile Asn Val Asn
    130                 135                 140

Thr His Glu Cys Tyr Leu Asn Glu Lys Gln Leu Ser Leu Thr Pro Thr
145                 150                 155                 160

Glu Phe Ser Ile Leu Arg Ile Leu Cys Glu Asn Lys Gly Asn Val Val
            165                 170                 175

Ser Ser Glu Leu Leu Phe His Glu Ile Trp Gly Asp Glu Tyr Phe Ser
            180                 185                 190

Lys Ser Asn Asn Thr Ile Thr Val His Ile Arg His Leu Arg Glu Lys
            195                 200                 205

Met Asn Asp Thr Ile Asp Asn Pro Lys Tyr Ile Lys Thr Val Trp Gly
    210                 215                 220

Val Gly Tyr Lys Ile Glu Lys
225                 230
```

(2) INFORMATION FOR SEQ ID NO:44:

(i) SEQUENCE CHARACTERISTICS:
        (A) LENGTH: 239 amino acids
        (B) TYPE: amino acid
        (D) TOPOLOGY: linear (ii) MOLECULE TYPE: protein (vi) ORIGINAL SOURCE:
        (A) ORGANISM: Escherichia coli (xi) SEQUENCE DESCRIPTION: SEQ ID NO:44:

```
Met Gln Glu Asn Tyr Lys Ile Leu Val Val Asp Asp Asp Met Arg Leu
1               5                   10                  15

Arg Ala Leu Leu Glu Arg Tyr Leu Thr Glu Gln Gly Phe Gln Val Arg
            20                  25                  30

Ser Val Ala Asn Ala Glu Gln Met Asp Arg Leu Leu Thr Arg Glu Ser
        35                  40                  45

Phe His Leu Met Val Leu Asp Leu Met Leu Pro Gly Glu Asp Gly Leu
    50                  55                  60

Ser Ile Cys Arg Arg Leu Arg Ser Gln Ser Asn Pro Met Pro Ile Ile
65                  70                  75                  80

Met Val Thr Ala Lys Gly Glu Glu Val Asp Arg Ile Val Gly Leu Glu
            85                  90                  95

Ile Gly Ala Asp Asp Tyr Ile Pro Lys Pro Phe Asn Pro Arg Glu Leu
            100                 105                 110

Leu Ala Arg Ile Arg Ala Val Leu Arg Arg Gln Ala Asn Glu Leu Pro
            115                 120                 125

Gly Ala Pro Ser Gln Glu Glu Ala Val Ile Ala Phe Gly Lys Phe Lys
    130                 135                 140

Leu Asn Leu Gly Thr Arg Glu Met Phe Arg Glu Asp Glu Pro Met Pro
145                 150                 155                 160

Leu Thr Ser Gly Glu Phe Ala Val Leu Lys Ala Leu Val Ser His Pro
            165                 170                 175

Arg Glu Pro Ile Ser Arg Asp Lys Leu Met Asn Leu Ala Arg Gly Arg
            180                 185                 190
```

|     |     |     |     |     |     |     |     |     |     |     |     |     |     |     |
| --- | --- | --- | --- | --- | --- | --- | --- | --- | --- | --- | --- | --- | --- | --- |
| Glu | Tyr | Ser | Ala | Met | Glu | Arg | Ser | Ile | Asp | Val | Gln | Ile | Ser | Arg | Leu |
|     |     | 195 |     |     |     |     | 200 |     |     |     |     | 205 |     |     |     |
| Arg | Arg | Met | Val | Glu | Glu | Asp | Pro | Ala | His | Pro | Arg | Tyr | Ile | Gln | Thr |
|     |     | 210 |     |     |     |     | 215 |     |     |     |     | 220 |     |     |     |
| Val | Trp | Gly | Leu | Gly | Tyr | Val | Phe | Val | Pro | Asp | Gly | Ser | Lys | Ala |
| 225 |     |     |     |     | 230 |     |     |     |     | 235 |     |     |     |     |

( 2 ) INFORMATION FOR SEQ ID NO:45:

( i ) SEQUENCE CHARACTERISTICS:
        ( A ) LENGTH: 229 amino acids
        ( B ) TYPE: amino acid
        ( D ) TOPOLOGY: linear ( i i ) MOLECULE TYPE: protein ( v i ) ORIGINAL SOURCE:
        ( A ) ORGANISM: Escherichia coli ( x i ) SEQUENCE DESCRIPTION: SEQ ID NO:45:

|     |     |     |     |     |     |     |     |     |     |     |     |     |     |     |     |
| --- | --- | --- | --- | --- | --- | --- | --- | --- | --- | --- | --- | --- | --- | --- | --- |
| Met | Ala | Arg | Arg | Ile | Leu | Val | Val | Glu | Asp | Glu | Ala | Pro | Ile | Arg | Glu |
| 1   |     |     |     | 5   |     |     |     |     | 10  |     |     |     |     | 15  |     |
| Met | Val | Cys | Phe | Val | Leu | Glu | Gln | Asn | Gly | Phe | Gln | Pro | Val | Glu | Ala |
|     |     |     | 20  |     |     |     |     | 25  |     |     |     |     | 30  |     |     |
| Glu | Asp | Tyr | Asp | Ser | Ala | Val | Asn | Gln | Leu | Asn | Glu | Pro | Trp | Pro | Asp |
|     |     | 35  |     |     |     |     | 40  |     |     |     |     | 45  |     |     |     |
| Leu | Ile | Leu | Leu | Asp | Trp | Met | Leu | Pro | Gly | Gly | Ser | Gly | Ile | Gln | Phe |
|     | 50  |     |     |     |     | 55  |     |     |     |     | 60  |     |     |     |     |
| Ile | Lys | His | Leu | Lys | Arg | Glu | Ser | Met | Thr | Arg | Asp | Ile | Pro | Val | Val |
| 65  |     |     |     |     | 70  |     |     |     |     | 75  |     |     |     |     | 80  |
| Met | Leu | Thr | Ala | Arg | Gly | Glu | Glu | Glu | Asp | Arg | Val | Arg | Gly | Leu | Glu |
|     |     |     |     | 85  |     |     |     |     | 90  |     |     |     |     | 95  |     |
| Thr | Gly | Ala | Asp | Asp | Tyr | Ile | Thr | Lys | Pro | Phe | Ser | Pro | Lys | Glu | Leu |
|     |     |     | 100 |     |     |     |     | 105 |     |     |     |     | 110 |     |     |
| Val | Ala | Arg | Ile | Lys | Ala | Val | Met | Arg | Arg | Ile | Ser | Pro | Met | Ala | Val |
|     |     | 115 |     |     |     |     | 120 |     |     |     |     | 125 |     |     |     |
| Glu | Glu | Val | Ile | Glu | Met | Gln | Gly | Leu | Ser | Leu | Asp | Pro | Thr | Ser | His |
|     | 130 |     |     |     |     | 135 |     |     |     |     | 140 |     |     |     |     |
| Arg | Val | Met | Ala | Gly | Glu | Glu | Pro | Leu | Glu | Met | Gly | Pro | Thr | Glu | Phe |
| 145 |     |     |     |     | 150 |     |     |     |     | 155 |     |     |     |     | 160 |
| Lys | Leu | Leu | His | Phe | Phe | Met | Thr | His | Pro | Glu | Arg | Val | Tyr | Ser | Arg |
|     |     |     |     | 165 |     |     |     |     | 170 |     |     |     |     | 175 |     |
| Glu | Gln | Leu | Leu | Asn | His | Val | Trp | Gly | Thr | Asn | Val | Tyr | Val | Glu | Asp |
|     |     |     | 180 |     |     |     |     | 185 |     |     |     |     | 190 |     |     |
| Arg | Thr | Val | Asp | Val | His | Ile | Arg | Arg | Leu | Arg | Lys | Ala | Leu | Glu | Pro |
|     |     | 195 |     |     |     |     | 200 |     |     |     |     | 205 |     |     |     |
| Gly | Gly | His | Asp | Arg | Met | Val | Gln | Thr | Val | Arg | Gly | Thr | Gly | Tyr | Arg |
|     | 210 |     |     |     |     | 215 |     |     |     |     | 220 |     |     |     |     |
| Phe | Ser | Thr | Arg | Phe |
| 225 |     |     |     |     |

( 2 ) INFORMATION FOR SEQ ID NO:46:

( i ) SEQUENCE CHARACTERISTICS:
        ( A ) LENGTH: 129 amino acids
        ( B ) TYPE: amino acid
        ( D ) TOPOLOGY: linear ( i i ) MOLECULE TYPE: protein ( v i ) ORIGINAL SOURCE:
    ( A ) ORGANISM: Escherichia coli ( x i ) SEQUENCE DESCRIPTION: SEQ ID NO:46:

```
Met Ala Asp Lys Glu Leu Lys Phe Leu Val Val Asp Asp Phe Ser Thr
1               5                   10                  15

Met Arg Arg Ile Val Arg Asn Leu Leu Lys Glu Leu Cys Phe Asn Asn
            20              25                  30

Val Glu Glu Ala Glu Asp Gly Val Asp Ala Leu Asn Lys Leu Gln Ala
        35              40                  45

Gly Gly Phe Gly Phe Ile Ile Ser Asp Trp Asn Met Pro Asn Met Asp
    50              55                  60

Gly Leu Glu Leu Leu Lys Thr Ile Arg Ala Asp Ser Ala Met Ser Ala
65              70                  75                      80

Leu Pro Val Leu Met Val Thr Ala Glu Ala Lys Lys Glu Asn Ile Ile
                85                  90                  95

Ala Ala Ala Gln Ala Gly Ala Ser Gly Tyr Val Val Lys Pro Phe Thr
            100             105                 110

Ala Ala Thr Leu Glu Glu Lys Leu Asn Lys Ile Phe Glu Lys Leu Gly
        115                 120                 125

Met
```

( 2 ) INFORMATION FOR SEQ ID NO:47:

( i ) SEQUENCE CHARACTERISTICS:
        ( A ) LENGTH: 9 amino acids
        ( B ) TYPE: amino acid
        ( D ) TOPOLOGY: linear ( i i ) MOLECULE TYPE: peptide ( v ) FRAGMENT TYPE: N-terminal ( v i ) ORIGINAL SOURCE:
        ( A ) ORGANISM: E. faecium
        ( B ) STRAIN: BM4147

( x i ) SEQUENCE DESCRIPTION: SEQ ID NO:47:

```
Met Asn Arg Ile Lys Val Ala Ile Leu
1               5
```

( 2 ) INFORMATION FOR SEQ ID NO:48:

( i ) SEQUENCE CHARACTERISTICS:
        ( A ) LENGTH: 10 base pairs
        ( B ) TYPE: nucleic acid
        ( C ) STRANDEDNESS: unknown
        ( D ) TOPOLOGY: linear ( i i ) MOLECULE TYPE: DNA (genomic)

( i x ) FEATURE:
        ( A ) NAME/KEY: RBS
        ( B ) LOCATION: 1..10

( x i ) SEQUENCE DESCRIPTION: SEQ ID NO:48:

TGAAAGGAGA        10

( 2 ) INFORMATION FOR SEQ ID NO:49:

( i ) SEQUENCE CHARACTERISTICS:
        ( A ) LENGTH: 10 base pairs
        ( B ) TYPE: nucleic acid
        ( C ) STRANDEDNESS: unknown
        ( D ) TOPOLOGY: linear (i i) MOLECULE TYPE: RNA (genomic)

(x i) SEQUENCE DESCRIPTION: SEQ ID NO:49:

UCUUUCCUCC 10

(2) INFORMATION FOR SEQ ID NO:50:

(i) SEQUENCE CHARACTERISTICS:
                (A) LENGTH: 23 base pairs
                (B) TYPE: nucleic acid
                (C) STRANDEDNESS: unknown
                (D) TOPOLOGY: linear (i i) MOLECULE TYPE: DNA (genomic)

(x i) SEQUENCE DESCRIPTION: SEQ ID NO:50:

GCTGCAGATA AAAATTTAGG AGG 23

(2) INFORMATION FOR SEQ ID NO:51:

(i) SEQUENCE CHARACTERISTICS:
                (A) LENGTH: 24 base pairs
                (B) TYPE: nucleic acid
                (C) STRANDEDNESS: unknown
                (D) TOPOLOGY: linear (i i) MOLECULE TYPE: DNA (genomic)

(x i) SEQUENCE DESCRIPTION: SEQ ID NO:51:

CGCATGCTAT TATAAAAGCC AGTC 24

(2) INFORMATION FOR SEQ ID NO:52:

(i) SEQUENCE CHARACTERISTICS:
                (A) LENGTH: 10 base pairs
                (B) TYPE: nucleic acid
                (C) STRANDEDNESS: unknown
                (D) TOPOLOGY: linear (i i) MOLECULE TYPE: DNA (genomic)

(x i) SEQUENCE DESCRIPTION: SEQ ID NO:52:

TGAAAGGGTG 10

(2) INFORMATION FOR SEQ ID NO:53:

(i) SEQUENCE CHARACTERISTICS:
                (A) LENGTH: 21 base pairs
                (B) TYPE: nucleic acid
                (C) STRANDEDNESS: unknown
                (D) TOPOLOGY: linear (i i) MOLECULE TYPE: rRNA (v i) ORIGINAL SOURCE:
                (A) ORGANISM: B. subtilis (x i) SEQUENCE DESCRIPTION: SEQ ID NO:53:

GGGGGGTTGG NNNNNNNNTT G 21

(2) INFORMATION FOR SEQ ID NO:54:

(i) SEQUENCE CHARACTERISTICS:
                (A) LENGTH: 19 base pairs
                (B) TYPE: nucleic acid
                (C) STRANDEDNESS: unknown
                (D) TOPOLOGY: linear (i i) MOLECULE TYPE: rRNA (vi) ORIGINAL SOURCE:
(A) ORGANISM: B. subtilis (xi) SEQUENCE DESCRIPTION: SEQ ID NO:54:

AGAACGAAAA NNNNNNATG                                                                                           19